US007667099B2

(12) United States Patent
Osteryoung et al.

(10) Patent No.: US 7,667,099 B2

(45) Date of Patent: Feb. 23, 2010

(54) PLASTID DIVISION AND RELATED GENES AND PROTEINS, AND METHODS OF USE

(75) Inventors: Katherine W. Osteryoung, Williamston, MI (US); Stanislav Vitha, Haslett, MI (US); Olga A. Koksharova, Moscow (RU); Hongbo Gao, East Lansing, MI (US)

(73) Assignee: Board of Trustees of Michigan State University, Lansing, MI (US)

( * ) Notice: Subject to any disclaimer, the term of this patent is extended or adjusted under 35 U.S.C. 154(b) by 124 days.

(21) Appl. No.: 10/600,070

(22) Filed: Jun. 20, 2003

(65) Prior Publication Data

US 2004/0139500 A1 Jul. 15, 2004

Related U.S. Application Data

(60) Provisional application No. 60/402,242, filed on Aug. 9, 2002, provisional application No. 60/390,140, filed on Jun. 20, 2002.

(51) Int. Cl.

| | |
|---|---|
| ***A01H 5/00*** | (2006.01) |
| ***A01H 5/10*** | (2006.01) |
| ***C12N 15/82*** | (2006.01) |
| ***C12N 15/29*** | (2006.01) |

(52) U.S. Cl. .................. 800/298; 536/23.2; 435/320.1; 435/418

(58) Field of Classification Search ....................... None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,940,838 | A | 7/1990 | Schilperoort et al. |
| 4,945,050 | A | 7/1990 | Sanford et al. |
| 4,965,188 | A | 10/1990 | Mullis et al. |
| 5,057,422 | A | 10/1991 | Bol et al. |
| 5,096,815 | A | 3/1992 | Ladner et al. |
| 5,173,410 | A | 12/1992 | Ahlquist |
| 5,187,267 | A | 2/1993 | Comai et al. |
| 5,198,346 | A | 3/1993 | Ladner et al. |
| 5,223,409 | A | 6/1993 | Ladner et al. |
| 5,352,605 | A | 10/1994 | Fraley |
| 5,451,513 | A | 9/1995 | Maliga et al. |
| 5,500,360 | A | 3/1996 | Ahlquist et al. |
| 5,501,967 | A | 3/1996 | Offringa et al. |
| 5,545,817 | A | 8/1996 | McBride et al. |
| 5,545,818 | A | 8/1996 | McBride et al. |
| 5,584,807 | A | 12/1996 | McCabe |
| 5,733,731 | A | 3/1998 | Schatz et al. |
| 5,811,238 | A | 9/1998 | Stemmer et al. |
| 5,824,877 | A | 10/1998 | Hinchee et al. |
| 5,830,721 | A | 11/1998 | Stemmer et al. |
| 5,837,458 | A | 11/1998 | Minshull et al. |
| 5,846,795 | A | 12/1998 | Ahlquist et al. |
| 5,866,785 | A | 2/1999 | Donson et al. |
| 5,965,794 | A | 10/1999 | Turpen |
| 5,977,438 | A | 11/1999 | Turpen et al. |
| 5,981,836 | A | 11/1999 | Osteryoung |
| 5,981,839 | A | 11/1999 | Kanuf et al. |
| 5,981,840 | A | 11/1999 | Zhao et al. |
| 6,051,757 | A | 4/2000 | Barton et al. |
| 6,063,947 | A | 5/2000 | DeBonte et al. |
| 6,812,382 | B1 | 11/2004 | Hitz et al. |

FOREIGN PATENT DOCUMENTS

| | | |
|---|---|---|
| EP | 0 292 435 | 11/1988 |
| WO | WO 88/06630 | 9/1988 |
| WO | WO 92/09690 | 6/1992 |
| WO | WO 93/07278 | 4/1993 |
| WO | WO 94/13822 | 6/1994 |
| WO | WO 95/14098 | 5/1995 |
| WO | WO 95/16783 | 6/1995 |

OTHER PUBLICATIONS

UniProt entry Q9FIG9 2001, www.pir.uniprot.org/cgi-bin/upEntry?id=Q9FIG9.*

Lazar et al, 1988, Mol. Cell. Biol. 8:1247-1252.*

Hill et al, 1998, Biochem. Biophys. Res. Comm. 244:573-577.*

Guo et al, 2004, Proc. Natl. Acad. Sci. USA 101: 9205-9210.*

Maple et al, Annals Botany 99:565-579.*

Osteryoung et al. (1998) "Chloroplast Division in Higher Plants Requires Members of Two Functionally Divergent Gene Families with Homology to Bacterial *ftsZ*," Plant Cell 10:1991-2004.

Jiang et al. (1998) "Multivesicular bodies: a mechanism to package lytic and storage functions in one organelle?" Trends Cell Biol 7:362-367.

Faguy and Doolittle (1998) "Cytoskeletal proteins: The evolution of cell division," Curr. Biol. 8:R338-341.

Lowe and Amos (1998) "Crystal structure of the bacterial cell-division protein FtsZ," Nature 391:203-206.

Bi and Lutkenhaus (1991) "FtsZ ring structure associated with division in *Escherichia coli*," Nature 354:161-164.

Addinall et al. (1996) "FtsZ Ring Formation in *fts* Mutants," J Bacteriol 178:3877-3884.

deBoer et al. (1988) "Isolation and Properties of *min*B, a Complex Genetic Locus Involved in Correct Placement of the Division Site in *Escherichia coli*," J Bacteriol 170:2106-2112.

(Continued)

*Primary Examiner*—Anne R Kubelik
(74) *Attorney, Agent, or Firm*—Medlen & Carroll, LLP

(57) ABSTRACT

The present invention relates to genes encoding proteins involved in prokaryotic type or plastid division and/or morphology and the encoded proteins, and in particular to isolated Ftn2 (ARC6), ARC5, and Fzo-like genes and polypeptides. The present invention also provides methods for using Ftn2 (ARC6), ARC5, and Fzo-like genes, and polypeptides.

12 Claims, 6 Drawing Sheets

OTHER PUBLICATIONS

Sun and Margolin (1998) "FtsZ Dynamics during the Division Cycle of Live *Escherichia coli* Cells," J Bacteriol 180:2050-2056.
Lutkenhaus (1998) "The regulation of bacterial cell divisions: a time and place for it," Curr Opin Microbiol 1:210-215.
Rothfield (1999) "Bacterial Cell Division," Annu. Rev. Genet. 33:423-448.
Rothfield and Justice (1997) "Bacterial Cell Division: The Cycle of the Ring," Cell 88:581-584.
Sullivan and Maddock (2000) "Bacterial division: Finding the dividing line," Curr. Biol. 10:R249-252.
McAndrew et al. (2001) "Colocalization of Plastid Division Proteins in the Chloroplast Stromal Compartment Estqablishes a New Functional Relationship between FtsZ1 and FtsZ2 in Higher Plants," Plant Physiol. 127:1656-1666.
Osteryoung et al. (2001) "The Plastid Division Machine," Annu. Rev. Plant Physiol. Plant Mol. Biol. 52:315-333.
Colletti et al. (2000) "A homologue of the bacterial cell division site-determining factor MinD mediates placement of the chloroplast division apparatus," Curr. Biol. 10:507-16.
Moehs et al. (2001) "Analysis of carotenoid biosynthetic gene expression during marigold petal development," Plant Mol. Biol. 45:281-93.
Wakasugi et al. (1997) "Complete nucleotide sequence of the chloroplast genome from the green alga *Chlorella vulgaris*: The existence of genes possibly involved in chloroplast division," Proc. Natl. Acad. Sci. USA 94:5967-72.
Itoh et al. (2001) "A Chloroplast Protein Homologous to the Eubacterial Topological Specificity Factor MinE Plays a Role in Chloroplast Division," Plant Physiol. 127:1644-1655.
Reddy et al. (2002) "Overexpression of the *Arabidopsis thaliana MinE1* bacterial division inhibitor homologue gene alters chloroplast size and morphology in transgenic *Arabidopsis* and tobacco plants," Planta. 215:167-176.
Margolin (1198) "A green light for the bacterial cytoskeleton," Trends Microbiol. 6:233-38.
Osteryoung (1998) "Plastid division: evidence for a prokaryotically derived mechanism," Curr Opin. Plant Biol. 1:475-79.
Marrison et al. (1999) "The distinctive roles of five different *ARC* genes in the chloroplast division process in *Arabidopsis*. " The Plant Journal 18(6): 651-662.
Ingram and Van Baalen C (1970) "Characteristics of a Stable, Filamentous Mutant of a Coccoid Blue-Green Alga," J. Bacteriol. 102:784-789.
Ingram et al. (1972) "Cell Division Mutations in the Blue-Green Bacterium *Agmenellum quadruplicatum* Strain BG1: a Comparison of the Cell Wall," J. Bacteriol. 111:614-621.
Ingram and Fisher (1973)"Novel Mutant Impaired in Cell Division: Evidence for a Positive Regulating Factor," J. Bacteriol. 113:999-1005.
Ingram and Fisher (1973) "Mechanism for the Regulation of Cell Division in *Agmenellum*," J. Bacteriol. 113:1006-1014.
Ingram and Blackwell (1975) "Isolation of a Small-Cell Mutant in the Blue-Green Bacterium *Agmenellum quadruplicatum*," J. Bacteriol. 123:743-746.
Doherty and Adams (1995) "Cloning and sequence of *ftsZ*and flanking regions from the cyanobacterium *Anabaena* PCC 7120," Gene: 93-99.
Zhang et al. (1995) "Analysis of genes encoding the cell division protein FtsZ and a glutathione synthetase homologue in the cynaobacteriaum *Anabaena* sp. PCC 7120," Res. Microbiol. 146:445-455.
Cai and Wolk (1997) "Nitrogen Deprivation of *Anabaena* sp. Strain PCC 7120 Elicits Rapid Activation of a Gene Cluster that is Essential for Uptake and Utilization of Nitrate," J. Bacteriol. 179:258-266.
Ernst et al. (1992) "Synthesis of Nitrogenase in Mutants of the Cyanobacterium *Anabaena* sp. Strain PCC 7120 Affected in Heterocyst Development or Metabolism," J. Bacteriol. 174:6025-6032.
Wolk et al. (1991) "Use of a transposon with luciferase as a reporter to identify environmentally responsive genes in a cyanobacterium," Proc. Natl. Acad. Sci. USA 88:5355-5359.
Dolganov and Grossman (1993) "Insertional Inactivation of Genes to Isolate Mutants of *Synechococcus* sp. Strain PCC 7942: Isolation of Filamentous Strains," J. Bacteriol. 175:7644-7651.
Ohtsuka and Hata (2000) "Molecular chaperone function of mammalian Hsp70 and Hsp40—a review," Int. J. Hyperthermia 16:231-45.
Cheetham and Caplan (1998) "Structure, function and evolution of DnaJ: conservation and adaptation of chaperone function," Cell Stress Chaperones 3:28-36.
Bukau and Horwich (1998) "The Hsp70 and Hsp60 Chaperone Machines," Cell 92:351-366.
Fink (1999) "Chaperone-Mediated Protein Folding," Physiological Rev. 79:425-449.
Gething (1997) "The difference with prokaryotes," Nature 388:329-331.
Hartl (1996) "Molecular chaperones in cellular protein folding," Nature 381;571-580.
Laufen et al. (1999) "Mechanism of regulation of Hsp70 chaperones by DnaJ cochaperones," Proc. Natl. Acad. Sci. USA 96:5452-5457.
Sikorski et al. (1990) "A Repeating Amino Acid Motif in *CDC23* Defines a Family of Proteins and a New Relationship among Genes Required for Mitosis and RNA Synthesis," Cell 60:307-317.
Das et al. (1998) "The structure of the tetratricopeptide repeats of protein phosphatase 5: implications for TPR-mediated protein-protein interactions," EMBO J. 17:1192-1199.
Lamb et al. (1995) "Tetratrico peptide repeat interactions: to TPR or not to TPR," Trends Biochem. Sci. 20:257-259.
Wilson et al. (1984) "The Structure of an Antigenic Determinant in a Protein," Cell 37:767.
Crea and Horn (1980) "Synthesis of oligonucleotides on cellulose by a phosphotriester method," Nucl. Acids Res. 8:2331.
Chow et al. (1981) "Synthesis of oligodeoxyribonucleotides on silica gel support," Nucl. Acids Res. 9:2807-2817.
Roberge et al. (1995) "A Strategy for a Convergent Synthesis of N-Linked Glycopeptides on a Solid Support," Science 269:202-204.
Sarkar et al. (1993) "Restriction-site PCR: A Direct Method of Unknown Sequence Retrieval Adjacent to a Known Locus by Using Universal Primers," PCR Methods Applic. 2:318-322.
Triglia et al. (1988) "A procedure for in vitro amplification of DNA segments that lie outside the boundaries of known sequences." Nucl. Acids Res. 16:8186.
Lagerstrom et al. (1991) "Capture PCR: Efficient Amplification of DNA Fragments Adjacent to a Known Sequence in Human and YAC DNA," PCR Methods Applic. 1:111-119.
Parker et al. (1991) "Targeted gene walking polymerase chain reaction," Nucl. Acids Res. 19:3055-60.
Back and Chappell (1996) "Identifying functional domains within terpene cyclases using a domain-swapping strategy," Proc. Natl. Acad. Sci. USA 93: 6841-6845.
Moore and Arnold (1996) "Directed evolution of a *para*-nitrobenzyl esterase for aqueous-organic solvents," Nat. Biotech. 14:458-67.
Eckert and Kunkel (1991) "DNA Polymerase Fidelity and the Polymerase Chain Reaction," PCR Methods Appl. 1:17-24.
Cadwell and Joyce (1992) "Randomization of Genes by PCR Mutagenesis," PCR Methods Appl. 2:28-33.
Zhao and Arnold (1997) "Optimization of DNA shuffling for high fidelity recombination," Nucl. Acids. Res. 25:1307-08.
Smith (1994) "The progeny of sexual PCR," Nature 370:324-25.
Stemmer (1994) "Rapid evolution of a protein in vitro by DNA shuffling," Nature 370:398-91.
Stemmer (1994) "DNA shuffling by random fragmentation and reassembly: In vitro recombination for molecular evolution." Proc. Natl. Acad. Sci. USA 91:10747-10751.
Zhang et al. (1997) "Directed evolution of a fucosidase from a galactosidase by DNA shuffling and screening." Proc. Natl. Acad. Sci. USA 94:4504-09.
Crameri et al. (1997) "Molecular evolution of an arsentate detoxification pathway by DNA shuffling," Nat. Biotech. 15:436-38.
Itakura et al. (1984) "Synthesis and Use of Synthetic Oligonucleotides," Annu. Rev. Biochem. 53:323.
Itakura et al. (1984) "Expression in *Escherichia coli* of a Chemically Synthesized Gene for the Hormone Somatostatin," Science 198:1056.

Ike et al. (1983) "Solid phase synthesis of polynucleotides. VIII. Synthesis of mixed oligodeoxyribonucleotides by the phosphotriester solid phase method," Nucl. Acid Res. 11:477.
Scott et al. (1980) "Searching for Peptide Ligands with an Epitope Library," Science 249:386-390.
Roberts et al. (1992) "Directed evolution of a protein: Selection of potent neutrophil elastase inhibitors displayed on M13 fusion phage." Proc. Natl. Acad. Sci. USA 89:2429-2433.
Devlin et al. (1990) "Random Peptide Libraries: A Source of Specific Protein Binding Molecules," Science 249: 404-406.
Cwirla et al. (1990) "Peptides on phage: A vast library of peptides for identifying ligands," Proc. Natl. Acad. Sci. USA 87: 6378-6382.
Ben-Bassat et al. (1987) "Processing of the Initiation Methionine from Proteins: Properties of the *Escherichia coli* Methionine Aminopeptidase and Its Gene Structure," J. Bacteriol., 169:751-757.
Miller et al. (1987) "N-terminal methionine-specific peptidase in *Salmonella typhimurium*," Proc. Natl. Acad. Sci. USA 84:2718-22.
Janknecht et al. (1991) "Rapid and efficient purification of native histidine-tagged protein expressed by recombinant vaccinia virus," Proc. Natl. Acad. Sci. USA 88:8972.
Marks et al. (1992) "Molecular Evolution of Proteins on Filamentous Phage," J. Biol. Chem. 267:16007-16010.
Griffiths et al. (1993) "Human anti-self antibodies with high specificity from phage display libraries," EMBO J. 12:725-734.
Clackson et al. (1991) "Making antibody fragments using phage display libraries," Nature 352:624-628.
Barbas et al. (1992) "Semisynthetic combinatorial antibody libraries: A chemical solution to the diversity problem," Proc. Natl. Acad. Sci., 89:4457-4461.
Wang et al. (1994) "Single Amino Acid Insertion Probe the a Subunit of the *Escherichia coli* $F_1F_0$-ATP Synthase," J. Biol. Chem. 269:3095-3099.
Balint (1993) "Antibody engineering by parsimonious mutagenesis," Gene 137:109-118.
Nagashima et al. (1993) "Alanine-scanning Mutagenesis of the Epidermal Growth Factor-like Domains of Human Thrombomodulin Identifies Critical Residues for Its Cofactor Activity," J. Biol. Chem. 268:2888-2892.
Cunningham et al. (1989) "High-Resolution Epitope Mapping of hGH-Receptor Interactions by Alanine-Scanning Mutagenesis," Science 244:1081-1085.
Brown et al. (1992) "The Promoter for the Procyclic Acidic Repetitive Protein (PARP) Genes of *Trypanosoma brucei* Shares Features with RNA Polymerase I Promoters," Mol. Cell. Biol. 12:2644-2652.
McKnight et al. (1986) "Transcriptional Control Signals of a Eukaryotic Protein-Coding Gene," Science 232-316.
Myers et al. (1986) "Fine Structure Gentic Analysis of a β-Globin Promoter," Science 232:613.
Gleba et al. (1999) "Use of plant roots for phytoremediation and molecular farming," Proc. Natl. Acad. Sci. USA 96: 5973-5977.
Weselake and Taylor (1999) "The study of storage lipid biosynthesis using microspore-derived cultures of oilseed rape," Prog. Lipid Res. 38: 401.
Chao et al. (1999) "Leucine Aminopeptidase RNAs, Proteins, and Activities Increase in Response to Water Deficity, Salinity, and the wound Signals Systemin, Methyl Jasmonate, and Abscisic Acid," Plant Physiol. 120:979-992.
Beachy et al. (1985) "Accumulation and assembly of soybean β-conglycinin in seeds of transformed petunia plants," EMBO J 4: 3047-3053.
Proudfoot (1991) "Poly(A) Signals," Cell 64:671.
Sanfacon et al. (1991) "A dissection of the cauliflower mosaic virus polyadenylation signal," Genes Dev. 5:141.
Mogen et al. (1990) "Upstream Sequences Other than AAUAAA are Required for Efficient Messenger RNA 3' -End Formation in Plants," Plant Cell 2:1261.
Ballas et al. (1989) "Efficient functioning of plant promoters and poly(A) sites in *Xenopus oocytes*," Nucl. Acids Res. 17:7891.
Joshi et al. (1987) "Putative plyadenylation signals in nuclear genes of higher plants: a compilation and analysis," Nucl. Acid Res. 15:9627.
Callis et al. (1987) "Introns increase gene expression in cultured maize cells," Genes Develop. 1:1183.
Kalderon et al. (1984) "A Short Amino Acid Sequence Able to Sepcify Nuclear Location," Cell 39:499.
Joshi (1987) "An inspection of the domain between putative TATA box and translation start site in 79 plant genes," Nucl. Acids Research 15:6643.
Bevan et al. (1983) "A chimaeric antibiotic resistance gene as a selectable marker for plant cell transformation," Nature 304:184.
White et al. (1990) "A cassette containing the *bar* gene of *Streptomyces hygroscopicus*: a selectable marker for plant transformation," Nucl Acids Res. 18:1062.
Blochlinger and Diggelmann (1984) "Hygromycin B Phosphotransferase as a Selectable Marker for DNA Transfer Experiments with Higher Eucaryotic Cells," Mol. Cell. Biol. 4:2929.
Bourouis et al. "Vectors containing a prokaryotic dihydrofolate reductase gene transform *Drosophila* cells to methotrexate-resistance," (1983) EMBO J. 2:1099.
Svab et al. (1990) "Stable transformation of plastids in higher plants," Proc. Natl. Acad. Sci. USA 87:8526.
Staub and Maliga (1992) "Long Regions of Homologous DNA are Incorporated into the Tobacco Plastid Genome by Transformation," Plant Cell 4:39.
Staub and Maliga (1993) "Accumulation of D1 polypeptide in tobacco plastids is regulated via the untranslated region of the *psb*A mRNA." EMBO J. 12:601.
Svab and Maliga (1993) "High-frequency plastid transformation in tobacco by s election for a chimeric *aadA* Gene," Proc. Natl. Acad. Sci. USA 90:913.
Fraley et al. (1982) "Liposome-mediated delibery of tobacco mosaic virus RNA into tobacco protoplasts: A sensitive assay for monitoring liposome-protoplast interactions," iProc. Natl. Acad. Sci. USA 79:1859.
Paszkowski et al. (1984) "Direct gene transfer to plants," EMBO J 3:2717.
Hayashimoto et al. (1990) "A Polyethylene Glycol-Mediated Protoplast Transformation System for Production of Fertile Transgenic Rice Plants," Plant Physiol. 93:857.
Fromm et al. (1985) "Expression of genes transferred into monocot and dicot plant cells by electroporation," Proc. Natl Acad. Sci. USA 82:5824.
Riggs et al. (1986) "Stable transformation of tobacco by electroporation: Evidence for plasmid concatenation," Proc. Natl. Acad. Sci. USA 83:5602.
Weising et al. (1988) "Foreign Genes in Plants: Transfer, Structure, Expression, and Applications," Annual Rev. Genet. 22:421.
Christou et al. (1988) "Stable Transformation of Soybean Callus by DNA-Coated Gold Particles," Plant Physiol. 87:671.
Klein et al. (1988) "Transfer of foreign genes into intact maize cells with high-velocity microprojectiles," Proc. Natl. Acad. Sci. USA 85:4305.
Gordon-Kamm et al. (1990) "Transformation of Maize Cells and Regeneration of Fertile Transgenic Plants," Plant Cell 2:603.
Koziel et al. (1996) "Transgenic Maize for the Control of European Corn Borrer and Other Maize Insect Pests," Annals of the NY Acad. of Sci. 792:164.
Shimamoto et al. (1989) "Fertile transfenic rice plants regenerated from transformed protoplasts," Nature 338:274.
Weeks et al. (1993) "Rapid Proudction of Multiple Independent Lines of Fertile Transgenic Wheat (*Triticum aestivum*)," Plant Physiol. 102: 1077.
Wan et al. (1994) "Generation of Large Numbers of Independently Transformed Fertile Barley Plants," Plant Physiol. 104: 37.
Casas et al. (1993) "Transfenic sorghum plants via microprojectile bombardment," Proc. Natl. Acad. Sci. USA 90:11212.
Nehra et al. (1994) "Self-fertile transfenic wheat plants regenerated from isolated scutellar tissues following microprojectile bombardment with two distinct gene constructs," The Plant Journal 5:285.
Schell (1987) "Transgenic Plants as Tools to Study the Molecular Organization of Plant Genes," Science 237:1176.
Sheehy et al. (1988) "Reduction of polygalacturonase activity in tomato fruit by antisense RNA," Proc. Natl. Acad. Sci. USA 85:8805-8809.

Ch'ng et al. (1989) "Antisense RNA complementary to 3' coding and noncoding sequences of creatine kinase is a potent inhibitor of translation in vivo," Proc. Natl. Acad. Sci. USA 86:10006-10010.
Haseloff et al. (1988) "Simple RNA enzynmes with new and highly specific endoribonuclease activities," Nature 334:585-591.
Merlo et al. (1998) "Ribozymes Targeted to Stearoyl-ACP Δ9 Desaturase mRNA Produce Heritable Increases of Stearic Acid in Transgenic Maize Leaves," Plant Cell 10: 1603-1621.
Napoli et al. (1990) "Introduction of a Chimeric Chalcone Synthase Gene into Petunia Results in Reversible Co-Suppression of Homologous Genes *in trans*," Plant Cell 2:279-289.
van der Krol et al. (1990) "Flavonoid Genes in Petunia: Addition of a Limited Number of Gene Copies May Lead to a Suppression of Gene Expression," Plant Cell 2:291-299.
Wesley et al. (2001) "Construct design for efficient, effective and high-throughput gene silencing in plants," Plant J. 27: 581-590.
Vitha et al. (2001) "FtsZ Ring Formation at the Chloroplast Division Site in Plants," J. Cell. Biol.153:111-120.
Altschul et al. (1990) "Basic Local Alignment Search Tool," J. Mol Biol. 215:403-10.
Emanuelsson et al. (2000) "Predicting Subcellular Localization of Proteins Based on their N-terminal Amino Acid Sequence," J. Mol Biol. 300:1005-16.
Tusnady and Simon (1998) "Principles Governing Amino Acid Composition of Integral Membrane Proteins: Application to Topology Prediction," J. Mol. Biol. 283:489-506.
Krogh et al. (2001) "Predicting Transmembrane Protein Topology with a Hidden Markov Model: Application to Complete Genomes," J. Mol Biol. 305:567-580.
Cserzo et al. (1997) "Preduction of transmembrane α-helices in prokaryotic membrane proteins: the dense alignment surface method," Prot. Eng. 10:673-676.
Corpet et al. (2000) "ProDom and ProDom-CG: tools for protein domain analysis and whole genome comparisons," Nucl. Acids Res. 28:267-9.
Burge and Karlin (1997) "Prediction of Complete Gene Structures in Human Genomic DNA," J. Mol. Biol. 215:403-10.
Ewing et al. (1998) "Base-Calling of Automated Sequencer Traces Using *Phred.* I. Accuracy Assessment," Genome Res. 8:175-185.
Koksharova and Wolk (2002) "A Novel Gene that Bears a DnaJ Motif Influences Byanobacterial Cell Division," J Bacterial. 184:5524-5528.
McAndrew et al. (2001) "Colocalization of Plastid Division Proteins in the Chloroplast Stromal Compartment Establishes a New Functional Relationship betweem FtsZ1 and FtsZ2 in Higher Plants," Plant Physiol. 127:1656-1666.
Dinkins et al. (2001) "Overexpression of the *Arabidopsis thaliana MinD1* gene alters chloroplast size and number in transgenic tobacco plants," Planta. 214:180-188.
Kanamaru et al. (2000) "Chloroplast Targeting, Distribution and Transcriptional Fluctuation of AtMinD1, a Eubacteria-Type Factor Critical for Chloroplast Division," Plant Cell Physiol. 41:1119-1128.
Bramhill (1997) " Bacterial Cell Division," Annu. Rev. Cell. Dev. Biol. 13:395-424.
Koksharova et al. (1998) "Genetic and biochemical evidence for distinct key functions of two highly divergent GAPDH genes in catabolic and anabolic carbon flow of the cyanobacterium *Synechocystis* sp. PCC6803," Plant Mol. Biol. 36:183-194.
Zhou et al. (1998) "Molecular Genetic Analysis of Transposase-End DNA Sequence Recognition: Cooperativity of Three Adjacent Base-pairs in Specific Interaction with a Mutant Tn5 Transposase," J. Mol. Biol. 276:913-925.
Robertson et al. (1996) "Characterization of Chloroplast Division Using the *Arabidopsis* Mutant *arc5*," Plant Physiol. 112:149-59.
Thompson (1994) "CLUSTAL W: improving the sensitivity of progressive multiple sequence alignment through sequence weighting, position-specific gap penalities and weight matrix choice," Nucl. Acids Res. 22:4673-4680.
Thompson et al. (1997) "The CLUSTAL_X windows interface: flexible strategies for multiple sequence alignment aided by quality analysis tools," Nucl. Acids Res. 25:4876-4882.
Danino et al. (2001) "Dynamin family of mechanoenzymes," Curr. Opin. Cell Biol. 13:454-460.
Hinshaw (2000) "Dynamin and Its Role in Membrane Fission," Annu. Rev. Cell Dev. Biol. 16:483-519.
Gu and Verma (1996) "Phragmoplastin, a dynamin-like protein associated with cell plate formation in plants," EMBO J. 15:695-704.
Arimura and Tsutsumi (2002) "A dynamin-like protein (ADL2b), rather than FtsZ, is involved in *Arbidopsis* mitochondrial division," Proc. Natl. Acad. Sci. USA 99 5727-5731.
Jin et al. (2001) "A New Dynamin-Like Protein, ADL6, is Involved in Trafficking from the *trans*-Golgi Network to the Central Vacuole in *Arabidopsis*, " Plant Cell 13:1511-1525.
Davis et al. (1998) "Soluble, highly fluorescent variants of green fluorescent protein (GFP) for use in higher plants," Plant Mol. Biol. 36:521-528.
Pyke and Leech (1994) "A Genetic Analysis of Chloroplast Division and Expansion in *Arabidopsis thaliana*," Plant Physiol. 104:201-207.
Miyagishima et al. (1999) "Real-time analyses of chloroplast and mitochondrial division and differences in the behavior of their dividing rings during contraction," Planta 207:343-353.
Miyagishima et al. (2001) "Plastid Division is Driven by a Complex Mechanism that Involves Differential Transition of the Bacterial and Eukaryotic Division Rings," Plant Cell 13:2257-2268.
Bleazard et al. (1999) "The dynamin-related GTPase Dnm1 regulates mitochondrial fission in yeast," Nature Cell Biol. 1:298-304.
Lee et al. (2002) "The Intermolecular Interaction between the PH Domain and the C-terminal Domain of *Arabidopsis* Dynamin-like 6 Determines Lipid Binding Specificity," J. Biol. Chem. 277:31842-31849.
Cline et al. (1984) "Thermolysin is a Suitable Protease for Probing the Surface of Intact Pea Chloroplasts," Plant Physiol. 75:675-678.
Schafer et al. (2002) "Dynamic2 and Cortactic Regulate Actin Assembly and Filament Organization," Curr. Biol. 12:1852-1857.
Hermann et al. (1998) "Mitrochondrial Fusion in Yeast Requires the Transmembrane GTPase Fzo1p," J. Cell. Biol. 143:359.
Rapaport et al. (1998) "Fzo1p is a Mitochondrial Outer Membrane Protein Essential for the Biogenesis of Functional Mitochondria in *Saccharomyces cerevisiae*," J. Biol. Chem. 273:20150.
Sesaki and Jensen (1999) "Division versus Fusion: Dnm1p and Fzo1p Antagonistically Regulate Mitochondrial Shape," J. Cell. Biol. 147:699.
Fritz et al. (2001) "Connection of the Mitochondrial Outer and Inner Membranes by Fzo1 is Critical for Organellar Fusion," J. Cell Biol 152:683.
Lazar et al. (1988) Mol. Cell. Biol. 8:12547-1252.
Hill et al. (1998) Biochem. Biophys. Res. Comm. 244:573-577.
Guo et al. (2004) Proc. Natl.. Acad. Sci. USA 101:9205-9210.
Maple et al. (2007) Annals Botany 99:565-679.
Vitha et al. (2003) The Plant Cell 15:1918-33.
Koksharova et al. (2002) J. Bacteriol. 184:5524-5528.

* cited by examiner

FIG. 3A

```
Anabena      6   QGKYAVRIPLDYYRILGLPLAASDEQLRQAYSDRIVQLPRREYSQAATASRKQLIEEAYVVLSDPKERSSYDQLYLAHAYDPD~NAATTKVAVENRGDSN
Nostoc       1   -----MRIPLDYYRILGLPLAASEEQLRQAYSDRIVQLPRREYSQAAISSRKQLIEEAYVVLSDPKQRSTYDQLYLAHAYDPD~NLAAAAVAQENRTEST
Pm_MED4      1   -----MELPLDHFRLIGVSPSATSEEILRAEQLRLDKTPDEGFTYEVLTQRSELLRLTADLLTDPDSRRDYENLLLN-G-----------------AS
Pm_MT9313    1   MAAQLVDLPIDHFRLLGVSPSADSEAILRALELREDRCPDQGFTHEVLIQRAELLRLSADLLTDPPRRQAYETALLELSRD---------------HP
Syn_PCC6803  1   -----MFIPLDFYRILGIPPQSGGETIEQAYQDRLLQLPRREFSDAAVTLRNQLLAIAYETLRDPEKRQAYDQEWWG-AMD---------------EAL
Scc_PCC7002  1   ----TVRIPLDYYRILCVPAKATTAQITQAYRDRLSQFPRREHNALATEARNRIIEQAFEVLSQTETRAVYDHELSGNMFRSLVPSRPKLPFPDRPSSDT
Scc_WH8102   5   GDLWTLDLPIDHFRLLGVSPSADPASILRRLQTRSDSPPDDGETHEGLLQRQALLHRSADLLTDPSERADYEAALLSLSAT----------------HP
rice        87   AAERSLPLQVDFYKVLGAEPHFLGDGIRRAFEARLAKPPQYGYSTDALVGRRQMLQIAHDTLMNQNSRTQYDRALSENR--------------------
Athal       79   RPERHVPIPIDFYQVLGAQTHFLTDGIRRAFEARVSKPPQFGFSDDALISRRQILQAACETLSNPRSRREYNEGLLDDE--------------------
potato      99   PSDHHISMPIDFYRVLGAEAHFLGDGIRRCYDARITKPPQYGYSQEALIGRRQILQAACETLADSTSRREYNQGLAQHE--------------------

                       210       220       230       240       250       260       270       280       290       300
                 ....|....|....|....|....|....|....|....|....|....|....|....|....|....|....|....|....|....|....|....|
Anabena    105   NGHFDVQSLSIEVSSEELIG-ALLILQELGEYELVLKLGRNYLGNQNGTASTRNGNHRTPEEFLDSSERPDILLTVALASLELGREQWQ--QGHYENAAL
Nostoc      95   KRGSDTQSLGIEITQDELVG-ALLILQELGEYELVLKLGRPYLVNKNSATSSRKSNNLADEEIYESAEHPDVVLTVALACLELGREQWQ--QGHYENAAI
Pm_MED4     75   ---------GLDLSSNREVA-GLILLWESGSSKEAFKITRKALQPPQTPALG-------------SSREADLTLLAALTSRDAAIQEQD--QRSYSNAAD
Pm_MT9313   84   GE-----TAGLDVSPSREVA-GLILLFEANSSHEVFHLASQGLQPPQSPTLG-------------SEREADLALLLALACRAAAAEEQE--QRRYEAAAS
Syn_PCC6803 79   GEALPLTTPELECSPEQEIG-ALLILLDLGEYELVVKYGEPVLHDPNPPAG---------------GLPQDYLLSVILAHWELSRERWQ--QQQYEFAAT
Scc_PCC7002 97   ELEALTAHQPTIDIAEKDLLGGLLLLLDLGEYELVLKWAAPYLKGKGKLVKEGKFG-------AVEIVEQELRLCLALAHWELSREQWL--QQHYEQAAL
Scc_WH8102  88   NE-----TVGLDLAASSEVA-GLILLWEAGAALEAFQLARQGLQPPQAPALG-------------SGREADLTLLAALACRDAARDEQQ--QRRYESAAQ
rice       165   -----EEALTMDIAWDKEAGEALAVLVT~~~~~~~~~~GEQLLLDRPPKRF----------------KQDVVLAMALAYVDLSRDAMAASPPDVIGCCE
Athal      157   -----EATVITDVPWDKVPG-ALCVLQEGGETEIVLRVGEALLKERLPKSF----------------KQDVVLVMALAFLDVSRDAMALDPPDFITGYE
potato     177   -----FDTILTPVPWDKVPG-AMCVL___________________________________________________________________________

                       310       320       330       340       350       360       370       380       390       400
                 ....|....|....|....|....|....|....|....|....|....|....|....|....|....|....|....|....|....|....|....|
Anabena    202   SLETGQEVLFSEGI---FPSVQAEIQADLYKLRPYRILELLALPQ--EKTIERHQGLDLLQSILDDRGGIDG---TGNDQSGLNIDDFLRFIQQLRHHLT
Nostoc     192   SLETGQELLVREGL---FSSIQAEIQADLYKLRPYRILELLALPQ--EKTAERSQGLELLQNLLEDRGGIDG---TNNDESGLNIDDFLRFIQQLRNHLT
Pm_MED4    151   FLQEGIQLLQRMGK---LGELRKTLEEDLVSLLPYRILDLLSRDL--NDYDSHKKGLSMLENLLIKRGGLEG-KNKSEYNDFLNQQEFESFFQQIKPFLT
Pm_MT9313  163   LLHDGIQLLQRMGK---LSEECHKLENDLDALLPYRILDLLSRDL--GDQVSHQEGLRLLDNFVSQRGGLEG-TAPSPAPGGLDQSEFDNFFKQIRKFLT
Syn_PCC6803 161 ASLKALARLQQDND---FPALEAEIRQELYRLRPYRILELLAKEG--QGEEQRQQGLALLQAMVQDRGGIEG---KGEDYSGLGNDDFLKFIHQLRCHLT
Scc_PCC7002 188 SGQKSQEELVDVAQ---FADLQQEIQGDLNRLRPYQVLELLALPE--SETQERQRGLQLLQEMLSARVGIDG---QGDDQSGLSIDDFLRFIQQLRSYLT
Scc_WH8102 167  LLRDGIELQQRMGK---LPDQQARLQQELDDLLPYRVLDLLSRDL--SDADARQQGISLLDQLVRDRGGLDPEGLDSETPAAMGQADFESFFQQIRRFLT
rice       234   VLERALKLLQEDGASNLAPDLLSQIDETLEEITPRCVLELLSLPIDTEHHKKRQEGLQGARNILWSVGRGGI-------ATVGGGFSREAFMNEAFLRMT
Athal      235   FVEEALKLLQEEGASSLAPDLRAQIDETLEEITPRYVLELLGLPLGDDYAAKRLNGLSGVRNILWSVGGGGA-------SALVGGLTREKFMNEAFLRMT
potato     197   ____________________________________________________________________________________________________
```

FIG. 3B

```
                   410       420       430       440       450       460       470       480       490       500
               ....|....|....|....|....|....|....|....|....|....|....|....|....|....|....|....|....|....|....|....|
Anabena     294 VAEQHKLFDGESK--RPSAVATYLAVYASIARGFTQRQPALTRHAKQILMRLSKR------------------QDVHLEQSLCALLGQTEEATRVLEL
Nostoc      284 VAEQHKLFEAQSK--RSSAVATYLAVYALIARGFAQRQPALTRQARQMLVRLGKR------------------QDVHLEQSLCALLGQTEEATRVLEL
Pm_MED4     245 VQDQIDLFLELQK--RGSSEAGELAFLSLTAIGFARRKPAKEFEARKILKKLNLSG-----------------LDSMPLIGCLDLLEADVEQSSARFLS
Pm_MT9313   257 VQEQVDLFLRWQQ--AGSADAGELGGLALAAVGFSRRKPERVQEARQHLERLQLDG-----------------CDPLPMLGCLDLLGDVGRAQERFLR
Syn_PCC6803 253 VAEQNALFLPESQ--RPSLVASYLAVHSLMAEGVKEQDPMAIVEAKSLIIQLENC------------------QDLALEKVICELLGQTEVVLAAIDQ
Scc_PCC7002 280 VQEQLDLFVAESK--RPSAAAAYLAVYALLAAGFSQRKPDLVVQAQTLLKRLGKR------------------QDVFLEQSICALLGQPSEANQLLEQ
Scc_WH8102  262 VQEQVDLFRGWFA--EGSIEAGCLAVFALAAAGYSRRKPEFLEQAREQLQRLVASD-----------------LDPMPLLGCLDLLGNVAEASLHFSA
rice        327 SIEQMDFFSKTPNSIPPEWFEIVNVALAHVAQAIISKRPQFIMMADDLFEQLQKFNIG----SHYAYDN----EMDLALERAFCSLLVGDVSKCRMWLGI
Athal       328 AAEQVDLFVATPSNIPAESFEVYEVALALVAQAFIGKKPHLEQDADKQFQQLQQAKVMAMEIPAMLYDTRNNWEIDFGLERGLCALLIGKVDECRMWLGL
potato      197 ____________________________________________________________________________________________________

                        510       520       530       540       550       560       570       580       590       600
               ....|....|....|....|....|....|....|....|....|....|....|....|....|....|....|....|....|....|....|
Anabena     373 SQEYEALALIREKSQD--------SPDLLPGLCLYAEQWLQNEVFPHFRDLSRQQASLKDYFANQQVQAYLEALPNDAETTNEWAVINRQSFSQPRGNSY
Nostoc      363 SQEYEALAFIREKSQD--------SPDLLPGLCLYAEQWLQHEVFPHFRDLANQQAFLKDYFANQQVQAYLEALPTDAQTTNEWAVINPQYF--PQ----
Pm_MED4     325 SSDEKLRDWLNNYPG-----------EKLEAICIFCKNWLENDVLVGYRDIDLKEIDLDSWFEDREIQEFIEQIEKKSNRTVF---K-SGPQN-------
Pm_MT9313   337 STDPRVKDCLNSHPG-----------DELAAFCEYCRSWLRGDVLPGYRDVDAEAVDLEAWFADRDVQAYVERIERSENRASS---L-GKAF--------
Syn_PCC6803 331 -GDPKIVAGLESKLAT--------GEDPLTAFYTFTEQWLEEEIVPYERDLSPETLSPKAYFNNPSVQQYLEQLEPDSFTT-------DNSF--------
Scc_PCC7002 359 SQEQEAIAYIQEQSEG--------APDLLPGLCLYGEQWLKTEVFSHERDLRQRLEDGSVSLTAYFADPEVQQYLDDLLTEAVPTP-------TP-----
Scc_WH8102  342 IRDEELLSWLAEHPG-----------DHLAAQCEYCRVWLERDVLPGYRDVDAAGVDLDAWFADRDVQAYVDRIDRQSARLG-----------------
rice        419 DNESSPYRDPKILEFIVTNSSISEENDLLPGLCKLLETWLIFEVFPRSRDTRGMQFRLGDYYDDPEVLSYLERMEGGGASHLA----------------
Athal       428 DSEDSQYRNPAIVEFVLENSNRDDNDDLP-GLCKLLETWLAGVVFPRFRDTKDKKFKLGDYYDDPMVLSYLERVEVVQGSPLA----------------
potato      197 ____________________________________________________________________________________________________

                        610       620       630       640       650       660       670       680       690       700
               ....|....|....|....|....|....|....|....|....|....|....|....|....|....|....|....|....|....|....|
Anabena     465 SGGTPVAKRPVGKANRPGEASTRPVPQRSHPSEVNRQFHQNRTPDPELPETSNHRRPESSNFTTARENISTTDAYTDNYPPEIPVERASRPVQPGVSGYT
Nostoc      448 ----------A---------KAKNTHFHNNSTKTSASFNHSRVPNPDLPETPTKETSEYPNFSPP--MWSSSGSIKSEVP---AAERMSRGTNQHLNGSA
Pm_MED4     402 -----------------K-PIFQAQESLKDSSTGPDLNSDNFEEGRLPLPGGVREDGQEVIEEN----IYTDE----II-------KNKSIEFYKYAIE
Pm_MT9313   413 ------------------------SGSSVKQPFPWAPLDPD----GILPLSLGGPDVGQPAADQ---------------------------------SSD
Syn_PCC6803 407 --------------------ASPALLSTATESETPMVHSSAALPDRPLTSTVPSRRGRSPRRSRD--DVFPSADNSSGLA----VTTLSPAIAYDTHSLG
Scc_PCC7002 438 ---------------HPDTESTAAPSEKPPETLQSETGVSPHPSRPAKVDSFEDLVTQTP-ATVPPAPPS-------------------------PGVA
Scc_WH8102  412 ------------------------SAATVTGAGLSSAPSAD----ASSPHEAALDDDHLPAEEA---------------------------------PSS
rice        501 -------------------A---AAAIAKLG-----AQATAALGTVKSNAIQAFN--------------------------------------------K
Athal       509 -------------------A---AAAMARIGAEHVKASAMQALQKVFPSRYTDRNSAEPKDVQE-----TVFSVD------PVGNNVGRDGEPGVFIAE
potato      197 ____________________________________________________________________________________________________
```

FIG. 3C

```
                      710       720       730       740       750       760       770       780       790       800
                 ....|....|....|....|....|....|....|....|....|....|....|....|....|....|....|....|....|....|....|....|
Anabena      565 QSTPPRQTPKRRRRK------KPQAVVNRGHSIHQQRQPSPS-TLGRKTRLLWIVLGSLGGILLFWLIVSTTFGWLKNVFFPAPSLQGEQLSIQISQPPL
Nostoc       525 KSAASGHNQKRRRRKPTPSASRERIPDNRPHSRRPRRRRTFANTIEGKTRLVWRVFISLVSILVFWVLATTTFGWLKNLFFPQPSPPDLQLFVQINQPPL
Pm_MED4      469 KIAELKFVFGEALEN--------YRIFNKSSYLTYLYAFLILFAFGLGVGFVRNNLKKPVQEKEIIDNSLSIN---ENKNVFYEGLNQDDKKKVLDNSKI
Pm_MT9313    453 EFASDGMAWIDRLAD--------LPRPTRPVLIGSVVFAALIAAF-AGFSLFGQRPRTSVST-------------------AADQPQVTAPPTATLQEEV
Syn_PCC6803  482 TNGIGGDSTSNGFSS-------NSAPESTSKHKSPRRRKKRVTIKPVRFGIFLLCLAGIVGGATALIINRTG-----D---PLGGLLEDPLDVFLDQPSE
Scc_PCC7002  497 PVTAALN-----PDPEASSASS-------KS--VSSKKSIGPWGAIAAIVGSVLLVVGLVRILSGLTTQEPLQVT---------LNGEPPLTIPSLDTAE
Scc_WH8102   452 DPANQRLS--NRLRW--------LAASLVVGLVAALAAAVMLRPR-ETAPVVLQ-PEPDRQD-------------------AVE-PKPSAQDSATLKPQA
rice         531 VFPLIEQLDRSAMENTKDGPGGYLENFDQENAPAHDSRNAALKIISAGALFALLAVIGAKYL-------------------PRKRPLSAIRSEHGSVAVA
Athal        576 AVRPSENFETNDYAIRAGVSESSVDETTVEMSVADMLKEASVKILAAGVAIGLISLFSQKYF-------------------LKSSSSFQRKDMVSSMESD
potato       197 ____________________________________________________________________________________________________
```

```
Human Dynamin-1     1 -----MGNRGMEDLIPLVNRLQDAFS------------AIGQNADLDLPQIAVVGGQSAGKSSVLENFVGR
Yeast Dnm1p         1 -----MAS--LEDLIPTVNKLQDVMY------------DSGIDT-LDLPILAVVGSQSSGKSSILETLVGR
ARC5                1 MAEVSAKSVTVEEMAEEDDAAIEERWSLYEAYNELHALAQELETPFEAPAVLVVGQQTDGKSALVEALMGF

Human Dynamin-1    64 VTRRPLVLQLVNATT------------------------------------------EYAEFLHCKGKKFT
Yeast Dnm1p        61 VTRRPLVLQLNNISPNSPLIEEDDNSVNPHDEVTKISGFEAGTKPLEYRGKERNHADEWGEFLHIPGKRFY
ARC5               81 KTRRPLTLHMKYDPQCQPP------------------------------------LCHLGSDDDPSVSLPK

Human_Dynamin-1   102 EAETDRVTGT-NKGISPVPINLRVYSPHVLNLTLVDLPGMTKVPVGDQ--PPDIEFQIRDMLMQFVTKENC
Yeast_Dnm1p       141 ENETARIAGK-DKGISKIPINLKVFSPHVLNLTLVDLPGITKVPIGEQ--PPDIEKQIKNLILDYIATPNC
ARC5              125 EAKNMRLEQEPCSPFSAKEIIVKVQYKYCPNLTIIDTPGLIAPAPGLKNRALQVQARAVEALVRAKMQHKE

Human_Dynamin-1   179 SDLANSDALKVAKEVDPQGQRTIGVITKLDLMDEGTDARDVLENKLLPLRRGYIGVVNRSQKDIDGKKDIT
Yeast_Dnm1p       218 VDLVNSESLKLAREVDPQGKRTIGVITKLDLMDSGTNALDILSGKMYPLKLGFVGVVNRSQQDIQLNKTVE
ARC5              205 SDWSIATTRRIVMQVDPELSRTIVVSTKLDTKIPQFSCSSDVEVFLSPP-------ASALDSSLLGDSPFF

Human_Dynamin-1   259 FLSHPSYRHLADRMGTPYLQKVLNQQLTNHIRDTLPGLRNKLQSQLLSIEKEVEEYKNFRPDDPARKTKAL
Y ast_Dnm1p       298 FRKEPVYRTISTKCGTRYLAKLLNQTLLSHIRDKLPDIKTKLNTLISQTEQELARYGGVGATTNESRASLV
ARC5              278 YGQDSVYKSNDEFKQAVSLREMEDIASLEKELGRELTKQEKSRIGISKLRLFLEELLWKRYKESVPLIIPL

Human_Dynamin-1   339 DFEKRIEGSGDQIDTYELSG-GARINRIFHERFPFELVKMEFDEKELRREISYAIKNIHGIRTGLFTPDMA
Yeast_Dnm1p       378 NFISSIDGTSSDINTKELCG-GARIYYIYNNVFGNSLKSIDPTSNLSVLDVRTAIRNSTGPRPTLFVPELA
ARC5              358 RKLDTVSKELSSLDEAKLKERGRTFHDLFLTKLSLLLKGTVVAPPDKPGETLQDERTQGGAFVGTDGLQFS

Human_Dynamin-1   418 KKIREPCLKCVDMVISELI-----------STVRQC-TKKLQQYPRLREEMERIVTTHIREREGRTKEQVM
Yeast_Dnm1p       457 KLLLEPSQRCVELVYEELM-----------KICHKCGSAELARYPKLKSMLIEVISELLRERLQPTRSYVE
ARC5              438 RLYGGAQYHRAMAEFRFLVGAIKCPPITREEIVNACGVEDIHDGTNYSRTACVIAVAKARETFEPFLHQLG

Human_Dynamin-1   486 MNTNHEDFIGFANAQQRSNQMNKKKTSGNQDEILVIRKGWLTINNIGIMKGGSKEYWFVLTAENLSWYKDD
Y ast_Dnm1p       526 INTNHPNFL---SATEAMDDIMKTRRKRNQE----LLKSKLSQQENGQTNGING------TSSISSNIDQD
ARC5              518 VLPISVYLLQKEGEYLSGHEVFLKEVASAFNSPVESTEKSCRDKCMEDLASTTR-------YVTWSLHNKN

Human_Dynamin-1   566 SVDNLKLRDVEKGFMSSKHIFALFN-TEQRNVYKDYRQLELACETQEEVDSWKASFLRAGVYPERVGDKEK
Yeast_Dnm1p       593 DGIDAESKQTKDKFLN--YFFGKDK-KGQPVFDASDKKRSIAGD------GNIEDFRNLQISDFSLGDIDD
ARC5              591 SPGGTEHNTTSGNALGFSLPQDALGGTTDTKSRSDVKLSHLASNIDSGSSIQTTEMRLADLLDSTLWNRKL

Human_Dynamin-1   645 DSPMHSMDPQLERQVETIRNLVDSYMAIVNKTVRDLMPKTIMHLMINNTKEFIFSELLANLYSCGDQNTLM
Yeast_Dnm1p       661 -----PLTEREELECELIKRLIVSYFDIIREMIEDQVPKAVMCLLVNYCKDSVQNRLVTKLYKETLFEELL
ARC5              668 --------IVYALVQQIFQGIREYFLASAELKFNCFLLMPIVDKLPALLREELENAFEDDLDSIFDITNER

Human_Dynamin-1   725 RDEMLRMYHALKEALSIIGNINTTTVSTPMPPPVDDSWLQVQSVPAGRRSPTSSPTPQRRAPAVPPARPGS
Ye st_Dnm1p       736 RELCVKSLGVYKKAATLISNIL-------------------------------------------------
ARC5              740 TEIELRRVKRIKEKFRVMNEKLNSHEFAQN--------LKAPSVQH-------------------------

Human_Dynamin-1   805 AGSALGGAPPVPSRPGASPDPFGPPPQVPSRPNRAPPGVPSRSGQASPSRPESPRPPFDL
Yeast_Dnm1p           ------------------------------------------------------------
ARC5                  ------------------------------------------------------------
```

FIG. 4

PLASTID DIVISION AND RELATED GENES AND PROTEINS, AND METHODS OF USE

This application claims priority to U.S. Provisional Patent Applications Ser. No. 60/402,242 filed on Aug. 9, 2002 and Ser. No. 60/390,140 filed on Jun. 20, 2002.

The present invention was funded in part with government support under grant number MCB 0092448 from the National Institutes of Health. The government may have certain rights in this invention.

FIELD OF THE INVENTION

The present invention relates to genes encoding proteins involved in prokaryotic-type or plastid division and/or morphology, and the encoded proteins, and in particular to isolated Ftn2 (ARC6), ARC5, and Fzo-like genes and polypeptides. The present invention also provides methods for using Ftn2 (ARC6), ARC5, and Fzo-like genes, and polypeptides.

BACKGROUND OF THE INVENTION

Plastids, the major organelles found only in plant and algal cells, are responsible for photosynthesis, for the storage of a wide variety of products, and for the synthesis of key molecules required for basic structural and functional aspects of plant cells. For example, plastids are responsible for the biosynthesis of purines and pyrimidines, and are the sole site of the synthesis of chlorophylls, carotenoids, certain amino acids (the "essential" amino acids), starches, fatty acids, and certain lipids.

Plastids are derived from proplastids, which are always present in young meristematic regions of a plant (a meristem is an undifferentiated region from which new cells arise). Proplastids can give rise to several different types of plastids, which types include: amyloplasts, unpigmented plastids which contain starch granules and which are especially common in storage organs, such as potato tubers; leucoplasts, colorless plastids involved in the synthesis of monoterpenes, the volatile compounds contained in essential oils and many of which are of commercial importance; chloroplasts, the green photosynthetic plastids responsible for energy capture via photosynthesis; and chromoplasts, yellow, orange, or red plastids, depending upon the particular combination of carotenes and xanthopylls present, and which are responsible for the colors of many fruits (tomatoes, oranges), flowers (buttercups, marigolds) and roots (carrots, sweet potatoes).

Plastids arise from the binary fission of existing plastids, independently of cell division. In root tips, shoots, and other meristems, proplastid division keeps pace with cell division, so the daughter cells possess approximately the same number of plastids as the parent cells; in angiosperms, this number is about 20 proplastids per cell. As cell expansion supersedes cell division, the number of plastids per cell increases due to continued plastid division. The number of plastids present in a mature plant cell is typically similar for a particular cell in a particular tissue; for example, an *Arabidopsis* leaf mesophyll cell typically contains about 120 chloroplasts. Thus, plastid division is essential for the maintenance of plastid populations in plant cells undergoing division, and for the accumulation of large chloroplast numbers in photosynthetic tissues.

Plastids are surrounded by a double membrane system which is made up of the outer and inner envelopes. The soluble interior portion of the plastid inside the inner envelope is the stroma; additional membrane structures may be present within the stroma, such as thylakoids. Thylakoids appear as interconnected stacked grana present in green chloroplasts, and contain the pigments necessary for light capture, such as chlorophyll. Thus, plastid division involves division of the outer and inner envelopes, as well as of the stroma and interior structures. As determined by ultra structural studies, plastid division begins with a constriction in the center of the plastid. Formation of the constriction is frequently associated with the appearance of an electron-dense annular structure termed the plastid dividing (PD) ring. In some electron micrographs of plastids from plants, the PD ring can be resolved into two concentric rings, an inner PD ring associated with the stromal surface of the inner envelope membrane, and an outer PD ring associated with the cytosolic surface of the outer envelope membrane. In other electron micrographs of plastids from red algae, yet a third PD ring is observed in the intermembrane space between the inner and outer envelope membranes. The constriction deepens and tightens, creating an extremely narrow isthmus before the two daughter plastids separate completely.

The mechanisms mediating plastid division are poorly understood, although it is believed that the PD rings are a dynamic macromolecular complex. It is also believed that this macromolecular complex is composed of numerous proteins that coordinate the mechanical activity required to constrict the plastid. Only a few components of the plastid division complex have been identified to date.

Plastid division is believed to have its evolutionary origin in a cyanobacterial endosymbiont that gave rise to chloroplasts (Osteryoung, K W et al. (1998) Plant Cell 10: 1991-2004). Thus, it has been proposed that the plastid division apparatus might have components in common with those involved in prokaryotic cell division, and in particular with cyanobacterial cell division (Possingham, J V and Lawrence M E (1983) Int. Rev. Cytol. 84: 1-56; and Suzuki, K et al (1994) J Cell Biol 63: 280-288). Genes from non-photosynthetic bacteria which play a role in division have been sequenced and identified. However, only a few of these genes involved in cyanobacterial division have been identified to date. One identified gene encodes bacterial FtsZ (from filamentation temperature-sensitive mutants, or fts mutants), which is a structural homologue to, and very likely the evolutionary precursor of, the eukaryotic tubulins (Erickson, H P (1998) Trends Cell Biol 7: 362-367; Faguy, D M and Doolittle W R (1998) Curr Biol 8: R338-341; Lowe, J and Amos L A (1998) Nature 391: 203-206) and Nogales, E et al. (1998) Nat Struct Biol 5: 451-458). FtsZ is well known to be a self-polymerizing, filament-forming GTPase, and it functions during bacterial cell division by assembling into a ring structure at the division site on the interior surface of the cytoplasmic membrane (Bi, E and Lutkenhaus J (1991) Nature 354: 161-164). The FtsZ ring assembly is required for the subsequent midcell localization of all other components of the cell division apparatus (Addinall, S G et al (1996) J Bacteriol 178: 3877-3884; and deBoer, P A J et al. (1988) J Bacteriol 170: 2106-2112); it remains associated with the leading edge of the division septum throughout cytokinesis, then it disassembles immediately following cell separation before rapidly reassembling at the center of the newly formed daughter cells (Addinall, S G et al (1996) J Bacteriol 178: 3877-3884; Bi, E and Lutkenhaus J (1991) Nature 354: 161-164; Butterfass, T (1988) in Division and Segregation of Organelles (Cambridge, UK; Cambridge University Press) pp 21-38; and Sun, Q and Margolin, W (1998) J Bacteriol 180: 2020-2056). In *E. coli*, placement of the FtsZ ring is governed by the minB operon, which encodes three gene products: MinC, MinD, and MinE (Lutkenhaus, J (1998) Curr Opin Microbiol 1: 210-215; Rothfield, L (1999) Annu Fev Genet 33: 423-448;

Rothfield, L I and Justice, S S (1997) Cell 88: 581-584; and Sullivan, S M and Maddock, J R (2000) Curr Biol 10: R249-252).

FtsZ genes have also been found in nuclear genomes of land plants, as determined from plant gene database analysis. The encoded proteins fall into two major groups, FtsZ1 and FtsZ2 (Osteryoung K W, Stokes K D, Rutherford S M, Percival A L, and Lee, W Y (1998), Plant Cell 10: 1991-2004). FtsZ1 family proteins appear to contain cleavable chloroplast transit peptides at their amino terminal ends that target them to the chloroplast stromal compartment (Emanuelsson O, Nielsen H, Brunak S, von Heijne G (2000) J. Mol. Biol. 300:1005-16), whereas members of the FtsZ2 family do not appear to possess easily recognizable chloroplast transit sequences. However, experimental evidence shows that both FtsZ1 and FtsZ2 proteins are imported into chloroplasts and localized in the stroma (McAndrew et al. (2001) *Plant Physiol.* 127:1656-1666). The FtsZ1 and FtsZ2 proteins are reported to colocalize to rings at the plastid midpoint in *Arabidopsis* and other plants, where members of both families assemble into rings on stromal surface of the inner envelope membranes (Osteryoung, K W and McAndrew, R S (2001) Annu Rev Plant Physiol Plant Mol Biol 52:315-333; and McAndrew et al. (2001) *Plant Physiol.* 127:1656-1666). These FtsZ proteins have been characterized both biochemically and microscopically during non-photosynthetic bacterial division; efforts are under way to similarly characterize these proteins in plants. (for a review, see Osteryoung, K and McAndrew R S (2002) Annu Rev Plant Physiol Mol Biol 52: 315-322; and McAndrew et al. (2001) *Plant Physiol.* 127: 1656-1666). A MinD protein has also been found encoded in plastid genomes of algae, as well as in the nuclear genomes of higher plants (Colletti K S, Tatersall E A, Pyke K A, Froelich A E, Stokes K D, Osteryoung K W (2000) Curr. Biol. 10:507-16,Moehs C P, Tian L, Osteryoung K W, DelaPenna D (2001) Plant Mol. Biol. In press); at least some of the MinD proteins include a cleavable chloroplast target sequence (Osteryoung, K and McAndrew R S (2002) Annu Rev Plant Physiol Mol Biol 52: 315-322). Reduced expression of MinD in *Arabidopsis* plants results in plants with asymmetrically constricted plastids (Colletti K S, Tatersall E A, Pyke K A, Froelich A E, Stokes K D, Osteryoung K W (2000) Curr. Biol. 10:507-16), suggesting that MinD also functions in plants to control the placement of the division ring to the center of the plastid. Both MinD as well as MinE are also encoded in the plastid genomes of unicellular algae (Wakasugi T, Nagai T, Kapoor M, Sugita M, Ito M, et al. (1997) Proc. Natl. Acad. Sci. USA 94:5967-72).

Currently, FtsZ, MinD, and MinE are the only obvious homologues of non-photosynthetic bacterial cell division genes known to exist in photosynthetic eukaryotes, and roles for MinE and MinD in plastid division have only recently been demonstrated, where they are involved in placement of the PD rings at the site of plastid constriction (Itoh et al. (2001) *Plant Physiol.* 127:1644-1655; Reddy et al. (2002) *Planta.* 215:167-176). Even the function of most of the other non-photosynthetic bacterial cell division proteins are not well understood, and they therefore cannot provide clues as to whether functional counterparts participate in plastid division. However, at least nine proteins localize to the division septum in *E. coli* (Margolin W (1198)Trends Microbiol. 6:233-38, Rothfield L I, Justice S S (1997) Cell 88:581-84), and the plastid division apparatus is likely to be at least as complex (Osteryoung K W, Pyke K A (1998) Curr Opin. Plant Biol. 1:475-79).

Therefore, there is a need to identify and characterize other genes involved in plastid division. The discovery of such genes is useful to further characterize the mechanism of plastid division. Moreover, these genes can then be manipulated to vary the number and size of plastids present in plant cells, in order to vary agronomic and horticultural characteristics of economically important plants, such as crop, ornamental, and woody plants.

SUMMARY OF THE INVENTION

The present invention relates to compositions comprising Ftn2, ARC5, and Fzo-like genes and polypeptides. The present invention is not limited to any particular nucleic acid or amino acid sequence. The present invention also provides methods for using Ftn2, ARC5, and Fzo-like genes and polypeptides.

Thus, the present invention provides an isolated nucleic acid sequence comprising an Ftn2 gene. The present invention also provides an isolated nucleic acid sequence comprising a sequence encoding an Ftn2 polypeptide. In some embodiments, the Ftn2 gene product functions in division of a photosynthetic prokaryote or a plastid. In particular embodiments, the nucleic acid sequence comprises SEQ ID NOs: 1, 3 or 4, or the coding sequence of SEQ ID NO:2.

The present invention also provides an isolated first nucleic acid sequence that hybridizes under conditions of high stringency to a second nucleic acid sequence comprising an Ftn2 gene. The present invention also provides an isolated first nucleic acid sequence that hybridizes under conditions of high stringency to a second nucleic acid sequence encoding an Ftn2 polypeptide. In some embodiments, a product of the first nucleic acid sequence functions in division of a photosynthetic prokaryote or a plastid. In particular embodiments, the second nucleic acid sequence is SEQ ID NOs: 1 or 4 or the coding sequence of SEQ ID NO:3.

The present invention also provides an isolated nucleic acid sequence comprising an Ftn2 gene, wherein the Ftn2 gene comprises at least one mutation. In some embodiments, the mutation is at least one nucleic acid substitution, nucleic acid addition, and/or nucleic acid deletion, and/or any combination of at least one nucleic acid substitution, nucleic acid addition, and/or nucleic acid deletion. The present invention also provides a nucleic acid sequence comprising an Ftn2 gene, where the gene encodes a variant of an Ftn2 polypeptide. In some embodiments, the variant is a mutant polypeptide, a truncated polypeptide, a fusion polypeptide, and/or any combination of a mutant polypeptide, a truncated polypeptide, and/or a fusion polypeptide. In particular embodiments, the isolated nucleic acid sequence comprises SEQ ID NO: 9 or the coding sequence of SEQ ID NO: 10.

The present invention also provides an isolated antisense sequence corresponding to a nucleic acid sequence comprising an Ftn2 gene. The present invention also provides an isolated antisense sequence corresponding to a nucleic acid sequence encoding an Ftn2 polypeptide.

The present invention also provides an siRNA targeted to an RNA transcribed from an Ftn2 gene. The present invention also provides an siRNA targeted to an RNA transcribed from a nucleic acid sequence encoding an Ftn2 protein. The present invention also provides an isolated nucleic acid sequence encoding an siRNA targeted to an RNA transcribed from an Ftn2 gene. The present invention also provides an isolated nucleic acid sequence encoding an siRNA targeted to an RNA transcribed from a nucleic acid sequence encoding an Ftn2 protein.

The present invention also provides compositions comprising any of the isolated nucleic acid sequences described above.

The present invention also provides any of the nucleic acid sequences described above operably linked to a heterologous promoter. The present invention also provides a vector comprising any of the nucleic acid sequences described above. In some embodiments, the vector comprises any of the nucleic acid sequences described above operably linked to a heterologous promoter.

The present invention also provides a purified protein, comprising an Ftn2 polypeptide. In some embodiments, the Ftn2 polypeptide functions in division of a photosynthetic prokaryote or a plastid. In particular embodiments, the protein comprises amino acid sequence SEQ ID NOs:2 or 4. The present invention also provides a purified protein, comprising a variant of an Ftn2 polypeptide. In some embodiments, the variant is a mutant polypeptide, a truncated polypeptide, a fusion polypeptide, and/or any combination of a mutant polypeptide, a truncated polypeptide, and/or a fusion polypeptide. In particular embodiments, the protein comprises amino acid sequence SEQ ID NO: 11.

The present invention also provides compositions comprising any of the purified proteins described above.

The present invention also provides an organism transformed with any of the nucleic acid sequences described above. In some embodiments, the organism is a plant or a microorganism. In other embodiments, the present invention provides a plant transformed with any of the nucleic acid sequences described above. In yet other embodiments, the present invention provides a plant cell transformed with any of the nucleic acid sequences described above. In yet other embodiments, the present invention provides a plant seed transformed with any of the nucleic acid sequences described above. In particular embodiments, the nucleic acid sequence comprises SEQ ID NOs: 1 or 4 or the coding sequence of SEQ ID NO:3.

The present invention also provides an organism transformed with a heterologous gene comprising an Ftn2 gene. In some embodiments, the organism is a plant or a microorganism. In other embodiments, the present invention provides a plant transformed with a heterologous gene comprising an Ftn2 gene. In yet other embodiments, the present invention provides a plant cell transformed with a heterologous gene comprising an Ftn2 gene. In yet other embodiments, the present invention provides a plant seed transformed with a heterologous gene comprising an Ftn2 gene. In particular embodiments, the nucleic acid sequence comprises SEQ ID NOs: 1 or 4 or the coding sequence of SEQ ID NO:3.

In additional embodiments, the present invention provides an isolated nucleic acid sequence comprising an ARC5 gene. In some embodiments, the present invention provides an isolated nucleic acid sequence comprising a sequence encoding an ARC5 polypeptide. In some embodiments, the ARC5 gene is selected from the group consisting of SEQ ID NOs: 11 and 14. In some embodiments, ARC5 polypeptide comprises an amino acid sequence selected from the group consisting of SEQ ID NOs: 13, 16, 17, and 18. In other embodiments, the present invention provides an isolated antisense sequence corresponding to a nucleic acid sequence comprising an ARC5 gene. In still other embodiments, the present invention provides an isolated antisense sequence corresponding to a nucleic acid sequence encoding an ARC5 polypeptide. In still further embodiments, the present invention provides an siRNA targeted to an RNA transcribed from an ARC5 gene. In yet other embodiments, the present invention provides an siRNA targeted to an RNA transcribed from a nucleic acid sequence encoding an ARC5 protein.

The present invention also provides an isolated first nucleic acid sequence that hybridizes under conditions of high stringency to a second nucleic acid sequence comprising an ARC5 gene. In some embodiments, a product of the first nucleic acid sequence functions in division of a photosynthetic prokaryote or a plastid.

The present invention additionally provides an isolated first nucleic acid sequence that hybridizes under conditions of high stringency to a second nucleic acid sequence encoding an ARC5 polypeptide. In some embodiments, a product of the first nucleic acid sequence functions in division of a photosynthetic prokaryote or a plastid. In some embodiments, the second nucleic acid sequence is SEQ ID NO: 11 or 14.

In still further embodiments, the present invention provides an isolated nucleic sequence comprising an ARC5 gene, wherein the ARC5 gene comprises at least one mutation. In some embodiments, the mutation is at least one nucleic acid substitution, addition, deletion, and/or any combination of at least one nucleic acid substitution, addition, and/or deletion.

In certain embodiments, the present invention provides a ARC5 nucleic acid sequence operably linked to a heterologous promoter. In some embodiments, the present invention provides vector comprising an ARC5 nucleic acid sequence. In other embodiments, the present invention provides a vector comprising an ARC5 nucleic acid sequence operably linked to a heterologous promoter.

In some embodiments, the present invention provides an isolated protein, comprising an ARC5 polypeptide; in particular embodiments, the ARC5 polypeptide comprises amino acid sequence SEQ ID NO:13, 16, 17, or 18. In other embodiments, the present invention provides an isolated protein, comprising a variant of an ARC5 polypeptide. In some embodiments, the variant is a mutant polypeptide, a truncated polypeptide, a fusion polypeptide, and/or any combination of a mutant polypeptide, a truncated polypeptide, and/or a fusion polypeptide.

In certain embodiments, the present invention provides an organism transformed with a heterologous gene comprising an ARC5 gene. In some embodiments, the organism includes, but is not limited to, a plant, an algae, or a microorganism. In other embodiments, the present invention provides a plant, a plant cell, or a plant seed transformed with a heterologous gene comprising an ARC5 gene. The present invention also provides an organism transformed with a heterologous gene encoding an ARC5 polypeptide, and a plant, plant cell, or plant seed transformed with a heterologous gene encoding an ARC5 polypeptide.

In additional embodiments, the present invention provides an isolated nucleic acid sequence comprising an Fzo-like gene. In some embodiments, the present invention provides an isolated nucleic acid sequence comprising a sequence encoding an Fzo-like polypeptide. In some embodiments, the Fzo-like gene is selected from the group consisting of SEQ ID NOs: 19 and 22. In some embodiments, the Fzo-like gene further comprises the nucleic acid sequence of SEQ ID NO:25 at the 3' terminus. In some embodiments, Fzo-like polypeptide comprises an amino acid sequence selected from the group consisting of SEQ ID NOs: 21 or 24. In other embodiments, the present invention provides an isolated antisense sequence corresponding to a nucleic acid sequence comprising an Fzo-like gene. In still other embodiments, the present invention provides an isolated antisense sequence corresponding to a nucleic acid sequence encoding an Fzo-like polypeptide. In still further embodiments, the present invention provides an siRNA targeted to an RNA transcribed from an Fzo-like gene. In yet other embodiments, the present invention provides an siRNA targeted to an RNA transcribed from a nucleic acid sequence encoding an Fzo-like protein.

The present invention also provides an isolated first nucleic acid sequence that hybridizes under conditions of high stringency to a second nucleic acid sequence comprising an Fzo-like gene. In some embodiments, a product of the first nucleic acid sequence functions in division of a photosynthetic prokaryote or a plastid.

The present invention additionally provides an isolated first nucleic acid sequence that hybridizes under conditions of high stringency to a second nucleic acid sequence encoding an Fzo-like polypeptide. In some embodiments, a product of the first nucleic acid sequence functions in division of a photosynthetic prokaryote or a plastid. In some embodiments, the second nucleic acid sequence is SEQ ID NO: 19 or 22. In some embodiments, the Fzo-like nucleic acid further comprises the nucleic acid sequence of SEQ ID NO:25 at the 3' terminus.

In still further embodiments, the present invention provides an isolated nucleic sequence comprising an Fzo-like gene, wherein the Fzo-like gene comprises at least one mutation. In some embodiments, the mutation is at least one nucleic acid substitution, addition, deletion, and/or any combination of at least one nucleic acid substitution, addition, and/or deletion.

In certain embodiments, the present invention provides a Fzo-like nucleic acid sequence operably linked to a heterologous promoter. In some embodiments, the present invention provides vector comprising an Fzo-like nucleic acid sequence. In other embodiments, the present invention provides a vector comprising an Fzo-like nucleic acid sequence operably linked to a heterologous promoter.

In some embodiments, the present invention provides an isolated protein, comprising an Fzo-like polypeptide; in particular embodiments, the Fzo-like polypeptide comprises amino acid sequence SEQ ID NO:21 or 24. In other embodiments, the present invention provides an isolated protein, comprising a variant of an Fzo-like polypeptide. In some embodiments, the variant is a mutant polypeptide, a truncated polypeptide, a fusion polypeptide, and/or any combination of a mutant polypeptide, a truncated polypeptide, and/or a fusion polypeptide.

In certain embodiments, the present invention provides an organism transformed with a heterologous gene comprising an Fzo-like gene. In some embodiments, the organism includes, but is not limited to, a plant, an algae, or a microorganism. In other embodiments, the present invention provides a plant, a plant cell, or a plant seed transformed with a heterologous gene comprising an Fzo-like gene. The present invention also provides an organism transformed with a heterologous gene encoding an Fzo-like polypeptide, and a plant, plant cell, or plant seed transformed with a heterologous gene encoding an Fzo-like polypeptide

DESCRIPTION OF THE FIGURES

FIG. 3 (SEQ ID NOS: 115-124) shows an alignment of plant and cyanobacterial Ftn2 full and partial sequences. Partial sequences are marked by asterisk (*). Not shown are the N-termini of the plant sequences, which contain chloroplast transit peptides. Light-gray and black columns indicate similarity and identity, respectively, greater than 80%. Gaps are indicated by a dash (-), missing sequence by an underline (_). Similarity and identity calculations do not include missing sequences. The Dna-J like domain is indicated by a solid line (▬) Putative myb domain is indicated by diamonds (♦). Site of truncation of the protein in arc6 mutant is marked by a triangle (▲) at position 398 of the alignment (residue 325 of AtFtn2).

FIG. 4 (SEQ ID NOS:195-197) shows an alignment of the AtARC5 gene with Dynamin-1 from *Homo sapiens* and Dnm1p from *Saccharomyces cerevisiae*. Gray boxes indicate completely conserved residues; yellow boxes are identical residues; cyan boxes are similar residues; dashes indicate gaps. The domain structure is indicated by the lines above the alignment. Red, GTPase domain; green, middle domain; blue, PH domain; lavender, GTPase effector domain; black, PR domain. The dotted underline indicates the sequence encoded by the alternatively spliced intron in ARC5. The triangle indicates the position of the arc5 mutation.

DEFINITIONS

Figure 1A:
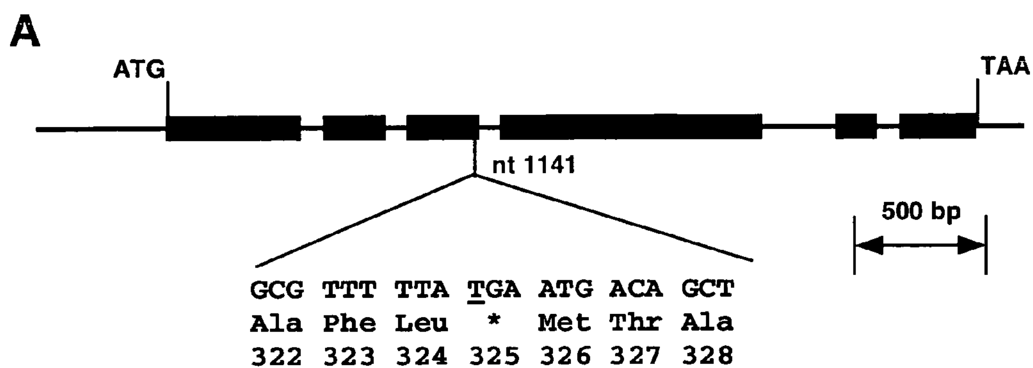
FIG. 1 shows the structure of the AtFtn2 gene (Panel A) and protein (Panel B). Panel A shows that the open reading frame is terminated by a TAA in-frame stop codon. The diagram depicts introns (thin lines) and exons (black boxes). Sizes are given in bp. The position of the arc6-1 mutation (C->T) at position 1141 is marked. The nucleotide sequences flanking the mutation (underlined) show the change of codon 325 (CGA in a wild type plant) into a premature stop (TGA) in arc6-1. Panel B shows the putative functional and conserved protein domain, which are depicted as wider black boxes; their numerical positions within the AtFtn2 sequence are also indicated. Black lines above the diagram delineate regions of AtFtn2 conserved among Ftn2 homologues. CT, chloroplast targeting signal.

To facilitate an understanding of the present invention, a number of terms and phrases as used herein are defined below:

The term "plant" is used in it broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells that are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure or a plant tissue.

The term "crop" or "crop plant" is used in its broadest sense. The term includes, but is not limited to, any species of plant or algae edible by humans or used as a feed for animals or used, or consumed by humans, or any plant or algae used in industry or commerce.

The term "oil-producing species" refers to plant species which produce and store triacylglycerol in specific organs, primarily in seeds. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species.

The term plant cell "compartments" or "organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The term "host cell" refers to any cell capable of replicating and/or transcribing and/or translating a heterologous gene.

The term "arc" refers to mutations observed in *Arabidopsis* which exhibition abnormal chloroplast accumulation and/or replication, and is an abbreviation for the designation "accumulation and replication of chloroplasts." Different arc mutants have been observed, and are indicated by a number after the arc designation: for example, arc1, arc2, etc.

The term "Ftn2" refers to a gene that when naturally occurring in a wild-type organism encodes an Ftn2 polypeptide. An Ftn2 polypeptide functions in prokaryotic-type division, such that a decreased amount of Ftn2 polypeptide in a prokaryote or a plant or algal cell compared to the amount typically present in wild-type results in incomplete division or no division of the prokaryote or plastid(s) in the plant or algal cell. As an illustrative but non-limiting example, in photosynthetic prokaryotes such as cyanobacteria, a decreased amount of Ftn2 polypeptide can result in long filamentous cells, up to many times longer than a wild-type cell. As an illustrative but non-limiting example, in plants such as *Arabidopsis*, a decreased amount of Ftn2 polypeptide can result in a single or a few very large chloroplasts present in a single leaf mesophyll cell.

An Ftn2 polypeptide is a protein (about 660 to about 800 amino acids long) which can be roughly defined by three regions. The N-terminal (about 420 amino acids) contains the DnaJ-like domain, and exhibits a high degree of homology among Ftn2 proteins obtained from different sources (about 20 to about 60% identity, and about 50 to about 80% similarity). The large central region (about 200 amino acids) is fairly variable, and exhibits a lower degree of homology among the different Ftn2 proteins (about 6% to about 20% identity, and about 20 to about 44% similarity). The C-terminal region (about 110 amino acids) is more highly conserved and in *Arabidopsis* Ftn2, contains putative myb domain (residues 677-690). The C-terminal region exhibits a higher degree of homology than the central region (about 15% to about 55% identity, and about 40 to about 70% similarity). The result is that when considered as a whole, homologous Ftn2 proteins possess about 15% or greater identity and about 38% or greater similarity to AtFtn2 protein. However, the N-terminal and C-terminal regions possess a higher degree of similarity and a higher degree of identity among the different Ftn2 proteins than do the whole proteins.

In *Arabidopsis*, a mutation in the Ftn2 gene results in an arc (accumulation and replication of chloroplasts) mutant, the arc6 mutant. The evidence described in Example 2, including the observations that the sequences of Ftn2 from a wild-type background and the sequences of arc6-1, arc6-2, and arc6-3 are essentially the same except that the a C->T transition at position 1141 in the gene results in a premature stop codon and results in a truncated protein of about 324 amino acids, and that the arc6 mutant is rescued by a wild-type copy of AtFtn2, indicates that AtFtn2 gene is ARC6.

The term "ARC5" refers to a gene that when naturally occurring in a wild-type organism encodes an ARC5 polypeptide. An ARC5 polypeptide functions in prokaryotic-type division, such that a decreased amount of ARC5 polypeptide in a prokaryote or a plant (including an algal) cell compared to the amount typically present in wild-type results in incomplete division or no division of the prokaryote or plastid(s) in the plant (including an algal) cell. As an illustrative but non-limiting example, in plants such as *Arabidopsis*, a decreased amount of ARC5 polypeptide can result in cells with about 5 to 10 chloroplasts per cell, where the chloroplasts are larger than in wild type, and constricted chloroplasts were frequently found.

An ARC5 polypeptide is a protein (of about 777 or about 741 amino acids long) which can be roughly defined by three regions. These regions, or motifs, are also found in other dynamin-like proteins: a conserved N-terminal GTPase domain, a pleckstrin homology (PH) domain shown in some proteins to mediate membrane association, and a C-terminal GTPase Effector Domain (GED) thought to interact directly with the GTPase domain and to mediate self-assembly.

In *Arabidopsis*, a mutation in the ARC5 gene results in an arc (accumulation and replication of chloroplasts) mutant, the arc5 mutant, as described in Example 6. Moreover, in *Arabidopsis*, two distinct cDNAs encoding ARC5 proteins with uninterrupted reading frames of 777 (87.2 kDa) or 741 (83.5 kDa) amino acids are found. These results indicate that the ARC5 transcript is alternatively spliced.

The term "Fzo-like" refers to a gene that when naturally occurring in a wild-type organism encodes an Fzo-like polypeptide. An Fzo-like polypeptide functions in prokaryotic-type division and/or morphology, such that a decreased amount of an Fzo-like polypeptide in a prokaryote or a plant (including an algal) cell compared to the amount typically present in wild-type results in incomplete division or no division and/or an abnormal morphology of the prokaryote or plastid(s) in the plant (including an algal) cell. As an illustrative but non-limiting example, in plants such as *Arabidopsis*, a T-DNA insertion in an Fzo-like gene can result in abnormalities in chloroplast size and number. Fzo-like polypeptide amino acid sequences are similar to the yeast Fzo1, which functions in the control of mitochondrial morphology in yeast. Fzo-like polypeptides are contemplated to comprise several domains: a chloroplast transit peptide, a GTPase domain and two predicted trans-membrane domains. In *Arabidopsis* Fzo-like polypeptide, the predicted chloroplast transit peptide is the first 54 amino acids, the GTPase domain is between amino acids 350-500, and the two predicted trans-membrane domains are close to each other in the region between amino acids 770-830.

It is contemplated that Ftn2, ARC5, and Fzo-like genes and proteins are present in, and thus can be isolated from and/or used in, any organism which possesses plastids, as well as any photosynthetic bacteria such as cyanobacteria; organisms which posses plastids include plants, both vascular and non-vascular, algae, and some parasitic protists which contain vestigial plastids.

The term "prokaryotic-type division" refers to division of a prokaryote, and in particular of a photosynthetic prokaryote, or of a plastid.

The term "morphology" refers to the form and/or structure of an organism, an organ, a tissue, a cell, an organelle, or a subcellular structure (for example, a membrane), and its development, and in particular to the form and/or structure and development of the form and/or structure of plastids in plants.

The terms "protein" and "polypeptide" refer to compounds comprising amino acids joined via peptide bonds and are used interchangeably.

As used herein, where "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule; furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "homology" when used in relation to amino acids refers to a degree of complementarity. There may be partial homology or complete homology (i.e., identity). "Sequence identity" refers to a measure of relatedness between two or more proteins, and is given as a percentage with reference to the total comparison length. The identity calculation takes into account those amino acid residues that are identical and in the same relative positions in their respective larger sequences. Calculations of identity may be performed by algorithms contained within computer programs.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferable greater than 75% sequence identity, and still more preferably greater than 90% sequence identity, with a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties (e.g., replacement of leucine with isoleucine). More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (See e.g., Anderson and Young, Quantitative Filter Hybridization (1985) *in Nucleic Acid Hybridization*). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q βreplicase, MDV-1 RNA is the specific template for the replicase (Kacian et al. (1972) Proc. Natl. Acad. Sci. USA, 69:3038). Other nucleic acid will not be replicated by this amplification enzyme. Similarly, in the case of T7 RNA polymerase, this amplification enzyme has a stringent specificity for its own promoters (Chamberlin et al. (1970) Nature, 228:227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics, 4:560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) *PCR Technology*, Stockton Press).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and *ubi*3 (see e.g., Garbarino and Belknap (1994) Plant Mol. Biol. 24:119-127) promoters. Such promoters have been used successfully to direct the expression of heterologous nucleic acid sequences in transformed plant tissue.

In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. (1989) *Molecular Cloning: A Laboratory Manual,* 2nd ed., Cold Spring Harbor Laboratory Press, New York, pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a-negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208, GV3101) are referred to as "nopaline-type" *Agrobacteria; Agrobacterium* strains which cause production of octopine (e.g., strain LBA4404, Ach5, B6) are referred to as "octopine-type" *Agrobacteria*; and *Agrobacterium* strains which cause production of agropine (e.g., strain EHA105, EHA101, A281) are referred to as "agropine-type" *Agrobacteria.*

The terms "bombarding", "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgenic" when used in reference to a plant or fruit or seed (i.e., a "transgenic plant". or "transgenic fruit" or a "transgenic seed" ) refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in one or more of its cells.

The terms “transformants” or “transformed cells” include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term “wild-type” when made in reference to a gene refers to a gene which has the characteristics of a gene isolated from a naturally occurring source. The term “wild-type” when made in reference to a gene product refers to a gene product which has the characteristics of a gene product isolated from a naturally occurring source. A wild-type gene is that which is most frequently observed in a population and is thus arbitrarily designated the “normal” or “wild-type” form of the gene. In contrast, the term “modified” or “mutant” when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term “antisense” refers to a deoxyribonucleotide sequence whose sequence of deoxyribonucleotide residues is in reverse 5' to 3' orientation in relation to the sequence of deoxyribonucleotide residues in a sense strand of a DNA duplex. A “sense strand” of a DNA duplex refers to a strand in a DNA duplex which is transcribed by a cell in its natural state into a “sense mRNA.” Thus an “antisense” sequence is a sequence having the same sequence as the non-coding strand in a DNA duplex. The term “antisense RNA” refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. “Ribozyme” refers to a catalytic RNA and includes sequence-specific endoribonucleases. “Antisense inhibition” refers to the production of antisense RNA transcripts capable of preventing the expression of the target protein.

The term “overexpression” refers to the production of a gene product in transgenic organisms that exceeds levels of production in normal or non-transformed organisms. The term “cosuppression” refers to the expression of a foreign gene which has substantial homology to an endogenous gene resulting in the suppression of expression of both the foreign and the endogenous gene. The term “altered levels” refers to the production of gene product(s) in transgenic organisms in amounts or proportions that differ from that of normal or non-transformed organisms.

The term “recombinant” when made in reference to a nucleic acid molecule refers to a nucleic acid molecule which is comprised of segments of nucleic acid joined together by means of molecular biological techniques. The term “recombinant” when made in reference to a protein or a polypeptide refers to a protein molecule which is expressed using a recombinant nucleic acid molecule.

The terms “Southern blot analysis” and “Southern blot” and “Southern” refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31-9.58).

The term “Northern blot analysis” and “Northern blot” and “Northern” as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52).

The terms “Western blot analysis” and “Western blot” and “Western” refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term “isolated” when used in relation to a nucleic acid, as in “an isolated oligonucleotide” refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a plant CPA-FAS includes, by way of example, such nucleic acid in cells ordinarily expressing a DES, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term “purified” refers to molecules, either nucleic or amino acid sequences, that are removed from their natural environment, isolated or separated. An “isolated nucleic acid sequence” is therefore a purified nucleic acid sequence. “Substantially purified” molecules are at least 60% free, preferably at least 75% free, and more preferably at least 90% free from other components with which they are naturally associated. The term “purified” or “to purify” also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DESCRIPTION OF THE INVENTION

The present invention relates to genes encoding proteins involved in plastid division and morphology, and the encoded proteins, and to methods of use of these genes and proteins. In particular, the present invention provides compositions comprising isolated Ftn2 (ARC6), ARC5, and Fzo-like genes and polypeptides. The present invention also provides methods for using Ftn2, ARC5, and Fzo-like genes, and polypeptides; such methods include but are not limited to altering plant phenotype by transgenic expression of Ftn2, ARC5, and Fzo-like genes and antisense genes. The description below provides specific, but not limiting, illustrative examples of embodiments of the present invention.

I. Identification of Prokaryotic-Type Plastid Division and Related Genes

Genes involved in plastid division can be identified and characterized by different routes. One route is to identify mutants in plastid division. Such mutants have been identified in *Arabidopsis*. A set of mutants, referred to as arc mutants (for accumulation and replication of chloroplasts), have been isolated and analyzed (Marrison J L et al. (1999) The Plant Journal 18(6): 651-662), the mesophyll chloroplasts differ considerably from wild type in number, size and shape. The arc mutant phenotypes are stable and result from single nuclear recessive mutation. Eleven independent nuclear ARC genes have been identified so far, and 5 arc mutants analyzed with respect to their effects on the stages of the proplastid and chloroplast division processes (Marrison J L et al. (1999) The Plant Journal 18(6): 651-662). These effects are summarized as follows: ARC1 is involved in the down-regulation of proplastid division, but is in a separate pathway from the other four ARC genes, and arc1 leads to increased proplastid division; ARC6 is involved in the initiation of both proplastid and chloroplast division, and arc6 completely suppresses proplastid and chloroplast division, but allows extended expansion until the chloroplasts are about 20 time larger than wild type chloroplasts; ARC11 is involved in the central positioning of the division constriction, and in arc11 the constriction is asymmetric; ARC3 controls chloroplast expansion, and the abnormally rapid expansion of arc3 chloroplasts prevents chloroplast division; ARC5 facilitates the separation of the two daughter plastids, and in arc5 the chloroplasts remain dumb-bell shaped and continue to expand (Marrison J L et al. (1999) The Plant Journal 18(6): 651-662). The map positions of ARC5 (on chromosome 3) and ARC 11 and ARC6 (both on chromosome 5) have also been reported (Marrison J L et al. (1999) The Plant Journal 18(6): 651-662).

However, these plastid division mutants have not yet led to the identification of specific genes involved in plastid division. Another route to identify such genes is based upon homology to genes in other organisms, where the homologs may carry out similar functions in plant plastids. For example, homologs to genes involved in cyanobacterial division may, if present in plants, have a role in plastid division. However, this route depends upon the prior identification of such genes.

The development of the present invention involved first the identification of cyanobacterial genes involved in cell division, then the identification of homologous genes in plants and other cyanobacteria.

A. Cyanobacterial Division Genes

Cyanobacteria are ancient relatives of chloroplasts and structurally similar to Gram-negative prokaryotes, and perform plant-type photosynthesis. Therefore, it is contemplated that genes present in cyanobacteria which are involved in cell division may have orthologs present in plants which are involved in plastid division.

To date, the genetic control of cell division has been studied much less in cyanobacteria than it has in *Escherichia coli, Bacillus subtilis* or *Caulobacter crescentus*. Morphologically aberrant mutants of cyanobacteria presumably impaired in cell division, recovered with high frequency after chemical mutagenesis (Ingram L O and Thurston E L (1970) Protoplasma 71:51-75; Ingram L O and Van Baalen C (1970) J. Bateriol. 102:784-789; Ingram LO, Van Baalen C and Fisher W D (1972) J. Bateriol. 11:614-621; Ingram L O and Fisher W. D.(1973a) J. Bacteriol. 113:995-1005; Ingram L O and Fisher W. D.(1973b) J. Bacteriol. 113:1006-1014; Ingram LO and Blackwell M M (1975) J. Bacteriol. 123:743-746; Zhevner V D, Glazer V M, and Shestakov S V (1973) Mikrobiologiya 42:290-297), were described almost three decades ago. Since that time, little information has been obtained about cyanobacterial genes that are involved in the regulation of cell division. Recently, a cyanobacterial gene that encodes an ortholog of cell division protein FtsZ has been cloned and sequenced from *Anabaena* PCC 7120 and other cyanobacteria (Doherty H M and Adams D G (1995) Gene: 93-99; Zhang C C, Huguenin S, and Friry A (1995) Res. Microbiol. 146:445-455). It is contemplated that the discovery of additional cyanobacterial genes involved in cell division and cell differentiation would enhance understanding of the mechanism and regulation of morphogenesis of both bacteria and plant chloroplasts, and that such genes would be useful to control such processes, for example in bacterial fermenters and in crop and horticultural plants.

In an effort to identify additional genes involved in cell division, transposon mutagenesis, using an improved transposon with an increase in rates of transposition of about two orders of magnitude, was applied to cyanobacteria. Effective transposons have been previously developed, resulting in Tn5 and its improved progeny, for example Tn5-1058, where Tn5-1058 and its progeny were characterized by (i) a much stronger promoter driving the antibiotic-resistance operon, (ii) enhanced transposition, and (iii) an *Escherichia coli* origin of replication within the transposon that facilitates recovery of the mutated gene. This vector allows the cloning of sequences contiguous with the transposon, by cutting genomic DNA with a restriction endonuclease that does not cut within the transposon, recircularizing in vitro, and transforming *E. coli* with the resulting ligation mixture (e.g., Black T A, Cai Y, and Wolk C P (1993) Mol. Microbiol. 9:77-84; Cai Y, and Wolk C P (1997) J. Bacteriol. 179:258-266; Ernst A, Black T, Cai Y, Panoff J M, Tiwari D N, and Wolk C P (1992) J. Bacteriol. 174:6025-6032; Wolk C P, Cai Y, and Panoff J M (1991) Proc. Natl. Acad. Sci. USA 88:5355-5359). The transposon subsequently developed by the inventors, Tn5-692, represented yet a further improved, demonstrating about a 100-fold increase in the rate of transposition. During the development of the present invention, the use of Tn5-692 provided large numbers of transposon mutants of *Anabaena variabilis* strain ATCC 29413 (PCC 7120) and of *Synechococcus* sp. PCC 7942. Of these transposon-derived mutants, two new cell division mutants of PCC 7942 have now been characterized.

Filamentous cyanobacterial cell division mutants described many years ago showed two distinct phenotypes (Ingram L O, and Fisher W D (1973a) J. Bacteriol. 113:999-1005): septate filaments containing cross-walls, apparently impaired in the terminal stages of cell separation; and serpentine forms that divide sporadically to produce multinucleoidal long cells. The gene mutated in a septate mutant of *Synechococcus* sp. strain PCC 7942 as a consequence of insertional inactivation (Dolganov N, and Grossman A R (1993) J. Bacteriol. 175:7644-7651) was identified and characterized.

By use of transposon mediated mutation, the inventors have discovered mutants of the second, serpentine phenotype. Cells of these mutants, designated FTN2 and FTN6 of *Synechococcus* sp. strain PCC 7942, have the appearance of long filaments that divide occasionally, at variable positions along the cell. Characterization of the protein Ftn2 revealed presence of a DnaJ domain, a (single) tetratricopeptide repeat (TPR) and a leucine zipper motif, which suggest that Ftn2 may function as part of a complex with one or more other proteins and may be regulatory.

DnaJ domains are characteristic of a family of molecular chaperones. Proteins in this family, from bacterial to human, have three distinct domains: (i) a highly conserved J domain of approximately 70 amino acids, often found near the N-terminus, which mediates interaction of DnaJ (a.k.a., Hsp40) with Hsp70 (DnaK) and regulates the ATPase activity of the latter; (ii) a glycine and phenylalanine (G/F)-rich region of unknown function that may act as a flexible linker; and (iii) a cysteine-rich region (C domain) that contains four CXXCXGXG (SEQ ID NO:207) motifs, and resembles a zinc-finger domain (Ohtsuka K, and Hata M (2000) Int. J. Hyperthermia). Although not originally identified as an fts gene, dnaJ shares with fts genes the property that its inactivation leads to a filamentous phenotype (Paciorek J, Kardys K, Lobacz B, and Wolska K I (1997) Acta Microbiol. Pol. 46:7-17). Cheetham and Caplan (Cheetham M E, and Caplan A J (1998) Cell Stress Chaperones 3:28-36) classified DnaJ/Hsp40 homologs into three groups: type I have all three of these domains; type II have only the J and G/F domains; and type III, like Ftn2, have only a J domain. DnaK proteins are highly versatile chaperones that assist a large variety of processes (Bukau B (1999 ed.) Molecular Chaperones and Folding Catalysts-Regulation, Cellular Function and Mechanisms, Hardwood, Amsterdam; Bukau B, and Horwich A L (1998) Cell 92:351-366; Cai Y, and Wolk C P (1997) J. Bacteriol. 179:258-266; Fink A (1999) Physiological Rev. 79:425-449; Gething M J (1997) Nature 388:329-331; Hartl F U (1996) Nature 381:571-579), from folding of newly synthesized proteins to facilitation of proteolytic degradation of unstable proteins (Laufen T, Mayer M P, and Heiter P (1995) Sci.USA 96:5452-5457). This functional diversity requires that DnaK proteins associate promiscuously with misfolded proteins or selectively with folded substrates, including with regulatory proteins of low abundance.

The tetratricopeptide repeat (TPR) of, typically, 34 amino acids was first described in the yeast cell division cycle regulator Cdc23p (Sikorski R S, Boguski M S, Goebl M, and Heieter P (1990) Cell 60:307-317) and was later found in many other proteins (Das A K, Cohen P W, and Barford D (1998) EMBO J. 17:1192-1199; Goebl M, and Yanagida M (1991) Trends Biochem. Sci. 16:173-177; Lamb J R, Tugendreich S, and Hieter P (1995) Trends Biochem. Sci. 20:257-259). TPRs are frequently present in tandem arrays of 3-16 copies, although single (as in FTN2) or paired TPRs are also common (; Lamb J R, Tugendreich S, and Hieter P (1995) Trends Biochem. Sci. 20:257-259). Processes involving TPR proteins include cell-cycle control, repression of transcription, response to stress, protein kinase inhibition, mitochondrial and peroxisomal protein transport, and neurogenesis (Goebl M, and Yanagida M (1991) Trends Biochem. Sci. 16:173-177). There appears to be no common biochemical function connecting TRP-containing proteins, although the TRP forms scaffolds that mediate protein-protein interactions and, often, the assembly of multiprotein complexes.

Ftn6 is homologous with hypothetical protein S111939 of PCC 6803 (BLAST score, 59; Expect=$10^{-08}$). ORF slr2041, situated 1325 bp from sll1939 on the opposite strand of DNA, predicts a cell-division protein, DivK.

B. Plant Plastid Division and Related Genes

The cyanobacterial Ftn2 genes and proteins were then used to search for homologous genes from *Arabidopsis*. Any such genes discovered were then characterized, in order to determine if in fact they are plastid division or related genes. *Arabidopsis* and cyanobacterial Ftn2 genes and proteins were then used to search for homologous genes from other cyanobacteria, plants, both vascular and non-vascular; and algae.

The product of the cyanobacterial Ftn2 gene from *Synechococcus* sp. strain PCC 7942 was discovered to share a similarity with an unknown protein of *Arabidopsis thaliana* (AB016888|Q9FIG9; BLAST score, 72.8; Expect=$1\times10^{-11}$). It was therefore contemplated that this ortholog was involved in plastid division in *Arabidopsis* cells. The encoded product of this *Arabidopsis* Ftn2 ortholog was predicted to posses a chloroplast transit peptide (from a web-based program (http://, followed by, HypothesisCreator.net/iPSORT/), with the amino acid sequence MEALS HVGIG LSPFQ LCRLP PATTK LRRSH (SEQ ID NO:28). The *Arabidopsis* protein was also predicted to possess a DnaJ domain profile according to ProfileScan (http://, followed by, www.isrec.isb-sib.ch/software/PFSCAN_form.html), and a Myb DNA-binding domain, according to InterProScan (http://, followed by, www.ebi.ac.uk/interpro/scan.html).

The inventors subsequently identified, sequenced and characterized the orthologous gene and protein from *Arabidopsis* (SEQ ID Nos: 1, 2, 3, 9, 10 and 11). Based upon these results, the inventors discovered a novel chloroplast division gene in *Arabidopsis thaliana*; because chloroplast division gene in *Arabidopsis thaliana* is a homologue of the recently identified cell division gene Ftn2 from a cyanobacterium *Synechococcus*, the *Arabidopsis* gene is designated AtFtn2.

The gene AtFtn2 is a nuclear gene coding for a chloroplast-targeted protein with an unconventional DnaJ-like N-terminal domain. The inventors further discovered that the *Arabidopsis* arc6 mutant, as described above and in which plastid division is completely blocked, and whose cells contain grossly enlarged chloroplasts, carries a point mutation in AtFtn2 resulting in premature termination of the translated protein. Moreover, the arc6 mutant phenotype can be rescued by a wild-type copy of AtFtn2. In the arc6 mutant, FtsZ filaments are highly fragmented and disorganized and do not form a ring at mid plastid typical for wild type chloroplasts. Therefore, it is contemplated that AtFtn2 is important for stability and/or assembly of the cytoskeletal plastid-dividing FtsZ protein rings.

The inventors have also discovered Ftn2 homologues in additional cyanobacterial and plant species, but not in completely and partially sequenced genomes of non-cyanobacterial prokaryotes and thus in which Ftn2 homologues appear to be absent.

Therefore, the inventors have discovered a novel gene family involved in plastid and in cyanobacterial prokaryotic division, the Ftn2 gene family. It is contemplated that Ftn2 genes and proteins are present in, and thus can be isolated from and/or used in, any organism which possess plastids; such organisms include plants, both vascular and non-vascular, algae, and some parasitic protists which contain vestigial plastids. It is also contemplated that Ftn2 genes and proteins are present in photosynthetic bacteria such as cyanobacteria.

The inventors have discovered additional genes involved in plastid division and/or morphology, ARC5 and Fzo-like genes.

Mutants of ARC5 exhibit defects in chloroplast constriction, have enlarged, dumbbell-shaped chloroplasts, and are rescued by a wild-type copy of ARC5. The ARC5 gene product shares similarity with the dynamin family of GTPases, which mediate endocytosis, mitochondrial division, and other organellar fission and fusion events in eukaryotes. Phylogenetic analysis showed that ARC5 is related to a group of dynamin-like proteins unique to plants. A green fluorescent protein (GFP)-ARC5 fusion protein localizes to a ring at the chloroplast division site. Chloroplast import and protease protection assays indicate that the ARC5 ring is positioned on the outer surface of the chloroplast. Thus, ARC5 is the first cytosolic component of the chloroplast division complex to be identified. ARC5 has no obvious counterparts in prokaryotes, suggesting that it evolved from a dynamin-related protein present in the eukaryotic ancestor of plants.

Fzo-like genes were discovered by searching the *Arabidopsis* genomic database using as the query sequence the yeast protein Fzo 1, which in the yeast functions in the control of mitochondrial morphology. The results indicated a related gene in *Arabidopsis*, referred to as Fzo-like gene, on chromosome 1, At1g03160 on BAC clone F10O3. At least two *Arabidopsis* lines with T-DNA insertions exhibited abnormalities in chloroplast size and number, indicating the Fzo-like genes functions in plastid division. Knock-out experiments demonstrate that chloroplast development and division are both impaired, where dumbbell-shape chloroplasts with constriction in the middle are frequently observed. Localization experiments with an Fzo-like/GFP fusion protein indicated that the fusion protein is localized to the vesicle-like structures associated with (or near) the chloroplast. The level of AtFzo-like-GFP is positively correlated with the numbers of the vesicle-like structures. Thus, AtFzo-like protein is involved in plastid division and/or morphology.

II. Prokaryotic-Type Division and Related Ftn2, ARC5, and Fzo-like Genes and Polypeptides A. Prokaryotic-Type Division and Related Genes The present invention provides compositions comprising an isolated nucleic acid sequence comprising prokaryotic-type division and related genes; in particular embodiments, the invention provides compositions comprising isolated Ftn2, ARC5, or Fzo-like genes. In some embodiments, the sequences comprise plant Ftn2, ARC5, or Fzo-like gene; in other embodiments, the sequences comprise *Arabidopsis* Ftn2, ARC5, or Fzo-like genes; in other embodiments, the sequences comprise algal Ftn2, ARC5, or Fzo-like genes; in other embodiments, the sequences comprise cyanobacterial Ftn2, ARC5, or Fzo-like genes. In different specific embodiments, isolated nucleic acid sequences comprise a nucleic acid sequence as described in, for example, Table 3, or encode an amino acid sequence as described in, for example, Table 3.

The present invention also provides compositions comprising an isolated nucleic acid sequence comprising an antisense sequence of prokaryotic-type division and related genes; in particular embodiments, the antisense sequences are directed to Ftn2, ARC5, or Fzo-like genes. In some embodiments, the sequences comprise an antisense sequence of a plant Ftn2, ARC5, or Fzo-like gene; in other embodiments, the sequences comprise an antisense sequence of an *Arabidopsis* Ftn2, ARC5, or Fzo-like gene; in other embodiments, the sequences comprise an antisense sequence of a cyanobacterial Ftn2, ARC5, or Fzo-like gene. In different specific embodiments, the sequences comprise antisense sequences of the sequences described, for example, in Table 3.

The present invention also provides compositions comprising an isolated nucleic acid sequence comprising a sequence encoding any of the Ftn2, ARC5, and Fzo-like polypeptides as described below, including but not limited to variants, homologs, truncation mutants, and fusion proteins.

B. Prokaryotic-Type Division and Related Ftn2, ARCS, and Fzo-like Polypeptides

The present invention provides compositions comprising purified prokaryotic-type division and related polypeptides; in particular embodiments, the polypeptides comprise Ftn2, ARC5, or Fzo-like polypeptides, as well as compositions comprising variants, homologs, mutants or fusion proteins thereof. In some embodiments, the polypeptide comprises a plant Ftn2, ARC5, or Fzo-like polypeptide; in other embodiments, the polypeptide comprises an *Arabidopsis* Ftn2, ARC5, or Fzo-like polypeptide; in other embodiments, the polypeptide comprises an algal Ftn2, ARC5, or Fzo-like polypeptide; in yet other embodiments, the polypeptide comprises a cyanobacterial Ftn2, ARC5, or Fzo-like polypeptide; in yet other embodiments, the polypeptide comprises a Cyanobacterial ftn2, ARC5, or FZO-like polypeptides In different specific embodiments, the polypeptide is encoded by a nucleic acid sequence described in, for example, Tables 3, 10, and 11, or comprises an amino acid sequence as described in, for example, Tables 3, 10 and 11.

Ftn2, ARC5, and Fzo-like polypeptides are involved in prokaryotic-type division and/or morphology.

In some embodiments, in both photosynthetic prokaryotes and plants, the Ftn2 polypeptide is contemplated to possess a DnaJ domain, a (single) tetratricopeptide repeat (TPR) and a leucine zipper motif, which domains indicate that the Ftn2 functions as part of a complex with one or more other proteins and is a regulatory protein. In plants, the Ftn2 polypeptide is contemplated to further possess an N-terminal plastid targeting sequence, and to be membrane bound. Although it is not necessary to understand the mechanism in order to practice the present invention, and the present invention is not intended to be limited to any particular mechanism or hypothesis, it is hypothesized that the Ftn2 proteins function in regulation of the assembly and stability of the FtsZ plastid dividing ring proteins. This hypothesis is based upon the observations noted above, that in the arc6 mutants (which lack Ftn2 proteins), little short FtsZ filaments, instead of PD rings, are observed (as described in Example 2).

Figure 2:
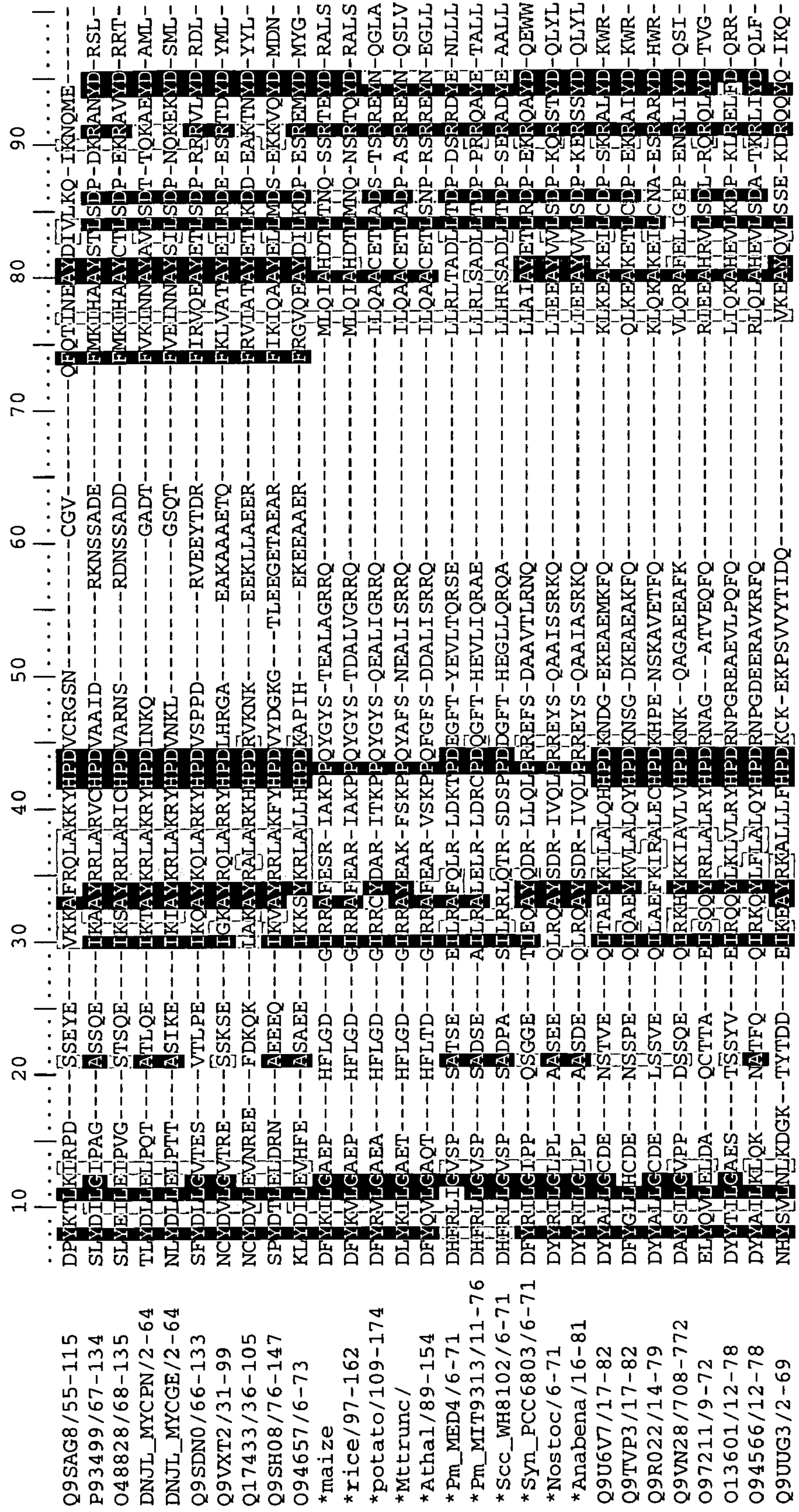
FIG. 2 (SEQ ID NOS: 86-114) shows a sequence alignment of DnaJ-like domains of plant and cyanobacterial Ftn2 proteins (indicated by asterisk) and DnaJ domains from Pfam database. Total about 270 DnaJ domains from the database were aligned with the ARC6 proteins. Shown in this figure are only selected DnaJ domains most similar to Ftn2 proteins. Black and gray columns indicate that identical or similar amino acid, respectively, was present in 70% of all aligned sequences at that position. The TrEMBL accession codes and location of the DnaJ domain within the protein are shown for the Pfam database records. For the ARC6 homologues, if the protein sequences were derived from EST records and did not encompass the initial M, the location of the DnaJ domain is not given.

An Ftn2 polypeptide is a very large protein (in *Arabidopsis*, it is about 800 to about 830 amino acids long); exemplary but non-limiting sequences are provided in FIGS. 2 and 6. An Ftn2 polypeptide can be roughly defined by three regions. The N-terminal contains the DnaJ-like domain, and is exhibits a high degree of homology among Ftn2 proteins obtained from different sources. The large central region is fairly variable, and exhibits a lower degree of homology among the different Ftn2 proteins. The C-terminal is more highly conserved, and therefore exhibits a higher degree of homology. The result is that when considered as a whole, homologous Ftn2 proteins possess about 15% or greater identity or about 38% or greater similarity to AtFtn2 protein. However, the N-terminal and C-terminal regions possess a higher degree of similarity and a higher degree of identity than do the whole proteins.

Thus, in some embodiments, an Ftn2 polypeptide of the present invention comprises at least one of the three regions described above, an N-terminus DnaJ-like domain, a variable central region, and a more conserved C terminal region, and possesses at least some of the Ftn2 characteristics as described above and in the Examples, where the characteristics include the effects of the absence or decrease in the amount of Ftn2 protein normally occurring in a cell.

In *Arabidopsis*, a mutation in the Ftn2 gene results in an arc (accumulation and replication of chloroplasts) mutant, the arc6 mutant. The evidence described in Example 2, including the observations that the sequences of Ftn2 from a wild-type background and the sequences of arc6-1, arc6-2, and arc6-3, are essentially the same except that the a C->T transition at position 1141 in the gene results in a premature stop codon and results in a truncated protein of about 324 amino acids, and that the arc6 mutant is rescued by a wild-type copy of AtFtn2, indicate that AtFtn2 gene is ARC6.

In some embodiments, ARC5 is also a fairly large protein of almost 800 amino acids; exemplary but non-limiting sequences are provided in SEQ ID Nos: 13 and 16-18. I*n Arabidopsis*, ARC5 exists in two forms, a longer form and a shorter form. The amino acid sequences of ARC5 were deduced from the cDNA sequence; the long form of the cDNA encodes a protein of 777 amino acids and 87.2 kDa, whereas the shorter form of the cDNA encodes a protein of 741 amino acids and 83.5 kDa. In addition, the ARC5 protein contains three motifs found in other dynamin-like proteins: a conserved N-terminal GTPase domain, a pleckstrin homology (PH) domain shown in some proteins to mediate membrane association, and a C-terminal GTPase Effector Domain (GED) thought to interact directly with the GTPase domain and to mediate self-assembly. The shorter cDNA encoded a protein of 741 amino acids and 83.5 kDa identical to that of the larger gene product except for the absence of 36 amino acids encoded by the sequence of the $15^{th}$ intron.

Thus, in some embodiments, an ARC5 polypeptide of the present invention comprises at least one of the three regions or motifs described above, a conserved N-terminal GTPase domain, a pleckstrin homology (PH) domain, and a C-terminal GTPase Effector Domain (GED), and possesses at least some of the ARC5 characteristics as described above and in the Examples, where the characteristics include the effects of the absence or decrease in the amount of ARC5 protein normally occurring in a cell.

The evidence described in Example 6, which includes the point mutation in At3g19730/At3g19720 in arc5, complementation of the mutant phenotype by the wild-type gene, and ability of a fragment from At3g19730/At3g19720 to confer an arc5-like phenotype in wild-type plants when expressed in the antisense orientation, indicate that the ARC5 locus and At3g19730/At3g19720 represent the same gene. Moreover, in *Arabidopsis*, the ARC5 transcript is alternatively spliced. The longer cDNA contained a sequence that was spliced out of the shorter cDNA as the $15^{th}$ intron; however, its presence in the longer cDNA did not interrupt the reading frame.

In some embodiments, an Fzo-like protein is also fairly large, of slightly more than about 640 amino acids; exemplary but non-limiting sequences are provided in SEQ ID Nos: 21 and 24. In *Arabidopsis*, an Fzo-like of about 642 amino acids has a predicted chloroplast transit peptide, a GTPase domain and two a predicted trans-membrane domains. The evidence described in Example 7 indicates that Fzo-like proteins are involved in plastid division and/or morphology. In some embodiments, An Fzo-like polypeptide Thus, in some embodiments, an Fzo-like polypeptide of the present invention comprises at least one of the regions described above, chloroplast transit peptide, a GTPase domain and two a predicted trans-membrane domains, and possesses at least some of the Fzo-like characteristics as described above and in the Examples, where the characteristics include the effects of the absence or decrease in the amount of ARC5 protein normally occurring in a cell.

In some embodiments of the present invention, the polypeptide is a purified product, obtained from expression of a native gene in a cell, while in other embodiments it may be a product of chemical synthetic procedures, and in still other embodiments it may be produced by recombinant techniques using a prokaryotic or eukaryotic host (e.g., by bacterial, yeast, higher plant, insect, and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In other embodiments, the present invention provides purified Ftn2, ARC5, and Fzo-like peptides encoded by any of the nucleic acid sequences described above and below, where the purified Ftn2, ARC5, and Fzo-like peptides are post-translationally modified. Such modifications include processing, such as by cleavage of peptide fragments. It is contemplated that newly translated AtFtn2 comprises a plastid peptide sequence, which is cleaved off during import of the protein into the plastid. Thus, AtFtn2 peptides of the present invention include newly translated Ftn2 proteins and post-translationally processed proteins.

Purification of Ftn2, ARC5, and Fzo-like Peptides

In some embodiments of the present invention, Ftn2, ARC5, and Fzo-like polypeptides purified from organisms are provided; such organisms may be transgenic organism, comprising a heterologous Ftn2, ARC5, or Fzo-like gene. The present invention provides purified Ftn2, ARC5, and Fzo-like polypeptides as well as a variant, homolog, mutant or fusion protein thereof, as described elsewhere.

The present invention also provides methods for recovering and purifying Ftn2, ARC5, and Fzo-like polypeptides from an organism; such organisms include single and multicellular organisms. Typically, the cells are first disrupted and fractionated before subsequent enzyme purification; disruption and fractionation methods are well-known. Purification methods are also well-known, and include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

The present invention further provides nucleic acid sequences having a coding sequence of the present invention (e.g., SEQ ID NOs: 1, 11, 14, 19, and 22) fused in frame to a marker sequence that allows for expression alone or both expression and purification of the polypeptide of the present invention. A non-limiting example of a marker sequence is a hexahistidine tag that may be supplied by a vector, for example, a pQE-30 vector which adds a hexahistidine tag to the N terminus of a plastid division and/or morphology polypeptide (e.g., Ftn2, ARC5, and Fzo-like) and which results in expression of the polypeptide in the case of a bacterial host, and more preferably by vector PT-23B, which adds a hexahistidine tag to the C terminal of an plastid division and/or morphology polypeptide and which results in improved ease of purification of the polypeptide fused to the marker in the case of a bacterial host, or, for example, the marker sequence may be a hemagglutinin (HA) tag when a mammalian host is used. The HA tag corresponds to an epitope derived from the influenza hemagglutinin protein (Wilson et al. (1984) Cell, 37:767).

Chemical Synthesis of Ftn2, ARC5, and Fzo-like Polypeptides

In an alternate embodiment of the invention, the coding sequence of an Ftn2, ARC5, or Fzo-like polypeptide is synthesized, whole or in part, using chemical methods well known in the art (See e.g., Caruthers et al. (1980) Nucl. Acids Res. Symp. Ser., 7:215-233; Crea and Horn (1980) Nucl. Acids Res., 9:2331; Matteucci and Caruthers (1980) Tetrahedron Lett., 21:719; and Chow and Kempe (1981) Nucl. Acids Res., 9:2807-2817). In other embodiments of the present invention, the protein itself is produced using chemical methods to synthesize either an entire Ftn2, ARC5, or Fzo-like amino acid sequence or a portion thereof. For example, peptides are synthesized by solid phase techniques, cleaved from the resin, and purified by preparative high performance liquid chromatography (See e.g., Creighton (1983) *Proteins Structures And Molecular Principles*, W H Freeman and Co, New York N.Y.). In other embodiments of the present invention, the composition of the synthetic peptides is confirmed by amino acid analysis or sequencing (See e.g., Creighton, supra).

Direct peptide synthesis can be performed using various solid-phase techniques (Roberge et al. (1995) Science, 269: 202-204) and automated synthesis may be achieved, for example, using ABI 431A Peptide Synthesizer (Perkin Elmer) in accordance with the instructions provided by the manufacturer. Additionally, an amino acid sequence of an Ftn2, ARC5, or Fzo-like polypeptide, or any part thereof, may be altered during direct synthesis and/or combined using chemical methods with other sequences to produce a variant polypeptide.

Generation of Ftn2, ARC5, and Fzo-like Polypeptide Antibodies

In some embodiments of the present invention, antibodies are generated to allow for the detection and characterization of Ftn2, ARC5, and Fzo-like proteins. The antibodies may be prepared using various immunogens. In one embodiment, the immunogen is an *Arabidopsis* Ftn2, ARC5, or Fzo-like peptide (e.g., an amino acid sequence as depicted in SEQ ID NOs:2, 13, 16, 17, 18, 21, 24, or fragments thereof) to generate antibodies that recognize *Arabidopsis* Ftn2, ARC5, and Fzo-like proteins; in another embodiment, the immunogen is a cyanobacterial Ftn2, ARC5, or Fzo-like peptide (e.g., an amino acid sequence as depicted in SEQ ID NO:5, or fragments thereof) to generate antibodies that recognize a cyanobacterial Ftn2, ARC5, or Fzo-like protein. In yet other embodiments, an antibody generated from an immunogenic Ftn2, ARC5, or Fzo-like peptide or fragment recognizes more than one Ftn2, ARC5, or Fzo-like protein or fragment; thus, in these embodiments, the antibodies are cross-reactive. In exemplary embodiments, an antibody prepared against an *Arabidopsis* Ftn2, ARC5, or Fzo-like peptide or fragment recognizes Ftn2, ARC5, or Fzo-like proteins from both *Arabidopsis* and cyanobacteria, and an antibody prepared against an cyanobacterial Ftn2, ARC5, or Fzo-like peptide or fragment recognizes Ftn2, ARC5, or Fzo-like proteins from both cyanobacteria and *Arabidopsis*. Such antibodies include, but are not limited to polyclonal, monoclonal, chimeric, single chain, Fab fragments, and Fab expression libraries.

Various procedures known in the art may be used for the production of polyclonal antibodies directed against a prokaryotic-type or plastid division and/or morphology gene (e.g., Ftn2, ARC5, or Fzo-like). For the production of antibody, various host animals can be immunized by injection with the peptide corresponding to an Ftn2, ARC5, or Fzo-like epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward an Ftn2, ARC5, or Fzo-like peptide, it is contemplated that any technique that provides for the production of antibody molecules by continuous cell lines in culture finds use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein (1975) Nature, 256:495-497), as well as the trioma technique, the human B-cell hybridoma technique (See e.g., Kozbor et al (1983) Immunol. Tod., 4:72), and the EBV-hybridoma technique to produce human monoclonal antibodies (Cole et al. (1985) in *Monoclonal Antibodies and Cancer Therapy*, Alan R. Liss, Inc., pp. 77-96).

In addition, it is contemplated that techniques described for the production of single chain antibodies (U.S. Pat. No. 4,946,778) find use in producing an Ftn2, ARC5, or Fzo-like peptide-specific single chain antibodies. An additional embodiment of the invention utilizes the techniques described for the construction of Fab expression libraries (Huse et al. (1989) Science, 246:1275-1281) to allow rapid and easy identification of monoclonal Fab fragments with the desired specificity for an Ftn2, ARC5, or Fzo-like peptide.

It is contemplated that any technique suitable for producing antibody fragments finds use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody is accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (e.g., using colloidal gold, enzyme or radioisotope labels, for example)? Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In some embodiments of the present invention, the foregoing antibodies are used in methods known in the art relating to the expression of an Ftn2, ARC5, or Fzo-like peptide (e.g., for Western blotting), measuring levels thereof in appropriate biological samples, etc. The antibodies can be used to detect Ftn2, ARC5, and Fzo-like peptides in a biological sample, as for example from a plant or from a cyanobacteria. The biological sample can be an extract of a tissue or cells, or a sample fixed for microscopic examination.

The biological samples are then be tested directly for the presence of an Ftn2, ARC5, or Fzo-like peptide using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of an Ftn2, ARC5, or Fzo-like peptide detected by immunoblotting (Western blotting). Immunoblotting techniques are generally more effective with antibodies generated against a peptide corresponding to an epitope of a protein, and hence, are particularly suited to the present invention.

III. Methods of Identifying Ftn2, ARC5, and Fzo-like Genes and Related Genes

Some embodiments of the present invention contemplate methods to isolate nucleic acid sequences encoding a prokaryotic-type or plastid division and/or morphology protein (e.g., Ftn2, ARC5, and Fzo-like proteins). In some embodiments, the methods involve first preparation of a cDNA library from an appropriate source, for example tissue or cells in which prokaryotic-type division occurs, such as in cyanobacteria or plants. The methods involve next subtracting highly abundant sequences from the library, sequencing the remaining library clones, and comparing the encoded amino acid sequences to the amino acid sequence of either cyanobacterial Ftn2 (for example, SEQ ID NO:5) or *Arabidopsis* Ftn2, ARC5, or Fzo-like (egg, SEQ ID NO:2, 13, 16, 17, 18, 21, and 24) to select putative Ftn2, ARC5, or Fzo-like peptide candidate ESTs. The methods involve next assembling a clone encoding a complete putative Ftn2, ARC5, or Fzo-like peptide, and characterizing the expression products of such sequences so discovered. Alternatively, the methods involve first an examination of an expressed sequence tag (EST) database from an appropriate source, for example tissue or cells in which prokaryotic-type division occurs, such as in cyanobacteria or plants, in order to discover novel potential Ftn2, ARC5, or Fzo-like encoding sequences. These methods next involve sequencing likely candidate sequences, and characterizing the expression products of such sequences so discovered.

Employing these methods resulted in the discovery of an *Arabidopsis* Ftn2, as described in illustrative Examples. The isolated novel coding sequence was demonstrated to encode an Ftn2, as described in the illustrative Examples. These methods were also used to discover other homologous Ftn2, ARC5, and Fzo-like genes, coding sequences, or ESTs from other plants, including vascular plant, and non-vascular plants such as mosses and ferns, and other cyanobacteria, as shown in Example 3, 6, and 7 (see Tables 3, 10, and 11). It is contemplated that these methods can also be used to discover other homologous Ftn2, ARC5, and Fzo-like genes, coding sequences, or ESTs from other plants, both vascular and non-vascular, algae, and other cyanobacteria. It is also contemplated that homologous Ftn2, ARC5, and Fzo-like genes are present in parasitic protists, which are unicellular eukaryotes containing vestigial plastids. These protists are sensitive to the herbicide ROUND-UP, and possess biosynthetic and metabolic pathways which are characteristic of plant plastids, although the protist plastid genome appears to be reduced compared to plant plastid genomes. Exemplary protists include but are not limited to the malarial protist *Plasmodium falciarum* and *Toxoplasma gondii.*

The Ftn2, ARC5, and Fzo-like coding sequences described above can be used to locate and isolate Ftn2, ARC5, and Fzo-like genes, by methods well known in the art. In some methods to isolate the gene, a $^{32}$P-radiolabeled Ftn2, ARC5, or Fzo-like coding sequence (or cDNA). from a particular source is used to screen, by DNA-DNA hybridization, a genomic or cDNA library constructed from the source genomic DNA. Single isolated clones that test positive for hybridization are proposed to contain part or all of the plastid division and/or morphology gene, and are sequenced. The sequence of a positive cloned Ftn2, ARC5, or Fzo-like genomic DNA is used to confirm the identity of the gene as an Ftn2, ARC5, or Fzo-like gene. If a particular clone encodes only part of the gene, additional clones that test positive for hybridization to an Ftn2, ARC5, or Fzo-like coding sequence (or cDNA) are isolated and sequenced. Comparison of the full-length sequence of the Ftn2, ARC5, or Fzo-like gene to the cDNA are used to determine the location of introns, if they are present.

Other methods for identifying other Ftn2, ARC5, or Fzo-like genes are also known. Such methods include utilizing structural predictions used to find related proteins. For example, protein motifs may be used to search for identical or similar proteins present in various databases, as well as their coding sequences (as described further below). Hydropathy profiles can also be used to search databases for similar protein profiles. In yet other methods, cross-hybridizing by Southern blot analysis can be used to screen libraries, and the hybridizing DNA sequenced.

IV. Additional Plastid Division and Related Genes

The present invention provides isolated nucleic acid sequences encoding a prokaryotic-type or plastid division and/or morphology gene (e.g., Ftn2, ARC5, or Fzo-like genes). For example, some embodiments of the present invention provide isolated polynucleotide sequences that are capable of hybridizing to Ftn2, ARC5, and Fzo-like coding sequences (for example, SEQ ID NOs: 1, 3, 4, 11, 12, 14, 15, 19, 20, 22, and 23) under conditions of low to high stringency as long as the polynucleotide sequence capable of hybridizing encodes a protein that retains a desired biological activity of the naturally occurring Ftn2, ARC5, or Fzo-like. In preferred embodiments, hybridization conditions are based on the melting temperature ($T_m$) of the nucleic acid binding complex and confer a defined “stringency” as explained above (See e.g., Wahl et al. (1987) Meth. Enzymol., 152:399-407, incorporated herein by reference).

In other embodiments, an isolated nucleic acid sequence encoding an Ftn2, ARC5, or Fzo-like peptide which is homologous to an Ftn2, ARC5, or Fzo-like as described in the Examples (for example, SEQ ID NOs; 2, 5, 13, 16, 17, 18, 21, and 24) is provided; in some embodiments, the sequence is obtained from a plant or cyanobacteria.

In other embodiments of the present invention, alleles of an Ftn2, ARC5, or Fzo-like gene are provided. In preferred embodiments, alleles result from a mutation, (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In other embodiments of the present invention, the polynucleotide sequence encoding an Ftn2, ARC5, or Fzo-like gene is extended utilizing the nucleotide sequences (e.g., SEQ ID NOs:3, 11, 14, 19, and 22) in various methods known in the art to detect upstream sequences such as promoters and regulatory elements. For example, it is contemplated that polymerase chain reaction (PCR) finds use in the present invention. This is a direct method that uses universal primers to retrieve unknown sequence adjacent to a known locus (Gobinda et al. (1993) PCR Methods Applic., 2:318-322). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR is used to amplify or extend sequences using divergent primers based on a known region (Triglia et al. (1988) Nucleic Acids Res., 16:8186). The primers may be designed using Oligo 4.0 (National Biosciences Inc, Plymouth Minn.), or another appropriate program, to be, for example, 22-30 nucleotides in length, to have a GC content of 50% or more, and to anneal to the target sequence at temperatures about 68-72 ° C. The method uses several restriction enzymes to generate a suitable fragment in the known region of a gene. The fragment is then circularized by intramolecular ligation and used as a PCR template. In yet another embodiment of the present invention, capture PCR (Lagerstrom et al. (1991) PCR Methods Applic., 1:111-119) is used. This is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR. In still other embodiments, walking PCR is utilized. Walking PCR is a method for targeted gene walking that permits retrieval of unknown sequence (Parker et al. (1991) Nucleic Acids Res., 19:3055-60). The PROMOTERFINDER kit (Clontech) uses PCR, nested primers and special libraries to “walk in” genomic DNA. This process avoids the need to screen libraries and is useful in finding intron/exon junctions. In yet other embodiments of the present invention, add TAIL PCR is used as a preferred method for obtaining flanking genomic regions, including regulatory regions (Lui and Whittier, (1995); Lui et al. (1995)).

Preferred libraries for screening for full length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic Libraries are useful for obtaining. introns and extending 5' sequence.

In yet other embodiments, databases containing complete or partial maps of a source genome can be utilized; exemplary genomes are described in Example 1. The flanking sequences can then be obtained from the database once an Ftn2, ARC5, or Fzo-like gene is identified from the source.

V. Variant Plastid Division Peptides

In some embodiments, the present invention provides isolated variants of the disclosed nucleic acid sequence encoding plastid division and/or morphology (e.g., Ftn2, ARC5, and Fzo-like) peptides, and the polypeptides encoded thereby; the peptide variants include mutants, fragments, fusion proteins or functional equivalents of Ftn2, ARC5, and Fzo-like peptides. Thus, nucleotide sequences of the present invention are engineered in order to alter an Ftn2, ARC5, or Fzo-like peptide coding sequence for a variety of reasons, including but not limited to alterations that modify the cloning, processing and/or expression of the gene product (such alterations include inserting new restriction sites, altering glycosylation patterns, and changing codon preference) as well as varying the regulatory and/or enzymatic activity (such changes include but are not limited to differing substrate affinities, differing substrate preferences and utilization, differing inhibitor affinities or effectiveness, differing reaction kinetics, varying subcellular localization, and varying protein processing and/or stability).

Mutants of an Ftn2, ARC5, or Fzo-like Peptide

Some embodiments of the present invention provide mutant forms of an Ftn2, ARC5, or Fzo-like peptide (i.e., muteins). In preferred embodiments, variants result from mutation, (i.e., a change in the nucleic acid sequence) and generally produce altered mRNAs or polypeptides whose structure or function may or may not be altered. Any given gene may have none, one, or many mutant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that is possible to modify the structure of a peptide having an activity (e.g., a prokaryotic-type or plastid division and morphology activity) for such purposes as altering the activity of the peptide. Such modified peptides are considered functional equivalents of peptides having an activity of an Ftn2, ARC5, or Fzo-like peptide as defined herein. A modified peptide can be produced in which the nucleotide sequence encoding the polypeptide has been altered, such as by substitution, deletion, or addition. In some embodiments, these modifications do not significantly reduce the synthetic activity of the modified enzyme. In other words, construct “X” can be evaluated in order to determine whether it is a member of the genus of modified or variant Ftn2, ARC5, and Fzo-like peptides of the present invention as defined functionally, rather than structurally. In some embodiments, the activity of variant Ftn2, ARC5, and Fzo-like peptides is evaluated by the methods described in Examples 2 or 6. For example, a variant Ftn2 can be evaluated in an arc6 mutant, as described in Example 2; an expressed functional Ftn2 peptide will partially or completely restore the mutant to a wild-type phenotype. Accordingly, in some embodiments the present invention provides nucleic acids encoding an Ftn2, ARC5, or Fzo-like peptide that complement the coding region of an Ftn2, ARC5, or Fzo-like coding sequence provided herein (for example, SEQ ID NOs: 1, 3, 4, 11, 14, 19, or 22).

As described above, mutant forms of Ftn2, ARC5, and Fzo-like peptides are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of Ftn2, ARC5, and Fzo-like peptides disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed. (1981) *Biochemistry*, pg. 17-21, 2nd ed, W H Freeman and Co.). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

Mutants of Ftn2, ARC5, and Fzo-like peptides can be generated by any suitable method well known in the art, including but not limited to site-directed mutagenesis, randomized "point" mutagenesis, and domain-swap mutagenesis in which portions of the Sterculia CPA-FAS cDNA are "swapped" with the analogous portion of other plant or bacterial CPA-FAS-encoding cDNAs (Back and Chappell (1996) PNAS 93: 6841-6845).

Variants may be produced by methods such as directed evolution or other techniques for producing combinatorial libraries of variants. Thus, the present invention further contemplates a method of generating sets of combinatorial mutants of the present Ftn2, ARC5, and Fzo-like proteins, as well as truncation mutants, and is especially useful for identifying potential variant sequences (i.e., homologs) that possess the biological activity of a Ftn2, ARC5, or Fzo-like (e.g., role in prokaryotic-type cell or plastid division and/or morphology). In addition, screening such combinatorial libraries is used to generate, for example, novel Ftn2, ARC5, or Fzo-like homologs that possess novel substrate specificities or other biological activities.

It is contemplated that Ftn2, ARC5, and Fzo-like coding nucleic acids (e.g., SEQ ID NOs: 1, 3, 4, 11, 14, 19, and 22 and fragments and variants thereof) can be utilized as starting nucleic acids for directed evolution. These techniques can be utilized to develop Ftn2, ARC5, or Fzo-like peptide variants having desirable properties such as increased synthetic activity or altered affinity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and. 5 (Moore and Arnold (1996) Nat. Biotech., 14, 458-67; Leung et al. (1989) Technique, 1:11-15; Eckert and Kunkel (1991) PCR Methods Appl., 1:17-24; Caldwell and Joyce (1992) PCR Methods Appl., 2:28-33; and Zhao and Arnold (1997) Nuc. Acids. Res., 25:1307-08). After mutagenesis, the resulting clones are selected for desirable activity (e.g., role in prokaryotic-type cell division, as described in Example 2). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith (1994) Nature, 370: 324-25; U.S. Pat. Nos. 5,837,458; 5,830,721; 5,811,238; 5,733,731). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer (1994) Nature, 370:398-91; Stemmer (1994) Proc. Natl. Acad. Sci. USA, 91, 10747-10751; Crameri et al. (1996) Nat. Biotech., 14:315-319; Zhang et al. (1997) Proc. Natl. Acad. Sci. USA, 94:4504-09; and Crameri et al. (1997) Nat. Biotech., 15:436-38). Variants produced by directed evolution can be screened for function in prokaryotic-type or plastid division and/or morphology by the methods described subsequently (see Example 2).

Homologs

Still other embodiments of the present invention provide isolated nucleic acid sequence encoding Ftn2, ARC5, and Fzo-like homologs, and the polypeptides encoded thereby. Some homologs of Ftn2, ARC5, and Fzo-like peptides have intracellular half-lives dramatically different than the corresponding wild-type protein. For example, the altered proteins are rendered either more stable or less stable to proteolytic degradation or other cellular process that result in destruction of, or otherwise inactivate plant CPA-FAS. Such homologs, and the genes that encode them, can be utilized to alter the activity of Ftn2, ARC5, and Fzo-like peptides by modulating the half-life of the protein. For instance, a short half-life can give rise to more Ftn2, ARC5, or Fzo-like peptide biological effects. Other homologs have characteristics that are either similar to wild-type Ftn2, ARC5, or Fzo-like peptides, or which differ in one or more respects from wild-type Ftn2, ARC5, or Fzo-like peptides.

The amino acid sequences of plant and cyanobacterial Ftn2 proteins were searched for protein motifs. One motif is a putative DnaJ domain (AtFtn2 residues 89-153; Scc_PCC7942_Ftn2 residues 6-70) as determined by the InterProScan program (InterPro accession IPR001623, Pfam conserved domain pfam00226). However, ClustalW alignment of this domain with all predicted DnaJ domains from the Pfam database (277 sequences) revealed that the central HPD motif essential for DnaJ proteins is not present in AtFtn2 or other plant and cyanobacterial ftn2 homologues (see FIG. 2).

Another domain discovered through a Pfam-HMM search in the plant Ftn2 proteins is a putative myb domain (residues 677-690, see FIGS. 1 and 3), albeit with low expectation value (0.63). Sequence alignment with entries from the Prosite database indicated that this motif represents only about a half of a typical myb domain.

Yet another domain in AtFtn2 is from one to three transmembrane domains; various software tools predicted up to three putative transmembrane helices (Table 2).

The Scc_PCC 7942_Ftn2 also possesses a single TPR repeat (residues 136-169) as determined by the InterProScan program, and a leucine zipper pattern (residues 234-255) as determined by the Prosite-Protein against PROSITE program (http://ca.expasy.org/tools/scnpsite.html/).

Accordingly, in some embodiments, the present invention provides an Ftn2 prokaryotic-type division peptide comprising at least the DnaJ-like domain (where the DnaJ-like domain is missing the central H PD amino acid (histidine-proline-aspartate), AtFtn2 residues 89-153; Scc_PCC 7942_Ftn2 residues 6-70), or the nucleic acid sequences corresponding thereto. In yet other embodiments of the present invention, it is contemplated that nucleic acid sequences suspected of encoding an Ftn2 homolog is screened by comparing motifs. In some embodiments, the deduced amino acid sequence can be analyzed for the presence of the DnaJ-like amino acid motif (AtFtn2 residues 89-153; Scc_PCC 7942_Ftn2 residues 6-70), the putative myb domain (AtFtn2 residues 677-690), TPR repeat (Scc_PCC7942_Ftn2 residues 136-169) or a leucine zipper pattern (Scc_PCC7942_Ftn2 residues 234-255).

In some embodiments of the combinatorial mutagenesis approach of the present invention, the amino acid sequences for a population of prokaryotic-type or plastid division and/or morphology peptides (e.g., Ftn2, ARC5, or Fzo-like) homologs are aligned, preferably to promote the highest homology possible. Such a population of variants can include, for example, Ftn2, ARC5, and Fzo-like homologs from one or more species, or Ftn2, ARC5, and Fzo-like homologs from the same species but which differ due to mutation. Amino acids that appear at each position of the aligned sequences are selected to create a degenerate set of combinatorial sequences.

In a preferred embodiment of the present invention, the combinatorial Ftn2, ARC5, or Fzo-like library is produced by way of a degenerate library of genes encoding a library of polypeptides that each include at least a portion of candidate Ftn2, ARC5, or Fzo-like -protein sequences. For example, a mixture of synthetic oligonucleotides is enzymatically ligated into gene sequences such that the degenerate set of candidate Ftn2, ARC5, or Fzo-like sequences are expressible as individual polypeptides, or alternatively, as a set of larger fusion proteins (e.g., for phage display) containing the set of Ftn2, ARC5, or Fzo-like sequences therein.

There are many ways by which the library of potential Ftn2, ARC5, or Fzo-like homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential Ftn2, ARC5, or Fzo-like sequences. The synthesis of degenerate oligonucleotides is well known in the art (See e.g., Narang (1983) Tetrahedron Lett., 39:3-9; Itakura et al. (1981) Recombinant DNA, in Walton (ed.), Proceedings of the 3rd Cleveland Symposium on Macromolecules, Elsevier, Amsterdam, pp 273-289; Itakura et al. (1984) Annu. Rev. Biochem., 53:323; Itakura et al. (1984) Science 198:1056; Ike et al. (1983) Nucl. Acid Res., 11:477). Such techniques have been employed in the directed evolution of other proteins (See e.g., Scott et al. (1980) Science, 249:386-390; Roberts et al. (1992) Proc. Natl. Acad. Sci. USA, 89:2429-2433; Devlin et al. (1990) Science, 249: 404-406; Cwirla et al. (1990) Proc. Natl. Acad. Sci. USA, 87: 6378-6382; as well as U.S. Pat. Nos. 5,223,409, 5,198,346, and 5,096,815).

Truncation Mutants of Ftn2, ARC5, or Fzo-like Proteins

In addition, the present invention provides isolated nucleic acid sequences encoding fragments of Ftn2, ARC5, or Fzo-like (i.e., truncation mutants), and the polypeptides encoded by such nucleic acid sequences. In preferred embodiments, the Ftn2, ARC5, or Fzo-like fragment is biologically active.

In some embodiments of the present invention, when expression of a portion of an Ftn2, ARC5, or Fzo-like protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol., 169:751-757) and *Salmonella typhimurium* and its in vitro activity has been demonstrated on recombinant proteins (Miller et al. (1990) Proc. Natl. Acad. Sci. USA, 84:2718-1722). Therefore, removal of an N-terminal methionine, if desired, can be achieved either in vivo by expressing such recombinant polypeptides in a host that produces MAP (e.g., *E. coli* or CM89 or *S. cerevisiae*), or in vitro by use of purified MAP.

Fusion Proteins Containing Ftn2, ARC5, or Fzo-like Proteins

The present invention also provides nucleic acid sequences encoding fusion proteins incorporating all or part of Ftn2, ARC5, or Fzo-like proteins, and the polypeptides encoded by such nucleic acid sequences. In some embodiments, the fusion proteins have an Ftn2, ARC5, or Fzo-like functional domain with a fusion partner. Accordingly, in some embodiments of the present invention, the coding sequences for the polypeptide (e.g., an Ftn2, ARC5, or Fzo-like functional domain) is incorporated as a part of a fusion gene including a nucleotide sequence encoding a different polypeptide. In one embodiment, a single fusion product polypeptide comprises an Ftn2, ARC5, or Fzo-like peptide fused to a marker protein; in some embodiments, the marker protein is GFP.

In some embodiments of the present invention, chimeric constructs code for fusion proteins containing a portion of an Ftn2, ARC5, or Fzo-like protein and a portion of another gene. In some embodiments, a fusion protein has biological activity similar to the wild type Ftn2, ARC5, or Fzo-like protein (e.g., have at least one desired biological activity of an Ftn2, ARC5, or Fzo-like protein). In other embodiments, the fusion protein has altered biological activity.

In other embodiments of the present invention, chimeric constructs code for fusion proteins containing an Ftn2, ARC5, or Fzo-like gene or portion thereof and a leader or other signal sequences which direct the protein to targeted subcellular locations. Such sequences are well known in the art, and direct proteins to locations such as the chloroplast, the mitochondria, the endoplasmic reticulum, the tonoplast, the golgi network, and the plasmalemma.

In addition to utilizing fusion proteins to alter biological activity, it is widely appreciated that fusion proteins can also facilitate the expression and/or purification of proteins, such as an Ftn2, ARC5, or Fzo-like protein of the present invention. Accordingly, in some embodiments of the present invention, an Ftn2, ARC5, or Fzo-like protein is generated as a glutathione-S-transferase (i.e., GST fusion protein). It is contemplated that such GST fusion proteins enables easy purification of an Ftn2, such as by the use of glutathione-derivatized matrices (See e.g., Ausabel et al. (eds.) (1991) Current Protocols in Molecular Biology, John Wiley & Sons, NY).

In another embodiment of the present invention, a fusion gene coding for a purification leader sequence, such as a poly-(His)/enterokinase cleavage site sequence at the N-terminus of the desired portion of an Ftn2, ARC5, or Fzo-like protein allows purification of the expressed Ftn2, ARC5, or Fzo-like fusion protein by affinity chromatography using a $Ni^2$+metal resin. In still another embodiment of the present invention, the purification leader sequence is then subsequently removed by treatment with enterokinase (See e.g., Hochuli et al. (1987) J. Chromatogr., 411:177; and Janknecht et al. Proc. Natl. Acad. Sci. USA, 88:8972). In yet other embodiments of the present invention, a fusion gene coding for a purification sequence appended to either the N (amino) or the C (carboxy) terminus allows for affinity purification; one example is addition of a hexahistidine tag to the carboxy terminus of an Ftn2, ARC5, or Fzo-like protein which was optimal for affinity purification.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See e.g., Current Protocols in Molecular Biology, supra).

Screening Gene Products

A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of Ftn2 homologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Accordingly, in some embodiment of the present invention, candidate Ftn2, ARC5, or Fzo-like gene products are displayed on the surface of a cell or viral particle, and the product detected by any of several methods. In other embodiments of the present invention, the gene library is cloned into the gene for a surface membrane protein of a bacterial cell, and the resulting fusion protein detected by panning (WO 88/06630; Fuchs et al. (1991) BioTechnol., 9:1370-1371; and Goward et al. (1992) TIBS 18:136-140). In other embodiments of the present invention, fluorescently labeled molecules that bind an Ftn2, ARC5, or Fzo-like peptide can be used to score for potentially functional Ftn2, ARC5, or Fzo-like homologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (See e.g., WO 90/02909; WO 92/09690; Marks et al. (1992) J. Biol. Chem., 267:16007-16010; Griffths et al. (1993) EMBO J., 12:725-734; Clackson et al. (1991) Nature, 352:624-628; and Barbas et al. (1992) Proc. Natl. Acad. Sci., 89:4457-4461).

In another embodiment of the present invention, the recombinant phage antibody system (e.g., RPAS, Pharmacia Catalog number 27-9400-01) is modified for use in expressing and screening of Ftn2, ARC5, or Fzo-like combinatorial libraries. The pCANTAB 5 phagemid of the RPAS kit contains the gene that encodes the phage gill coat protein. In some embodiments of the present invention, the Ftn2, ARC5, or Fzo-like combinatorial gene library is cloned into the phagemid adjacent to the gIII signal sequence such that it is expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate Ftn2, ARC5, or Fzo-like gene insert. The resulting recombinant phage contain phagemid DNA encoding a specific candidate Ftn2, ARC5, or Fzo-like protein and display one or more copies of the corresponding fusion coat protein. In some embodiments of the present invention, the phage-displayed candidate proteins that are capable of, for example, interacting with other prokaryotic-type proteins, are selected or enriched by panning. The bound phage is then isolated, and if the recombinant phage express at least one copy of the wild type gIII coat protein, they will retain their ability to infect *E. coli*. Thus, successive rounds of reinfection of *E. coli* and panning will greatly enrich for Ftn2, ARC5, or Fzo-like homologs, which can then be screened for further biological activities.

In light of the present disclosure, other forms of mutagenesis generally applicable will be apparent to those skilled in the art in addition to the aforementioned rational mutagenesis based on conserved versus non-conserved residues. For example, Ftn2, ARC5, or Fzo-like homologs can be generated and screened using, for example, alanine scanning mutagenesis and the like (Rufet al. (1994) Biochem., 33:1565-1572; Wang et al. (1994) J. Biol. Chem., 269:3095-3099; Balint (1993) Gene 137:109-118; Grodberg et al. (1993) Eur. J. Biochem., 218:597-601; Nagashima et al. (1993) J. Biol. Chem., 268:2888-2892; Lowman et al. (1991) Biochem., 30:10832-10838; and Cunningham et al. (1989) Science, 244:1081-1085), by linker scanning mutagenesis (Gustin et al. (1993) Virol., 193:653-660; Brown et al. (1992) Mol. Cell. Biol., 12:2644-2652; McKnight et al. Science, 232:316); or by saturation mutagenesis (Meyers et al. (1986) Science, 232:613).

VI. Expression of Cloned Plastid Division and Related Genes

In other embodiment of the present invention, nucleic acid sequences corresponding to plastid division and/or morphology (e.g., Ftn2, ARC5, or Fzo-like) genes, homologs and mutants as described above may be used to generate recombinant DNA molecules that direct the expression of the encoded protein product in appropriate host cells.

As will be understood by those of skill in the art, it may be advantageous to produce Ftn2, ARC5, or Fzo-like -encoding nucleotide sequences possessing non-naturally occurring codons. Therefore, in some preferred embodiments, codons preferred by a particular prokaryotic or eukaryotic host (Murray et al (1989) Nucl. Acids Res., 17) can be selected, for example, to increase the rate of Ftn2, ARC5, or Fzo-like expression or to produce recombinant RNA transcripts having desirable properties, such as a longer half-life, than transcripts produced from naturally occurring sequence.

A. Vectors for Production of Plastid Division and Related Proteins

The nucleic acid sequences of the present invention may be employed for producing polypeptides by recombinant techniques. Thus, for example, the nucleic acid sequence may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic sequences as broadly described above (e.g., SEQ ID NOs: 1, 3, 4, 11, 14, 19, and 22). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, a nucleic acid sequence of the present invention within an expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of Plastid Division and Related Polypeptides

In a further embodiment, the present invention provides host cells comprising any of the above-described constructs. In some embodiments of the present invention, the host cell is a higher eukaryotic cell (e.g., a plant cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman (1981) Cell 23:175), 293T, C127, 3T3, HeLa and BHK cell lines, NT-1 (tobacco cell culture line), root cell and cultured roots in rhizosecretion (Gleba et al. (1999) Proc Natl Acad Sci USA 96: 5973-5977).Other examples include microspore-derived cultures of oilseed rape. (Weselake R J and Taylor D C (1999) Prog. Lipid Res. 38: 401), and transformation of pollen and microspore culture systems. Yet other examples include red and green algal cells. Further examples are described in the Examples.

The constructs in host cells can be used in a conventional manner to produce the gene product encoded by any of the recombinant sequences of the present invention described above. In some embodiments, introduction of the construct into the host cell can be accomplished by calcium phosphate transfection, DEAE-Dextran mediated transfection, or electroporation (See e.g., Davis et al. (1986) Basic Methods in Molecular Biology). Alternatively, in some embodiments of the present invention, a polypeptide of the invention can be synthetically produced by conventional peptide synthesizers.

Proteins can be expressed in eukaryotic cells, yeast, bacteria, or other cells under the control of appropriate promoters. Cell-free translation systems can also be employed to produce such proteins using RNAs derived from a DNA construct of the present invention. Appropriate cloning and expression vectors for use with prokaryotic and eukaryotic hosts are described by Sambrook, et al. (1989) *Molecular Cloning: A Laboratory Manual*, Second Edition, Cold Spring Harbor, N.Y.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

C. Transgenic Plants, Seeds, and Plant Parts

In other embodiments, the present invention provides plants, seeds, plant cells and/or plant parts comprising any of the above-described constructs. Plants are transformed with a heterologous gene encoding an Ftn2, ARC5, or Fzo-like protein or transformed with a fusion gene encoding a fusion polypeptide expressing an Ftn2, ARC5, or Fzo-like protein according to procedures well known in the art. It is contemplated that the heterologous genes are utilized to alter the level of the proteins encoded by the heterologous genes. It is further contemplated that the heterologous genes are utilized to change the phenotype of the transgenic plants; such changes in phenotype are contemplated to include but not be limited to change in plastid size, number per cell, and shape.

Plants

The methods of the present invention are not limited to any particular plant. Indeed, a variety of plants are contemplated in different embodiments, including but not limited to tomato, potato, tobacco, pepper, nice, corn, barley, wheat, *Brassica, Arabidopsis*, sunflower, soybean, poplar, and pine. In some embodiments, plants include oil-producing species, which are plant species that produce and store triacylglycerol in specific organs, primarily in seeds; fatty acids are synthesized in the plastid. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of genes encoding metabolites synthesized in the plastid. Other plants include plants that synthesize desirable compounds in the plastid, such as production of carotenoid pigments, as for example in tomatoes and marigolds, and production of starch, as for example in corn and potatoes.

Vectors

The methods of the present invention contemplate the use of a heterologous gene encoding an Ftn2, ARC5, or Fzo-like polypeptide, as described above. Such genes include any of the sequences described above, including variants and fragments.

Heterologous genes intended for expression in plants are first assembled in expression cassettes comprising a promoter. Methods that are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y).

In general, these vectors comprise a nucleic acid sequence of the invention encoding an Ftn2, ARC5, or Fzo-like polypeptide (as described above) operably linked to a promoter and other regulatory sequences (e.g., enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al. (1999) Plant Physiol 120: 979-992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat No. 5,187,267); a tetracycline-inducible promoter (U.S. Pat No. 5,057,422); and seed-specific promoters, such as those for seed storage proteins (e.g., phaseolin, napin, oleosin, and a promoter for soybean beta conglycin (Beachy et al. (1985) EMBO J. 4: 3047-3053)). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tm1 terminator, the pea rbcS E9 terminator, and the nopaline and octopine synthase terminator (See e.g., Odell et al. (1985) Nature 313:810; Rosenberg et al. (1987) Gene, 56:125; Guerineau et al. (1991) Mol. Gen. Genet., 262:141; Proudfoot (1991) Cell, 64:671; Sanfacon et al. Genes Dev., 5:141; Mogen et al. (1990) Plant Cell, 2:1261; Munroe et al. (1990) Gene, 91:151; Ballad et al. (1989) Nucleic Acids Res. 17:7891; Joshi et al (1987) Nucleic Acid Res., 15:9627).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Calais et al. (1987) Genes Develop. 1:1183). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Calderone et al. (1984) Cell 39:499; Lassoer et al. (1991) Plant Molecular Biology 17:229), a plant translational consensus sequence (Joshi (1987) Nucleic Acids Research 15:6643), an intron (Luehrsen and Walbot (1991) Mol. Gen. Genet. 225:81), and the like, operably linked to the nucleic acid sequence encoding plant CPA-FAS.

In preparing the construct comprising a nucleic acid sequence encoding an Ftn2, ARC5, or Fzo-like polypeptide, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19:259; Bevan et al. (1983) Nature 304:184), the bar gene which confers resistance to the herbicide phosphinothricin (White et al (1990) Nucl Acids Res. 18:1062; Spencer et al. (1990) Theor. Appl. Genet. 79:625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some preferred embodiments, the vector is adapted for use in an *Agrobacterium* mediated transfection process (See e.g., U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. NO. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention is utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted plant CPA-FAS polynucleotide of the present invention can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention, where the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278).

Transformation Techniques

Once a nucleic acid sequence encoding an Ftn2, ARC5, or Fzo-like polypeptide is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos. 5,451,513; 5,545,817; 5,545,818; PCT application WO 95/16783); these techniques also result in plastid transformation. The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. (1990) PNAS, 87:8526; Staub and Maliga, (1992) Plant Cell, 4:39). The presence of cloning sites between these markers allowed creation of a plastid targeting vector introduction of foreign DNA molecules (Staub and Maliga (1993) EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202:179). In still other embodiments, the vector is transferred into the plant cell by using polyethylene glycol (Krens et al. (1982) Nature, 296:72; Crossway et al. (1986) BioTechniques, 4:320); fusion of protoplasts with other entities, either minicells, cells, lysosomes or other fusible lipid-surfaced bodies (Fraley et al. (1982) Proc. Natl. Acad. Sci., USA, 79:1859); protoplast transformation (EP 0 292 435); direct gene transfer (Paszkowski et al. (1984) EMBO J., 3:2717; Hayashimoto et al. (1990) Plant Physiol. 93:857).

In still further embodiments, the vector may also be introduced into the plant cells by electroporation. (Fromm, et al. (1985) Pro. Natl Acad. Sci. USA 82:5824; Riggs et al. (1986) Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del.). (See e.g., U.S. Pat. NO. 4,945,050; and McCabe et al. (1988) Biotechnology 6:923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al (1990) Bio/Technology 8:736 (rice); European Patent Application EP 0 332 581 (orchardgrass and other Pooideae); Vasil et al. (1993) Biotechnology, 11:1553 (wheat); Weeks et al. (1993) Plant Physiol., 102:1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5:263 (cotton); Casas et al. (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat).

In addition to direct transformation, in some embodiments, the vectors comprising a nucleic acid sequence encoding an Ftn2, ARC5, or Fzo-like polypeptide of the present invention are transferred using *Agrobacterium*-mediated transformation (Hinchee et al. (1988) Biotechnology, 6:915; Ishida et al. (1996) Nature Biotechnology 14:745). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237: 1176). Species which are susceptible infection by *Agrobacterium* may be transformed in vitro. Alternatively, plants may be transformed in vivo, such as by transformation of a whole plant by Agrobacteria infiltration of adult plants, as in a "floral dip" method (Bechtold N, Ellis J, Pelletier G (1993) Cr. Acad. Sci. III-Vie 316: 1194-1199).

Regeneration

After selecting for transformed plant material that can express the heterologous gene encoding a plastid division and/or morphology polypeptide (e.g., Ftn2, ARC5, or Fzo-like polypeptide), whole plants are regenerated. Plant regeneration from cultured protoplasts is described in Evans et al. (1983) Handbook of Plant Cell Cultures, Vol. 1: (MacMillan Publishing Co. New York); and Vasil I. R. (ed.), Cell Culture and Somatic Cell Genetics of Plants, Acad. Press, Orlando, Vol. I (1984), and Vol. III (1986). It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

Generation of Transgenic Lines

Transgenic lines are established from transgenic plants by tissue culture propagation. The presence of nucleic acid sequences encoding exogenous Ftn2, ARC5, or Fzo-like polypeptides of the present invention (including mutants or variants thereof) may be transferred to related varieties by traditional plant breeding techniques.

These transgenic lines are then utilized for evaluation of plastid division and/or morphology and agronomic traits. Evaluation of plastid division and/or morphology includes examination of plastid size, number, and shape in the transgenic lines, and comparison to these characteristics in wild-type parent lines. A difference of at least about 10%, preferably of at least about 25%, and more preferably of at least about 50%, from these characteristics in wild-type plants, is indicative of homologous plastid division and/or morphology gene activity in the transgenic lines.

VII. Manipulation of Ftn2, ARC5, and Fzo-like Levels and Function in Plants

Altering the expression of Ftn2, ARC5, or Fzo-like or homologues in crop species via genetic engineering using antisense, RNAi, cosuppression, or overexpression strategies, introducing Ftn2, ARC5, or Fzo-like homologues from plants, algae or cyanobacteria into plants, algae, or cyanobacteria, is contemplated to result in changes in plastid size, shape and/or number. Such changes are contemplated to occur in all types of plastids including chloroplasts, chromoplasts, leucoplasts and amyloplasts, and in all organs including leaves, roots, stems, petals, and seeds depending on the specificity of the promoters used in the construction of the transgenes.

Alterations in plastid size, shape and/or number via genetic engineering of Ftn2, ARC5, or Fzo-like expression in agronomically or horticulturally important plant and algal species is contemplated to result in improved productivity and/or increased vigor due to enhanced photosynthetic capacity, and/or to allow enhanced production of commercially important compounds that accumulate in plastids either naturally or as a result of genetic engineering. Examples of compounds that naturally accumulate in plastids include vitamin E, provitamin A, essential (aromatic) amino acids, pigments (carotenes, xanthophylls, chlorophylls), starch, and lipids. Plants with altered plastid size or number have further applications in improving the efficiency of plastid transformation technologies that are used for the introduction of transgenes into the plastid genome.

It is contemplated, therefore, that the nucleic acids encoding an Ftn2, ARC5, or Fzo-like polypeptide of the present invention may be utilized to either increase or decrease the level of Ftn2, ARC5, or Fzo-like mRNA and/or protein in transfected cells as compared to the levels in wild-type cells. Such transgenic cells have great utility, including but not limited to further research as to the effects of the overexpression of Ftn2, ARC5, or Fzo-like, and as to the effects as to the underexpression or lack of Ftn2, ARC5, or Fzo-like genes. In particular embodiments, the cells are plant cells.

Accordingly, in some embodiments, expression in plants by the methods described above leads to the overexpression of Ftn2, ARC5, or Fzo-like genes in transgenic plants, plant tissues, plant cells, or seeds.

In other embodiments of the present invention, Ftn2, ARC5, or Fzo-like encoding polynucleotides are utilized to decrease the level of Ftn2, ARC5, or Fzo-like mRNA and/or protein in transgenic plants, plant tissues, plant cells, or seeds as compared to wild-type plants, plant tissues, plant cells, or seeds. One method of reducing Ftn2, ARC5, or Fzo-like expression utilizes expression of antisense transcripts. Antisense RNA has been used to inhibit plant target genes in a tissue-specific manner (e.g., van der Krol et al. (1988) Biotechniques 6:958-976). Antisense inhibition has been shown using the entire cDNA sequence as well as a partial cDNA sequence (e.g., Sheehy et al. (1988) Proc. Natl. Acad. Sci. USA 85:8805-8809; Cannon et al. (1990) Plant Mol. Biol. 15:39-47). There is also evidence that 3' non-coding sequence fragment and 5' coding sequence fragments, containing as few as 41 base-pairs of a 1.87 kb cDNA, can play important roles in antisense inhibition (Ch'ng et al. (1989) Proc. Natl. Acad. Sci. USA 86:10006-10010).

Accordingly, in some embodiments, an Ftn2, ARC5, or Fzo-like encoding-nucleic acid of the present invention (e.g., SEQ ID NOs: 13, 11, 14, 19, and 22 and fragments and variants thereof) are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, Solanum nodiflorum mottle virus and subterranean clover mottle virus. The design and use of target RNA-specific ribozymes is described in Haseloff, et al. (1988) Nature 334:585-591. Ribozymes targeted to the mRNA of a lipid biosynthetic gene, resulting in a heritable increase of the target enzyme substrate, have also been described (Merlo AO et al. (1998) Plant Cell 10:1603-1621).

Another method of reducing Ftn2, ARC5, or Fzo-like expression utilizes the phenomenon of cosuppression or gene silencing (See e.g., U.S. Pat. NO. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (e.g., Napoli et al. (1990) Plant Cell 2:279-289; van der Krol et al. (1990) Plant Cell 2:291-299; Smith et al. (1990) Mol. Gen. Genetics 224: 477-481). Accordingly, in some embodiments the nucleic acid sequences encoding an Ftn2, ARC5, or Fzo-like polypeptide of the present invention (e.g. including SEQ ID NOs 1, 3, 11, 14, 19, and 22 and fragments and variants thereof) are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants which are over-expressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

An effective method to down regulate a gene is by hairpin RNA constructs. Guidance to the design of such constructs for efficient, effective and high throughput gene silencing have been described (Wesley S V et al. (2001) Plant J. 27:581-590).

VIII. Herbicide Targets

In some embodiments, the plastid division and/or morphology genes of the present invention find use as herbicide targets. The present invention is not limited to a particular mechanism. Indeed, an understanding of the mechanism is not necessary to practice the present invention. Nonetheless, it is contemplated that, based on the fact that ARC6 is found in plants and cyanobacteria but not in animals, fungi or other eukaryotes, the gene product has use as an herbicide target.

EXPERIMENTAL

The following examples are provided in order to demonstrate and further illustrate certain preferred embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); WT (wild type); nt (nucleotide(s)); na (nucleic acid(s)); aa (amino acid(s)); arc (accumulation and replication of chloroplasts; refers to mutations observed in *Arabidopsis* which exhibition abnormal chloroplast accumulation and/or replication)

EXAMPLES

The following examples describe the identification and characterization of several Ftn2 coding sequences and encoded amino acid sequences from cyanobacteria and plants, both vascular and non-vascular. A cyanobacterial cell division gene Ftn2 (accession AF421196) was isolated from *Synechococcus* sp. WH8102 (as described in Examples 4 and 5). The product of this Ftn2 gene was then discovered to be similar to an unknown protein of *Arabidopsis thaliana*, as well as to predicted products of ORFs from an *Anabaena* strain, a *Nostoc punctiforme*, and a presumptive gene from a *Synechocystis* strain. The *Arabidopsis* Ftn2 gene, which encodes a protein similar to the *Synechococcus* Ftn2 protein, was then isolated, sequenced, and characterized (as described in Examples 1 and 2). The two encoded Ftn2 protein products were then used to discover other Ftn2 encoding nucleic acid and amino acid sequences from other plants and cyanobacteria (as described in Example 3).

Example 1

Materials and Methods Utilized to Identify and Characterize Ftn2 Genes

This example describes the materials and methods used to identify and characterize Ftn2 genes in plants and other cyanobacteria.

Gene and Protein Names

The cyanobacterial cell division gene Ftn2 (accession AF421196) was isolated from *Synechococcus* sp. WH8102 as described below (and in Koksharova and (2002) J Bacterial: in press in preparation). Although the initial designation of this gene as Ftn2 conflicts with existing records for ferritin type 2 protein gene Ftn2 (e.g., accession AJ306614), in this description the designation Ftn2 refers to the cyanobacterial cell division gene and its plant homologues. Because the Ftn2 plant homologue was isolated and identified in *Arabidopsis* arc6 mutant (as described in Example 2 below), the ARC6 gene (and ARC6 protein) designations may be used. These denote the same entities as AtFtn2 gene and AtFtn2 protein, respectively.

For clarity, the species abbreviation is used as the first part of the name: AtFtn2 (*Arabidopsis thaliana*), StFtn2 (*Solanum tuberosum*, potato), ZmFtn2 (*Zea mays*, maize), OsFtn2 (*Oryza sativa*, rice), *Nostoc*_Ftn2 (*Nostoc punctiforme* ATCC 29133), MtFtn2 (*Medicago truncatula*), Pm_MED4_Ftn2 (*Protochlorococcus marinus* MED4), Pm_MIT9313_Ftn2 (*Protochlorococcus marinus* MIT 9313), Scc_WH8102_Ftn2 (*Synechococcus* WH8102), Syn_PCC6803_Ftn2 (*Synechocystis* PCC6803, NP_441990), and *Anabena*_Ftn2 (*Anabena* PCC 7120). The DNA and/or protein accession numbers are listed in Table 3 in Example 3 below.

Plant Material

The wild type (WT) *Arabidopsis thaliana*, ecotype Wassiljevskija (Ws), transgenic plants expressing AtFtsZ1-1 or AtFtsZ2-1 antisense constructs (Osteryoung et al.(1998) Plant Cell. 10:1991-2004), AtFtsZ1-1 sense constructs (Stokes et al., 2000) and AtFtsZ2-1-cmyc sense constructs (Vitha et al.(2001) J. Cell. Biol.153:111-119) (all in ecotype Columbia Col-0 background), the *Arabidopsis* chloroplast division mutants arc6-1, arc6-2 and arc6-3 (Ws-2 background) and arc3 (Landsberg erecta background) were grown for five weeks in a growth chamber as described previously (Osteryoung et al.(1998) Plant Cell. 10:1991-2004).

Amplification and Sequencing of AtFtn2

Genomic DNA was isolated from WT and arc6-11, arc6-2 and arc6-3 young leaf tissue using the Plant DNAzol reagent (Invitrogen, Carlsbad, Calif.) according to the manufacturer's instructions. The AtFtn2 genomic fragment was amplified with the Pfu Turbo DNA polymerase (Stratagene, La Jolla, Calif.) using the primers 5' TGTCCAAATTTTATGTGACACTCC 3' (forward) (SEQ ID NO:29) and 5' TTGTGAAAGGCTTGAATGTAAGA 3' (reverse) (SEQ ID NO:30). The amplification product of~3.8 kb contained the whole AtFtn2 coding sequence flanked by a 0.5 kb 5' and a 0.2 kb 3' regions. The amplified product was cloned into a SmaI-digested pBluescript vector (Startagene). For each plant genotype, DNA isolation, PCR amplification, and cloning of the product were carried out independently for three individual plants to minimize amplification errors. The resulting plasmid DNA was then pooled for each genotype and sequenced in both directions. Sequencer reads were processed, assembled into contigs, and viewed using Phrap, Phred and Consed (see the Software Tools section).

Complementation of the arc6-1 Mutant

The PCR-amplified genomic fragment containing AtFtn2 (see above) was cloned into a SmaI site of a pBJ97 shuttle vector, excised with NotI and inserted into a plant transformation vector pMLBART (both vectors obtained from Karl Gordon, CSIRO, Canberra, Australia via John Bowman, University of California, Davis), a derivative of pART27 (Gleave, 1992), that confers resistance to the herbicide glufosinate as a selectable marker. *Agrobacterium*-mediated transformation of WT and arc6-1 plants and selection of the glufosinate-resistant T1 plants were performed as described previously (Vitha et al., 2001).

Microscopy

Chloroplast phenotypes were assessed in tips from fully expanded leaves of four week old plants as described previously (Osteryoung et al.(1998) Plant Cell. 10:1991-2004). Cells containing 1-4 chloroplasts were scored as having severe plastid phenotype. The intermediate phenotype was characterized by 10-30 chloroplasts per cell, while cells containing 50 or more chloroplasts were scored as having WT-like phenotype. Images were recorded with Nikon Coolpix 995 (Nikon Corporation, Tokyo, Japan) digital camera.

Immunoblotting and Immunofluorescence of AtFtsZ

Immunoblotting with leaf tissue extracts and immunofluorescence microscopy of leaf mesophyll chloroplasts were performed as previously described (Stokes et al. (2000) *Arabidopsis* Plant Physiol. 124:1668-1677; Vitha et al.(2001) J. Cell. Biol.153:111-119) using rabbit antipeptide antibodies specific to AtFtsZ1 and AtFtsZ2 (antibodies were designated 1-1A and 2-1A, respectively). For immunofluorescence labeling, a goat anti-rabbit Oregon Green 488 conjugate (Molecular Probes, Eugene, Oreg.) was used at 1:200 dilution. Specimens were viewed with Olympus BH-2 and Leica DMR A2 microscopes equipped with epifluorescence illumination, 100×oil immersion objectives, FITC fluorescence filter sets (excitation 455-495 nm, emission 512-575 nm) and CCD cameras Optronics (Goleta, Calif.) DEI 750 and Qimaging (Burnaby, B.C., Canada) Retiga 1350ex, respectively. The images were taken either as a single optical section or as a stack of images with spacing 0.5 μm between slices. Image stacks were processed and projected (Brightest Point method) with Imagej ver. 1.27 software (http://rsb.info.nih.gov/ij/) and further adjusted and cropped using Adobe Photoshop 6.0 (Adobe Systems Inc., San Jose, Calif.).

Databases and Software Tools

DNA and protein sequence databases were searched with tblastn and blastn (Altschul et al. (1990) J. Mol Biol. 215: 403-10) at National Center for Biotechnology Information (NCBI; at http://, followed by, www.ncbi.nlm.nih.gov), and in the *Arabidopsis thaliana* database at Munich Information Center for Protein Sequences (MIPS; at http://, followed by, mips.gsf.de/proj/thal/db/index.html). Preliminary sequence data for *Synechococcus* sp. strain WH8102, strain MED4, *Protochlorococcus marinus* strain MT9313 and *Nostoc punctiforme* strain ATCC 29133 were obtained from the DOE Joint Genome Institute (JGI) (at http://, followed by, .jgi.doe-.gov/JGI_microbial/html/index.html). The *Anabena* sp. PCC 7120 sequence was obtained from the Kazusa DNA Research Institute, Japan (at http://, followed by, .kazusa.or.jp/cyano/). The preliminary *Synechococcus* sp. PCC 7002 sequence was obtained from NCBI through a tblastn search of microbial genomes (http://www, followed by, .ncbi.nlm.nih.gov/cgi-bin/Entrez/genom_table_cgi).

For predictions of subcellular protein targeting, TargetP ver. 1.01 (Emanuelsson et al.(2000) J. Mol Biol. 300:1005-16) (at http://www, followed by, .cbs.dtu.dk/services/TargetP/) and Predotar ver. 0.5 (at http://www, followed by, .inra.fr/Internet/Produits/Predotar/) were used. Prediction of transmembrane domain was performed with HMMTOP ver. 2.0 (Tusnady and Simon (1998) J. Mol Biol. 283:489-506; Tusnady and Simon (2001) Bioinformatics 17:849-50) (at http://www, followed by, .enzim.hu/hmmtop/), TMHMM ver. 2.0 (Krogh et al. (2001) J. mol Biol. 305:567-580) (at http://www, followed by, .cbs.dtu.dk/services/TMHMM-2.0/), DAS (Cserzo et al. (1997) Pro t Eng. 10:673-676) (at http://www, followed by, .sbc.su.se/~miklos/DAS/), SOSUI (Hirokawa et al. (1998) Bioinformatics 14:378-379(at http://, followed by, sosui.proteome.bio.tuat.ac.jp/sosuiframe0E.html), Split (Juretic et al. (2002) J. Chem Inf Comp Sci: in press) (at http, followed by, ://pref.etfos.hr/split-4.0/); TMPRED (Hofmann and Stoffel (1993) Biol Chem Hoppe-Seyler 374:166) (at http://www, followed by, .ch.embnet.org/software/TMPRED_form.html) and TopPred2 (Claros and von Heijne (1994) Comput Appl Biosci 10:685-686) (at http://, followed by, bioweb.pasteur.fr/seqanal/interfaces/toppred.html). Identification of conserved domains was facilitated by searches in the ProDom Protein domain database (Corpet et al. (2000) Nucleic Acids Res. 28:267-9) (at http://, followed by, prodes.toulouse.inra.fr/prodom/doc/prodom.html) and through the Conserved Domain Database and Search Service, v1.54 at NCBI (at http :/www, followed by, .ncbi.nlm.nih.gov/Structure/cdd/cdd.shtml). The PredictProtein service (at http://www, followed by, .embl-heidelberg.de/predictprotein/predictprotein.html) was further used as interface to access multiple tools for the primary and secondary structure analysis.

The exon/intron prediction for the rice Ftn2 homologue from the genomic DNA sequence combined results from several algorithms: GeneScan (Burge and Karlin (1997) J Mol Biol. 215:403-10) (at http://, followed by, genes.mit.edu/GENSCAN.html), GrailEXP v3.3 (Xu and Uberbacher (1997) J Compt Biol. 4:325-38) (at http://, followed by, compbio.ornl.gov/grailexp/), FGENESH 1.1 (at http://, followed by, genomic.sanger.ac.uk/gf/gf.shtml) and Genie (Kulp et al. (1996) Proc Int Conf Intell Syst Mol Biol. 4:134-42) (at http://, followed by, www.fruitfly.org/seq_tools/genie.html). The exon/intron predictions were then compared to the available rice ESTs and to the homology regions with the *Arabidopsis* AtFtn2 identified in tblastn search. Sequence manipulation, multiple alignments and shading of aligned sequences were performed using BioEdit 5.09 (at http://, followed by, www.mbio.ncsu.edu/BioEdit/bioedit.html). DNA sequencing reads were processed using the Phred basecaller (Ewing et al. (1998) Genome Res. 8:175-185, assembled with Phrap assembler and contig assemblies then viewed with Consed (at http://, followed by, www.phrap.org/).

Example 2

Characterization of *Arabidopsis* Ftn2 Gene and Protein

This example describes the identification, isolation, and characterization of an Ftn2 gene from *Arabidopsis*.

Identification of *Arabidopsis* arc6 Mutation

Available mapping data for the arc6-1 mutant (Marrison et al. (1999) Plant J. 18:651-662; Rutherford (1996) In Dept of Biology, University of York, York 161-209) suggested that the mutation is located on chromosome 5, between the markers m247 and DFR, very close to the marker g4028. The tblastn search of *Arabidopsis* genome with the *Synechococcus* sp. WH8102 Ftn2 cell division gene (as described below, and in Koksharova and Wolk (2002) J Bacterial: in press) in preparation) (see Table 3 below) revealed a homologue on chromosome 5, At5g42480 (Accession number NM_123613) in close proximity to the genetic markers mentioned above. This gene was designated AtFtn2. The gene was sequenced from the wild-type and arc6-1 plants, where the sequence included the flanking regions of about 500 nt 5' and 200 nt 3'. Compared to the wild type AtFtn2 gene, arc6 showed two nucleotide differences. The first difference was found at position 1141: T in arc6, C in the WT-Ws, close to the end of exon 3, resulting in a premature stop codon (TGA) in arc6 and a truncated protein of 324 amino acids (FIGS. 1, 2). The second difference was found at position 1790: G in arc6, A in WT-Ws. This difference was attributed to slightly different genetic backgrounds of arc6-1 (Ws-2) and the WT used (Ws, unknown subtype), since the published sequence of WT-Columbia (NM_123613) was identical to that of arc6 in this area.

Sequencing of arc6-2 and arc6-3 revealed a mutation identical to that in arc6-1. To further confirm this result and to ascertain that the arc6-2 and arc6-3 were not accidentally mislabeled or confused with arc6-1, the region of interest was sequenced from additional arc6-2 and arc6-3 mutants obtained from the Nottingham *Arabidopsis* Stock Centre (seed stock number N286 and N287, respectively). These mutants, too, carried the same mutation as arc6-1.

The arc6 Mutation is Rescued by a Wild-Type Copy of AtFtn2

Genomic AtFtn2 DNA, containing about 0.5 kb 5' and 0.2 kb 3' region, was introduced into the arc6-1 and WT plants via *Agrobacterium*-mediated floral-dip transformation. T1 plants carrying the selection marker were assessed for leaf chloroplast size and numbers. Most T1 plants of the arc6-1 background showed less severe plastid phenotypes than the parent arc6-1 mutant. Plastids were more numerous and smaller, and approximately 80% of the T1 plants had WT-like phenotypes (Table 1). A majority of the plants with the WT background had normal (WT-like) phenotypes, even though some plants showed occasional clusters of cells with enlarged, irregularly shaped chloroplasts.

TABLE 1

Leaf mesophyll chloroplast phenotypes in T1 plants carrying AtFtn2 transgene.

| Genetic background | # plants total | WT-like phenotypes | Intermediate plastid size, number | Severe chloroplast phenotype |
|---|---|---|---|---|
| WT Ws | 205 | 191 | 0 | 14 |
| Arc6-1 | 120 | 97 | 18 | 5 |

Characterization of AtFtn2 Gene and Protein: a Plastid-Targeted Protein with an Unconventional DnaJ-Like Domain The AtFtn2 genomic sequence has 6 exons (FIG. 1). The presence of EST and full length cDNA in the sequence database (Table 3 below) indicates that the gene is expressed. Both the predicted and the experimentally determined full length cDNA coding sequences (Table 3 below) have 2406 nt encoding a protein of 801 aa, with putative N-terminal chloroplast targeting sequence of 67 aa predicted by TargetP. Chloroplast targeting was also predicted by Predotar (targeting scores 0.738 and 0.979 for TargetP and Predotar, respectively).

A search for protein motifs with InterProScan revealed a putative DnaJ domain (AtFtn2 residues 89-153), InterPro accession IPR001623, Pfam conserved domain pfam00226. However, ClustalW alignment of this domain with all predicted DnaJ domains from the Pfam database (277 sequences) revealed that the central Histidine-Proline-Aspartate (HPD) motif typical for DnaJ proteins is not present in AtFtn2 or in other plant and cyanobacterial Ftn2 homologues (FIG. 2). In addition to the DnaJ-like domain, the Pfam-HMM search identified a putative myb domain (residues 677-690, see FIG. 2) albeit with low expectation value (0.63). Sequence alignment with myb domains from the Prosite database indicated that only a second half of the putative myb domain is present in AtFtn2.

Annotation for AtFtn2 in the MIPS database (mips.gsf.de/cgi-bin/proj/thal/gv_report?mdh9+At5g42480) stated that AtFtn2 is a membrane protein Furthermore, preliminary results from the ongoing proteomics project at Michigan State University, which is directed at identifying components of the chloroplast envelope, indicated that AtFtn2 is present in the envelope membrane fraction from isolated *Arabidopsis* chloroplasts. Up to three putative transmembrane helices were predicted, using different software tools (Table 2).

TABLE 2

Putative transmembrane (TM) regions in AtFtn2

| Prediction program | TM region |
|---|---|
| HMMTOP | 297-314, 615-632 |
| DAS | 207-215, 354-356, 621-630 |
| TopPred 2 | 56-76, 295-315, 615-635 |
| Tmpred | 46-71, 297-313, 619-634 |
| SOSUI | 615-636 |
| Split | 615-634 |
| TMHMM | None |

Plastid-Dividing Cytoskeletal FtsZ Rings and Filaments are Severely Disrupted in arc6

Immunoblots showed that levels of the cytoskeletal, chloroplast-dividing proteins AtFtsZ1 and AtFtsZ2 were slightly lower in arc6-1 and arc6-2 mutants_compared to the WT. Immunofluorescence labeling of arc6 leaf chloroplasts was done with antibodies specific to AtFtsZ1 and AtFtsZ2. The mmunolabeling was highly specific for the target proteins, as indicated by the controls where the antibodies were omitted, as well as by previous results (Vitha et al. (2001) J Cell Biol. 153:111-119). These earlier results also demonstrated that AtFtsZ1 and AtFtsZ2 proteins are colocalized in FtsZ filaments and rings, in both the current set of WT and mutant plants (McAndrew et al. (2001) *Plant Physiol.* 127:1656-1666; (Vitha et al. (2001) J Cell Biol. 153:111-119).

In WT leaf chloroplasts, AtFtsZ1 and AtFtsZ2 are localized in rings at mid-plastids. In contrast, arc6 plastids show numerous short and disorganized AtFtsZ filaments. To investigate the possibility that the fragmentation and disruption of FtsZ rings and filaments is a consequence of the gross enlargement of the chloroplast rather than being directly related to the arc6 mutation, AtFtsZ localization patterns were analyzed in several mutant or transgenic plants with very large chloroplasts. Plants carrying antisense or overexpression constructs of AtFtsZ1-1, AtFtsZ2-1 or AtMinD, the chloroplast division-site determining factor (Colletti et al. (2000) Curr Biol. 10:507-516), as well as the arc3 mutant of *Arabidopsis* (Marrison et al. (1999) Plant J. 18:651-662) were used. The results indicate that intact FtsZ rings and/or long FtsZ1 and FtsZ2 filaments can assemble in large chloroplasts as well as in the WT. However, overexpression of AtMinD caused disruption and fragmentation of FtsZ rings and filaments, an effect somewhat similar to the FtsZ pattern in arc6. This is consistent with the suggested role of AtMinD in preventing FtsZ ring assembly at improper sites (Dinkins et al. (2001) Planta. 214:180-188; Kanamaru et al. (2000) Plant Cell Physiol. 41:1119-1128).

Example 3

Ftn2 Homologues in Other Plants and Cyanobacteria

This example describes the identification of other Ftn2 homologues in other plants and in cyanobacteria.

Tblastn search with AtFtn2 and *Synechococcus* sp. WH8102 Ftn2 proteins as a query revealed homologues in all publicly available fully sequenced cyanobacterial genomes and also in rice (*Oryza sativa*) non-annotated genomic DNA sequence (Table 3). Additionally, a number of ESTs representing ftn2 homologues from vascular plants, as well as a moss (*Physcomitrella patens*) and a fern (*Ceratopteris richardii*) homologue, were identified (Table 3). No ftn2 homologues were found in non-cyanobacterial prokaryotes.

TABLE 3

Homologues of Ftn2
Results of tblastn search with the *Arabidopsis* AtFtn2 protein sequence.
For ESTs, the reading frame and the area of match with AtFtn2 are indicated.

| Species | ORF/Gene name | Accession # (DNA) | Protein Accession # | Type[2] | Frame, tblastn match with *Arabidopsis* ARC6 |
|---|---|---|---|---|---|
| *Arabidopsis thaliana* | At5g42480[1] ARC6 | NM_123613 AB016888[13] | NP_199063 BAB10489 | Gen | |
| *Arabidopsis thaliana* | | AI998415 | | EST | −3; 642–801 |
| *Arabidopsis thaliana* | At5g42480 | AY091075 | AAM13895 | cDNA | Full length cDNA |
| *Medicago truncatula* | | AL382914 | | EST | +3; 623–717 |
| *Medicago truncatula* | | AL382915 | | EST | +3; 693–801 |
| *Medicago truncatula* | | BI268376 | | EST | +3; 33–239 |
| *Medicago truncatula* | | AW696905 | | EST | +2; 95–121<br>+3; 121–258<br>+1; 244–277 |
| *Gossypium arboreum* | | BQ410207 | | EST | −2; 679–798 |
| *Gossypium arboreum* | | BQ410206 | | EST | +2; 679–801 |
| *Glycine max* | | AW472683 | | EST | +2; 173–221 |
| *Solanum tuberosum* | | BE472035 | | EST | +3; 1–177 |
| *Beta vulgaris* | | BQ490457 | | EST | +3; 585–691 |
| *Populus balsamifera* | | BI120337 | | EST | +1; 316–409 |
| *Mesembryanthemum crystallinum* | | AI043508 | | EST | +1; 747–801 |
| *Oryza sativa* | | AU095068 | | EST | +3; 501–576 |
| *Oryza sativa* | | AU183658 | | EST | +3; 286–381 |
| *Oryza sativa* | | AU058418 | | EST | +3; 286–384 |
| *Oryza sativa*[7] | | BK000999 | | cDNA | |
| *Triticum aestivum* | | BQ238871 | | EST | +3; 710–801 |

TABLE 3-continued

Homologues of Ftn2
Results of tblastn search with the *Arabidopsis* AtFtn2 protein sequence.
For ESTs, the reading frame and the area of match with AtFtn2 are indicated.

| Species | ORF/Gene name | Accession # (DNA) | Protein Accession # | Type[2] | Frame, tblastn match with *Arabidopsis* ARC6 |
|---|---|---|---|---|---|
| *Triticum aestivum* | | BJ263824 | | EST | −3; 679–801 |
| *Triticum aestivum* | | BJ258222 | | EST | +1; 129–287 |
| *Triticum aestivum* | | BE490117 | | EST | +3; 186–362 |
| *Triticum monococcum* | | BQ169059 | | EST | −2; 708–801 |
| *Triticum monococcum* | | BG607272 | | EST | +1; 267–413 |
| *Hordeum vulgare* | | BJ482132 | | EST | +2; 165–294 |
| *Hordeum vulgare* | | AJ463103 | | EST | +2; 708–801 |
| *Hordeum vulgare* | | AJ485539 | | EST | +1; 666–784 |
| *Hordeum vulgare* | | BJ464825 | | EST | +2; 249–457 |
| *Hordeum vulgare* | | AJ485537 | | EST | +1; 666–801 |
| *Hordeum vulgare* | | BI949952 | | EST | +3; 666–801 |
| *Hordeum vulgare* | | AV833644 | | EST | +3; 290–472 |
| *Hordeum vulgare* | | AV921157 | | EST | −3; 683–801 |
| *Sorghum bicolor* | | BE917942 | | EST | +1; 671–801 |
| *Sorghum bicolor* | | BE918523 | | EST | +2; 613–752 |
| *Zea mays* | | BQ048486 | | EST | −1; 200–366 |
| *Zea mays* | | BM498278 | | EST | +3; 34–185 |
| *Zea mays* | | BM498757 | | EST | −3; 211–358 |
| *Zea mays* | | AW331058 | | EST | +2; 673–798 |
| *Ceratopteris richardii* | | BE641509 | | EST | +3; 305–488 |
| *Physcomitrella patens* | | BI437111 | | EST | +2; 669–799 |
| *Protochlorococcus marinus* MED4 | Contig1, Gene_533[5] | | | Gen | |
| *Protochlorococcus marinus* MT9313 | Contig1, gene2677[6] | | | Gen | |
| *Synechococcus* sp. PCC 7002 | Contig05130 2-306[3] | | | Gen | |
| *Synechococcus* sp. PCC 7942 | Ftn2 | AF421196 | AAL16071 | Gen | |
| *Anabena* PCC 7120 | all2707 | AP003590[8] NC_003272[9] | BAB74406 NP_486747 | Gen | |
| *Nostoc punctiforme* ATCC 29133 | Contig493 Gene 84[4] | | | Gen | |
| *Synechocystis* sp. PCC 6803 | sll0169 | NC_000911[10] D63999[11] | NP_441990 BAA10060 | Gen | |
| *Arabidopsis thaliana* | At3g19180 | AY074283 | AAL66980 | cDNA | Full length cDNA |
| *Arabidopsis thaliana* | At3g19180 | NC_003074[12] | NP_188549 | Gen | |
| *Synechococcus* sp. WH8102 | Gene 3082 | | | | |
| *Thermosynechococcus elongatus* BP-1 | tlr0758 | | | GEN | |
| *Trichodesmium erythraeum* IMS101 | Contig97 Gene 8639 | | | GEN | |
| *Chlamydomonas reinhardtii* | genie.294.6 (Scaffold294, nt 47288–51078) | | | GEN | |
| *Prunus persica* (peach) | | BU046755 | | EST | +1; 315–508 |
| *Helianthus annuus* | | BU035730 | | EST | +1; 627–801 |
| *Helianthus annuus* | | BQ977057 | | EST | +1; 664–801 |
| *Populus tremula* | | BU889000 | | EST | +1; 613–759 |

[1]Standard *Arabidopsis* ORF name (http://, followed by, arabidopsis.org/info/guidelines.html)
[2]Type of DNA sequence: EST (Expressed Sequence Tag), cDNA (full length cDNA), Gen (Genomic DNA)
[3]Unfinished fragment of the genome, Joint Genome Institute (JGI)
[4]Draft analysis; http://, followed by, genome.orn1.gov/microbial/npun/31may01/npun.html
[5]draft analysis http://, followed by, genome.orn1.gov/microbial/pmar_med/
[6]Draft analysis http://, followed by, genome.orn1.gov/microbial/pmar_mit/
[7]AAAA0100502 Predicted Gen sequence from shotgun sequencing data, see Methods; BK000999 cDNA sequence
[8]complement (211130 . . . 213526)
[9]complement (3300430 . . . 3302826)
[10]complement (2314780 . . . 2316924)
[11]complement (47521 . . . 49665)
[12]bases 6632806 . . . 6639031
[13]bases 64077 . . . 67114; gene id: MDH9.18

In order to obtain putative protein sequence of the rice Ftn2 from the genomic sequence, results from several gene prediction programs, EST database records and tblastn alignment with AtFtn2 (see Example 1) were combined. It is contemplated that the rice Ftn2 (OsFtn2) is encoded on the reverse strand of the contig (Accession AAAA01000502) and has 7 exons (8785-8486, 8104-7874, 7743-7546, 7380-7120, 7022-6158, 5923-5790, 5510-5217). The predicted protein has 760 amino acids.

TargetP analysis of the full length rice and partial potato Ftn2 sequences, for which the N-terminal portions were complete and included the initial M, identified putative chloroplast targeting signals of 40 and 76 aa, respectively, with prediction scores 0.961 and 0.583. Predotar predicted chloroplast targeting for the rice (score 0.928) but not potato Ftn2 (score 0.032).

Figure 1B:
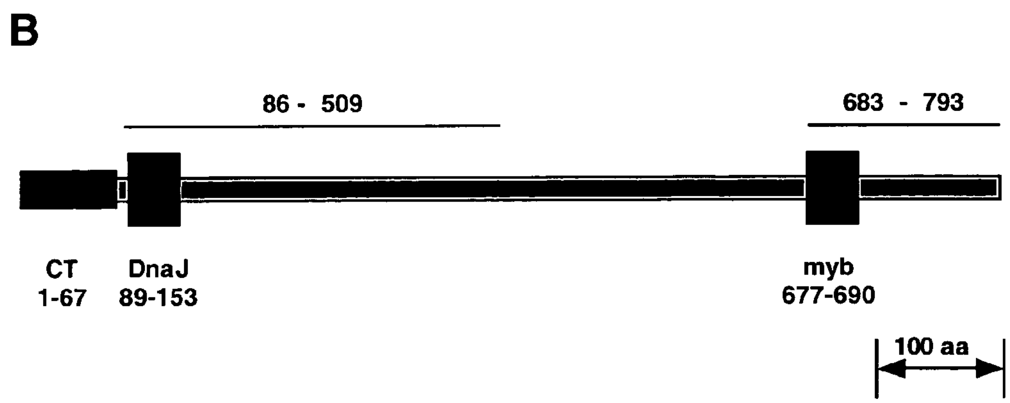

ClustalW alignment of full and partial Ftn2 protein sequences (FIG. 3) showed that the N-terminal, and to a lesser degree also the C-terminal, regions of these proteins are conserved and separated by a highly divergent central area (FIG. 1B). The cyanobacterial homologues shared approximately 20% identity and 40% similarity with AtFtn2, while scores for the rice homologue were 47% and 68%, respectively (Table 4).

TABLE 4

Similarity and identity scores of Ftn2 homologues compared *Arabidopsis* AtFtn2. Sequence alignment does not include the N-terminal portion with chloroplast targeting signals - the first 74 amino acids of AtFtn2 were removed

| Species | % Identities | % Similarities |
|---|---|---|
| *Anabena* PCC 7120 | 19 | 38 |
| *Nostoc punctiforme* ATCC 29133 | 19 | 39 |
| *Protochlorococcus marinus* MED4 | 15 | 38 |
| *Protochlorococcus marinus* MT9313 | 16 | 40 |
| *Synechocystis* sp. PCC 6803 | 19 | 40 |
| *Synechococcus* WH8102 | 17 | 38 |
| *Oryza sativa* | 47 | 68 |

Tblastn search with AtFtn2 also revealed an *Arabidopsis* membrane protein of unknown function, At3g19180 (Table 3), which showed a 21% and 44% identity and similarity, respectively, with AtFtn2. This protein is 970 aa long and contains an N-terminal targeting sequence. However, the targeting prediction is controversial: it is either a chloroplast (TargetP score 0.723) or a mitochondrial (Predotar score 0.846) target. A number of ESTs from maize, barley, sorghum, wheat and tomato were found in tblastn search using At3g19180 as a query.

Example 4

Materials and Methods Utilized to Identify and Characterize Cyanobacterial Ftn2 Genes This example describes the materials and methods used to identify and characterize cyanobacterial Ftn2 genes. The designation "Ftn2" refers to the mutant phenotype in which cell division is inhibited, resulting cells that are longer than wild-type cells, or filamentous in appearance. In classical studies of filamentous temperature-sensitive mutants of *E. coli* affected in cell division (Bramhill D (1997) Annu. Rev. Cell. Dev. Biol. 13:395-424), the corresponding genes were designated fts; therefore, by analogy, the cell division mutants isolated as described below were initially designated FTN-mutants (Filamentous, TransposoN-derived), and the corresponding genes, Ftn.

Bacterial Strains, Plasmids, and Culture Conditions

Wild type *Synechococcus* sp. strain PCC 7942 and its derivatives (Table 5) were grown in BG11 medium (Rippka R J, et al. (1979) J. Gen. Microbiol. 111:1-61). Wild type *Anabaena*sp. strain PCC 7120 and its derivatives were grown in media with or without nitrate supplementation as described by Hu et al. (Hu N T et al. (1982) Virology 114:236-246). Derivative strains were grown in the presence of appropriate antibiotics. Cyanobacterial cells were grown in 125-ml Erlenmeyer flasks at 30° C. in the light (about 3,500 ergs $cm^{-2} s^{-1}$) on a rotary shaker. Growth and plasmid transformation of *E. coli*, selection, and testing of transformants were performed as described (Sambrook J et al. (1989) Molecular Cloning, a laboratory manual, $2^{nd}$ ed., Cold Spring Harbor Laboratory Press, Cold Spring Harbor, N.Y.). Plasmids with or without transposon Tn5-692 were transferred to PCC 7942 and to *Anabaena*sp. strain PCC 7120 by conjugation with *E. coli* strain HB101 bearing pRL443, pRL528, and pRL692 (Cohen M F et al. (1998) Methods Enzymol 297:3-17). Plasmids pRL2462 and pRL2463 (see Table 5) were introduced into *Synechococcus* sp. strain PCC 7942 by transformation (Koksharova O et al. (1998) Plant Mol. Biol. 36:183-194).

TABLE 5

Cyanobacterial strains and plasmids used

| Strain or plasmid | Derivation and/or relevant characteristics | Source |
|---|---|---|
| *Synechococcus* sp. strain | | |
| PCC 7942 | Wild type | L. Sherman |
| FTN2 | $Sm^rSp^rEm^r$; Tn5-692 mutant | This study |
| FTN6 | $Sm^rSp^rEm^r$; Tn5-692 mutant | This study |
| *Anabaena* sp. strain | | |
| PCC 7120 | Wild type | R. Haselkorn |
| $FTN2_A$ | $Nm^r$; PCC 7120::pRL2471 | This study |
| $FTN6_A$ | $Nm^r$; PCC 7120::pRL2474 | This study |
| Plasmids | | |
| pRL443 | $Ap^rTc^r$; $Km^s$ derivative of RP4 | (19) |
| pRL498 | $Km^r$; positive selection cloning vector | (20) |
| pRL528 | $Cm^r$; bears avaIM and eco47IIM | (19) |
| pRL692 | $Em^rSm^rSp^r$, bears Tn5-692 | This study |
| pRL2462 | $Sm^rSp^r$; chromosomal DNA from FTN2 cut with SalI, religated, and transformed to *E. coli* | This study |

TABLE 5-continued

| Cyanobacterial strains and plasmids used | | |
|---|---|---|
| Strain or plasmid | Derivation and/or relevant characteristics | Source |
| pRL2463 | Sm$^r$Sp$^r$; chromosomal DNA from FTN6 cut with SalI, religated, and transformed to *E. coli* | This study |
| pRL2464 | Ap$^r$; pBluescript ® SK(+)(Stratagene) cut with XbaI and ligated to SpeI-SpeI fragment from pRL2463 | This study |
| pRL2465 | Ap$^r$; pBluescript ® SK(+) cut with XbaI and SalI, ligated to XbaI-SalI fragment from pRL2463 | This study |
| pRL2466 | Ap$^r$; pBluescript ® SK(+) cut with XbaI and SalI, ligated to XbaI-SalI fragment from pRL2462 | This study |
| pRL2468 | Ap$^r$; pBluescript ® SK(+) cut with SpeI and SalI, ligated to SpeI-SalI fragment from pRL2462 | This study |
| pRL2471 | Km$^r$; pRL498 with truncated PCR copy of Ftn$2_A$ | This study |
| pRL2474 | Km$^r$; pRL498 with truncated PCR copy of Ftn$6_A$ | This study |
| PRL2733 | Sm$^r$Sp$^r$; chromosomal DNA of FTN2 cut with BlnI, religated and transformed to *E. coli* | This study |

[a]Ap, ampicillin;
Em, erythtomycin;
Km, kanamycin;
[r]resistant;
[s]sensitive;
Sm, streptomycin;
Sp, spectinomycin;
Tc, tetracycline.

Transposon Mutagenesis of *Synechococcus* sp. Strain PCC 7942

Transposon Tn5-692 (in plasmid pRL692: GenBank accession no. AF424805) is a derivative of transposon Tn5 that confers resistance to erythromycin (Em), spectinomycin (Sp), and streptomycin (Sm); contains a pMB1 oriV; and bears mutations (Zhou M et al. (1998) J Mol. Biol. 276:913-925) that increase its rate of transposition ca. 100-fold relative to pRL1058 (Wolk C P et al. (2000) Heterocyst formation in *Anabaena*, pp. 83-104 In: Y. V. Brun and L. J. Shimkets (ed), Prokaryotic Development, American Society for Microbiology, Washington). Plates with filter-borne cells were incubated 48 h at 30° C. (light intensity, 1,500 ergs $cm^{-1}$ $s^{-1}$), and the filters then transferred onto solid BG11 medium containing 10 μg $ml^{-1}$, each, of erythromycin and spectinomycin. Antibiotic-resistant colonies appeared 10-15 days later.

Mutant Selection and Microscopy

Mutants exhibiting a filamentous phenotype spread extensively on solid medium. Mutant cells grown in liquid medium were examined by microscopy, and photographed at 400 and 800 times magnification with a Zeiss (Carl Zeiss, D-7082, Oberkochen, Germany) Axiophot microscope. Samples were prepared for electron microscopy and micrographed by S. Burns, MSU Center for Electron Optics.

Cloning and Sequencing of *Synechococcus* PCC 7942 Ftn Genes

Transposon Tn5-692 contains an oriV active in *E. coli*. Therefore, to clone PCC 7942 DNA contiguous with the transposon, DNA recovered from FTN2 was cut separately with SalI and BlnI, whose targets are absent from the transposon, circularized with T4 DNA ligase, and transformed to *E. coli* DH5α, yielding plasmids pRL2462 and pRL2733, respectively, and DNA recovered from FTN6 was cut with SalI, circularized, and transformed to DH5α, yielding pRL2463. Fragments contiguous with the transposon were subcloned to pBluescript SK(+) (Stratagene, La Jolla, Calif. 92037, USA) and sequenced. To compare sequences of Ftn2 and Ftn6 from the FTN mutants and from wild-type *Synechococcus* sp. strain PCC 7942, genomic DNA from wild-type PCC 7942 was isolated as described by Koksharova et al. (Koksharova O et al. Plant Mol. Biol. 36:183-194) and PCR amplifications and sequencing were performed with gene specific primers (Table 6). With the exception of the final 183 bp of Ftn2, which were sequenced only from pRL2733 as template, all portions of Ftn2 and Ftn6 were sequenced on both strands of DNA derived from a transposon recovery and on both strands of DNA PCR-amplified from wild type DNA; where there was any possible inconsistency, multiple independently PCR-amplified fragments of DNA were sequenced. The sequences of Ftn2 and Ftn6 have been submitted to GenBank under accession nos. AF21196 and AF21197, respectively.

TABLE 6

| DNA primers for PCR and sequencing of Ftn2 and Ftn6 of *Synechococcus* sp. PCC 7942 | | |
|---|---|---|
| Primers | Used for PCR | Used for sequencing |
| Ftn2-specific | | |
| Cpw267 5'-CCGAATTCTCTGTGTTGGCG-3' (D) (SEQ ID NO:31) | + | + |
| Cpw268 5'-AAGCTTCGTACAGACCCTGCTGAC-3' (R) (SEQ ID NO:32) | + | |

TABLE 6-continued

DNA primers for PCR and sequencing of Ftn2 and Ftn6 of *Synechococcus* sp. PCC 7942

| Primers | Used for PCR | Used for sequencing |
|---|---|---|
| Cpw338 5'-GGTAAGTTGACGGTCAAG-3' (D) (SEQ ID NO:33) | + | + |
| Cpw339 5'-CGATAGGGCCGTAGCTGTC-3' (R) (SEQ ID NO:34) | + | + |
| Cpw355 5'-GGTTAACTTGTGATCGAAC-3' (R) (SEQ ID NO:35) | + | + |
| Cpw376 5'-GCAGCCAGTCTGCCCTAG-3' (D) (SEQ ID NO:36) | | + |
| Cpw377 5'-GCGCAGTCCTTTCTTGAGG-3' (R) (SEQ ID NO:37) | | + |
| Cpw384 5'-CTGACCGGTGAGGTTCTGC-3' (D) (SEQ ID NO:38) | | + |
| Cpw386 5'-CCAGGAATCGCTGAACATTC-3'(R) (SEQ ID NO:39) | | + |
| Cpw387 5'-GCGATCGCGGTAGCTTTCGG-3' (R) (SEQ ID NO:40) | | + |
| Cpw400 5'-CTAGGCAGTGTACGTTC-3' (D) (SEQ ID NO:41) | | + |
| Ftn6-specific | | |
| Cpw269 5'-CCGAATTCGTGACCTCTACCCGTACTGC-3'(D) (SEQ ID NO:42) | + | + |
| Cpw270 5'-CCAAGCTTCGTTTTATAAAGGCGCTCAG-3'(R) (SEQ ID NO:43) | + | + |
| Cpw340 5'-CTGCTCGTGAGCAATTTGC-3' (D) (SEQ ID NO:44) | + | + |
| Cpw341 5'-CCGTTCTGAAAGGCTC-3' (R) (SEQ ID NO:45) | + | + |
| Cpw396 5'-CAGTGAATTGTAATAC-3' (D) (SEQ ID NO:46) | | + |
| Cpw398 5'-GAAATAGCCATCGCGAGC-3'(R) (SEQ ID NO:47) | | + |

Insertional Inactivation of Ftn2 and Ftn6 Orthologs in *Anabaena* sp. strain PCC 7120

Orthologs $Ftn2_A$ of Ftn2 and $Ftn6_A$ of Ftn6 were identified in the genome of *Anabaena* sp. strain PCC7120 by tblastn and blastn search against the complete Anabena genome database at the Kazusa DNA Research Institute (kazusa.or.jp/cyano/anabaena). Copies of (i) $Ftn2_A$ and (ii) $Ftn6_A$ truncated at both ends were prepared by PCR with isolated genomic DNA of PCC 7120 as template using:

(i) CPW263, 5'-CCGAATTCGTGGCAGTGGAAAATCGTGGG-3' (SEQ ID NO:48), as direct primer and CPW264, 5'-CCGAATTCCACTTGCACGATTGGGATC-3'(SEQ ID NO:49), as reverse primer and;

(ii) CPW265, 5'-CCGAATTCGCCCTACTCATTAACTATAG-3' (SEQ ID NO:50), as direct primer and CPW266, 5'-CCGAATTCCGGAGCGATCGCTTGTTTG-3' (SEQ ID NO:51), as reverse primer. The PCR-generated copies were cloned in the EcoRI site of pRL498 (16), and the clones transferred by conjugation to wild-type PCC 7120, with selection on AA+nitrate agar medium (Fink A (1999) Physiological Rev. 79:6025-6032) containing 25 μg neomycin $ml_{-1}$.

Southern Hybridization

Southern hybridization was performed as described by Sambrook et al. (45), with digoxigenin-dUTP-labelled probes (DIG DNA Labeling Kit, Roche Diagnostics Corp., Indianapolis, Ind.). Probes for Southern analysis were prepared by PCR with the following primers: Ftn2, CPW 267 and CPW 268; Ftn6, CPW 269 and CPW 270 (see Table 2); $Ftn2_A$, CPW263 and CPW264; and $Ftn6_A$, CPW265 and CPW266 (see above).

Example 5

Identification, Isolation, and Characterization of Cyanobacterial Ftn2 Gene and Protein This example describes the identification, isolation, and characterization of an Ftn2 gene from cyanobacteria.

Transposon Mutagenesis and Analysis of Ftn Genes of *Synechococcus* sp. Strain PCC 7942

When *Synechococcus* sp. strain PCC 7942 was mutagenized with transposon Tn5-692, about 3000 $Em^rSp^r$, dense, round mutant colonies with regular margins were accompanied by 39 spreading colonies with irregular borders that were comprised of very elongated cells. In classical studies of filamentous temperature-sensitive mutants of *E. coli* affected in cell division (6), the corresponding genes were designated fts. Therefore, by analogy, the transposon-derived cell division mutants were designated FTN-mutants (Filamentous, TransposoN-derived) and the corresponding genes, Ftn. Two such mutants whose irregular colonies are composed of cells that are longer than wild-type cells, designated FTN2 and FTN6, were further characterized. The cells of FTN2 are very long, up to 100-fold the length of wild-type cells, whereas the cells of FTN6 are only up to 20 times longer than those of the parental strain. Because the septation of these serpentine cells was not easily visualized by light microscopy, the cells were negatively stained with uranyl acetate, and examined by electron microscopy. The cells of both mutants usually divided asymmetrically. Plasmids pRL2462, pRL2463, and pRL2733 contain transposon DNA and contiguous PCC 7942 DNA. The first two were transformed to PCC 7942. All spectinomycin- and erythromycin-resistant transformants were filamentous, establishing that the mutations were closely linked to the transposon. Mutants FTN2 and FTN6 are completely segregated.

DNA contiguous with the transposon was subcloned from pRL2462 to pBluescript SK(+) as XbaI-SalI and SpeI-SalI fragments, producing plasmids pRL2466 and pRL2468, respectively, and from pRL2463 to pBluescript SK(+) as XbaI-SalI and SpeI-SpeI fragments, producing plasmids pRL2465 and pRL2464, respectively. Part of plasmid pRL2733 was sequenced with primers. The expected 9-bp duplication adjacent to the site of insertion of the transposon was found in the case of FTN6, but the same two transposon-proximal 9-bp sequences differed at one position (TGCAG-GCG[C/T]) as recovered from FTN2. To resolve this difference, and to determine whether the sequences determined with the transposon-mutated genes were identical to the wild-type sequences, both genes were amplified piecewise by PCR from wild-type PCC 7942 and the products of PCR were sequenced. Independent PCR amplifications confirmed that the sequence TGCAGGCGC is adjacent to the position of the transposon in Ftn2.

In FTN2 and FTN6, the transposon was inserted in single-copy open reading frames (ORFs) that were denoted Ftn2 and Ftn6. Ftn2 predicts a 631-amino acid protein (SEQ ID NO: 5) that shows greatest similarity to the predicted products of an ORF designated $Ftn2_A$ from *Anabaena* sp. strain PCC 7120 (bp 3302826-3300430 in the chromosome; BLAST score, 278; Expect=$3\times10^{-75}$; [1]), a *Nostoc punctiforme* ORF (BLAST score, 263; Expect=$1\times10^{-70}$), and presumptive gene sll0169 of *Synechocystis* sp. strain PCC 6803 (BLAST score, 218; Expect=$2\times10^{-55}$).

The InterProScan program (http://www, followed by, ebi. ac.uk/interpro/scan.html) shows the presence in Ftn2 of a DnaJ N-terminal domain (amino acid residues 6-70) and a single TPR repeat (amino acid residues 136-169. The Prosite-Protein against PROSITE program (http://ca.expasy.org/ tools/scnpsite.html/) shows the presence in Ftn2 of a leucine zipper pattern (amino acid residues 234-255; Table 7). Ftn2 and its cyanobacterial and plant orthologs show the presence of a DnaJ N-terminal domain, but are otherwise, as are Ftn6 and its orthogs, dissimilar from the products of known division-related genes (Bramhill D (1997) Annu. Rev. Cell. Dev. Biol. 13:395-424).

TABLE 7

Characteristics of Ftn2 and its homologs

| Protein and organism | Number of aa | MW (kDa) | pI | Domains or pattern |
|---|---|---|---|---|
| Ftn2 | | | | |
| *Synechococcus* sp. PCC 7942 | 648 | 72.4 | 5 | 1. DnaJ N-terminal domain (aa 6-70)<br>2. TPR repeat (aa 136-169)<br>3. Leucine zipper (aa 234-255) |
| $Ftn2_A$ | | | | |
| *Anabaena* sp. PCC 7120 Ftn2 ortholog | 798 | 90.1 | 6.3 | 1. DnaJ N-terminal domain (aa 16-80) |
| *Nostoc punctiforme* | 768 | 87.4 | 6.8 | 1. DnaJ N-terminal domain (aa 16-80)<br>2. ATP/GTP binding site motif A (P-loop) (aa 566-573) |
| S110169 | | | | |
| *Synechocystis* PCC 6803 AB016888 | 714 | 79.4 | 4.7 | 1. DnaJ N-terminal domain (aa 6-70) |
| *Arabidopsis thaliana* | 801 | 88.3 | 4.6 | 1. DnaJ domain profile (aa 89-153)<br>2. Myb DNA-binding domain (aa 677-690) |

aa = amino acid residues

The gene Ftn6 predicts a 152-amino acid protein that shows greatest similarity to an ORF from contig 630 of *N. punctiforme* (BLAST score, 80; E=$3\times10^{-16}$), an ORF from *Anabaena* sp. strain PCC 7120 denoted $Ftn6_A$ (bp 1903579-1902896 in the chromosome; BLAST score, 77.8; E=$10^{-15}$) and a predicted protein, Sll1939, from *Synechocystis* sp. strain PCC 6803 (BLAST score, 59; E=$1\times10^{-08}$).

Inactivation of the FtnA Genes of *Anabaena* sp. Strain PCC 7120

*Anabaena* sp. strain PCC 7120, a filamentous cyanobacterium, is capable of cellular differentiation ((Wolk C P et al. (2000) Heterocyst formation in *Anabaena*, pp. 83-104 In: Y. V. Brun and L. J. Shimkets (ed), Prokaryotic Development, American Society for Microbiology, Washington). Experiments to mutate the *Anabaena* sp. orthologs $Ftn2_A$ and $Ftn6_A$ were undertaken to observe whether the effects of inactivating these genes would be similar to those observed in *Synechococcus*, and whether there might be an effect on differentiation.

A truncated, PCR-generated copy of each gene was cloned in pRL498, producing plasmids pRL2471 and pRL2474, respectively. Cells of $Ftn2_A$ and $Ftn6_A$ *Anabaena* sp., i.e., of PCC 7120:pRL2471 and PCC 7120:pRL2474, grown in the presence of nitrate were often up to twice as long as cells of the wild-type strain. In medium free of combined nitrogen, both mutants formed very elongated vegetative cells (those of $Ftn2_A$ were up to 60-fold longer than those of the wild-type strain); heterocysts of nearly normal size (but also sometimes up to 4-fold larger, with an increase in both length and width); and also enlarged akinete-like cells. Because mutant $FTN2_A$ is not completely segregated, gene $Ftn2_A$ may be important for viability of *Anabaena*. Mutant $FTN6_A$ is completely segregated.

Example 6

Identification of ARC5

This Example describes the identification of the *Arabidopsis* ARC5 gene.

The arc5 mutation was induced by EMS mutation in *Arabidopsis* strain Landsberg erecta and identified as a chloroplast division mutant by microscopic screening (Robertson et al., (1996) Plant Physiol 112(1): 149-59. Phenotypes were analyzed as previously described (Osteryoung, K. W. et al. (1998) Plant Cell 10, 1991-2004), except that the images were recorded with a Coolpix 995 digital camera (Nikon Corporation, Tokyo, Japan). arc5 cells were found to have about 5 to 10 chloroplasts per cell. The chloroplasts are larger than in wild type. Constricted chloroplasts were frequently found. The proportion of constricted chloroplasts varied in different plants.

The arc5 mutation was previously mapped between markers nga 162 (20.6 cM) and AtD MC1 (32.6 cM) on chromosome 3 (Marrison et al., 1999 Plant J 18(6): 651-62). To fine-map the position of arc5, an $F_2$ population was generated from a cross between arc5 and Col-0 wild type. 1720 mutant plants out of 7000 $F_2$ plants were selected and their DNA was extracted for PCR marker-based mapping. Markers were generated using the primer sets shown in Table 8:

TABLE 8

Primer Sequences

| BAC Clone name | Primer sequences for PCR | Marker type |
|---|---|---|
| MDC8 | GATTAATGAGACTATATATGAGAG (SEQ ID NO:52) and ATCTGCATAACTTCAATTGAACTG (SEQ ID NO:53) | INDEL |
| MCB22 | GAACCCCCAGAATATCAACATC (SEQ ID NO:54) and GCTCTGATGGTGATTCTGGTAAC (SEQ ID NO:55) | INDEL |
| MVI11 | GTAGCATTCTTTAGAGATTGATCTAG (SEQ ID NO:56) and TATTCGAGTTTGAAATTATGATTTATGC (SEQ ID NO:57) | INDEL |
| MLD14 | GCTACAGTTCTCAACCGGTAAATC (SEQ ID NO:58) and CATAAGCTTTTATGCTCCAAAATAGTCTC (SEQ ID NO:59) | INDEL |
| T31J18 | CTTGATCTTGTGTTCTGACATCTC (SEQ ID NO:60) and CTAAACTATTCACAAATGCCATAGACG (SEQ ID NO:61) | CAPS, cut by DraI |
| MMB12 | AGCCGTCTTGTCCCATCATTAAAG (SEQ ID NO:62) and GCACAAACAAACAGGGTCAATAGTTA (SEQ ID NO:63) | CAPS marker, cut by EcoRV |
| F16J14 | TTAAAGTGAAGCTTAAGCAGAGG (SEQ ID NO:64) and CATTGTTAGAAAGTCAACACTTTG (SEQ ID NO:65) | INDEL |
| MSA6 | GCAAGACATAACCAATGAACAAG (SEQ ID NO:66) GACACGTATGCGTTTCTAAGAG (SEQ ID NO:67) | INDEL |
| MAL21 | CTCCAACTTCAAGCAAAACGGATG (SEQ ID NO:68) and CTCTGTTTTTTGGGCTAGTGATGG (SEQ ID NO:69) | INDEL |
| MPN9 | GCATACCCAATATCCTTTGTGC (SEQ ID NO:70) and GATAGTATAACCAGAGGTTGGAG (SEQ ID NO:71) | CAPS marker, cut by Tsp509I |

The results indicated that arc5 was located either on BAC clone MMB12 or MPN9, which overlap. The following three additional markers were generated, but no recombination between these and arc5 was observed.

TABLE 9

Primer Sequences

| BAC Clone name | Primer sequences for PCR | Marker type |
|---|---|---|
| MMB12 | GAATCTTCTCAAACTGAAATCCACC (SEQ ID NO:72) and TCGAAAGGAAGATCGGTGAACC (SEQ ID NO:73) | CAPS marker, cut by TaqI |
| MPN9 | GATTGTGCTATGGTTCAGGAGTTC (SEQ ID NO:74) and CATCAGCTATAACCTCCTCAGTG (SEQ ID NO:75) | CAPS marker, cut by AccI |
| MPN9 | ACTGACTATAAGGACCCCTCAAAC (SEQ ID NO:76) and GTTGACCATAATTCATCCACCACTATTA (SEQ ID NO:77) | INDEL but cut by HindIII |

The mapping studies narrowed down the interval of chromosome III containing arc5 to a 92-kb region comprising DNA spanning the overlap between MMB12 and MPN9.

To identify the DNA corresponding to arc5, BAC insert DNA from MMB12 and MPN9 was double-digested with HincII and HindIII. The digested fragments were inserted between 35S promoter and OCS terminator in the plant transformation vector pART27 (Gleave, 1992 Plant Molecular Biology 20: 1203-1207) to make a small transformable antisense/sense library. The library was transferred to *Agrobacterium tumefaciens* strain GV3101, and used to transform wild type *Arabidopsis* plants (Col-0) by floral dipping. 120 transformants were screened by microscopy for chloroplast division defects. Two plants were found to have only a few large chloroplasts per cell. The fragments between the 35S promoter and OCS terminator in the transgenes from these two plants were amplified by PCR and sequenced. One plant carried a transgene containing a fragment of the BAC backbone DNA, and another fragment from At3g19730 in the antisense orientation. The other plant also carried the same fragment from At3g19730 in the antisense orientation, as well as a second fragment from At3g19760. Based on these findings, it was predicted that the arc5 gene corresponded to At3g19730, which is predicted to be a dynamin-like protein. To confirm the plastid division phenotype in the transgenic plants was from this gene, an antisense transgene was constructed containing the fragment from At3g19730 carried by the two plants described above, and transformed into wild-type *Arabidopsis* (Col-0). 80 transformed plants were screened under the microscope. 20% of the transformants displayed fully expanded cells with fewer and larger chloroplasts than in wild type. These phenotypes resembled those in arc5. This further confirmed that At3g19730 functioned in chloroplast division and is ARC5.

In the NCBI database, At3g19720 and At3g19730 were annotated as a single gene, MMB12.21. Based on the alignment of MMB12.21 to the other dynamin-like proteins in *Arabidopsis*, it appeared that NCBI's annotation of this region was more accurate. Thus, they may be referred to as At3g19730/At3g19720; moreover, the annotated start codon for At3g19730 and stop codon for At3g19720 represent the true start and stop codons of this gene. The whole region of MMB12.21 in the arc5 mutant, and well as in wild-type Landsberg erecta, was sequenced. The data revealed a G-to-A mutation (C-to-T on the opposite strand) at nucleotide 60730 of MMB12. This mutation caused a change from the tryptophan codon "TGG" to the stop codon "TAG", in the $5^{th}$ exon of MMB 12.21. This mutation also created a new restriction enzyme cutting site—Xba I.

To determine whether the wild type ARC5 gene could complement the mutation, the predicted ARC5 gene (a transgene containing the predicted At3g19730/At3g19720 locus plus 1.9 kb and 1.1 kb of the 5' and 3' flanking DNA, respectively) was amplified from the DNA of BAC MMB12 by PCR using the primers 5'-GGAATTCCGAGTCGAGTTGCTTTGTTG-3' (SEQ ID NO:78) and 5'-CGTCTAGAGCTTACCTCAAAGGTACATGGA-3' (SEQ ID NO:79). The PCR product was digested with EcoRI and ligated into a derivative of the transformation vector pLH7000 (http://www.dainet.de/baz/jb2000/jb_2000direkt.htm) digested with EcoRI and SmaI. The construct was transferred to *A. tumefaciens* GV3101 and introduced into arc5 plants by floral dipping. The phenotypes of the $T_1$ plants were determined by microscopy. Microscopic analysis of $T_1$ transgenic plants indicated that the chloroplast division defect in the mutant was fully or partially rescued by the wild-type transgene.

Thus, from the results described above, which include the point mutation in At3g19730/At3g19720 in arc5, complementation of the mutant phenotype by the wild-type gene, and ability of a fragment from At3g19730/At3g19720 to confer an arc5-like phenotype in wild-type plants when expressed in the antisense orientation, indicate that the ARC5 locus and At3g19730/At3g19720 represent the same gene.

A cDNA for ARC5 was isolated using RT-PCR. Based on the sequencing data and ORF analysis, primers were chosen to amplify a region from 93 bp upstream of the predicted start codon to 152 bp downstream of the stop codon. After the cDNA fragments were cloned into Bluescript K S+vector, two distinct cDNAs encoding proteins with uninterrupted reading frames of 777 or 741 amino acids were found. These results indicate that the ARC5 transcript is alternatively spliced. The longer cDNA contained a sequence that was spliced out of the shorter cDNA as the $15^{th}$ intron; however, its presence in the longer cDNA did not interrupt the reading frame. Table 10 shows the SEQ ID NOs for ARC5 nucleic acids and proteins. The NCBI annotation is included in Table 10, as indicated.

The protein sequences were blasted against the NCBI protein database. The amino acid sequences of ARC5 were deduced from the cDNA sequence; the long form of the cDNA encodes a protein of 777 amino acids and 87.2 kDa, whereas the shorter form of the cDNA encodes a protein of 741 amino acids and 83.5 kDa. The sequence alignment was performed with the CLUSTALW multiple alignment program (Thompson, J. D. et al. (1994) *Nucleic Acids Res.* 22, 4673-4680) at the Biology Workbench 3.2 website (http://, followed by, biowb.sdsc.edu/). Protein sequences used for the phylogenetic analysis were aligned with Clustal X (Thompson, J. D. et al. (1997) *Nucleic Acids Res.* 25, 4876-4882) using default settings. Neighbor joining and maximum parsimony analyses were performed using PAUP version 4.0b10 (Swofford, D.L. (1998) PAUP*. *Phylogenetic Analysis Using Parsimony (*and Other Methods). Version*4.0b10 (Sinauer Associates, Sunderland, Mass.)) with default settings except for ties being randomly broken. Neighbor-joining and maximum parsimony analyses produced topologically identical trees. Bootstrap analyses were performed on the neighbor-joining and maximum parsimony trees with one thousand replications. GENBANK® accession numbers for proteins aligned with ARC5 (longer form, accession no. AY212885) are as follows: human Dynamin-1 (NP_004399), yeast Dnm1p (NP_013100), At1g53140 (NP_175722), rice dynamin like protein (BAB56031), ADL6 (AAF22291), At5g42080 (NP_568602), Glycine phragmoplastin (AAB05992), tobacco phragmoplastin (CAB56619), At2g44590 (NP_181987), human Dynamin II (NP_004936), ADL2a (NP_567931), ADL2b (NP_565362), rice ADL2-like protein (BAB86118), worm Drp-1(AAL56621) and human Dnm1p/Vps1p-like protein (JC5695).

The results, shown in FIG. 4, showed that the protein can be aligned over its entire length with numerous members of the dynamin family; most of the regions of the protein sequences can be aligned with the protein sequence of dynamin-I (GI# 4758182). Thus, the ARC5 protein contains three motifs found in other dynamin-like proteins: a conserved N-terminal GTPase domain, a pleckstrin homology (PH) domain shown in some proteins to mediate membrane association, and a C-terminal GTPase Effector Domain (GED) thought to interact directly with the GTPase domain and to mediate self-assembly (Danino, D. & Hinshaw, J. E. (2001) *Curr. Opin. Cell Biol.* 13, 454-460; and Hinshaw, J. E. (2000) *Annu. Rev. Cell Dev. Biol.* 16, 483-519). The shorter cDNA encoded a protein of 741 amino acids and 83.5 kDa identical to that of the larger gene product except for the absence of 36 amino acids encoded by the sequence of the $15^{th}$ intron. These results suggest that the ARC5 transcript is alternatively spliced. Alternative splicing of dynamin genes in several other organisms has also been documented (Hinshaw, J. E. (2000) *Annu. Rev. Cell Dev. Biol.* 16, 483-519).

Phylogenetic analysis was performed to investigate the relationship between ARC5 and other members of the dynamin family of proteins. Only full-length sequences were used, though EST data indicate that related proteins are present in many plants and in green algae. ARC5 clustered with a group of proteins found in plants, but was in a distinct clade from other dynamin-like proteins in *Arabidopsis* with functions in cell-plate formation and mitochondrial division (Gu, X. & Verma, D. P. (1996) *EMBO J* 15, 695-704; and Arimura, S.-i. & Tsutsumi, N. (2002) *Proc. Natl. Acad. Sci.* USA 99, 5727-5731). Surprisingly, the ARC5-like proteins clustered near ADL6, another *Arabidopsis* dynamin-like protein involved in vesicle trafficking from the trans-Golgi network to the vacuole in plants (37 Jin, J. B. et al. (2001) *Plant Cell* 13, 1511-1526).

Based on the similarity of ARC5 to dynamin and its relatives, ARC5 is contemplated to represent a new class of a dynamin-like proteins that functions specifically in chloroplast division.

The subcellular localization of ARC5 was investigated by expressing a GFP-ARC5 fusion protein in transgenic plants. The GFP sequence was amplified from plasmid smRS-GFP (Davis, S. J. & Vierstra, R. D. (1998) *Plant Mol. Biol.* 36, 521-528) with the primers 5'-CGGGATCCATGAGTAAAGGAGAAGAACT-3' (SEQ ID NO:80) and 5'-GCTCTAGATAGTTCATCCATGCCATGT-3' (SEQ ID NO:81). The PCR product was digested with BamHI and XbaI. The ARC5 coding region and 1.1 kb of the 3' flanking DNA were amplified from the MMB12 BAC clone with primers 5'-GGACTAGTACGATGGCGGAAGTATCAGC-3' (SEQ ID NO:82) and 5'-CGGGATCCGCACCGAAGGAGCCTTTAGATT-3' (SEQ ID NO:83). The PCR product was digested with SpeI and EcoRI. cDNA fragments encoding GFP and ARC5 were subcloned into Bluescript K S+(Stratagene) that had been digested with EcoRI and BamHI to create a GFP-ARC5 fusion construct. The ARC5 promoter was amplified from MMB12 with primers 5'-GACTAGTTGGCTCAACGCTTACCTCAA-3' (SEQ ID NO:84) and 5'-CGGGATCCGCCATCGTCTCTTACGA-3' (SEQ ID NO:85), and cloned into Bluescript KS +(Stratagene) between the SpeI and BamHI sites. The promoter fragment was then subcloned into the plasmid containing the GFP-ARC5 fusion construct at the 5' end of the fusion. The resulting plasmid was digested with SpeI and EcoRI, and the promoter-GFP-ARC5 cassette was subcloned into a derivative of the transformation vector pLH7000 (http://, followed by, www.dainet.de/baz/jb2000/jb_2000direkt.htm). The plasmid was transferred to *A. tumefaciens* GV3101 and used to transform wild-type *A. thaliana* plants (Col-0) as described above. The GFP-ARC5 localization pattern was visualized by fluorescence microscopy in $T_1$ plants. For in vivo detection of green fluorescent protein (GFP), fresh leaf tissue was mounted in water and viewed with an L5 filter set (excitation 455 nm to 495 nm, emission 512 to 575 nm) and a 100×oil immersion objective of a Leica DMR A2 microscope (Leica Microsystems, Wetzlar, Germany) equipped with epifluorescence illumination. Images were captured with a cooled CCD camera (Retiga 1350EX, Qimaging, Burnaby, British Columbia, Canada) and processed with Adobe Photoshop imaging software (Adobe Systems, San Jose, Calif.).

Because overexpression of chloroplast FtsZ proteins can result in a dominant-negative phenotype (Vitha, S. et al. (2001) *J. Cell Biol.* 153, 111-119), the native ARC5 promoter was used to create the GFP-ARC5 transgene for expression in wild-type plants (Col-0). Fluorescence microscopy showed that the fusion protein was localized in a ring-like pattern at the site of the chloroplast constriction. This ring could be faintly detected in unconstricted chloroplasts, suggesting that ARC5 may act at an earlier stage of division than previously hypothesized (Pyke, K. A. & Leech, R. M. (1994) Plant Physiol. 104, 201-207; and Robertson, E. J. et al. (1996) Plant Physiol. 112, 149-159). However, ARC5 is not required for FtsZ ring formation, the earliest known event in the assembly of the chloroplast division apparatus (Miyagishima, S. et al. (1999) Planta 207, 343-353; Miyagishima, S. et al. (2001) Plant Cell 13, 2257-2268; and 40 Bleazard, W. et al. (1999) Nature Cell Biol. 1, 298-304), since the FtsZ ring can be detected in the arc5 mutant. The GFP-ARC5 fusion protein was most obvious in visibly constricted chloroplasts, perhaps as a consequence of ring thickening during constriction. Similar localization patterns have been described for FtsZ1 and FtsZ2 (Vitha, S. et al. (2001) J. Cell Biol. 153, 111-119).

Even though ARC5 mediates chloroplast division, it is not predicted by subcellular targeting prediction programs to be imported to the chloroplast. To further define the topology of the ARC5-containing ring with respect to the chloroplast envelope membranes, in vitro chloroplast import and protease protection assays were employed. Transcription/translation reactions, chloroplast isolation, in vitro import reactions, proteolytic treatments, and post-import fractionation and analysis were performed as described (McAndrew, R. S. et al. (2001) Plant Physiol. 127, 1656-1666). The longer ARC5 cDNA, after subcloning into Bluescript KS+ as described above, was used for these experiments.

A radiolabeled translation product corresponding to the longer ARC5 cDNA was generated by coupled transcription/translation, then incubated with isolated pea chloroplasts. Subsequent fractionation of the chloroplasts indicated that the translation product was associated with the membrane fraction, but was not processed. The binding of the ARC5 translation product to isolated chloroplasts may be effected in part by the PH domain, which has been shown to mediate lipid binding of other dyanamin-like proteins (Hinshaw, J. E. (2000) Annu. Rev. Cell Dev. Biol. 16, 483-519; and 38 Lee, S. H. et al. (2002) *J. Biol. Chem.* 277, 31842-31849). In contrast, two chloroplast-targeted control proteins, one localized to the inner envelope and the other to the stroma, were processed upon import, consistent with the presence of N-terminal transit peptides, and associated with the membrane and soluble chloroplast fractions, respectively. In addition, the two control proteins were both protected from proteolysis by thermolysin, which does not penetrate the outer envelope (Cline, K. et al. (1984) Plant Physiol. 75, 675-678), whereas the ARC5 translation product was fully degraded by this protease. These data provide evidence that the ARC5-containing ring represented by the GFP-ARC5 fusion protein is situated on the cytosolic surface of the outer chloroplast envelope membrane. The position of ARC5 on the chloroplast surface is topologically equivalent to that of Dnm1p, a dynamin-like protein that mediates mitochondrial division in yeast (Bleazard, W. et al. (1999) Nature Cell Biol. 1, 298-304).

Blast searching indicates a second homologue of ARC5. It is predicted that this gene also functions in chloroplast division. This is based upon the observation of a slow but continued chloroplast division in arc5, which may be due to the presence of the second ARC5. homologue (At1g53140) in a duplicated region of the *Arabidopsis* genome (Pyke, K. A. & Leech, R. M. (1994) *Plant Physiol.* 104, 201-207), and whose function might overlap that of ARC5. Table 10 shows the coding and protein sequences for ARC5, as well as the NCBI and MIPS predicted protein sequence of the ARC5 homologue.

TABLE 10

| ARC5 | |
|---|---|
| Gene | SEQ ID NO |
| ARC5 Genomic (BAC MMB12(GB: AP000417)) | 11 |
| ARC5 cDNA | 12 |
| ARC5 Protein | 13 |
| NCBI ARC5 Genomic (BAC MMB12(GB: AP000417)) | 14 |
| NCBI ARC5 cDNA | 15 |
| NCBI ARC5 Protein | 16 |
| NCBI ARC5 Homologue (protein) | 17 |
| MIPS ARC5 Homologue (protein) | 18 |
| ARC5 Genomic[1] | 26; 27[2] |

Dynamin and its relatives are large GTPases that participate in a variety of organellar fission and fusion events in eukaryotes, including budding of endocytic and Golgi-derived vesicles, mitochondrial fission, mitochondrial fusion, and plant cell plate formation (reviewed in Danino, D. & Hinshaw, J. E. (2001) Curr. Opin. Cell Biol. 13, 454-460; and Hinshaw, J. E. (2000) Annu. Rev. Cell Dev. Biol. 16, 483-519). Dynamin has also been shown to regulate actin assembly and organization at membranes (Schafer, D. A. et al. (2002) Curr. Biol. 12, 1852-1857). ARC5 defines a new class of dynamin-like proteins that function specifically in plastid division, and its identification extends the range of cellular processes in which dynamin-like proteins participate.

Example 7

Identification of Fzo-Like Plastid Division Gene

This Example describes the identification of an Fzo-like gene of *Arabidopsis*. A blast search of the *Arabidopsis* database using as the query sequence the yeast protein Fzo1, which functions in the control of mitochondrial morphology in yeast (Hermann et al 1998 J. Cell. Biol. 143:359; Rapaport et al. 1998 J. Biol. Chem. 273:20150; Sesaki and Jensen 1999 J. Cell. Biol. 147:699; Fritz et al. 2001 J. Cell Biol 152:683), revealed a related gene, designated Fzo-like gene, on chromosome 1, At1g03160 on BAC clone F10O3.

A Blast search of the Salk T-DNA insertion database identified 8 lines of *Arabidopsis* with T-DNA insertions in this gene. The seeds for these lines were obtained and germinated, and the resulting plants examined by microscopy for chloroplast division defects in leaves. Two lines exhibited abnormalities in chloroplast size and number, suggesting that At1g03160 functions in chloroplast division.

The open reading frame is predicted to contain a chloroplast transit peptide, further suggesting a role for in chloroplast division. Thus, Fzo-like protein is contemplated to possess several domains: a chloroplast transit peptide, a GTPase domain and two predicted trans-membrane domains. In *Arabidopsis* Fzo-like polypeptide, the predicted chloroplast transit peptide is the first 54 amino acids, the GTPase domain is between amino acids 350-500, and the two predicted trans-membrane domains are close to each other in the region between amino acids 770-830. EST information indicates that the 3' end of this gene probably resides in the neighboring BAC F15K9.

Knock-out of AtFzo-like results in impaired chloroplast development and division, and affects the growth and development of plant. Zero to ten chloroplasts of differing sizes are observed per cell in knock-out plants. The dumbbell-shape chloroplasts with constriction in the middle are frequently observed. The mutant plants looks yellow, smaller than wild type plants and flower later.

Localization experiments of AtFzo-like protein in the cell were performed as described above for ARC6, where AtFzo-like was fused to GFP. The results that AtFzo-like-GFP is localized to the vesicle-like structures associated with (or near) the chloroplast. The level of AtFzo-like-GFP is positively correlated with the numbers of the vesicle-like structures.

Table 11 shows the SEQ ID NOs for the Fzo-like nucleic acid and protein sequences. Both the MIPS and the NCBI cDNA and translations are provided.

TABLE 11

| Fzo-Like Gene | |
|---|---|
| Gene | SEQ ID NO |
| MIPS Fzo Genomic | 19 |
| MIPS Fzo cDNA | 20 |
| MIPS Fzo Protein | 21 |
| NCBI Fzo Genomic | 22 |
| NCBI Fzo cDNA | 23 |
| NCBI Fzo Protein | 24 |
| 3' Fzo Genomic (BAC F15K9) | 25 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, and molecular biology or related fields are intended to be within the scope of the following claims.

We claim:

1. A vector comprising SEQ ID NO:3.

2. The vector of claim 1, wherein said vector further comprises a heterologous promoter.

3. A cell transformed with said vector of claim 1.

4. The cell of claim 3, wherein said cell is a plant cell or a microorganism cell.

5. A plant transformed with a heterologous gene comprising a nucleic acid sequence encoding SEQ ID NO: 2, wherein said gene encodes a product that functions in division of a photosynthetic prokaryote or a plastid.

6. A plant cell of said plant of claim 5.

7. A plant seed of said plant of claim 5, wherein said seed comprises said heterologous gene.

8. The plant of claim 5, wherein said nucleic acid is operably linked to a heterologous promoter.

9. A vector comprising a nucleic acid sequence encoding an amino acid sequence that comprises SEQ ID NO: 2.

10. The vector of claim 9, wherein said vector further comprises a heterologous promoter.

11. A cell transformed with said vector of claim 9.

12. The cell of claim 11, wherein said cell is a plant cell or a microorganism cell.

* * * * *

SEQUENCE LISTING

```
<160> NUMBER OF SEQ ID NOS: 208

<210> SEQ ID NO 1
<211> LENGTH: 2406
<212> TYPE: DNA
```

<213> ORGANISM: Arabidopsis thaliana

<400> SEQUENCE: 1

```
atggaagctc tgagtcacgt cggcattggt ctctccccat tccaattatg ccgattacca     60
ccggcgacga caaagctccg acgtagccac aacacctcta caactatctg ctccgccagc    120
aaatgggccg accgtcttct ctccgacttc aatttcacct ccgattcctc ctcctcctcc    180
ttcgccaccg ccaccaccac cgccactctc gtctctctgc caccatctat tgatcgtccc    240
gaacgccacg tccccatccc cattgatttc taccaggtat taggagctca aacacatttc    300
ttaaccgatg gaatcagaag agcattcgaa gctagggttt cgaaaccgcc gcaattcggt    360
ttcagcgacg acgctttaat cagccggaga cagattcttc aagctgcttg cgaaactctg    420
tctaatcctc ggtctagaag agagtacaat gaaggtcttc ttgatgatga agaagctaca    480
gtcatcactg atgttccttg ggataaggtt cctggggctc tctgtgtatt gcaagaaggt    540
ggtgagactg agatagttct tcgggttggt gaggctctgc ttaaggagag gttgcctaag    600
tcgtttaagc aagatgtggt tttagttatg gcgcttgcgt ttctcgatgt ctcgagggat    660
gctatggcat tggatccacc tgattttatt actggttatg agtttgttga ggaagctttg    720
aagcttttac aggaggaagg agcaagtagc cttgcaccgg atttacgtgc acaaattgat    780
gagactttgg aagagatcac tccgcgttat gtcttggagc tacttggctt accgcttggt    840
gatgattacg ctgcgaaaag actaaatggt ttaagcggtg tgcggaatat tttgtggtct    900
gttggaggag gtggagcatc agctcttgtt gggggtttga cccgtgagaa gtttatgaat    960
gaggcgtttt tacgaatgac agctgctgag caggttgatc tttttgtagc taccccaagc   1020
aatattccag cagagtcatt tgaagtttac gaagttgcac ttgctcttgt ggctcaagct   1080
tttattggta agaagccaca ccttttacag gatgctgata agcaattcca gcaacttcag   1140
caggctaagg taatggctat ggagattcct gcgatgttgt atgatacacg gaataattgg   1200
gagatagact tcggtctaga aaggggactc tgtgcactgc ttataggcaa agttgatgaa   1260
tgccgtatgt ggttgggctt agacagtgag gattcacaat ataggaatcc agctattgtg   1320
gagtttgttt tggagaattc aaatcgtgat gacaatgatg atctccctgg actatgcaaa   1380
ttgttggaaa cctggttggc aggggttgtc tttcctaggt tcagagacac caaagataaa   1440
aaatttaaac tcggggacta ctatgatgat cctatggttt tgagttactt ggaaagagtg   1500
gaggtagttc agggttctcc tttagctgct gctgcaacta tggcaaggat tggagccgag   1560
catgtgaaag ctagtgctat gcaggcactg cagaaagttt ttccttcccg ctatacagat   1620
agaaactcgg ctgaacccaa ggatgtgcaa gagacagtgt ttagtgtaga tcctgttggt   1680
aacaatgtag gccgtgatgg tgagcctggt gtctttattg cagaagctgt aagaccctct   1740
gaaaactttg aaactaatga ttatgcaatt cgagctgggg tctcagagag tagcgttgat   1800
gaaactactg ttgaaatgtc cgttgctgat atgttaaagg aggcaagtgt gaagatccta   1860
gctgctggtg tggcaattgg actgatttca ctgttcagcc agaagtattt tcttaaaagc   1920
agctcatctt ttcaacgcaa ggatatggtt tcttctatgg aatctgatgt cgctaccata   1980
gggtcagtca gagctgacga ttcagaagca cttcccagaa tggatgctag gactgcagag   2040
aatatagtat ccaagtggca gaagattaag tctctggctt ttgggcctga tcaccgcata   2100
gaaatgttac cagaggtttt ggatgggcga atgctgaaga tttggactga cagagcagct   2160
gaaactgcgc agcttgggtt ggtttatgat tatacactgt tgaaactatc tgttgacagt   2220
gtgacagtct cagcagatgg aacccgtgct ctggtggaag caactctgga ggagtctgct   2280
```

-continued

```
tgtctatctg atttggttca tccagaaaac aatgctactg atgtcagaac ctacacaaca   2340

agatacgaag ttttctggtc caagtcaggg tggaaaatca ctgaaggctc tgttcttgca   2400

tcataa                                                               2406
```

<210> SEQ ID NO 2
<211> LENGTH: 801
<212> TYPE: PRT
<213> ORGANISM: Arabidopsis thaliana

<400> SEQUENCE: 2

```
Met Glu Ala Leu Ser His Val Gly Ile Gly Leu Ser Pro Phe Gln Leu
1               5                   10                  15

Cys Arg Leu Pro Pro Ala Thr Thr Lys Leu Arg Arg Ser His Asn Thr
            20                  25                  30

Ser Thr Thr Ile Cys Ser Ala Ser Lys Trp Ala Asp Arg Leu Leu Ser
        35                  40                  45

Asp Phe Asn Phe Thr Ser Asp Ser Ser Ser Ser Ser Phe Ala Thr Ala
    50                  55                  60

Thr Thr Thr Ala Thr Leu Val Ser Leu Pro Pro Ser Ile Asp Arg Pro
65                  70                  75                  80

Glu Arg His Val Pro Ile Pro Ile Asp Phe Tyr Gln Val Leu Gly Ala
                85                  90                  95

Gln Thr His Phe Leu Thr Asp Gly Ile Arg Arg Ala Phe Glu Ala Arg
            100                 105                 110

Val Ser Lys Pro Pro Gln Phe Gly Phe Ser Asp Asp Ala Leu Ile Ser
        115                 120                 125

Arg Arg Gln Ile Leu Gln Ala Ala Cys Glu Thr Leu Ser Asn Pro Arg
    130                 135                 140

Ser Arg Arg Glu Tyr Asn Glu Gly Leu Leu Asp Asp Glu Glu Ala Thr
145                 150                 155                 160

Val Ile Thr Asp Val Pro Trp Asp Lys Val Pro Gly Ala Leu Cys Val
                165                 170                 175

Leu Gln Glu Gly Gly Glu Thr Glu Ile Val Leu Arg Val Gly Glu Ala
            180                 185                 190

Leu Leu Lys Glu Arg Leu Pro Lys Ser Phe Lys Gln Asp Val Val Leu
        195                 200                 205

Val Met Ala Leu Ala Phe Leu Asp Val Ser Arg Asp Ala Met Ala Leu
    210                 215                 220

Asp Pro Pro Asp Phe Ile Thr Gly Tyr Glu Phe Val Glu Glu Ala Leu
225                 230                 235                 240

Lys Leu Leu Gln Glu Glu Gly Ala Ser Ser Leu Ala Pro Asp Leu Arg
                245                 250                 255

Ala Gln Ile Asp Glu Thr Leu Glu Glu Ile Thr Pro Arg Tyr Val Leu
            260                 265                 270

Glu Leu Leu Gly Leu Pro Leu Gly Asp Asp Tyr Ala Ala Lys Arg Leu
        275                 280                 285

Asn Gly Leu Ser Gly Val Arg Asn Ile Leu Trp Ser Val Gly Gly Gly
    290                 295                 300

Gly Ala Ser Ala Leu Val Gly Gly Leu Thr Arg Glu Lys Phe Met Asn
305                 310                 315                 320

Glu Ala Phe Leu Arg Met Thr Ala Ala Glu Gln Val Asp Leu Phe Val
                325                 330                 335

Ala Thr Pro Ser Asn Ile Pro Ala Glu Ser Phe Glu Val Tyr Glu Val
```

```
            340                 345                 350

Ala Leu Ala Leu Val Ala Gln Ala Phe Ile Gly Lys Lys Pro His Leu
        355                 360                 365

Leu Gln Asp Ala Asp Lys Gln Phe Gln Gln Leu Gln Gln Ala Lys Val
    370                 375                 380

Met Ala Met Glu Ile Pro Ala Met Leu Tyr Asp Thr Arg Asn Asn Trp
385                 390                 395                 400

Glu Ile Asp Phe Gly Leu Glu Arg Gly Leu Cys Ala Leu Leu Ile Gly
                405                 410                 415

Lys Val Asp Glu Cys Arg Met Trp Leu Gly Leu Asp Ser Glu Asp Ser
            420                 425                 430

Gln Tyr Arg Asn Pro Ala Ile Val Glu Phe Val Leu Glu Asn Ser Asn
        435                 440                 445

Arg Asp Asp Asn Asp Asp Leu Pro Gly Leu Cys Lys Leu Leu Glu Thr
    450                 455                 460

Trp Leu Ala Gly Val Val Phe Pro Arg Phe Arg Asp Thr Lys Asp Lys
465                 470                 475                 480

Lys Phe Lys Leu Gly Asp Tyr Tyr Asp Asp Pro Met Val Leu Ser Tyr
                485                 490                 495

Leu Glu Arg Val Glu Val Val Gln Gly Ser Pro Leu Ala Ala Ala Ala
            500                 505                 510

Thr Met Ala Arg Ile Gly Ala Glu His Val Lys Ala Ser Ala Met Gln
        515                 520                 525

Ala Leu Gln Lys Val Phe Pro Ser Arg Tyr Thr Asp Arg Asn Ser Ala
    530                 535                 540

Glu Pro Lys Asp Val Gln Glu Thr Val Phe Ser Val Asp Pro Val Gly
545                 550                 555                 560

Asn Asn Val Gly Arg Asp Gly Glu Pro Gly Val Phe Ile Ala Glu Ala
                565                 570                 575

Val Arg Pro Ser Glu Asn Phe Glu Thr Asn Asp Tyr Ala Ile Arg Ala
            580                 585                 590

Gly Val Ser Glu Ser Ser Val Asp Glu Thr Thr Val Glu Met Ser Val
        595                 600                 605

Ala Asp Met Leu Lys Glu Ala Ser Val Lys Ile Leu Ala Ala Gly Val
    610                 615                 620

Ala Ile Gly Leu Ile Ser Leu Phe Ser Gln Lys Tyr Phe Leu Lys Ser
625                 630                 635                 640

Ser Ser Ser Phe Gln Arg Lys Asp Met Val Ser Ser Met Glu Ser Asp
                645                 650                 655

Val Ala Thr Ile Gly Ser Val Arg Ala Asp Asp Ser Glu Ala Leu Pro
            660                 665                 670

Arg Met Asp Ala Arg Thr Ala Glu Asn Ile Val Ser Lys Trp Gln Lys
        675                 680                 685

Ile Lys Ser Leu Ala Phe Gly Pro Asp His Arg Ile Glu Met Leu Pro
    690                 695                 700

Glu Val Leu Asp Gly Arg Met Leu Lys Ile Trp Thr Asp Arg Ala Ala
705                 710                 715                 720

Glu Thr Ala Gln Leu Gly Leu Val Tyr Asp Tyr Thr Leu Leu Lys Leu
                725                 730                 735

Ser Val Asp Ser Val Thr Val Ser Ala Asp Gly Thr Arg Ala Leu Val
            740                 745                 750

Glu Ala Thr Leu Glu Glu Ser Ala Cys Leu Ser Asp Leu Val His Pro
        755                 760                 765
```

Glu Asn Asn Ala Thr Asp Val Arg Thr Tyr Thr Thr Arg Tyr Glu Val
770 775 780

Phe Trp Ser Lys Ser Gly Trp Lys Ile Thr Glu Gly Ser Val Leu Ala
785 790 795 800

Ser

<210> SEQ ID NO 3
<211> LENGTH: 3667
<212> TYPE: DNA
<213> ORGANISM: Arabidopsis thaliana

<400> SEQUENCE: 3
tgttctgcat taaggagaat acaattataa gcaatttgtc ttgatttcaa caagattttg 60
cttggctata ggattcattg gctctgtttg cttttacatt tacatgtcat aatagtttcg 120
aattttacac atttcagttg gatgttaaga aaagagaggg aattgatggg gttttgtggg 180
tttaaacttt aaagtagtca agaattaagt cattggttta ctgttgctct atatgtgtaa 240
aatgaaggca actccaacgg ttcttaggtg gaatagatta tttagacgat ttaacatcat 300
aaagtccgtg gcgactgtaa catcatagat tgttttttat ttttttcagt agctggtgat 360 gtttttgat ttaacttata ctactcaaaa tcaaaattcc ataaacccta gacgaccaaa 420
cagtctcttc aatatgtaaa acagaacaaa gtttttgtag tagcctaaaa agacactccc 480
atggaagctc tgagtcacgt cggcattggt ctctccccat tccaattatg ccgattacca 540
ccggcgacga caaagctccg acgtagccac aacacctcta caactatctg ctccgccagc 600
aaatgggccg accgtcttct ctccgacttc aatttcacct ccgattcctc ctcctcctcc 660
ttcgccaccg ccaccaccac cgccactctc gtctctctgc caccatctat tgatcgtccc 720
gaacgccacg tccccatccc cattgatttc taccaggtat taggagctca aacacatttc 780
ttaaccgatg gaatcagaag agcattcgaa gctagggttt cgaaaccgcc gcaattcggt 840
ttcagcgacg acgctttaat cagccggaga cagattcttc aagctgcttg cgaaactctg 900
tctaatcctc ggtctagaag agagtacaat gaaggtcttc ttgatgatga agaagctaca 960
gtcatcactg atgttccttg ggataaggta atttcgattt cggaataata aagtttcttc 1020
gttttaattt catgaattgg ataaaggaag gaacttttat ctagtgaagg ttcctggggc 1080
tctctgtgta ttgcaagaag gtggtgagac tgagatagtt cttcgggttg gtgaggctct 1140
gcttaaggag aggttgccta agtcgtttaa gcaagatgtg gttttagtta tggcgcttgc 1200
gtttctcgat gtctcgaggg atgctatggc attggatcca cctgatttta ttactggtta 1260
tgagtttgtt gaggaagctt tgaagctttt acaggtagtt tgacttgctt tggtaatttg 1320
acgagcgttg gctttataag aactttcttg atttgatact ttgttattga gtcttgtgta 1380
ggaggaagga gcaagtagcc ttgcaccgga tttacgtgca caaattgatg agactttgga 1440
agagatcact ccgcgttatg tcttggagct acttggctta ccgcttggtg atgattacgc 1500
tgcgaaaaga ctaaatggtt taagcggtgt gcggaatatt ttgtggtctg ttggaggagg 1560
tggagcatca gctcttgttg gggggtttgac ccgtgagaag tttatgaatg aggcgttttt 1620
acgaatgaca gctgctgagc aggtatacag tttagatacc tttttttaat ttctttagca 1680
tgatataact ttaggtttct cattttaatg tatgttgtgt ggtaggttga tctttttgta 1740
gctaccccaa gcaatattcc agcagagtca tttgaagttt acgaagttgc acttgctctt 1800
gtggctcaag cttttattgg taagaagcca caccttttac aggatgctga taagcaattc 1860

-continued

```
cagcaacttc agcaggctaa ggtaatggct atggagattc ctgcgatgtt gtatgataca   1920

cggaataatt gggagataga cttcggtcta gaaaggggac tctgtgcact gcttataggc   1980

aaagttgatg aatgccgtat gtggttgggc ttagacagtg aggattcaca atataggaat   2040

ccagctattg tggagtttgt tttggagaat tcaaatcgtg atgacaatga tgatctccct   2100

ggactatgca aattgttgga aacctggttg gcaggggttg tctttcctag gttcagagac   2160

accaaagata aaaaatttaa actcggggac tactatgatg atcctatggt tttgagttac   2220

ttggaaagag tggaggtagt tcagggttct cctttagctg ctgctgcaac tatggcaagg   2280

attggagccg agcatgtgaa agctagtgct atgcaggcac tgcagaaagt tttccttcc    2340

cgctatacag atagaaactc ggctgaaccc aaggatgtgc aagagacagt gtttagtgta   2400

gatcctgttg gtaacaatgt aggccgtgat ggtgagcctg gtgtctttat tgcagaagct   2460

gtaagaccct ctgaaaactt tgaaactaat gattatgcaa ttcgagctgg ggtctcagag   2520

agtagcgttg atgaaactac tgttgaaatg tccgttgctg atatgttaaa ggaggcaagt   2580

gtgaagatcc tagctgctgg tgtggcaatt ggactgattt cactgttcag ccagaagtat   2640

tttcttaaaa gcagctcatc ttttcaacgc aaggatatgg tttcttctat ggaatctgat   2700

gtcgctacca taggtatgat taaatgatgc aattttcata tatctgcatt gctcaaaata   2760

tgcttgtttt gtgagctaag aacatagttc ccacttaata catgtcccaa aagttgtacc   2820

aagattaaca agttgctgag taaatttcac taattatgct gcttgaattt tttgatcaaa   2880

ctgtagacag aaatgtaaat ttcactctca acatttctgt ttagaataac gtaggattag   2940

agattgcctt agtgtggctt tgtccaactt ttctttcctt gatttttttc ttttcgattt   3000

agggtcagtc agagctgacg attcagaagc acttcccaga atggatgcta ggactgcaga   3060

gaatatagta tccaagtggc agaagattaa gtctctggct tttgggcctg atcaccgcat   3120

agaaatgtta ccagaggtga gggaataaat ctacaattca atcaattgtg tgaaaactgt   3180

tggacatgat tatagtctgg tgccttgttt gattctgtta tttataggtt ttggatgggc   3240

gaatgctgaa gatttggact gacagagcag ctgaaactgc gcagcttggg ttggtttatg   3300

attatacact gttgaaacta tctgttgaca gtgtgacagt ctcagcagat ggaacccgtg   3360

ctctggtgga agcaactctg gaggagtctg cttgtctatc tgatttggtt catccagaaa   3420

acaatgctac tgatgtcaga acctacacaa caagatacga agttttctgg tccaagtcag   3480

ggtggaaaat cactgaaggc tctgttcttg catcataata tactcatatg tagcatgtct   3540

gagcttgcga gattctcttt gttctgtaaa ttctctctct aagttagtgt ttataaatga   3600

acacaaaaaa attaacgttc ttggcacacc cttttccttg atctaaacta taacataagg   3660

gctacaa                                                             3667
```

<210> SEQ ID NO 4
<211> LENGTH: 2469
<212> TYPE: DNA
<213> ORGANISM: Synechococcus PCC7942

<400> SEQUENCE: 4

```
cttgccgact aaaggctaag catcgccatt ccttagatta aagcagtctg tcggcggcgc     60

tgtgccggtt aacaccagtc tgtcgctgac agcggtgcct ttctggggct tgcctgtggg    120

gcgagtaacc gatcgctggg ataagagttg gtgcttctgg ctctcaagaa tagggttttc    180

cgtcgcgtat tcccgatcac atccccctgt gtctgctacg gagataacgc cgatcactca    240

acagaattgg taagttgacg gtcaagttgg gatgatgaag tcggctcaag ctggcgatcc    300
```

-continued

```
ggatctggtg ggtgttctgt gcgtattcct ctcgattact accgaattct ctgtgttggc    360
gtgcaagcct cggcagacaa acttgccgaa agctaccgcg atcgcctcaa ccaatcgccc    420
tcccatgagt tttcagagct ggcattgcag gcgcggcggc aactcctcga agcagcgatt    480
gctgagctga gtgatcccga acagcgcgat cgctacgatc gccgcttttt tcagggcggt    540
ctggaagcga ttgaaccaag cctagaactc gaagactggc agcgaattgg agccctgctg    600
atcctgctgg aattggggga atacgatcgc gtttcgcaac tggctgagga actcctgcca    660
gactacgacg cgagcgcaga agtacgcgat cagttcgcgc ggggtgatat cgccttggcg    720
atcgcactat cccagcaatc cctcggtcga gaatgccgtc agcagggtct gtacgaacag    780
gccgcccagc actttggccg cagccagtct gccctagccg atcatcagcg ctttcctgaa    840
ctgagtcgaa ccctgcacca agaacaagga cagctacggc cctatcgcat tttggagcgg    900
ttggcccagc ccttgactgc cgatagcgat cgccagcagg gtttgctgtt gttgcaggcg    960
atgttggacg accggcaggg cattgaaggc cctggggatg atggctcggg gctgaccctt   1020
gataactttt tgatgtttct ccagcaaatt cgcggctatc tgaccctggc tgaacagcag   1080
ttgctgtttg aatcggaagc gcgtcggccc tcgccggctg cgagcttttt tgcctgctac   1140
accctgattg cgcggggctt ttgcgatcac caaccctcgt tgatccatcg cgccagcttg   1200
ctcttgcatg aactcaagag ccgcatggat gtgcacatcg aacaggcgat cgccagccta   1260
ttgctcggac agcccgaaga agctgaggcg ctactcgtcc agagccaaga tgaggaaacc   1320
ctcagccaaa tccgtgccct agcccaaggg gaagccctga tcgtcggttt gtgccgattc   1380
acggaaacct ggctagcgac caaggtattt ccggatttcc gcgacctcaa ggaaaggact   1440
gcgccgctgc agccctactt tgacgacccc gatgtccaga cctatctgga tgcgatcgtg   1500
gagttgccgt ccgatttgat gccaacgccg ctacccgttg agccgcttga ggtgcgatcg   1560
tcgttgctgg ccaaggaact gccgacccca gcaacgcctg gtgtagctcc accccctcgc   1620
cgccgtcgcc gcgatcgctc cgaacgtcct gctcgcacgg ccaaacgctt gcccttgccc   1680
tggattggtt tgggggttgt ggtggttctc ggcggtggaa caggggtttg ggcttggcga   1740
tcgcgttcca attccacccc gccgaccccg ccccccgtgg ttcaaacgct gcctgaggcg   1800
gtacctgccc cttcgcccgc gccagttacc gttgccctcg atcgggctca ggctgaaact   1860
gtgttgcaaa actggttggc cgctaaagct gcagccttgg ggcctcaata cgatcgcgat   1920
cgcttagcga cggtgctgac cggtgaggtt ctgcagactt ggcagggttt ttctagccag   1980
caggccaaca cccagctcac atcacagttc gatcacaagt taaccgtcga ctcagttcag   2040
ctcagtgacg gtgatcaacg agcagtagtc caagccaagg tcgatgaagt tgagcaggtc   2100
tatcgaggcg accagctgct cgaaacgcgc cgagatttgg gcttggtgat ccgctaccag   2160
ctcgtgcgcg agaacaacat ctggaaaatt gcttcgatta gtttggtgcg ctaggaattc   2220
gcaaggggtg aacccccctgc ggtcttttct gtagatcccc tagagcgatc gcagaatgtt   2280
cagcgattcc tggatgtgcg cttgggcatt caagagtgaa tcaaaaatgt ggcgcacctt   2340
gccctctttg tcgatcacat aagtgacgcg acccggaatc acaaacaggg ttttgggcac   2400
gccataggtt tgacggaggc gatcgcctgc atcgctcagc agttggaagg gcaagttgta   2460
tttctgggc                                                           2469
```

<210> SEQ ID NO 5
<211> LENGTH: 631
<212> TYPE: PRT

<213> ORGANISM: Synechococcus PCC7942

<400> SEQUENCE: 5

```
Met Arg Ile Pro Leu Asp Tyr Tyr Arg Ile Leu Cys Val Gly Val Gln
1               5                   10                  15

Ala Ser Ala Asp Lys Leu Ala Glu Ser Tyr Arg Asp Arg Leu Asn Gln
            20                  25                  30

Ser Pro Ser His Glu Phe Ser Glu Leu Ala Leu Gln Ala Arg Arg Gln
        35                  40                  45

Leu Leu Glu Ala Ala Ile Ala Glu Leu Ser Asp Pro Glu Gln Arg Asp
    50                  55                  60

Arg Tyr Asp Arg Arg Phe Phe Gln Gly Gly Leu Glu Ala Ile Glu Pro
65                  70                  75                  80

Ser Leu Glu Leu Glu Asp Trp Gln Arg Ile Gly Ala Leu Leu Ile Leu
                85                  90                  95

Leu Glu Leu Gly Glu Tyr Asp Arg Val Ser Gln Leu Ala Glu Glu Leu
            100                 105                 110

Leu Pro Asp Tyr Asp Ala Ser Ala Glu Val Arg Asp Gln Phe Ala Arg
        115                 120                 125

Gly Asp Ile Ala Leu Ala Ile Ala Leu Ser Gln Gln Ser Leu Gly Arg
    130                 135                 140

Glu Cys Arg Gln Gln Gly Leu Tyr Glu Gln Ala Ala Gln His Phe Gly
145                 150                 155                 160

Arg Ser Gln Ser Ala Leu Ala Asp His Gln Arg Phe Pro Glu Leu Ser
                165                 170                 175

Arg Thr Leu His Gln Glu Gln Gly Gln Leu Arg Pro Tyr Arg Ile Leu
            180                 185                 190

Glu Arg Leu Ala Gln Pro Leu Thr Ala Asp Ser Asp Arg Gln Gln Gly
        195                 200                 205

Leu Leu Leu Leu Gln Ala Met Leu Asp Asp Arg Gln Gly Ile Glu Gly
    210                 215                 220

Pro Gly Asp Asp Gly Ser Gly Leu Thr Leu Asp Asn Phe Leu Met Phe
225                 230                 235                 240

Leu Gln Gln Ile Arg Gly Tyr Leu Thr Leu Ala Glu Gln Gln Leu Leu
                245                 250                 255

Phe Glu Ser Glu Ala Arg Arg Pro Ser Pro Ala Ala Ser Phe Phe Ala
            260                 265                 270

Cys Tyr Thr Leu Ile Ala Arg Gly Phe Cys Asp His Gln Pro Ser Leu
        275                 280                 285

Ile His Arg Ala Ser Leu Leu Leu His Glu Leu Lys Ser Arg Met Asp
    290                 295                 300

Val His Ile Glu Gln Ala Ile Ala Ser Leu Leu Leu Gly Gln Pro Glu
305                 310                 315                 320

Glu Ala Glu Ala Leu Leu Val Gln Ser Gln Asp Glu Glu Thr Leu Ser
                325                 330                 335

Gln Ile Arg Ala Leu Ala Gln Gly Glu Ala Leu Ile Val Gly Leu Cys
            340                 345                 350

Arg Phe Thr Glu Thr Trp Leu Ala Thr Lys Val Phe Pro Asp Phe Arg
        355                 360                 365

Asp Leu Lys Glu Arg Thr Ala Pro Leu Gln Pro Tyr Phe Asp Asp Pro
    370                 375                 380

Asp Val Gln Thr Tyr Leu Asp Ala Ile Val Glu Leu Pro Ser Asp Leu
385                 390                 395                 400
```

-continued

```
Met Pro Thr Pro Leu Pro Val Glu Pro Leu Glu Val Arg Ser Ser Leu
                405                 410                 415

Leu Ala Lys Glu Leu Pro Thr Pro Ala Thr Pro Gly Val Ala Pro Pro
            420                 425                 430

Pro Arg Arg Arg Arg Arg Asp Arg Ser Glu Arg Pro Ala Arg Thr Ala
        435                 440                 445

Lys Arg Leu Pro Leu Pro Trp Ile Gly Leu Gly Val Val Val Val Leu
    450                 455                 460

Gly Gly Gly Thr Gly Val Trp Ala Trp Arg Ser Arg Ser Asn Ser Thr
465                 470                 475                 480

Pro Pro Thr Pro Pro Pro Val Val Gln Thr Leu Pro Glu Ala Val Pro
                485                 490                 495

Ala Pro Ser Pro Ala Pro Val Thr Val Ala Leu Asp Arg Ala Gln Ala
            500                 505                 510

Glu Thr Val Leu Gln Asn Trp Leu Ala Ala Lys Ala Ala Ala Leu Gly
        515                 520                 525

Pro Gln Tyr Asp Arg Asp Arg Leu Ala Thr Val Leu Thr Gly Glu Val
    530                 535                 540

Leu Gln Thr Trp Gln Gly Phe Ser Ser Gln Gln Ala Asn Thr Gln Leu
545                 550                 555                 560

Thr Ser Gln Phe Asp His Lys Leu Thr Val Asp Ser Val Gln Leu Ser
                565                 570                 575

Asp Gly Asp Gln Arg Ala Val Val Gln Ala Lys Val Asp Glu Val Glu
            580                 585                 590

Gln Val Tyr Arg Gly Asp Gln Leu Leu Glu Thr Arg Arg Asp Leu Gly
        595                 600                 605

Leu Val Ile Arg Tyr Gln Leu Val Arg Glu Asn Asn Ile Trp Lys Ile
    610                 615                 620

Ala Ser Ile Ser Leu Val Arg
625                 630
```

<210> SEQ ID NO 6
<211> LENGTH: 1390
<212> TYPE: DNA
<213> ORGANISM: Synechococcus PCC7942

<400> SEQUENCE: 6

```
ctcgatactt gggagttgaa cacagagtag tagtctaagt aacaactgct cgtgagcaat     60

ttgctacact ttttaccaaa ttttgagctc agttttcgcg aaaactggga tgttgagttg    120

aaccctcagc agcaaaattg taccgcctga gacttttacc gttttattcg gccatctggg    180

aacaatcgcc ctggagctta ttgtgacctc tacccgtact gccgttattg ccttgttaga    240

acgctatttc gagctgtcgg cagcgcgagc agcagaggtc ttgcagcaac tgcgatcgca    300

ccaccctgaa gcctggattt atcccgccac agtcgaggcg atttaccaag gccgttaccg    360

ctgggtgtcg atcgcacaaa tccttgctct gtggcagcgg cgcgggcaga tcaactgcca    420

cttcagtgca gactatgagc gcttgttgct cggtgaagtt ccagagcaac ccgatcgcat    480

caatgttgag acgcggctcc ctgcgatcgc catgaccttg ccttgggtgc cagaacagcc    540

tggagaagca ttcgtgccag cgcaagatca gtcgggttta actgagcgcc tttataaaac    600

gttggtcaaa gcgggcagcg attgcgctgg gtaggcttag aacagttgcc atccaaactt    660

gagagtgccc gttcggccag ccaagagaat tccaagagcc tttcagaacg gacaacaatt    720

ctgctctaca atcaagcccg agtgaagagg cggcgggcta ttggctgaat ggcaaaaaac    780
```

-continued

```
atcattcttt cagcaatcgt gggttatacc tacgacaaaa ttgacctatt cttaacttct     840

gcactccgta acacctcagc agatattctt ttaattgcat caagtccttc agcccaactc     900

cgtcatcagt tattgagttc acctcgggtc aaactcgttg atgtgaacct tcaaggtgaa     960

ccagctgaaa tggtatttcg ccgtttcttt attgccaagg agattttggc gagaatcgaa    1020

gcagatgaaa ttctcttgag cgatgctcgc gatgtctatt tccaatctga cccttttggt    1080

gtccaagggg ttttatttgc cgaggaacct cagctaatcg caaactgtaa agtcaatagc    1140

agctggataa aaaaatactt aggagaggat gagtttcaag ccatttctcc taatccaatt    1200

ctctgcgggg gcaaccatgt gctggatgcc accaaggcct ttagcctgac gttgaccaca    1260

ccagaagaaa ttgttgggct gcccgagagt ttgctggcct tggcggctca agctgctcaa    1320

gccgctggtg aaacagaggc aacacccgaa gccggccctt ggcgaatcac cctcgacttc    1380

ccaagctttg                                                           1390
```

<210> SEQ ID NO 7
<211> LENGTH: 152
<212> TYPE: PRT
<213> ORGANISM: Synechococcus PCC7942

<400> SEQUENCE: 7

```
Met Gly Thr Ile Ala Leu Glu Leu Ile Val Thr Ser Thr Arg Thr Ala
1               5                   10                  15

Val Ile Ala Leu Leu Glu Arg Tyr Phe Glu Leu Ser Ala Ala Arg Ala
            20                  25                  30

Ala Glu Val Leu Gln Gln Leu Arg Ser His His Pro Glu Ala Trp Ile
        35                  40                  45

Tyr Pro Ala Thr Val Glu Ala Ile Tyr Gln Gly Arg Tyr Arg Trp Val
    50                  55                  60

Ser Ile Ala Gln Ile Leu Ala Leu Trp Gln Arg Arg Gly Gln Ile Asn
65                  70                  75                  80

Cys His Phe Ser Ala Asp Tyr Glu Arg Leu Leu Leu Gly Glu Val Pro
                85                  90                  95

Glu Gln Pro Asp Arg Ile Asn Val Glu Thr Arg Leu Pro Ala Ile Ala
            100                 105                 110

Met Thr Leu Pro Trp Val Pro Glu Gln Pro Gly Glu Ala Phe Val Pro
        115                 120                 125

Ala Gln Asp Gln Ser Gly Leu Thr Glu Arg Leu Tyr Lys Thr Leu Val
    130                 135                 140

Lys Ala Gly Ser Asp Cys Ala Gly
145                 150
```

<210> SEQ ID NO 8

<400> SEQUENCE: 8

000

<210> SEQ ID NO 9
<211> LENGTH: 2406
<212> TYPE: DNA
<213> ORGANISM: Arabidopsis thaliana

<400> SEQUENCE: 9

```
atggaagctc tgagtcacgt cggcattggt ctctccccat tccaattatg ccgattacca      60

ccggcgacga caaagctccg acgtagccac aacacctcta caactatctg ctccgccagc     120
```

-continued

```
aaatgggccg accgtcttct ctccgacttc aatttcacct ccgattcctc ctcctcctcc    180

ttcgccaccg ccaccaccac cgccactctc gtctctctgc caccatctat tgatcgtccc    240

gaacgccacg tccccatccc cattgatttc taccaggtat taggagctca aacacatttc    300

ttaaccgatg gaatcagaag agcattcgaa gctagggttt cgaaaccgcc gcaattcggt    360

ttcagcgacg acgctttaat cagccggaga cagattcttc aagctgcttg cgaaactctg    420

tctaatcctc ggtctagaag agagtacaat gaaggtcttc ttgatgatga agaagctaca    480

gtcatcactg atgttccttg ggataaggtt cctggggctc tctgtgtatt gcaagaaggt    540

ggtgagactg agatagttct tcgggttggt gaggctctgc ttaaggagag gttgcctaag    600

tcgtttaagc aagatgtggt tttagttatg gcgcttgcgt ttctcgatgt ctcgagggat    660

gctatggcat tggatccacc tgattttatt actggttatg agtttgttga ggaagctttg    720

aagcttttac aggaggaagg agcaagtagc cttgcaccgg atttacgtgc acaaattgat    780

gagactttgg aagagatcac tccgcgttat gtcttggagc tacttggctt accgcttggt    840

gatgattacg ctgcgaaaag actaaatggt ttaagcggtg tgcggaatat tttgtggtct    900

gttggaggag gtggagcatc agctcttgtt gggggtttga cccgtgagaa gtttatgaat    960

gaggcgtttt tatgaatgac agctgctgag caggttgatc tttttgtagc taccccaagc   1020

aatattccag cagagtcatt tgaagtttac gaagttgcac ttgctcttgt ggctcaagct   1080

tttattggta agaagccaca ccttttacag gatgctgata agcaattcca gcaacttcag   1140

caggctaagg taatggctat ggagattcct gcgatgttgt atgatacacg gaataattgg   1200

gagatagact tcggtctaga aaggggactc tgtgcactgc ttataggcaa agttgatgaa   1260

tgccgtatgt ggttgggctt agacagtgag gattcacaat ataggaatcc agctattgtg   1320

gagtttgttt tggagaattc aaatcgtgat gacaatgatg atctccctgg actatgcaaa   1380

ttgttggaaa cctggttggc aggggttgtc tttcctaggt tcagagacac caaagataaa   1440

aaatttaaac tcggggacta ctatgatgat cctatggttt tgagttactt ggaaagagtg   1500

gaggtagttc agggttctcc tttagctgct gctgcagcta tggcaaggat tggagccgag   1560

catgtgaaag ctagtgctat gcaggcactg cagaaagttt ttccttcccg ctatacagat   1620

agaaactcgg ctgaacccaa ggatgtgcaa gagacagtgt ttagtgtaga tcctgttggt   1680

aacaatgtag gccgtgatgg tgagcctggt gtctttattg cagaagctgt aagaccctct   1740

gaaaactttg aaactaatga ttatgcaatt cgagctgggg tctcagagag tagcgttgat   1800

gaaactactg ttgaaatgtc cgttgctgat atgttaaagg aggcaagtgt gaagatccta   1860

gctgctggtg tggcaattgg actgatttca ctgttcagcc agaagtattt tcttaaaagc   1920

agctcatctt ttcaacgcaa ggatatggtt tcttctatgg aatctgatgt cgctaccata   1980

gggtcagtca gagctgacga ttcagaagca cttcccagaa tggatgctag gactgcagag   2040

aatatagtat ccaagtggca gaagattaag tctctggctt ttgggcctga tcaccgcata   2100

gaaatgttac cagaggtttt ggatgggcga atgctgaaga tttggactga cagagcagct   2160

gaaactgcgc agcttgggtt ggtttatgat tatacactgt tgaaactatc tgttgacagt   2220

gtgacagtct cagcagatgg aacccgtgct ctggtggaag caactctgga ggagtctgct   2280

tgtctatctg atttggttca tccagaaaac aatgctactg atgtcagaac ctacacaaca   2340

agatacgaag ttttctggtc caagtcaggg tggaaaatca ctgaaggctc tgttcttgca   2400

tcataa                                                              2406
```

-continued

<210> SEQ ID NO 10
<211> LENGTH: 3667
<212> TYPE: DNA
<213> ORGANISM: Arabidopsis thaliana

<400> SEQUENCE: 10

```
tgttctgcat taaggagaat acaattataa gcaatttgtc ttgatttcaa caagattttg     60
cttggctata ggattcattg gctctgtttg cttttacatt tacatgtcat aatagtttcg    120
aattttacac atttcagttg gatgttaaga aaagagaggg aattgatggg gttttgtggg    180
tttaaacttt aaagtagtca agaattaagt cattggttta ctgttgctct atatgtgtaa    240
aatgaaggca actccaacgg ttcttaggtg gaatagatta tttagacgat ttaacatcat    300
aaagtccgtg gcgactgtaa catcatagat tgttttttat ttttttcagt agctggtgat    360
gtttttgat ttaacttata ctactcaaaa tcaaaattcc ataaacccta gacgaccaaa    420
cagtctcttc aatatgtaaa acagaacaaa gtttttgtag tagcctaaaa agacactccc    480
atggaagctc tgagtcacgt cggcattggt ctctccccat tccaattatg ccgattacca    540
ccggcgacga caaagctccg acgtagccac aacacctcta caactatctg ctccgccagc    600
aaatgggccg accgtcttct ctccgacttc aatttcacct ccgattcctc ctcctcctcc    660
ttcgccaccg ccaccaccac cgccactctc gtctctctgc caccatctat tgatcgtccc    720
gaacgccacg tccccatccc cattgatttc taccaggtat taggagctca aacacatttc    780
ttaaccgatg gaatcagaag agcattcgaa gctagggttt cgaaaccgcc gcaattcggt    840
ttcagcgacg acgctttaat cagccggaga cagattcttc aagctgcttg cgaaactctg    900
tctaatcctc ggtctagaag agagtacaat gaaggtcttc ttgatgatga agaagctaca    960
gtcatcactg atgttccttg ggataaggta atttcgattt cggaataata aagtttcttc   1020
gttttaattt catgaattgg ataaaggaag gaacttttat ctagtgaagg ttcctggggc   1080
tctctgtgta ttgcaagaag gtggtgagac tgagatagtt cttcgggttg gtgaggctct   1140
gcttaaggag aggttgccta agtcgtttaa gcaagatgtg gttttagtta tggcgcttgc   1200
gtttctcgat gtctcgaggg atgctatggc attggatcca cctgatttta ttactggtta   1260
tgagtttgtt gaggaagctt tgaagctttt acaggtagtt tgacttgctt tggtaatttg   1320
acgagcgttg gctttataag aactttcttg atttgatact ttgttattga gtcttgtgta   1380
ggaggaagga gcaagtagcc ttgcaccgga tttacgtgca caaattgatg agactttgga   1440
agagatcact ccgcgttatg tcttggagct acttggctta ccgcttggtg atgattacgc   1500
tgcgaaaaga ctaaatggtt taagcggtgt gcggaatatt ttgtggtctg ttggaggagg   1560
tggagcatca gctcttgttg gggggtttgac ccgtgagaag tttatgaatg aggcgttttt   1620
atgaatgaca gctgctgagc aggtatacag tttagatacc tttttttaat ttctttagca   1680
tgatataact ttaggtttct cattttaatg tatgttgtgt ggtaggttga tctttttgta   1740
gctaccccaa gcaatattcc agcagagtca tttgaagttt acgaagttgc acttgctctt   1800
gtggctcaag cttttattgg taagaagcca cacctttttac aggatgctga taagcaattc   1860
cagcaacttc agcaggctaa ggtaatggct atggagattc ctgcgatgtt gtatgataca   1920
cggaataatt gggagataga cttcggtcta gaaaggggac tctgtgcact gcttataggc   1980
aaagttgatg aatgccgtat gtggttgggc ttagacagtg aggattcaca atataggaat   2040
ccagctattg tggagtttgt tttggagaat tcaaatcgtg atgacaatga tgatctccct   2100
ggactatgca aattgttgga aacctggttg gcaggggttg tctttcctag gttcagagac   2160
```

-continued

```
accaaagata aaaaatttaa actcggggac tactatgatg atcctatggt tttgagttac   2220

ttggaaagag tggaggtagt tcagggttct cctttagctg ctgctgcagc tatggcaagg   2280

attggagccg agcatgtgaa agctagtgct atgcaggcac tgcagaaagt tttccttcc   2340

cgctatacag atagaaactc ggctgaaccc aaggatgtgc aagagacagt gtttagtgta   2400

gatcctgttg gtaacaatgt aggccgtgat ggtgagcctg gtgtctttat tgcagaagct   2460

gtaagaccct ctgaaaactt tgaaactaat gattatgcaa ttcgagctgg ggtctcagag   2520

agtagcgttg atgaaactac tgttgaaatg tccgttgctg atatgttaaa ggaggcaagt   2580

gtgaagatcc tagctgctgg tgtggcaatt ggactgattt cactgttcag ccagaagtat   2640

tttcttaaaa gcagctcatc ttttcaacgc aaggatatgg tttcttctat ggaatctgat   2700

gtcgctacca taggtatgat taaatgatgc aattttcata tatctgcatt gctcaaaata   2760

tgcttgtttt gtgagctaag aacatagttc ccacttaata catgtcccaa aagttgtacc   2820

aagattaaca agttgctgag taaatttcac taattatgct gcttgaattt tttgatcaaa   2880

ctgtagacag aaatgtaaat ttcactctca acatttctgt ttagaataac gtaggattag   2940

agattgcctt agtgtggctt tgtccaactt ttctttcctt gatttttttc ttttcgattt   3000

agggtcagtc agagctgacg attcagaagc acttcccaga atggatgcta ggactgcaga   3060

gaatatagta tccaagtggc agaagattaa gtctctggct tttgggcctg atcaccgcat   3120

agaaatgtta ccagaggtga gggaataaat ctacaattca atcaattgtg tgaaaactgt   3180

tggacatgat tatagtctgg tgccttgttt gattctgtta tttataggtt ttggatgggc   3240

gaatgctgaa gatttggact gacagagcag ctgaaactgc gcagcttggg ttggtttatg   3300

attatacact gttgaaacta tctgttgaca gtgtgacagt ctcagcagat ggaacccgtg   3360

ctctggtgga agcaactctg gaggagtctg cttgtctatc tgatttggtt catccagaaa   3420

acaatgctac tgatgtcaga acctacacaa caagatacga agttttctgg tccaagtcag   3480

ggtggaaaat cactgaaggc tctgttcttg catcataata tactcatatg tagcatgtct   3540

gagcttgcga gattctcttt gttctgtaaa ttctctctct aagttagtgt ttataaatga   3600

acacaaaaaa attaacgttc ttggcacacc cttttccttg atctaaacta taacataagg   3660

gctacaa                                                             3667
```

<210> SEQ ID NO 11
<211> LENGTH: 7980
<212> TYPE: DNA
<213> ORGANISM: Arabidopsis thaliana

<400> SEQUENCE: 11

```
actgtaaatt ttgataaata aaaaaaaaca aaaaaaagat cgccaaatca tatttcatac     60

tatcagattt aaacaatata atttgttcga cgatacagaa atattttacc tcacaggaag    120

aggttgcgca gaaggagcca tggatgtgtt tgttcgagtc gagttgcttt gttgtaagta    180

ggtaattgca agaaacttga gttgtctata aagctttgga atacttctct ttatatatac    240

gtttacaaca attttttttt tttttttttt tctattttta caacaaattg tttttttatta    300

taataataaa cttaaacgaa aataaataat atctctttgt tctatttctt aaaaaagaaa    360

ttagcttgta gtacttcaac gtatcttaac tctttagtct ttagtaggta tatatcatct    420

atttatttat ttttattttt tttatattac gattatagtg tacgtacgta tttattaatc    480

aaaaataact tggtagaagt aaaaagaaaa tgattttttt tttactcagt gatcagtttt    540

acgtttattc aaaaataagt tgtagtttcc ttcttaatat tcaagttata tgactaaaaa    600
```

-continued

```
ttggtcggtt aatttactat taagattaat cggaaactct agttagatca cgagataatc    660

atcacgtgga gaaacatttg gttcttgtca cgtggagaaa acgttaagct tattttttac    720

ttctttatta tatttttgag gaaatggttg aaagaaagag agtgtttaaa atgtgaatgc    780

gctcgtagtt aggtggaggt taatgggtag gagggtaggt catatgtgta ttagtgatgg    840

ataaaaatta aaaacataaa aaaaacttca agctgtaaat aatctaataa aagaacatag    900

aaatataatc aaagaaccat ttaactaaat aaatactttc gattcaaata gcatatttct    960

aagttccaag aatagctatc ctctatccac atgttacatt tttttttct ttttcacatc   1020

catatagttt ttaaaataat tttctagatg gtatttttta ttcgacattt ttttttcctt   1080

ttagatttac tgattataat ttatttagaa ataaatgata cgactgtcgt ttctacaaaa   1140

ctgaaatttg caaacattgg accaaaaagc gaaaccttaa tcacttgaaa cgacaacgtt   1200

ctttagtatg tttttggaca tacaaagtac acataagatg ttccctcact cttcgattgt   1260

ttcttaacct aatataatta agcaatattg aacttgagtc actcaatgct gcaccgaagg   1320

agcctttaga ttttgagcaa attcatgaga gtttagcttc tcattcatca ctctgaattt   1380

ctcttttatc ctctttatct gtccaaaaca tgacacataa cataatgtta gttctcctgc   1440

atacttccaa tggcaaatag aaaaaagaga cattgatcat agaagtcagt ttggtttacc   1500

cttctgagct cgatctctgt gctccgtttc ttttgatcaa gtgattgccg gagattcgtg   1560

atgtcgaaga tactatcgag gtcgtcttca aatgcgtttt ccaactcttc ccggagaaga   1620

gcaggtaact tatcaacgat gggcattaga agaaaacagt tgaactgcag aacaaaagaa   1680

aacacagata caaacttttt aaaagaaaag tcattttaaa agcaagaaga atctgagtaa   1740

aaactgaagt aggagcaaac ctttaactca gcagaggcga gaaagtactc tcgtatgccc   1800

tggaatatct gttggaccaa tgcgtacaca attctctcag aggaaggagc aagcttgcgg   1860

ttccaaagtg tgctatctag aagatcagcc aaccgcattt ctgttgtctg aatactggaa   1920

cctgaatcga tgtttgaggc gagatggctt agctttacat ctgatcttga cttggtgtct   1980

gttgtgccac ctaatgcatc ttggggaaga ctaaatccta tggcattacc tgatgtcgta   2040

ttatgctctg ttccaccaaa tgagtccaag aattgacgta gaccagctcg gttctacata   2100

acattgagaa acgaaaacta ctcaatcaga aacggatact tgatggtatg tacacaactc   2160

aattggattg aaacagagct atagggctgt agcaatgacc ttgttgtgaa gagaccatgt   2220

aacatagcga gttgtacttg ctaaatcctc catacatctg caaacaatat aaaatccaaa   2280

gggtgatcaa tcactaaagc tcactagaac acaggtagga ggcaccgaca tggtaagaac   2340

aggaattgga aatagaatta cttgtcacga catgattttt ctgtggactc cacaaaactg   2400

ttgaatgctg aagcaacccg cttgagaaac acctcatgcc cacttaaata ttcaccttct   2460

ttctattcaa atttagaaca tacatcaaaa aatttgctgg aaagggatca tgagtatgat   2520

accgtcaaac caaagaaaac agtacctacc tgaagaagat atacagaaat tggaagcaat   2580

ctcttgagaa tgtgtagaag cctcgcccct aactatatca acgcaaaaca aacgaaaatg   2640

agaactggaa aaaactttct gtatggaaag agaaacatgt gaataacaaa atttcagatg   2700

aaagtattcc caaacatagt ttctgtaagc agaacatgtt tactcgataa ctcttatgca   2760

caaataagtt ccagcaaatc tcaaaactga atggtagtat gatttcaata tataacgtta   2820

tatttcattt tttttttac gtacagtaca ccttaactaa ttagtaaaat tgctttccat   2880

cctccacgaa agaaaaagaa aaaagtagct atatctatgt cacctgatga aggaaaggtt   2940
```

-continued

```
caaacgtctc acgagccttc gcaactgcta taacacaagc tgttctacaa cagcaaataa   3000

gagaaagaga ataagaggcc atagaaaaca tgacaaacgt tgcagctcag attagatact   3060

gaaaggggtc tgggatgcaa agacaataaa ttgagaagtg tgttgcatgt cagtcaatcc   3120

tatgatacct ggaatagttt gttccatcat gaatatcctc aactccacat gcatttacaa   3180

tttcctccct cgttattggg ggacatttga tagcaccaac tagaaaacga aactcagcca   3240

tggcacggtg atattgtgca cccccataga gacgcatccc tgcattctgt aaaatgaaag   3300

ataatctggt tatggtctct cataattctt gaaggtccaa cgaagtatct cttttatttg   3360

tttccaatac attattcttt ggcacatatg tttcatgcgg tcaaatttat cttccatcat   3420

attataatcc atgtacaaga acaagacaac tggatttgaa gaccatgccc agcttgctct   3480

ataaagtcca acaatattct gcttcaggga aagacttacc ggtattagct tatgtgaaaa   3540

ctggagacca tcagtaccaa caaatgctcc tccttgtgtc ctttcatctt gcagtgtctc   3600

acctgaaaaa caccatgaga aattattaac aatcaaagaa cccaacataa agagaatgct   3660

gttataaaat gtgcttctgc cagtaaccaa agtatcatga ccaatgattg attgattagc   3720

atacatcatt ccatgtgtaa tcatcgcagt ctggtgaccc agtcgaattg aacaatatgc   3780

atttaactaa actgattttg caaaagtcca atttaacaac acccagaaac aagaaaagtt   3840

tatgccaaag aagttgacta gcagagaaca gagcagtaac attaccaaat ttatctggag   3900

gggccacaac tgttcccttc aataacagcg ataactgatc aagaaaaata taaacaaaac   3960

aggtgagaaa acacagcact gatcaatact aacaaaggta cttcgtacgt caatcagaaa   4020

atatgacgca gcaattttaa agtcttaagg gcatccaaca caaaaagttt acagccattc   4080

tgaatttgta gcaagtccta gatatcattt actgtagcat aattttatat gtgtcagtaa   4140

tcaataaaca aatttgtttt tatgtgtcag tagttaataa accaaaaaaa aagagaagtt   4200

tacacaaatg aacttgttgt aattatacaa aaactattaa tccacgagtc caggcaaaaa   4260

tgaaaaggta tgggaaggtg taaatagaaa tctaaaaaaa cgaaatgctc tctacagtta   4320

ccttggttaa gaagagatca tggaaagtcc tgcctctctc tttgagtttt gcttcatcca   4380

aagagctgca ttgaaaggaa ttattcaacc tccaatgagt tatattttct ataaatcagt   4440

agctaacaat taaactgcct aaaatcaagt agacattttc agacaaaaca aattgcgacc   4500

taagttcctt gctcacggta tccagctttc tgactgtact gcggtactcc tttcctaaca   4560

gtggaatgat caatggaaca ctctctttgt acctggaaag agaagggcat caagactaca   4620

gcgaaaagta aactacaata gaaacagagg ctggaaaaat cagagttaaa acaacagtta   4680

taccttttcc agagtagttc ttccagaaac aacctcagtt tactgatgcc aatcctactc   4740

ttttcctgtt ttgtcagtaa acggcccaac ttcttctcta aagatgcaat gtcttccatt   4800

tctctaagtg acacagcctg taataaaaac cacacatagt ttagaaaaag acctgtttaa   4860

cttgtttaag gaatcagaca gcagagcaga gacctgtttg aactcgtcat tagacttata   4920

cactgaatcc tgtccatagc caactcttcc agaaggcaca gacgtgaaaa aaggagaatc   4980

gcccaataag gagctgtcaa gtgcgcttgc aggaggtgag agaaagactt ccacgtcaga   5040

tgaacatgag aattgaggga ttttagtgtc aagctttgta gaaacaacaa ttgtcctaga   5100

aagctcagga tcaacctaca tgaacgagaa acaaacttta acaaaaataa agacaaggtt   5160

agacgcaatg gagttacgtc aagcaacgta cttgcatcac tatccttcga gtggttgcaa   5220

tgctccagtc actgctatct tcgaggcata aaatgatgaa ctctttgtgt tgcatctttg   5280

ctcggactag agcttccaca gcccgtgctt gaacctaaga aaaagaacaa gtaacccact   5340
```

-continued

```
ctcaaataaa gcaaaaccaa aacatgaaat cagccacgga attggctgga agccataaga   5400
aaaaacaacc tgaagagctc ggtttttcag tcctggtgca ggagcaataa gtccaggtgt   5460
atcaatgatg gtaaggtttg gacaatactt atactggact ttcacaataa tctcctttgc   5520
agagaatggg ctacatggct cttgctccag cctcatgttc tcagcctcaa tatatgccta   5580
actccaaatc atataacaaa tttcgttaac atgagcattt cgcttctcta caataaacct   5640
aagtacttgt gtttctcaac attcgtcaaa atcttcccag aatttatacg cagaaacaag   5700
caattgaaga agcacaagta ataataataa caaaacacct gaatttgtga gagagatttg   5760
ggaagagaaa cggaaggatc atcatcagat ccgagatgac aaagcgggaa ttgacactga   5820
ggatcgtact tcatatggag agtaatcggc cgacgagtct tggttccgcc gccgacatgg   5880
ttaaattgaa accccataag agcttccaca agcgcacttt taccgtcggt ctgctgtccc   5940
accacaagaa ccgccggtgc ttcgaacggc gtctccaatt cctgcgccaa agcgtgtaac   6000
tcgttgtaag cttcgtaaag actccaccgc tcctcaatcg cagcgtcgtc ctcttccgcc   6060
atttcctcaa ccgtcaccga ttttgctgat acttccgcca tcgtctctta cgaaaatgag   6120
caagaggaag agtaagagta agagagtgtc tcttatttct tctactcttt agttttcgtc   6180
gccgttcctt tttccgccat ggaattagca gatacggcta atttcaattt ttgtcaaaag   6240
aaatattttt tgtgttttaa tctcacgcgc atccatggcg cgttgagtca acgttgtaat   6300
agttctccgc taaatttaaa taaaagagcg cgtaaggaga gagtttaagg attttttttt   6360
tttggtcggc aaatacaaag gatttgcttt gtcttgacca atagtatatg cagaaatatt   6420
atctcaaagg atttgtgata actatgtagt acagaattgt gattattgga tgagaaacca   6480
gaaatatttt gagcaaatga cgacttgtta atttactatt ttttcatttc ttaaaggtct   6540
ctcttgtgta actatgatta aaattgaaat agtgactttt attgttacga catggaacaa   6600
atcaacgagt tctattgtta aagagagaca ttgatgaatg taacaaaact gtggcttaga   6660
agccgaaagg agacttagtt cggtgtccctc cttcaccgta ttgctcgttc cattttctca   6720
attcgttcat tgtcgtcgcg tcgtatgcca ctgacggact tacctgcaaa ttacattaca   6780
atgacgcaat ttcgataatg caaacaccag gggaaaaaac atgaatagag atgatgatga   6840
tgttttttaa gagattgatc aataccttag ctttggattg aatgaagtcg tccaaactca   6900
gtggtcgtag atcaggggac gcatttgtta ccgagtcctg ataattcgac gtttcaaaag   6960
catggagtga gtacaaaaat tatttttcgt aacaacagaa atcaactgtg tgggtttatg   7020
catgtcctta ccttgttttc ttcttgtaac aattcttgaa caggtctgta tgcagctgct   7080
atgcatagat tctgcaatgt aagaaaaagaa aaggaatcag aactactgtg ttgaatcata   7140
ctcgaacttg taaatgaaac cccgaatgac caaaccttta gatcgcttcc tgaatatcct   7200
tcggtttcct ttgcaagttt atcaaactcg aaaccagttt caagattttc tggtgtcaga   7260
aatatcttca atatcttcaa ccggttttcc gcatctggta aatccacata tatcctataa   7320
acacaagcct caatacaatt atcgaaaaga tacaaatatt ccaaaggaga aattacttga   7380
aagcttaaat taccgtcttg gtagcctacg aatgacagcg tcatcaagat caaaaggtcg   7440
gttggtggca ccgagaatga gaatcctttg gctatctttt gatctgagtc catcccaagc   7500
tgccataaac tcatttctca ttcttcgtgt tgcctcgtgc tcaaaagcac caccacgagc   7560
acccaacaaa ctgtcaacct atacgacaac aaaataaatt acagttagtc cttgagtaac   7620
acattttacg catcacaaaa gtattcctca taaaaagcaa taaccgaaat tgaaaagtga   7680
```

-continued

```
tataaagcta aacaatttct cacctcatca acaaatataa tgacgggggc tagtttgctt   7740

gcaaaagaga acaaagcctt cgtgagcttc tctgcatctc caaaccactg tgccaaacaa   7800

tggacgaaat tgacttaaat cagaaccaat cagaggtaaa gttggaaaga gatttactct   7860

aagttacaat cggcattgac aataataagt cgatgaccgg ggtggaaaag tttttcttat   7920

gtcattagat attctcctta tttatatgaa gatgtttaca aagtggaata tcaacgtgac   7980
```

<210> SEQ ID NO 12
<211> LENGTH: 2678
<212> TYPE: DNA
<213> ORGANISM: Arabidopsis thaliana

<400> SEQUENCE: 12

```
gaaattagcc gtatctgcta attccatggc ggaaaaagga acggcgacga aaactaaaga     60

gtagaagaaa taagagacac tctcttactc ttactcttcc tcttgctcat tttcgtaaga    120

gacgatggcg gaagtatcag caaaatcggt gacggttgag gaaatggcgg aagaggacga    180

cgctgcgatt gaggagcggt ggagtcttta cgaagcttac aacgagttac acgctttggc    240

gcaggaattg gagacgccgt tcgaagcacc ggcggttctt gtggtgggac agcagaccga    300

cggtaaaagt gcgcttgtgg aagctcttat ggggtttcaa tttaaccatg tcggcggcgg    360

aaccaagact cgtcggccga ttactctcca tatgaagtac gatcctcagt gtcaattccc    420

gctttgtcat ctcggatctg atgatgatcc ttccgtttct cttcccaaat ctctctcaca    480

aattcacgca tatattgagg ctgagaacat gaggctggag caagagccat gtagcccatt    540

ctctgcaaag gagattattg tgaaagtcca gtataagtat tgtccaaacc ttaccatcat    600

tgatacacct ggacttattg ctcctgcacc aggactgaaa aaccgagctc ttcaggttca    660

agcacgggct gtggaagctc tagtccgagc aaagatgcaa cacaaagagt tcatcatttt    720

atgcctcgaa gatagcagtg actggagcat tgcaaccact cgaaggatag tgatgcaagt    780

tgatcctgag ctttctagga caattgttgt ttctacaaag cttgacacta aaatccctca    840

attctcatgt tcatctgacg tggaagtctt tctctcacct cctgcaagcg cacttgacag    900

ctccttattg ggcgattctc ctttttttcac gtctgtgcct tctggaagag ttggctatgg    960

acaggattca gtgtataagt ctaatgacga gttcaaacag gctgtgtcac ttagagaaat   1020

ggaagacatt gcatctttag agaagaagtt gggccgttta ctgacaaaac aggaaaagag   1080

taggattggc atcagtaaac tgaggttgtt tctggaagaa ctactctgga aaaggtacaa   1140

agagagtgtt ccattgatca ttccactgtt aggaaaggag taccgcagta cagtcagaaa   1200

gctggatacc gtgagcaagg aacttagctc tttggatgaa gcaaaactca aagagagagg   1260

caggactttc catgatctct tcttaaccaa gttatcgctg ttattgaagg gaacagttgt   1320

ggcccctcca gataaatttg gtgagacact gcaagatgaa aggacacaag gaggagcatt   1380

tgttggtact gatggtctcc agttttcaca taagctaata cagaatgcag ggatgcgtct   1440

ctatgggggt gcacaatatc accgtgccat ggctgagttt cgttttctag ttggtgctat   1500

caaatgtccc ccaataacga gggaggaaat tgtaaatgca tgtggagttg aggatattca   1560

tgatggaaca aactattcca gaacagcttg tgttatagca gttgcgaagg ctcgtgagac   1620

gtttgaacct ttccttcatc agttaggggc gaggcttcta cacattctca agagattgct   1680

tccaatttct gtatatcttc ttcagaaaga aggtgaatat ttaagtgggc atgaggtgtt   1740

tctcaagcgg gttgcttcag cattcaacag ttttgtggag tccacagaaa aatcatgtcg   1800

tgacaaatgt atggaggatt tagcaagtac aactcgctat gttacatggt ctcttcacaa   1860
```

```
caagaaccga gctggtctac gtcaattctt ggactcattt ggtggaacag agcataatac   1920

gacatcaggt aatgccatag gatttagtct tccccaagat gcattaggtg gcacaacaga   1980

caccaagtca agatcagatg taaagctaag ccatctcgcc tcaaacatcg attcaggttc   2040

cagtattcag acaacagaaa tgcggttggc tgatcttcta gatagcacac tttggaaccg   2100

caagcttgct ccttcctctg agagaattgt gtacgcattg gtccaacaga tattccaggg   2160

catacgagag tactttctcg cctctgctga gttaaagttc aactgttttc ttctaatgcc   2220

catcgttgat aagttacctg ctcttctccg ggaagagttg gaaaacgcat ttgaagacga   2280

cctcgatagt atcttcgaca tcacgaatct ccggcaatca cttgatcaaa agaaacggag   2340

cacagagatc gagctcagaa gggtaaagag gataaaagag aaattcagag tgatgaatga   2400

gaagctaaac tctcatgaat ttgctcaaaa tctaaaggct ccttcggtgc agcattgagt   2460

gactcaagtt caatattgct taattatatt aggttaagaa acaatcgaag agtgagggaa   2520

catcttatgt gtactttgta tgtccaaaaa catactaaag aacgttgtcg tttcaagtga   2580

ttaaggtttc gctttttggt ccaatgtttg caaatttcag ttttgtagaa acgacagtcg   2640

tatcatttat ttctaaataa attataatca gtaaatct                           2678


<210> SEQ ID NO 13
<211> LENGTH: 777
<212> TYPE: PRT
<213> ORGANISM: Arabidopsis thaliana

<400> SEQUENCE: 13

Met Ala Glu Val Ser Ala Lys Ser Val Thr Val Glu Glu Met Ala Glu
1               5                   10                  15

Glu Asp Asp Ala Ala Ile Glu Glu Arg Trp Ser Leu Tyr Glu Ala Tyr
            20                  25                  30

Asn Glu Leu His Ala Leu Ala Gln Glu Leu Glu Thr Pro Phe Glu Ala
        35                  40                  45

Pro Ala Val Leu Val Val Gly Gln Gln Thr Asp Gly Lys Ser Ala Leu
    50                  55                  60

Val Glu Ala Leu Met Gly Phe Gln Phe Asn His Val Gly Gly Gly Thr
65                  70                  75                  80

Lys Thr Arg Arg Pro Ile Thr Leu His Met Lys Tyr Asp Pro Gln Cys
                85                  90                  95

Gln Phe Pro Leu Cys His Leu Gly Ser Asp Asp Asp Pro Ser Val Ser
            100                 105                 110

Leu Pro Lys Ser Leu Ser Gln Ile His Ala Tyr Ile Glu Ala Glu Asn
        115                 120                 125

Met Arg Leu Glu Gln Glu Pro Cys Ser Pro Phe Ser Ala Lys Glu Ile
    130                 135                 140

Ile Val Lys Val Gln Tyr Lys Tyr Cys Pro Asn Leu Thr Ile Ile Asp
145                 150                 155                 160

Thr Pro Gly Leu Ile Ala Pro Ala Pro Gly Leu Lys Asn Arg Ala Leu
                165                 170                 175

Gln Val Gln Ala Arg Ala Val Glu Ala Leu Val Arg Ala Lys Met Gln
            180                 185                 190

His Lys Glu Phe Ile Ile Leu Cys Leu Glu Asp Ser Ser Asp Trp Ser
        195                 200                 205

Ile Ala Thr Thr Arg Arg Ile Val Met Gln Val Asp Pro Glu Leu Ser
    210                 215                 220
```

-continued

```
Arg Thr Ile Val Val Ser Thr Lys Leu Asp Thr Lys Ile Pro Gln Phe
225                 230                 235                 240

Ser Cys Ser Ser Asp Val Glu Val Phe Leu Ser Pro Pro Ala Ser Ala
                245                 250                 255

Leu Asp Ser Ser Leu Leu Gly Asp Ser Pro Phe Phe Thr Ser Val Pro
            260                 265                 270

Ser Gly Arg Val Gly Tyr Gly Gln Asp Ser Val Tyr Lys Ser Asn Asp
        275                 280                 285

Glu Phe Lys Gln Ala Val Ser Leu Arg Glu Met Glu Asp Ile Ala Ser
    290                 295                 300

Leu Glu Lys Lys Leu Gly Arg Leu Leu Thr Lys Gln Glu Lys Ser Arg
305                 310                 315                 320

Ile Gly Ile Ser Lys Leu Arg Leu Phe Leu Glu Glu Leu Leu Trp Lys
                325                 330                 335

Arg Tyr Lys Glu Ser Val Pro Leu Ile Ile Pro Leu Leu Gly Lys Glu
            340                 345                 350

Tyr Arg Ser Thr Val Arg Lys Leu Asp Thr Val Ser Lys Glu Leu Ser
        355                 360                 365

Ser Leu Asp Glu Ala Lys Leu Lys Glu Arg Gly Arg Thr Phe His Asp
    370                 375                 380

Leu Phe Leu Thr Lys Leu Ser Leu Leu Leu Lys Gly Thr Val Val Ala
385                 390                 395                 400

Pro Pro Asp Lys Phe Gly Glu Thr Leu Gln Asp Glu Arg Thr Gln Gly
                405                 410                 415

Gly Ala Phe Val Gly Thr Asp Gly Leu Gln Phe Ser His Lys Leu Ile
            420                 425                 430

Gln Asn Ala Gly Met Arg Leu Tyr Gly Gly Ala Gln Tyr His Arg Ala
        435                 440                 445

Met Ala Glu Phe Arg Phe Leu Val Gly Ala Ile Lys Cys Pro Pro Ile
    450                 455                 460

Thr Arg Glu Glu Ile Val Asn Ala Cys Gly Val Glu Asp Ile His Asp
465                 470                 475                 480

Gly Thr Asn Tyr Ser Arg Thr Ala Cys Val Ile Ala Val Ala Lys Ala
                485                 490                 495

Arg Glu Thr Phe Glu Pro Phe Leu His Gln Leu Gly Ala Arg Leu Leu
            500                 505                 510

His Ile Leu Lys Arg Leu Leu Pro Ile Ser Val Tyr Leu Leu Gln Lys
        515                 520                 525

Glu Gly Glu Tyr Leu Ser Gly His Glu Val Phe Leu Lys Arg Val Ala
    530                 535                 540

Ser Ala Phe Asn Ser Phe Val Glu Ser Thr Glu Lys Ser Cys Arg Asp
545                 550                 555                 560

Lys Cys Met Glu Asp Leu Ala Ser Thr Thr Arg Tyr Val Thr Trp Ser
                565                 570                 575

Leu His Asn Lys Asn Arg Ala Gly Leu Arg Gln Phe Leu Asp Ser Phe
            580                 585                 590

Gly Gly Thr Glu His Asn Thr Thr Ser Gly Asn Ala Ile Gly Phe Ser
        595                 600                 605

Leu Pro Gln Asp Ala Leu Gly Gly Thr Thr Asp Thr Lys Ser Arg Ser
    610                 615                 620

Asp Val Lys Leu Ser His Leu Ala Ser Asn Ile Asp Ser Gly Ser Ser
625                 630                 635                 640

Ile Gln Thr Thr Glu Met Arg Leu Ala Asp Leu Leu Asp Ser Thr Leu
```

-continued

```
                645                 650                 655

Trp Asn Arg Lys Leu Ala Pro Ser Ser Glu Arg Ile Val Tyr Ala Leu
            660                 665                 670

Val Gln Gln Ile Phe Gln Gly Ile Arg Glu Tyr Phe Leu Ala Ser Ala
        675                 680                 685

Glu Leu Lys Phe Asn Cys Phe Leu Leu Met Pro Ile Val Asp Lys Leu
    690                 695                 700

Pro Ala Leu Leu Arg Glu Glu Leu Glu Asn Ala Phe Glu Asp Asp Leu
705                 710                 715                 720

Asp Ser Ile Phe Asp Ile Thr Asn Leu Arg Gln Ser Leu Asp Gln Lys
                725                 730                 735

Lys Arg Ser Thr Glu Ile Glu Leu Arg Arg Val Lys Arg Ile Lys Glu
            740                 745                 750

Lys Phe Arg Val Met Asn Glu Lys Leu Asn Ser His Glu Phe Ala Gln
        755                 760                 765

Asn Leu Lys Ala Pro Ser Val Gln His
    770                 775
```

<210> SEQ ID NO 14
<211> LENGTH: 6900
<212> TYPE: DNA
<213> ORGANISM: Arabidopsis thaliana

<400> SEQUENCE: 14

```
actgtaaatt ttgataaata aaaaaaaaca aaaaaaagat cgccaaatca tatttcatac     60

tatcagattt aaacaatata atttgttcga cgatacagaa atattttacc tcacaggaag    120

aggttgcgca gaaggagcca tggatgtgtt tgttcgagtc gagttgcttt gttgtaagta    180

ggtaattgca agaaacttga gttgtctata aagctttgga atacttctct ttatatatac    240

gtttacaaca attttttttt tttttttttt tctattttta caacaaattg tttttttatta    300

taataataaa cttaaacgaa aataaataat atctctttgt tctatttctt aaaaaagaaa    360

ttagcttgta gtacttcaac gtatcttaac tctttagtct ttagtaggta tatatcatct    420

atttatttat ttttattttt tttatattac gattatagtg tacgtacgta tttattaatc    480

aaaaataact tggtagaagt aaaaagaaaa tgattttttt tttactcagt gatcagtttt    540

acgtttattc aaaaataagt tgtagtttcc ttcttaatat tcaagttata tgactaaaaa    600

ttggtcggtt aatttactat taagattaat cggaaactct agttagatca cgagataatc    660

atcacgtgga gaaacatttg gttcttgtca cgtggagaaa acgttaagct tattttttac    720

ttctttatta tatttttgag gaaatggttg aaagaaagag agtgtttaaa atgtgaatgc    780

gctcgtagtt aggtggaggt taatgggtag gagggtaggt catatgtgta ttagtgatgg    840

ataaaaatta aaaacataaa aaaaacttca agctgtaaat aatctaataa aagaacatag    900

aaatataatc aaagaaccat ttaactaaat aaatactttc gattcaaata gcatatttct    960

aagttccaag aatagctatc ctctatccac atgttacatt ttttttttct ttttcacatc   1020

catatagttt ttaaaataat tttctagatg gtattttttta ttcgacattt tttttcctt   1080

ttagatttac tgattataat ttatttagaa ataaatgata cgactgtcgt ttctacaaaa   1140

ctgaaatttg caaacattgg accaaaaagc gaaaccttaa tcacttgaaa cgacaacgtt   1200

ctttagtatg tttttggaca tacaaagtac acataagatg ttccctcact cttcgattgt   1260

ttcttaacct aatataatta agcaatattg aacttgagtc actcaatgct gcaccgaagg   1320

agcctttaga ttttgagcaa attcatgaga gtttagcttc tcattcatca ctctgaattt   1380
```

-continued

```
ctcttttatc ctctttatct gtccaaaaca tgacacataa cataatgtta gttctcctgc   1440
atacttccaa tggcaaatag aaaaaagaga cattgatcat agaagtcagt ttggtttacc   1500
cttctgagct cgatctctgt gctccgtttc ttttgatcaa gtgattgccg gagattcgtg   1560
atgtcgaaga tactatcgag gtcgtcttca aatgcgtttt ccaactcttc ccggagaaga   1620
gcaggtaact tatcaacgat gggcattaga agaaaacagt tgaactgcag aacaaaagaa   1680
aacacagata caaacttttt aaaagaaaag tcattttaaa agcaagaaga atctgagtaa   1740
aaactgaagt aggagcaaac ctttaactca gcagaggcga gaaagtactc tcgtatgccc   1800
tggaatatct gttggaccaa tgcgtacaca attctctcag aggaaggagc aagcttgcgg   1860
ttccaaagtg tgctatctag aagatcagcc aaccgcattt ctgttgtctg aatactggaa   1920
cctgaatcga tgtttgaggc gagatggctt agctttacat ctgatcttga cttggtgtct   1980
gttgtgccac ctaatgcatc ttggggaaga ctaaatccta tggcattacc tgatgtcgta   2040
ttatgctctg ttccaccaaa tgagtccaag aattgacgta gaccagctcg gttctacata   2100
acattgagaa acgaaaacta ctcaatcaga aacggatact tgatggtatg tacacaactc   2160
aattggattg aaacagagct atagggctgt agcaatgacc ttgttgtgaa gagaccatgt   2220
aacatagcga gttgtacttg ctaaatcctc catacatctg caaacaatat aaaatccaaa   2280
gggtgatcaa tcactaaagc tcactagaac acaggtagga ggcaccgaca tggtaagaac   2340
aggaattgga aatagaatta cttgtcacga catgattttt ctgtggactc cacaaaactg   2400
ttgaatgctg aagcaacccg cttgagaaac acctcatgcc cacttaaata ttcaccttct   2460
ttctattcaa atttagaaca tacatcaaaa aatttgctgg aaagggatca tgagtatgat   2520
accgtcaaac caaagaaaac agtacctacc tgaagaagat atacagaaat tggaagcaat   2580
ctcttgagaa tgtgtagaag cctcgcccct aactatatca acgcaaaaca aacgaaaatg   2640
agaactggaa aaaactttct gtatggaaag agaaacatgt gaataacaaa atttcagatg   2700
aaagtattcc caaacatagt ttctgtaagc agaacatgtt tactcgataa ctcttatgca   2760
caaataagtt ccagcaaatc tcaaaactga atggtagtat gatttcaata tataacgtta   2820
tatttcattt tttttttac gtacagtaca ccttaactaa ttagtaaaat tgctttccat   2880
cctccacgaa agaaaaagaa aaaagtagct atatctatgt cacctgatga aggaaaggtt   2940
caaacgtctc acgagccttc gcaactgcta taacacaagc tgttctacaa cagcaaataa   3000
gagaaagaga ataagaggcc atagaaaaca tgacaaacgt tgcagctcag attagatact   3060
gaaaggggtc tgggatgcaa agacaataaa ttgagaagtg tgttgcatgt cagtcaatcc   3120
tatgatacct ggaatagttt gttccatcat gaatatcctc aactccacat gcatttacaa   3180
tttcctccct cgttattggg ggacatttga tagcaccaac tagaaaacga aactcagcca   3240
tggcacggtg atattgtgca cccccataga gacgcatccc tgcattctgt aaaatgaaag   3300
ataatctggt tatggtctct cataattctt gaaggtccaa cgaagtatct cttttatttg   3360
tttccaatac attattcttt ggcacatatg tttcatgcgg tcaaatttat cttccatcat   3420
attataatcc atgtacaaga acaagacaac tggatttgaa gaccatgccc agcttgctct   3480
ataaagtcca acaatattct gcttcaggga aagacttacc ggtattagct tatgtgaaaa   3540
ctggagacca tcagtaccaa caaatgctcc tccttgtgtc ctttcatctt gcagtgtctc   3600
acctgaaaaa caccatgaga aattattaac aatcaaagaa cccaacataa agagaatgct   3660
gttataaaat gtgcttctgc cagtaaccaa agtatcatga ccaatgattg attgattagc   3720
```

-continued

```
atacatcatt ccatgtgtaa tcatcgcagt ctggtgaccc agtcgaattg aacaatatgc   3780
atttaactaa actgattttg caaaagtcca atttaacaac acccagaaac aagaaaagtt   3840
tatgccaaag aagttgacta gcagagaaca gagcagtaac attaccaaat ttatctggag   3900
gggccacaac tgttcccttc aataacagcg ataactgatc aagaaaaata taaacaaaac   3960
aggtgagaaa acacagcact gatcaatact aacaaaggta cttcgtacgt caatcagaaa   4020
atatgacgca gcaattttaa agtcttaagg gcatccaaca caaaaagttt acagccattc   4080
tgaatttgta gcaagtccta gatatcattt actgtagcat aattttatat gtgtcagtaa   4140
tcaataaaca aatttgtttt tatgtgtcag tagttaataa accaaaaaaa aagagaagtt   4200
tacacaaatg aacttgttgt aattatacaa aaactattaa tccacgagtc caggcaaaaa   4260
tgaaaaggta tgggaaggtg taaatagaaa tctaaaaaaa cgaaatgctc tctacagtta   4320
ccttggttaa gaagagatca tggaaagtcc tgcctctctc tttgagtttt gcttcatcca   4380
aagagctgca ttgaaaggaa ttattcaacc tccaatgagt tatattttct ataaatcagt   4440
agctaacaat taaactgcct aaaatcaagt agacattttc agacaaaaca aattgcgacc   4500
taagttcctt gctcacggta tccagctttc tgactgtact gcggtactcc tttcctaaca   4560
gtggaatgat caatggaaca ctctctttgt acctggaaag agaagggcat caagactaca   4620
gcgaaaagta aactacaata gaaacagagg ctggaaaaat cagagttaaa acaacagtta   4680
taccttttcc agagtagttc ttccagaaac aacctcagtt tactgatgcc aatcctactc   4740
ttttcctgtt ttgtcagtaa acggcccaac ttcttctcta aagatgcaat gtcttccatt   4800
tctctaagtg acacagcctg taataaaaac cacacatagt ttagaaaaag acctgtttaa   4860
cttgtttaag gaatcagaca gcagagcaga gacctgtttg aactcgtcat tagacttata   4920
cactgaatcc tgtccatagc caactcttcc agaaggcaca gacgtgaaaa aaggagaatc   4980
gcccaataag gagctgtcaa gtgcgcttgc aggaggtgag agaaagactt ccacgtcaga   5040
tgaacatgag aattgaggga ttttagtgtc aagctttgta gaaacaacaa ttgtcctaga   5100
aagctcagga tcaacctaca tgaacgagaa acaaacttta acaaaaataa agacaaggtt   5160
agacgcaatg gagttacgtc aagcaacgta cttgcatcac tatccttcga gtggttgcaa   5220
tgctccagtc actgctatct tcgaggcata aaatgatgaa ctctttgtgt tgcatctttg   5280
ctcggactag agcttccaca gcccgtgctt gaacctaaga aaaagaacaa gtaacccact   5340
ctcaaataaa gcaaaaccaa aacatgaaat cagccacgga attggctgga agccataaga   5400
aaaaacaacc tgaagagctc ggtttttcag tcctggtgca ggagcaataa gtccaggtgt   5460
atcaatgatg gtaaggtttg gacaatactt atactggact ttcacaataa tctcctttgc   5520
agagaatggg ctacatggct cttgctccag cctcatgttc tcagcctcaa tatatgccta   5580
actccaaatc atataacaaa tttcgttaac atgagcattt cgcttctcta caataaacct   5640
aagtacttgt gtttctcaac attcgtcaaa atcttcccag aatttatacg cagaaacaag   5700
caattgaaga agcacaagta ataataataa caaaacacct gaatttgtga gagagatttg   5760
ggaagagaaa cggaaggatc atcatcagat ccgagatgac aaagcgggaa ttgacactga   5820
ggatcgtact tcatatggag agtaatcggc cgacgagtct tggttccgcc gccgacatgg   5880
ttaaattgaa accccataag agcttccaca agcgcacttt taccgtcggt ctgctgtccc   5940
accacaagaa ccgccggtgc ttcgaacggc gtctccaatt cctgcgccaa agcgtgtaac   6000
tcgttgtaag cttcgtaaag actccaccgc tcctcaatcg cagcgtcgtc ctcttccgcc   6060
atttcctcaa ccgtcaccga ttttgctgat acttccgcca tcgtctctta cgaaaatgag   6120
```

-continued caagaggaag agtaagagta agagagtgtc tcttatttct tctactcttt agttttcgtc 6180
gccgttcctt tttccgccat ggaattagca gatacggcta atttcaattt ttgtcaaaag 6240
aaatattttt tgtgttttaa tctcacgcgc atccatggcg cgttgagtca acgttgtaat 6300
agttctccgc taaatttaaa taaaagagcg cgtaaggaga gagtttaagg attttttttt 6360
tttggtcggc aaatacaaag gatttgcttt gtcttgacca atagtatatg cagaaatatt 6420
atctcaaagg atttgtgata actatgtagt acagaattgt gattattgga tgagaaacca 6480
gaaatatttt gagcaaatga cgacttgtta atttactatt ttttcatttc ttaaaggtct 6540
ctcttgtgta actatgatta aaattgaaat agtgactttt attgttacga catggaacaa 6600
atcaacgagt tctattgtta aagagagaca ttgatgaatg taacaaaact gtggcttaga 6660
agccgaaagg agacttagtt cgggtccctc cttcaccgta ttgctcgttc cattttctca 6720
attcgttcat tgtcgtcgcg tcgtatgcca ctgacggact tacctgcaaa ttacattaca 6780
atgacgcaat ttcgataatg caaacaccag gggaaaaaac atgaatagag atgatgatga 6840 tgtttttaa gagattgatc aataccttag ctttggattg aatgaagtcg tccaaactca 6900

<210> SEQ ID NO 15
<211> LENGTH: 2319
<212> TYPE: DNA
<213> ORGANISM: Arabidopsis thaliana

<400> SEQUENCE: 15
atggcggaag tatcagcaaa atcggtgacg gttgaggaaa tggcggaaga ggacgacgct 60
gcgattgagg agcggtggag tctttacgaa gcttacaacg agttacacgc tttggcgcag 120
gaattggaga cgccgttcga agcaccggcg gttcttgtgg tgggacagca gaccgacggt 180
aaaagtgcgc ttgtggaagc tcttatgggg tttcaattta accatgtcgg cggcggaacc 240
aagactcgtc ggccgattac tctccatatg aagtacgatc ctcagtgtca attcccgctt 300
tgtcatctcg gatctgatga tgatccttcc gtttctcttc ccaaatctct ctcacaaatt 360
caggcatata ttgaggctga gaacatgagg ctggagcaag agccatgtag cccattctct 420
gcaaaggaga ttattgtgaa agtccagtat aagtattgtc caaaccttac catcattgat 480
acacctggac ttattgctcc tgcaccagga ctgaaaaacc gagctcttca ggttcaagca 540
cgggctgtgg aagctctagt ccgagcaaag atgcaacaca aagagttcat cattttatgc 600
ctcgaagata gcagtgactg gagcattgca accactcgaa ggatagtgat gcaagttgat 660
cctgagcttt ctaggacaat tgttgtttct acaaagcttg acactaaaat ccctcaattc 720
tcatgttcat ctgacgtgga agtctttctc tcacctcctg caagcgcact tgacagctcc 780
ttattgggcg attctccttt tttcacgtct gtgccttctg gaagagttgg ctatggacag 840
gattcagtgt ataagtctaa tgacgagttc aaacaggctg tgtcacttag agaaatggaa 900
gacattgcat ctttagagaa gaagttgggc cgtttactga caaaacagga aaagagtagg 960
attggcatca gtaaactgag gttgtttctg gaagaactac tctggaaaag gtacaaagag 1020
agtgttccat tgatcattcc actgttagga aaggagtacc gcagtacagt cagaaagctg 1080
gataccttat cgctgttatt gaagggaaca gttgtggccc ctccagataa atttggtgag 1140
acactgcaag atgaaaggac acaaggagga gcatttgttg gtactgatgg tctccagttt 1200
tcacataagc taataccgaa tgcagggatg cgtctctatg gggggtgcaca atatcaccgt 1260 gccatggctg agtttcgttt tctagttggt gctatcaaat gtcccccaat aacgagggag 1320

-continued

```
gaaattgtaa atgcatgtgg agttgaggat attcatgatg gaacaaacta ttccagaaca   1380
gcttgtgtta tagcagttgc gaaggctcgt gagacgtttg aacctttcct tcatcagaaa   1440
gtttttttcca gttctcattt tcgtttgttt tgcgttgata tagttagggg cgaggcttct   1500
acacattctc aagagattgc ttccaatttc tgtatatctt cttcaggtag gtactgtttt   1560
ctttggtttg acggtgaata tttaagtggg catgaggtgt ttctcaagcg ggttgcttca   1620
gcattcaaca gttttgtgga gtccacagaa aaatcatgtc gtgacaaatg tatggaggat   1680
ttagcaagta caactcgcta tgttacatgg tctcttcaca acaagaaccg agctggtcta   1740
cgtcaattct tggactcatt tggtggaaca gagcataata cgacatcagg taatgccata   1800
ggatttagtc ttccccaaga tgcattaggt ggcacaacag acaccaagtc aagatcagat   1860
gtaaagctaa gccatctcgc ctcaaacatc gattcaggtt ccagtattca gacaacagaa   1920
atgcggttgg ctgatcttct agatagcaca ctttggaacc gcaagcttgc tccttcctct   1980
gagagaattg tgtacgcatt ggtccaacag atattccagg gcatacgaga gtactttctc   2040
gcctctgctg agttaaagtt caactgtttt cttctaatgc ccatcgttga taagttacct   2100
gctcttctcc gggaagagtt ggaaaacgca tttgaagacg acctcgatag tatcttcgac   2160
atcacgaatc tccggcaatc acttgatcaa aagaaacgga gcacagagat cgagctcaga   2220
aggataaaga ggataaaaga gaaattcaga gtgatgaatg agaagctaaa ctctcatgaa   2280
tttgctcaaa atctaaaggc tccttcggtg cagcattga                          2319
```

<210> SEQ ID NO 16
<211> LENGTH: 772
<212> TYPE: PRT
<213> ORGANISM: Arabidopsis thaliana

<400> SEQUENCE: 16

```
Met Ala Glu Val Ser Ala Lys Ser Val Thr Val Glu Glu Met Ala Glu
1               5                   10                  15

Glu Asp Asp Ala Ala Ile Glu Glu Arg Trp Ser Leu Tyr Glu Ala Tyr
            20                  25                  30

Asn Glu Leu His Ala Leu Ala Gln Glu Leu Glu Thr Pro Phe Glu Ala
        35                  40                  45

Pro Ala Val Leu Val Val Gly Gln Gln Thr Asp Gly Lys Ser Ala Leu
    50                  55                  60

Val Glu Ala Leu Met Gly Phe Gln Phe Asn His Val Gly Gly Gly Thr
65                  70                  75                  80

Lys Thr Arg Arg Pro Ile Thr Leu His Met Lys Tyr Asp Pro Gln Cys
                85                  90                  95

Gln Phe Pro Leu Cys His Leu Gly Ser Asp Asp Asp Pro Ser Val Ser
            100                 105                 110

Leu Pro Lys Ser Leu Ser Gln Ile Gln Ala Tyr Ile Glu Ala Glu Asn
        115                 120                 125

Met Arg Leu Glu Gln Glu Pro Cys Ser Pro Phe Ser Ala Lys Glu Ile
    130                 135                 140

Ile Val Lys Val Gln Tyr Lys Tyr Cys Pro Asn Leu Thr Ile Ile Asp
145                 150                 155                 160

Thr Pro Gly Leu Ile Ala Pro Ala Pro Gly Leu Lys Asn Arg Ala Leu
                165                 170                 175

Gln Val Gln Ala Arg Ala Val Glu Ala Leu Val Arg Ala Lys Met Gln
            180                 185                 190

His Lys Glu Phe Ile Ile Leu Cys Leu Glu Asp Ser Ser Asp Trp Ser
```

-continued

```
        195                 200                 205

Ile Ala Thr Thr Arg Arg Ile Val Met Gln Val Asp Pro Glu Leu Ser
    210                 215                 220

Arg Thr Ile Val Val Ser Thr Lys Leu Asp Thr Lys Ile Pro Gln Phe
225                 230                 235                 240

Ser Cys Ser Ser Asp Val Glu Val Phe Leu Ser Pro Pro Ala Ser Ala
                245                 250                 255

Leu Asp Ser Ser Leu Leu Gly Asp Ser Pro Phe Phe Thr Ser Val Pro
            260                 265                 270

Ser Gly Arg Val Gly Tyr Gly Gln Asp Ser Val Tyr Lys Ser Asn Asp
        275                 280                 285

Glu Phe Lys Gln Ala Val Ser Leu Arg Glu Met Glu Asp Ile Ala Ser
    290                 295                 300

Leu Glu Lys Lys Leu Gly Arg Leu Leu Thr Lys Gln Glu Lys Ser Arg
305                 310                 315                 320

Ile Gly Ile Ser Lys Leu Arg Leu Phe Leu Glu Glu Leu Leu Trp Lys
                325                 330                 335

Arg Tyr Lys Glu Ser Val Pro Leu Ile Ile Pro Leu Leu Gly Lys Glu
            340                 345                 350

Tyr Arg Ser Thr Val Arg Lys Leu Asp Thr Leu Ser Leu Leu Leu Lys
        355                 360                 365

Gly Thr Val Val Ala Pro Pro Asp Lys Phe Gly Glu Thr Leu Gln Asp
    370                 375                 380

Glu Arg Thr Gln Gly Gly Ala Phe Val Gly Thr Asp Gly Leu Gln Phe
385                 390                 395                 400

Ser His Lys Leu Ile Pro Asn Ala Gly Met Arg Leu Tyr Gly Gly Ala
                405                 410                 415

Gln Tyr His Arg Ala Met Ala Glu Phe Arg Phe Leu Val Gly Ala Ile
            420                 425                 430

Lys Cys Pro Pro Ile Thr Arg Glu Glu Ile Val Asn Ala Cys Gly Val
        435                 440                 445

Glu Asp Ile His Asp Gly Thr Asn Tyr Ser Arg Thr Ala Cys Val Ile
    450                 455                 460

Ala Val Ala Lys Ala Arg Glu Thr Phe Glu Pro Phe Leu His Gln Lys
465                 470                 475                 480

Val Phe Ser Ser Ser His Phe Arg Leu Phe Cys Val Asp Ile Val Arg
                485                 490                 495

Gly Glu Ala Ser Thr His Ser Gln Glu Ile Ala Ser Asn Phe Cys Ile
            500                 505                 510

Ser Ser Ser Gly Arg Tyr Cys Phe Leu Trp Phe Asp Gly Glu Tyr Leu
        515                 520                 525

Ser Gly His Glu Val Phe Leu Lys Arg Val Ala Ser Ala Phe Asn Ser
    530                 535                 540

Phe Val Glu Ser Thr Glu Lys Ser Cys Arg Asp Lys Cys Met Glu Asp
545                 550                 555                 560

Leu Ala Ser Thr Thr Arg Tyr Val Thr Trp Ser Leu His Asn Lys Asn
                565                 570                 575

Arg Ala Gly Leu Arg Gln Phe Leu Asp Ser Phe Gly Gly Thr Glu His
            580                 585                 590

Asn Thr Thr Ser Gly Asn Ala Ile Gly Phe Ser Leu Pro Gln Asp Ala
        595                 600                 605

Leu Gly Gly Thr Thr Asp Thr Lys Ser Arg Ser Asp Val Lys Leu Ser
    610                 615                 620
```

His Leu Ala Ser Asn Ile Asp Ser Gly Ser Ser Ile Gln Thr Thr Glu
625 630 635 640

Met Arg Leu Ala Asp Leu Leu Asp Ser Thr Leu Trp Asn Arg Lys Leu
645 650 655

Ala Pro Ser Ser Glu Arg Ile Val Tyr Ala Leu Val Gln Gln Ile Phe
660 665 670

Gln Gly Ile Arg Glu Tyr Phe Leu Ala Ser Ala Glu Leu Lys Phe Asn
675 680 685

Cys Phe Leu Leu Met Pro Ile Val Asp Lys Leu Pro Ala Leu Leu Arg
690 695 700

Glu Glu Leu Glu Asn Ala Phe Glu Asp Asp Leu Asp Ser Ile Phe Asp
705 710 715 720

Ile Thr Asn Leu Arg Gln Ser Leu Asp Gln Lys Lys Arg Ser Thr Glu
725 730 735

Ile Glu Leu Arg Arg Ile Lys Arg Ile Lys Glu Lys Phe Arg Val Met
740 745 750

Asn Glu Lys Leu Asn Ser His Glu Phe Ala Gln Asn Leu Lys Ala Pro
755 760 765

Ser Val Gln His
770

<210> SEQ ID NO 17
<211> LENGTH: 841
<212> TYPE: PRT
<213> ORGANISM: Arabidopsis thaliana

<400> SEQUENCE: 17

Met Gln Glu Leu Tyr Thr Asn Arg Thr Val Leu Asn Arg Pro Arg Phe
1 5 10 15

Ala Val Asn Val Arg Pro Thr Arg Leu Lys Arg Asn Gln Gln Ser Gln
20 25 30

Ser Lys Met Gln Ser His Ser Lys Asp Pro Ile Asn Ala Glu Ser Arg
35 40 45

Ser Arg Phe Glu Ala Tyr Asn Arg Leu Gln Ala Ala Ala Val Ala Phe
50 55 60

Gly Glu Lys Leu Pro Ile Pro Glu Ile Val Ala Ile Gly Gly Gln Ser
65 70 75 80

Asp Gly Lys Ser Ser Leu Leu Glu Ala Leu Leu Gly Phe Arg Phe Asn
85 90 95

Val Arg Glu Val Glu Met Gly Thr Arg Arg Pro Leu Ile Leu Gln Met
100 105 110

Val His Asp Leu Ser Ala Leu Glu Pro Arg Cys Arg Phe Gln Ile Ser
115 120 125

Arg Ile Phe Phe Val Glu Leu Ala Ile Leu Ile Thr Asp Leu Asp Glu
130 135 140

Asp Ser Glu Glu Tyr Gly Ser Pro Ile Val Ser Ala Thr Ala Val Ala
145 150 155 160

Asp Val Ile Arg Ser Arg Thr Glu Ala Leu Leu Lys Lys Thr Lys Thr
165 170 175

Ala Val Ser Pro Lys Pro Ile Val Met Arg Ala Glu Tyr Ala His Cys
180 185 190

Pro Asn Leu Thr Ile Ile Asp Thr Pro Gly Phe Val Leu Lys Ala Lys
195 200 205

Lys Gly Glu Pro Glu Thr Thr Pro Asp Glu Ile Leu Ser Met Val Lys

-continued

```
    210                 215                 220

Ser Leu Ala Ser Pro Pro His Arg Ile Leu Leu Phe Leu Gln Gln Ser
225                 230                 235                 240

Ser Val Glu Trp Cys Ser Ser Leu Trp Leu Asp Ala Val Arg Glu Ile
                245                 250                 255

Asp Ser Ser Phe Arg Arg Thr Ile Val Val Val Ser Lys Phe Asp Asn
            260                 265                 270

Arg Leu Lys Glu Phe Ser Asp Arg Gly Glu Val Asp Arg Tyr Leu Ser
        275                 280                 285

Ala Ser Gly Tyr Leu Gly Glu Asn Thr Arg Pro Tyr Phe Val Ala Leu
    290                 295                 300

Pro Lys Asp Arg Ser Thr Ile Ser Asn Asp Glu Phe Arg Arg Gln Ile
305                 310                 315                 320

Ser Gln Val Asp Thr Glu Val Ile Arg His Leu Arg Glu Gly Val Lys
                325                 330                 335

Gly Gly Phe Asp Glu Glu Lys Phe Arg Ser Cys Ile Gly Phe Gly Ser
            340                 345                 350

Leu Arg Asp Phe Leu Glu Ser Glu Leu Gln Lys Arg Tyr Lys Glu Ala
        355                 360                 365

Ala Pro Ala Thr Leu Ala Leu Leu Glu Glu Arg Cys Ser Glu Val Thr
    370                 375                 380

Asp Asp Met Leu Arg Met Asp Met Lys Ile Gln Ala Thr Ser Asp Val
385                 390                 395                 400

Ala His Leu Arg Lys Ala Ala Met Leu Tyr Thr Ala Ser Ile Ser Asn
                405                 410                 415

His Val Gly Ala Leu Ile Asp Gly Ala Ala Asn Pro Ala Pro Glu Gln
            420                 425                 430

Trp Gly Lys Thr Thr Glu Glu Glu Arg Gly Glu Ser Gly Ile Gly Ser
        435                 440                 445

Trp Pro Gly Val Ser Val Asp Ile Lys Pro Pro Asn Ala Val Leu Lys
    450                 455                 460

Leu Tyr Gly Gly Ala Ala Phe Glu Arg Val Ile His Glu Phe Arg Cys
465                 470                 475                 480

Ala Ala Tyr Ser Ile Glu Cys Pro Pro Val Ser Arg Glu Lys Val Ala
                485                 490                 495

Asn Ile Leu Leu Ala His Ala Gly Arg Gly Gly Gly Arg Gly Val Thr
            500                 505                 510

Glu Ala Ser Ala Glu Ile Ala Arg Thr Ala Ala Arg Ser Trp Leu Ala
        515                 520                 525

Pro Leu Leu Asp Thr Ala Cys Asp Arg Leu Ala Phe Val Leu Gly Ser
    530                 535                 540

Leu Phe Glu Ile Ala Leu Glu Arg Asn Leu Asn Gln Asn Ser Glu Tyr
545                 550                 555                 560

Glu Lys Lys Thr Glu Asn Met Asp Gly Tyr Val Gly Phe His Ala Ala
                565                 570                 575

Val Arg Asn Cys Tyr Ser Arg Phe Val Lys Asn Leu Ala Lys Gln Cys
            580                 585                 590

Lys Gln Leu Val Arg His His Leu Asp Ser Val Thr Ser Pro Tyr Ser
        595                 600                 605

Met Ala Cys Tyr Glu Asn Asn Tyr His Gln Gly Gly Ala Phe Gly Ala
    610                 615                 620

Tyr Asn Lys Phe Asn Gln Ala Ser Pro Asn Ser Phe Cys Phe Glu Leu
625                 630                 635                 640
```

-continued

```
Ser Asp Thr Ser Arg Asp Glu Pro Met Lys Asp Gln Glu Asn Ile Pro
                645                 650                 655

Pro Glu Lys Asn Asn Gly Gln Glu Thr Thr Pro Gly Lys Gly Gly Glu
            660                 665                 670

Ser His Ile Thr Val Pro Glu Thr Pro Ser Pro Asp Gln Pro Cys Glu
        675                 680                 685

Ile Val Tyr Gly Leu Val Lys Lys Glu Ile Gly Asn Gly Pro Asp Gly
    690                 695                 700

Val Gly Ala Arg Lys Arg Met Ala Arg Met Val Gly Asn Arg Asn Ile
705                 710                 715                 720

Glu Pro Phe Arg Val Gln Asn Gly Gly Leu Met Phe Ala Asn Ala Asp
                725                 730                 735

Asn Gly Met Lys Ser Ser Ser Ala Tyr Ser Glu Ile Cys Ser Ser Ala
            740                 745                 750

Ala Gln His Phe Ala Arg Ile Arg Glu Val Leu Val Glu Arg Ser Val
        755                 760                 765

Thr Ser Thr Leu Asn Ser Gly Phe Leu Thr Pro Cys Arg Asp Arg Leu
    770                 775                 780

Val Val Ala Leu Gly Leu Asp Leu Phe Ala Val Asn Asp Asp Lys Phe
785                 790                 795                 800

Met Asp Met Phe Val Ala Pro Gly Ala Ile Val Val Leu Gln Asn Glu
                805                 810                 815

Arg Gln Gln Leu Gln Lys Arg Gln Lys Ile Leu Gln Ser Cys Leu Thr
            820                 825                 830

Glu Phe Lys Thr Val Ala Arg Ser Leu
        835                 840


<210> SEQ ID NO 18
<211> LENGTH: 817
<212> TYPE: PRT
<213> ORGANISM: Arabidopsis thaliana

<400> SEQUENCE: 18

Met Ala Asn Ser Asn Thr Tyr Leu Thr Thr Pro Thr Lys Thr Pro Ser
1               5                   10                  15

Ser Arg Arg Asn Gln Gln Ser Gln Ser Lys Met Gln Ser His Ser Lys
            20                  25                  30

Asp Pro Ile Asn Ala Glu Ser Arg Ser Arg Phe Glu Ala Tyr Asn Arg
        35                  40                  45

Leu Gln Ala Ala Ala Val Ala Phe Gly Glu Lys Leu Pro Ile Pro Glu
    50                  55                  60

Ile Val Ala Ile Gly Gly Gln Ser Asp Gly Lys Ser Ser Leu Leu Glu
65                  70                  75                  80

Ala Leu Leu Gly Phe Arg Phe Asn Val Arg Glu Val Glu Met Gly Thr
                85                  90                  95

Arg Arg Pro Leu Ile Leu Gln Met Val His Asp Leu Ser Ala Leu Glu
            100                 105                 110

Pro Arg Cys Arg Phe Gln Asp Glu Asp Ser Glu Glu Tyr Gly Ser Pro
        115                 120                 125

Ile Val Ser Ala Thr Ala Val Ala Asp Val Ile Arg Ser Arg Thr Glu
    130                 135                 140

Ala Leu Leu Lys Lys Thr Lys Thr Ala Val Ser Pro Lys Pro Ile Val
145                 150                 155                 160

Met Arg Ala Glu Tyr Ala His Cys Pro Asn Leu Thr Ile Ile Asp Thr
```

-continued

```
                165                 170                 175

Pro Gly Phe Val Leu Lys Ala Lys Lys Gly Glu Pro Glu Thr Thr Pro
            180                 185                 190

Asp Glu Ile Leu Ser Met Val Lys Ser Leu Ala Ser Pro Pro His Arg
        195                 200                 205

Ile Leu Leu Phe Leu Gln Gln Ser Ser Val Glu Trp Cys Ser Ser Leu
    210                 215                 220

Trp Leu Asp Ala Val Arg Glu Ile Asp Ser Ser Phe Arg Arg Thr Ile
225                 230                 235                 240

Val Val Val Ser Lys Phe Asp Asn Arg Leu Lys Glu Phe Ser Asp Arg
                245                 250                 255

Gly Glu Val Asp Arg Tyr Leu Ser Ala Ser Gly Tyr Leu Gly Glu Asn
            260                 265                 270

Thr Arg Pro Tyr Phe Val Ala Leu Pro Lys Asp Arg Ser Thr Ile Ser
        275                 280                 285

Asn Asp Glu Phe Arg Arg Gln Ile Ser Gln Val Asp Thr Glu Val Ile
    290                 295                 300

Arg His Leu Arg Glu Gly Val Lys Gly Gly Phe Asp Glu Glu Lys Phe
305                 310                 315                 320

Arg Ser Cys Ile Gly Phe Gly Ser Leu Arg Asp Phe Leu Glu Ser Glu
                325                 330                 335

Leu Gln Lys Arg Tyr Lys Glu Ala Ala Pro Ala Thr Leu Ala Leu Leu
            340                 345                 350

Glu Glu Arg Cys Ser Glu Val Thr Asp Asp Met Leu Arg Met Asp Met
        355                 360                 365

Lys Ile Gln Ala Thr Ser Asp Val Ala His Leu Arg Lys Ala Ala Met
    370                 375                 380

Leu Tyr Thr Ala Ser Ile Ser Asn His Val Gly Ala Leu Ile Asp Gly
385                 390                 395                 400

Ala Ala Asn Pro Ala Pro Glu Gln Trp Gly Lys Thr Thr Glu Glu Glu
                405                 410                 415

Arg Gly Glu Ser Gly Ile Gly Ser Trp Pro Gly Val Ser Val Asp Ile
            420                 425                 430

Lys Pro Pro Asn Ala Val Leu Lys Leu Tyr Gly Gly Ala Ala Phe Glu
        435                 440                 445

Arg Val Ile His Glu Phe Arg Cys Ala Ala Tyr Ser Ile Glu Cys Pro
    450                 455                 460

Pro Val Ser Arg Glu Lys Val Ala Asn Ile Leu Leu Ala His Ala Gly
465                 470                 475                 480

Arg Gly Gly Gly Arg Gly Val Thr Glu Ala Ser Ala Glu Ile Ala Arg
                485                 490                 495

Thr Ala Ala Arg Ser Trp Leu Ala Pro Leu Leu Asp Thr Ala Cys Asp
            500                 505                 510

Arg Leu Ala Phe Val Leu Gly Ser Leu Phe Glu Ile Ala Leu Glu Arg
        515                 520                 525

Asn Leu Asn Gln Asn Ser Glu Tyr Glu Lys Lys Thr Glu Asn Met Asp
    530                 535                 540

Gly Tyr Val Gly Phe His Ala Ala Val Arg Asn Cys Tyr Ser Arg Phe
545                 550                 555                 560

Val Lys Asn Leu Ala Lys Gln Cys Lys Gln Leu Val Arg His His Leu
                565                 570                 575

Asp Ser Val Thr Ser Pro Tyr Ser Met Ala Cys Tyr Glu Asn Asn Tyr
            580                 585                 590
```

```
His Gln Gly Gly Ala Phe Gly Ala Tyr Asn Lys Phe Asn Gln Ala Ser
        595                 600                 605

Pro Asn Ser Phe Cys Phe Glu Leu Ser Asp Thr Ser Arg Asp Glu Pro
    610                 615                 620

Met Lys Asp Gln Glu Asn Ile Pro Pro Glu Lys Asn Asn Gly Gln Glu
625                 630                 635                 640

Thr Thr Pro Gly Lys Gly Gly Glu Ser His Ile Thr Val Pro Glu Thr
                645                 650                 655

Pro Ser Pro Asp Gln Pro Cys Glu Ile Val Tyr Gly Leu Val Lys Lys
            660                 665                 670

Glu Ile Gly Asn Gly Pro Asp Gly Val Gly Ala Arg Lys Arg Met Ala
        675                 680                 685

Arg Met Val Gly Asn Arg Asn Ile Glu Pro Phe Arg Val Gln Asn Gly
    690                 695                 700

Gly Leu Met Phe Ala Asn Ala Asp Asn Gly Met Lys Ser Ser Ser Ala
705                 710                 715                 720

Tyr Ser Glu Ile Cys Ser Ser Ala Ala Gln His Phe Ala Arg Ile Arg
                725                 730                 735

Glu Val Leu Val Glu Arg Ser Val Thr Ser Thr Leu Asn Ser Gly Phe
            740                 745                 750

Leu Thr Pro Cys Arg Asp Arg Leu Val Val Ala Leu Gly Leu Asp Leu
        755                 760                 765

Phe Ala Val Asn Asp Asp Lys Phe Met Asp Met Phe Val Ala Pro Gly
    770                 775                 780

Ala Ile Val Val Leu Gln Asn Glu Arg Gln Gln Leu Gln Lys Arg Gln
785                 790                 795                 800

Lys Ile Leu Gln Ser Cys Leu Thr Glu Phe Lys Thr Val Ala Arg Ser
                805                 810                 815

Leu


<210> SEQ ID NO 19
<211> LENGTH: 4283
<212> TYPE: DNA
<213> ORGANISM: Arabidopsis thaliana

<400> SEQUENCE: 19

ttcatgttct tagaagttct aaattttgat catctcttat ttgaaagctc aactaaaata      60

gctatgatat cattccctga tgctacgtac taggttttta aattcataca cacacaaatc     120

tataattaaa acttgttaaa ttcatacaca caaaggacaa atcttcttcg tattaaaaaa     180

gatggaggct ctggaacatc tagtggtgcc gtatcactta cttgactggt tcaagccgtt     240

tgtctttgtt tggaagaagt aaatttaatt gtgggagagg gatttcacga atttaaatct     300

gtttttctcc cttttcgtgg tatactttgg accttttgga tatgaacaca tatgtgaaaa     360

cgttaattca tgtgtttgaa aagtaattaa tcgcgccgtc cgtcttatag ctttgggatg     420

ggccaatagg atatttaaga gataagaaaa ctaatcagaa acacagacga aggtatctca     480

ctctctctct ttctctctcc atgagaactc taatctctca ccggcaatgt gtgacgtcac     540

cgtttcttat ctccgccgca tctccaccgt ttcctggccg gtgctttaag ttatcctcct     600

ttactcctcc acgtcatagg cgtttttctt ctctctcgat cagaaacatt tcgcatgaat     660

ccgccgatca gacttcttct tctaggccgc gaactcttta tcctggtggt tacaagcgtc     720

ccgaactcgc cgttcccggt ttacttctcc ggctagacgc cgacgaggtt atgagcggga     780
```

-continued

```
atcgtgaaga gactcttgat ttggtcgacc gtgctttagc taaatcggtt caaatcgtcg    840
tgattgatgg cggagccacc gctggtaagc tctacgaggc ggcttgtttg ctgaaatcac    900
ttgtcaaagg ccgtgcttac ctcttgatcg ctgaacgtgt tgatatcgcc tccgccgttg    960
gtgctagtgg tgttgctctc tccgacgaag gtaacaactg atttcattca gttttagcat   1020
ttaatttctc atagagtgag ttttgtctct caatgctatg tacaggtctt ccggcgattg   1080
tggcgagaaa cacattgatg ggatccaacc ccgactcggt acttcttcca ctggtagctc   1140
ggattgtgaa ggatgttgat tctgctctaa ttgcctcaag ctccgagggt gctgatttcc   1200
ttatacttgg atctggtgaa gaagatacgc aagtggcgga ttctttgttg aagagcgtga   1260
aaataccgat atatgtgact tgcagaggca atgaagaagc taaagaagaa ttgcagttac   1320
tgaaatcagg tgtttctggt tttgttattt cgttgaaaga tttgcgttct tctagggatg   1380
tagctcttcg ccagagtctt gatggagctt atgttgtaaa taatcatgag acacaaaata   1440
tgaatgaact gccggagaaa aagaattctg ctggcttcat aaaattagag gacaaacaga   1500
aactaatagt agaaatggag aaatctgtgt tgagagagac gattgaaatc atccacaagg   1560
cggctccact ggtgattttt atttcaaaca tttggtagtt gaagtcaatt ttttgaaatg   1620
gttctaagta ggtttttgtg tggttataat atggtttcat ttacttcttc gactattttt   1680
cattaacaga tggaggaagt ctcccttcta attgatgctg tttctcggat cgatgagccg   1740
tttctgatgg ttatagtggt aattctgcac tcaactccgt caaattgtga ttccaggaat   1800
ttgcattggt attagctcta tattcattcc agaaacattt tagttacaca cttttgccag   1860
cactagatag cttgagatac aatgggcatg cttctagtca cttgtccttt agtgcttctc   1920
aatatcttct ttcgtcgcct atgactatga tgtttcgctt cttcttttgt tctgtctatg   1980
cttctcttct taatttgctt atggatctgg ttgtaaggga actgcatatt tcttaactgt   2040
accatctgct tgtgtacata gttttttcgc tttcttgtga cttgtgagta tgccgttctt   2100
ggaagatgtt ttaagtggga caagttgcct ttatgattca aaatagtttt tgtatggata   2160
attaattgga atccacaatt tgctggtact agggggaatt taactctgga aaatcaacgg   2220
ttatcaatgc acttcttggg aagagatacc tgaaagaagg ggtagtcccc actaccaatg   2280
aaatcacgtt tctgtgctac tctgacttgg aatccgaaga gcaacaacgt tgccaaacac   2340
atccagatgg ccaatatgta tgctatcttc ctgcaccaat acttaaggat gtgagtaatt   2400
caaaattcta ccatcgcagt cctgaatttt tactaattat ttggaggaat tgatttgggt   2460
tgttctcctt tcgagcagat aaatattgtt gacacacctg ggaccaatgt gatccttcaa   2520
aggcaacagc gtcttacaga agaatttgtt ccacgtgcag atttgcttgt ttttgttctt   2580
tctgctgacc gccctttaac tgaaagtgag gtagaagtta ccgttttact tggcatgtta   2640
gttgttgttg tttttgctca atatgtatct gcctaagtag cttgttagat ctatttttca   2700
cgaaagtagt tagttaagtc atgtatagac catcaagacc ttgtgtaggg aagggaaagt   2760
tgtcactagg ttgaatgcat atatcaaggt tttgttgatt ataaatttaa actagactaa   2820
tttattttca aagtaatgag tgttatagct attgctggaa ccagtatgtc ctgttggtcc   2880
atattttggt aaagcttagg ccaatacatt tgagaggtga gttgttattg gtacagcaaa   2940
actgatttta cgtccatggc aaattgtatg taaatgatca tctacgaagt actaacctta   3000
tgaatatttg gttcttattt tgaaaatctg aaaaagtttc aaaagaagga ataagcttct   3060
caatgtcatc atacccatgt catttctatc tctacctctg gagcttcctg ctgtcttgat   3120
tttactgtag gctgatttac atctcattgc gtttgtcagg ttgcgtttct ccggtacaca   3180
```

-continued

```
cagcagtgga aaaagaaatt tgtgtttatt ctgaataaat ctgatatcta tcgtgatgct   3240
cgtgaggttt atcagaaaca atatttatgt cttttccttg atagtctctg taattgctgg   3300
atttttcttg actaaagatt aattttactg ctgcagcttg aggaagctat ttcatttgtt   3360
aaagagaata cacggaagtt gcttaataca gaaaatgtga tattgtatcc ggtgtccgca   3420
cggtctgctc ttgaggcgaa gctttcaaca gcttctttgg ttggcagaga tgatcttgag   3480
atcgcagatc ctggttctaa ttggagagtc cagagcttca atgaacttga gaaatttctt   3540
tatagcttct tggatagctc aacagctacc gggatggaga gaataaggct taaattggag   3600
acacccatgg cgattgctga gcgtctcctt tcttctgtgg aagctcttgt gagacaagat   3660
tgcctagctg ctagggaaga cttggcttca gcagacaaga ttatcagtcg aactaaagaa   3720
tacgcgctta agatggaata tgagagcatt tcttggagaa ggcaggctct ctcgttggta   3780
taaattctat tagatattat cttgttgaat cacgaaggag gaaattggat tgttctaact   3840
tggctttttt gtgttttgta ctctggcttt tatcgcagat tgataatgcc agattacaag   3900
ttgttgatct gataggaact accctgcgac tatcaagcct tgatcttgcg atctcgtacg   3960
tgttcaaagg ggaaaaatcg gcctcagtag cagctacatc caaagttcaa ggtgaaatac   4020
tcgctccagc actcacaaat gcgaaagtaa gtgtgatgct ttattctttg agtattggcc   4080
taactgggga catgttggtc atatatatga ggtctgagat atagtcacta ttcatgcaga   4140
aagtaaatat tgtctaacaa tgtcttgttg tgacctgatt gactttacat ttcactgttt   4200
gcaggaattg cttggaaaat atgctgaatg gctacaatca aatactgccc gtgaagggag   4260
tctgtctctg aaatcattcg aaa                                            4283
```

<210> SEQ ID NO 20
<211> LENGTH: 1929
<212> TYPE: DNA
<213> ORGANISM: Arabidopsis thaliana

<400> SEQUENCE: 20

```
atgagaactc taatctctca ccggcaatgt gtgacgtcac cgtttcttat ctccgccgca     60
tctccaccgt ttcctggccg gtgctttaag ttatcctcct ttactcctcc acgtcatagg    120
cgtttttctt ctctctcgat cagaaacatt tcgcatgaat ccgccgatca gacttcttct    180
tctaggccgc gaactcttta tcctggtggt tacaagcgtc ccgaactcgc cgttcccggt    240
ttacttctcc ggctagacgc cgacgaggtt atgagcggga atcgtgaaga gactcttgat    300
ttggtcgacc gtgctttagc taaatcggtt caaatcgtcg tgattgatgg cggagccacc    360
gctggtaagc tctacgaggc ggcttgtttg ctgaaatcac ttgtcaaagg ccgtgcttac    420
ctcttgatcg ctgaacgtgt tgatatcgcc tccgccgttg gtgctagtgg tgttgctctc    480
tccgacgaag gtcttccggc gattgtggcg agaaacacat tgatgggatc caaccccgac    540
tcggtacttc ttccactggt agctcggatt gtgaaggatg ttgattctgc tctaattgcc    600
tcaagctccg agggtgctga tttccttata cttggatctg gtgaagaaga tacgcaagtg    660
gcggattctt tgttgaagag cgtgaaaata ccgatatatg tgacttgcag aggcaatgaa    720
gaagctaaag aagaattgca gttactgaaa tcaggtgttt ctggttttgt tatttcgttg    780
aaagatttgc gttcttctag ggatgtagct cttcgccaga gtcttgatgg agcttatgtt    840
gtaaataatc atgagacaca aaatatgaat gaactgccgg agaaaaagaa ttctgctggc    900
ttcataaaat tagaggacaa acagaaacta atagtagaaa tggagaaatc tgtgttgaga    960
```

-continued

```
gagacgattg aaatcatcca caaggcggct ccactgatgg aggaagtctc ccttctaatt   1020
gatgctgttt ctcggatcga tgagccgttt ctgatggtta tagtgggggga atttaactct   1080
ggaaaatcaa cggttatcaa tgcacttctt gggaagagat acctgaaaga aggggtagtc   1140
cccactacca atgaaatcac gtttctgtgc tactctgact tggaatccga agagcaacaa   1200
cgttgccaaa cacatccaga tggccaatat gtatgctatc ttcctgcacc aatacttaag   1260
gatataaata ttgttgacac acctgggacc aatgtgatcc ttcaaaggca acagcgtctt   1320
acagaagaat ttgttccacg tgcagatttg cttgtttttg ttctttctgc tgaccgccct   1380
ttaactgaaa gtgaggttgc gtttctccgg tacacacagc agtggaaaaa gaaatttgtg   1440
tttattctga ataaatctga tatctatcgt gatgctcgtg agcttgagga agctatttca   1500
tttgttaaag agaatacacg gaagttgctt aatacagaaa atgtgatatt gtatccggtg   1560
tccgcacggt ctgctcttga ggcgaagctt tcaacagctt ctttggttgg cagagatgat   1620
cttgagatcg cagatcctgg ttctaattgg agagtccaga gcttcaatga acttgagaaa   1680
tttctttata gcttcttgga tagctcaaca gctaccggga tggagagaat aaggcttaaa   1740
ttggagacac ccatggcgat tgctgagcgt ctcctttctt ctgtggaagc tcttgtgaga   1800
caagattgcc tagctgctag ggaagacttg gcttcagcag acaagattat cagtcgaact   1860
aaagaatacg cgcttaagat ggaatatgag agcatttctt ggagaaggca ggctctctcg   1920
ttggtataa                                                           1929
```

<210> SEQ ID NO 21
<211> LENGTH: 642
<212> TYPE: PRT
<213> ORGANISM: Arabidopsis thaliana

<400> SEQUENCE: 21

```
Met Arg Thr Leu Ile Ser His Arg Gln Cys Val Thr Ser Pro Phe Leu
1               5                   10                  15

Ile Ser Ala Ala Ser Pro Pro Phe Pro Gly Arg Cys Phe Lys Leu Ser
            20                  25                  30

Ser Phe Thr Pro Pro Arg His Arg Arg Phe Ser Ser Leu Ser Ile Arg
        35                  40                  45

Asn Ile Ser His Glu Ser Ala Asp Gln Thr Ser Ser Ser Arg Pro Arg
    50                  55                  60

Thr Leu Tyr Pro Gly Gly Tyr Lys Arg Pro Glu Leu Ala Val Pro Gly
65                  70                  75                  80

Leu Leu Leu Arg Leu Asp Ala Asp Glu Val Met Ser Gly Asn Arg Glu
                85                  90                  95

Glu Thr Leu Asp Leu Val Asp Arg Ala Leu Ala Lys Ser Val Gln Ile
            100                 105                 110

Val Val Ile Asp Gly Gly Ala Thr Ala Gly Lys Leu Tyr Glu Ala Ala
        115                 120                 125

Cys Leu Leu Lys Ser Leu Val Lys Gly Arg Ala Tyr Leu Leu Ile Ala
    130                 135                 140

Glu Arg Val Asp Ile Ala Ser Ala Val Gly Ala Ser Gly Val Ala Leu
145                 150                 155                 160

Ser Asp Glu Gly Leu Pro Ala Ile Val Ala Arg Asn Thr Leu Met Gly
                165                 170                 175

Ser Asn Pro Asp Ser Val Leu Leu Pro Leu Val Ala Arg Ile Val Lys
            180                 185                 190

Asp Val Asp Ser Ala Leu Ile Ala Ser Ser Ser Glu Gly Ala Asp Phe
```

-continued

```
        195                 200                 205

Leu Ile Leu Gly Ser Gly Glu Glu Asp Thr Gln Val Ala Asp Ser Leu
    210                 215                 220

Leu Lys Ser Val Lys Ile Pro Ile Tyr Val Thr Cys Arg Gly Asn Glu
225                 230                 235                 240

Glu Ala Lys Glu Glu Leu Gln Leu Leu Lys Ser Gly Val Ser Gly Phe
                245                 250                 255

Val Ile Ser Leu Lys Asp Leu Arg Ser Ser Arg Asp Val Ala Leu Arg
            260                 265                 270

Gln Ser Leu Asp Gly Ala Tyr Val Val Asn Asn His Glu Thr Gln Asn
        275                 280                 285

Met Asn Glu Leu Pro Glu Lys Lys Asn Ser Ala Gly Phe Ile Lys Leu
    290                 295                 300

Glu Asp Lys Gln Lys Leu Ile Val Glu Met Glu Lys Ser Val Leu Arg
305                 310                 315                 320

Glu Thr Ile Glu Ile Ile His Lys Ala Ala Pro Leu Met Glu Glu Val
                325                 330                 335

Ser Leu Leu Ile Asp Ala Val Ser Arg Ile Asp Glu Pro Phe Leu Met
            340                 345                 350

Val Ile Val Gly Glu Phe Asn Ser Gly Lys Ser Thr Val Ile Asn Ala
        355                 360                 365

Leu Leu Gly Lys Arg Tyr Leu Lys Glu Gly Val Val Pro Thr Thr Asn
    370                 375                 380

Glu Ile Thr Phe Leu Cys Tyr Ser Asp Leu Glu Ser Glu Glu Gln Gln
385                 390                 395                 400

Arg Cys Gln Thr His Pro Asp Gly Gln Tyr Val Cys Tyr Leu Pro Ala
                405                 410                 415

Pro Ile Leu Lys Asp Ile Asn Ile Val Asp Thr Pro Gly Thr Asn Val
            420                 425                 430

Ile Leu Gln Arg Gln Gln Arg Leu Thr Glu Glu Phe Val Pro Arg Ala
        435                 440                 445

Asp Leu Leu Val Phe Val Leu Ser Ala Asp Arg Pro Leu Thr Glu Ser
    450                 455                 460

Glu Val Ala Phe Leu Arg Tyr Thr Gln Gln Trp Lys Lys Lys Phe Val
465                 470                 475                 480

Phe Ile Leu Asn Lys Ser Asp Ile Tyr Arg Asp Ala Arg Glu Leu Glu
                485                 490                 495

Glu Ala Ile Ser Phe Val Lys Glu Asn Thr Arg Lys Leu Leu Asn Thr
            500                 505                 510

Glu Asn Val Ile Leu Tyr Pro Val Ser Ala Arg Ser Ala Leu Glu Ala
        515                 520                 525

Lys Leu Ser Thr Ala Ser Leu Val Gly Arg Asp Asp Leu Glu Ile Ala
    530                 535                 540

Asp Pro Gly Ser Asn Trp Arg Val Gln Ser Phe Asn Glu Leu Glu Lys
545                 550                 555                 560

Phe Leu Tyr Ser Phe Leu Asp Ser Ser Thr Ala Thr Gly Met Glu Arg
                565                 570                 575

Ile Arg Leu Lys Leu Glu Thr Pro Met Ala Ile Ala Glu Arg Leu Leu
            580                 585                 590

Ser Ser Val Glu Ala Leu Val Arg Gln Asp Cys Leu Ala Ala Arg Glu
        595                 600                 605

Asp Leu Ala Ser Ala Asp Lys Ile Ile Ser Arg Thr Lys Glu Tyr Ala
    610                 615                 620
```

Leu Lys Met Glu Tyr Glu Ser Ile Ser Trp Arg Arg Gln Ala Leu Ser
625 630 635 640

Leu Val

<210> SEQ ID NO 22
<211> LENGTH: 6060
<212> TYPE: DNA
<213> ORGANISM: Arabidopsis thaliana

<400> SEQUENCE: 22
actgtcacaa agaactagaa aaggcaagca aaactcaact atgtcaaaag tgtcacttag 60
attgattctt gaatagcgag acgaagtatc tgggaaaata cggtactgaa ttaacatctc 120
cgtcagatca taggttcgga ttgaacagat gacacaatta aacaatgatg aagatcaaga 180
cactttaatc gactgaattc tagttagaac ttagactaaa agtatttaat acttgaagct 240
caccacttct cgaatatctt gttccaatcg ttttgatgtg gttccggcac tcaagttctg 300
tattgttttc aagctgactt tatcagtttt ctgaagtaag tcatatgtgt ctatgcccaa 360
ttgcgttttt gaattgacat atgttggcca tttgttttcg aatgatttca gagacagact 420
cccttcacgg gcagtatttg attgtagcca ttcagcatat tttccaagca attcctgcaa 480
acagtgaaat gtaaagtcaa tcaggtcaca acaagacatt gttagacaat atttactttc 540
tgcatgaata gtgactatat ctcagacctc atatatatga ccaacatgtc cccagttagg 600
ccaatactca aagaataaag catcacactt actttcgcat ttgtgagtgc tggagcgagt 660
atttcacctt gaactttgga tgtagctgct actgaggccg atttttcccc tttgaacacg 720
tacgagatcg caagatcaag gcttgatagt cgcagggtag ttcctatcag atcaacaact 780
tgtaatctgg cattatcaat ctgcgataaa agccagagta caaaacacaa aaaagccaag 840
ttagaacaat ccaatttcct ccttcgtgat tcaacaagat aatatctaat agaatttata 900
ccaacgagag agcctgcctt ctccaagaaa tgctctcata ttccatctta agcgcgtatt 960
ctttagttcg actgataatc ttgtctgctg aagccaagtc ttccctagca gctaggcaat 1020
cttgtctcac aagagcttcc acagaagaaa ggagacgctc agcaatcgcc atgggtgtct 1080
ccaatttaag ccttattctc tccatcccgg tagctgttga gctatccaag aagctataaa 1140
gaaatttctc aagttcattg aagctctgga ctctccaatt agaaccagga tctgcgatct 1200
caagatcatc tctgccaacc aaagaagctg ttgaaagctt cgcctcaaga gcagaccgtg 1260
cggacaccgg atacaatatc acattttctg tattaagcaa cttccgtgta ttctctttaa 1320
caaatgaaat agcttcctca agctgcagca gtaaaattaa tctttagtca agaaaaatcc 1380
agcaattaca gagactatca aggaaaagac ataaatattg tttctgataa acctcacgag 1440
catcacgata gatatcagat ttattcagaa taaacacaaa tttctttttc cactgctgtg 1500
tgtaccggag aaacgcaacc tgacaaacgc aatgagatgt aaatcagcct acagtaaaat 1560
caagacagca ggaagctcca gaggtagaga tagaaatgac atgggtatga tgacattgag 1620
aagcttattc cttcttttga aactttttca gattttcaaa ataagaacca aatattcata 1680
aggttagtac ttcgtagatg atcatttaca tacaatttgc catggacgta aaatcagttt 1740
tgctgtacca ataacaactc acctctcaaa tgtattggcc taagctttac caaaatatgg 1800
accaacagga catactggtt ccagcaatag ctataacact cattactttg aaaataaatt 1860
agtctagttt aaatttataa tcaacaaaac cttgatatat gcattcaacc tagtgacaac 1920
tttcccttcc ctacacaagg tcttgatggt ctatacatga cttaactaac tactttcgtg 1980

-continued

```
aaaaatagat ctaacaagct acttaggcag atacatattg agcaaaaaca acaacaacta   2040
acatgccaag taaaacggta acttctacct cactttcagt taaagggcgg tcagcagaaa   2100
gaacaaaaac aagcaaatct gcacgtggaa caaattcttc tgtaagacgc tgttgccttt   2160
gaaggatcac attggtccca ggtgtgtcaa caatatttat ctgctcgaaa ggagaacaac   2220
ccaaatcaat tcctccaaat aattagtaaa aattcaggac tgcgatggta gaattttgaa   2280
ttactcacat ccttaagtat tggtgcagga agatagcata catattggcc atctggatgt   2340
gtttggcaac gttgttgctc ttcggattcc aagtcagagt agcacagaaa cgtgatttca   2400
ttggtagtgg ggactacccc ttctttcagg tatctcttcc caagaagtgc attgataacc   2460
gttgattttc cagagttaaa ttccccctag taccagcaaa ttgtggattc caattaatta   2520
tccatacaaa aactattttg aatcataaag gcaacttgtc ccacttaaaa catcttccaa   2580
gaacggcata ctcacaagtc acaagaaagc gaaaaaacta tgtacacaag cagatggtac   2640
agttaagaaa tatgcagttc ccttacaacc agatccataa gcaaattaag aagagaagca   2700
tagacagaac aaaagaagaa gcgaaacatc atagtcatag gcgacgaaag aagatattga   2760
gaagcactaa aggacaagtg actagaagca tgcccattgt atctcaagct atctagtgct   2820
ggcaaaagtg tgtaactaaa atgtttctgg aatgaatata gagctaatac caatgcaaat   2880
tcctggaatc acaatttgac ggagttgagt gcagaattac cactataacc atcagaaacg   2940
gctcatcgat ccgagaaaca gcatcaatta gaagggagac ttcctccatc tgttaatgaa   3000
aaatagtcga agaagtaaat gaaaccatat tataaccaca caaaaaccta cttagaacca   3060
tttcaaaaaa ttgacttcaa ctaccaaatg tttgaaataa aaatcaccag tggagccgcc   3120
ttgtggatga tttcaatcgt ctctctcaac acagatttct ccatttctac tattagtttc   3180
tgtttgtcct ctaattttat gaagccagca gaattctttt tctccggcag ttcattcata   3240
ttttgtgtct catgattatt tacaacataa gctccatcaa gactctggcg aagagctaca   3300
tccctagaag aacgcaaatc tttcaacgaa ataacaaaac cagaaacacc tgatttcagt   3360
aactgcaatt cttctttagc ttcttcattg cctctgcaag tcacatatat cggtattttc   3420
acgctcttca acaaagaatc cgccacttgc gtatcttctt caccagatcc aagtataagg   3480
aaatcagcac cctcggagct tgaggcaatt agagcagaat caacatcctt cacaatccga   3540
gctaccagtg gaagaagtac cgagtcgggg ttggatccca tcaatgtgtt tctcgccaca   3600
atcgccggaa gacctgtaca tagcattgag agacaaaact cactctatga gaaattaaat   3660
gctaaaactg aatgaaatca gttgttacct tcgtcggaga gagcaacacc actagcacca   3720
acggcggagg cgatatcaac acgttcagcg atcaagaggt aagcacggcc tttgacaagt   3780
gatttcagca aacaagccgc ctcgtagagc ttaccagcgg tggctccgcc atcaatcacg   3840
acgatttgaa ccgatttagc taaagcacgg tcgaccaaat caagagtctc ttcacgattc   3900
ccgctcataa cctcgtcggc gtctagccgg agaagtaaac cgggaacggc gagttcggga   3960
cgcttgtaac caccaggata aagagttcgc ggcctagaag aagaagtctg atcggcggat   4020
tcatgcgaaa tgtttctgat cgagagagaa gaaaaacgcc tatgacgtgg aggagtaaag   4080
gaggataact taaagcaccg gccaggaaac ggtggagatg cggcggagat aagaaacggt   4140
gacgtcacac attgccggtg agagattaga gttctcatgg agagagaaag agagagagtg   4200
agataccttc gtctgtgttt ctgattagtt ttcttatctc ttaaatatcc tattggccca   4260
tcccaaagct ataagacgga cggcgcgatt aattactttt caaacacatg aattaacgtt   4320
```

-continued

```
ttcacatatg tgttcatatc caaaaggtcc aaagtatacc acgaaaaggg agaaaaacag   4380

atttaaattc gtgaaatccc tctcccacaa ttaaatttac ttcttccaaa caaagacaaa   4440

cggcttgaac cagtcaagta agtgatacgg caccactaga tgttccagag cctccatctt   4500

ttttaatacg aagaagattt gtcctttgtg tgtatgaatt taacaagttt taattataga   4560

tttgtgtgtg tatgaattta aaaacctagt acgtagcatc agggaatgat atcatagcta   4620

ttttagttga gctttcaaat aagagatgat caaaatttag aacttctaag aacatgaacg   4680

aataaacaac tattttcttt tcaaaccaac taaggtagat ggtcactgaa agtatataca   4740

tcagataaaa gttgcttgtt attccagatg aagttggacc gagaaaaaaa aaagttactt   4800

gttattcaat atgtttggat ctttgtcttg cagattgcta tatagggttg ataatgggct   4860

tcgttgtaat gggtatacag tgtataagaa tcggccttgt gcaaccaatc ctaatatgtg   4920

tgtctcatta aggtaagtgc ttaagattag aagagtaaaa cacttgactt atcaactatg   4980

tcaactaagg gttctatatt tttattaaat aaaaaataat tgaatatttt ttagaatgat   5040

ttaataaatt taatgctatt gtttgattta aatgtataat tcaccgcgag aagaaatttt   5100

ataactcaaa ttttaaagtt ttaagttgta tttgtttatt ttgttaaatg tttaatattg   5160

tataattgta ttttgattgt tgtttctcgg atttcacccg tagtacatca tcccatatta   5220

atatcgaatc aaacccgtca attctaaaat ttcacccgtg gtagtattta attgtataat   5280

tatattttaa ttgtcattct aagatttcac tcctaattct atcgcaaatt attatcaacc   5340

caaaccagtc aattctaaaa tatcacccgt agtacaccat cccatattaa tatcgaatca   5400

agcccgtcaa ttctaggatt tcacccgtgg tagtatttaa ttgtataatt atattttaat   5460

tgtcattcta ggatttcact cctaattcta tcgcaaatta ttatcaaccc aaaccagtca   5520

attctaaaat atcacccgta gtacaccatc ccatattaat atcgattcaa actcgtcaat   5580

tctaggattt cgctcgtggt agtatttaat tgtataatta tattttaatt gtcattttaa   5640

ctcctagttc tatcgcaaat tcttatcaac ccaaacagtc aattctaaaa tttcacccgt   5700

agtataaagt ttaaatattt ataatattta aatttcttat aaaagaatca aaatgtgttt   5760

taaaaaaatt aaagttttaa gttttttttt tttaatattg ttaattttgt ttagtgttta   5820

agattatata attacattat gattgtcatt atatgttttt ctccatagca tactatccca   5880

tgttattatc cactcaaacc tgtcacacca tataaccccg tcccgtgaaa ttaaacacaa   5940

atttgtcatt ttattataaa tttcaaatat ttataaaatt agaaacttca aaaaagatta   6000

atattgaccc aaacttcatc attgaatttt gagtgttata tctaagattt ctctcgcaat   6060
```

<210> SEQ ID NO 23
<211> LENGTH: 2469
<212> TYPE: DNA
<213> ORGANISM: Arabidopsis thaliana

<400> SEQUENCE: 23

```
atggaggctc tggaacatct agtgctttgg gatgggccaa taggatattt aagagataag     60

aaaactaatc agaaacacag acgaaggtat ctcactctct ctctttctct ctccatgaga    120

actctaatct ctcaccggca atgtgtgacg tcaccgtttc ttatctccgc cgcatctcca    180

ccgtttcctg gccggtgctt taagttatcc tcctttactc ctccacgtca taggcgtttt    240

tcttctctct cgatcagaaa catttcgcat gaatccgccg atcagacttc ttcttctagg    300

ccgcgaactc tttatcctgg tggttacaag cgtcccgaac tcgccgttcc cggtttactt    360

ctccggctag acgccgacga ggttatgagc gggaatcgtg aagagactct tgatttggtc    420
```

-continued

```
gaccgtgctt tagctaaatc ggttcaaatc gtcgtgattg atggcggagc caccgctggt    480
aagctctacg aggcggcttg tttgctgaaa tcacttgtca aaggccgtgc ttacctcttg    540
atcgctgaac gtgttgatat cgcctccgcc gttggtgcta gtggtgttgc tctctccgac    600
gaaggtcttc cggcgattgt ggcgagaaac acattgatgg gatccaaccc cgactcggta    660
cttcttccac tggtagctcg gattgtgaag gatgttgatt ctgctctaat tgcctcaagc    720
tccgagggtg ctgatttcct tatacttgga tctggtgaag aagatacgca agtggcggat    780
tctttgttga agagcgtgaa aataccgata tatgtgactt gcagaggcaa tgaagaagct    840
aaagaagaat tgcagttact gaaatcaggt gtttctggtt ttgttatttc gttgaaagat    900
ttgcgttctt ctagggatgt agctcttcgc cagagtcttg atggagctta tgttgtaaat    960
aatcatgaga cacaaaatat gaatgaactg ccggagaaaa agaattctgc tggcttcata   1020
aaattagagg acaaacagaa actaatagta gaaatggaga aatctgtgtt gagagagacg   1080
attgaaatca tccacaaggc ggctccactg atggaggaag tctcccttct aattgatgct   1140
gtttctcgga tcgatgagcc gtttctgatg gttatagtgg gggaatttaa ctctggaaaa   1200
tcaacggtta tcaatgcact tcttgggaag agatacctga aagaaggggt agtccccact   1260
accaatgaaa tcacgtttct gtgctactct gacttggaat ccgaagagca acaacgttgc   1320
caaacacatc cagatggcca atatataaat attgttgaca cacctgggac caatgtgatc   1380
cttcaaaggc aacagcgtct tacagaagaa tttgttccac gtgcagattt gcttgttttt   1440
gttctttctg ctgaccgccc tttaactgaa agtgaggtag aagttaccgt tttacttggc   1500
atggaaggga aagttgtcac taggttgaat gcatatatca aggttgcgtt tctccggtac   1560
acacagcagt ggaaaaagaa atttgtgttt attctgaata aatctgatat ctatcgtgat   1620
gctcgtgagc ttgaggaagc tatttcattt gttaaagaga atacacggaa gttgcttaat   1680
acagaaaatg tgatattgta tccggtgtcc gcacggtctg ctcttgaggc gaagctttca   1740
acagcttctt tggttggcag agatgatctt gagatcgcag atcctggttc taattggaga   1800
gtccagagct tcaatgaact tgagaaattt ctttatagct tcttggatag ctcaacagct   1860
accgggatgg agagaataag gcttaaattg gagacaccca tggcgattgc tgagcgtctc   1920
ctttcttctg tggaagctct tgtgagacaa gattgcctag ctgctaggga agacttggct   1980
tcagcagaca agattatcag tcgaactaaa gaatacgcgc ttaagatgga atatgagagc   2040
atttcttgga gaaggcaggc tctctcgttg attgataatg ccagattaca agttgttgat   2100
ctgataggaa ctaccctgcg actatcaagc cttgatcttg cgatctcgta cgtgttcaaa   2160
ggggaaaaat cggcctcagt agcagctaca tccaaagttc aaggtgaaat actcgctcca   2220
gcactcacaa atgcgaaaga attgcttgga aaatatgctg aatggctaca atcaaatact   2280
gcccgtgaag ggagtctgtc tctgaaatca ttcgaaaaca aatggccaac atatgtcaat   2340
tcaaaaacgc aattgggcat agacacatat gacttacttc agaaaactga taaagtcagc   2400
ttgaaaacaa tacagaactt gagtgccgga accacatcaa aacgattgga acaagatatt   2460
cgagaagtg                                                           2469
```

<210> SEQ ID NO 24
<211> LENGTH: 823
<212> TYPE: PRT
<213> ORGANISM: Arabidopsis thaliana

<400> SEQUENCE: 24

-continued

```
Met Glu Ala Leu Glu His Leu Val Leu Trp Asp Gly Pro Ile Gly Tyr
1               5                   10                  15

Leu Arg Asp Lys Lys Thr Asn Gln Lys His Arg Arg Arg Tyr Leu Thr
            20                  25                  30

Leu Ser Leu Ser Leu Ser Met Arg Thr Leu Ile Ser His Arg Gln Cys
        35                  40                  45

Val Thr Ser Pro Phe Leu Ile Ser Ala Ala Ser Pro Pro Phe Pro Gly
    50                  55                  60

Arg Cys Phe Lys Leu Ser Ser Phe Thr Pro Pro Arg His Arg Arg Phe
65                  70                  75                  80

Ser Ser Leu Ser Ile Arg Asn Ile Ser His Glu Ser Ala Asp Gln Thr
                85                  90                  95

Ser Ser Ser Arg Pro Arg Thr Leu Tyr Pro Gly Gly Tyr Lys Arg Pro
            100                 105                 110

Glu Leu Ala Val Pro Gly Leu Leu Leu Arg Leu Asp Ala Asp Glu Val
        115                 120                 125

Met Ser Gly Asn Arg Glu Glu Thr Leu Asp Leu Val Asp Arg Ala Leu
    130                 135                 140

Ala Lys Ser Val Gln Ile Val Val Ile Asp Gly Gly Ala Thr Ala Gly
145                 150                 155                 160

Lys Leu Tyr Glu Ala Ala Cys Leu Leu Lys Ser Leu Val Lys Gly Arg
                165                 170                 175

Ala Tyr Leu Leu Ile Ala Glu Arg Val Asp Ile Ala Ser Ala Val Gly
            180                 185                 190

Ala Ser Gly Val Ala Leu Ser Asp Glu Gly Leu Pro Ala Ile Val Ala
        195                 200                 205

Arg Asn Thr Leu Met Gly Ser Asn Pro Asp Ser Val Leu Leu Pro Leu
    210                 215                 220

Val Ala Arg Ile Val Lys Asp Val Asp Ser Ala Leu Ile Ala Ser Ser
225                 230                 235                 240

Ser Glu Gly Ala Asp Phe Leu Ile Leu Gly Ser Gly Glu Glu Asp Thr
                245                 250                 255

Gln Val Ala Asp Ser Leu Leu Lys Ser Val Lys Ile Pro Ile Tyr Val
            260                 265                 270

Thr Cys Arg Gly Asn Glu Glu Ala Lys Glu Glu Leu Gln Leu Leu Lys
        275                 280                 285

Ser Gly Val Ser Gly Phe Val Ile Ser Leu Lys Asp Leu Arg Ser Ser
    290                 295                 300

Arg Asp Val Ala Leu Arg Gln Ser Leu Asp Gly Ala Tyr Val Val Asn
305                 310                 315                 320

Asn His Glu Thr Gln Asn Met Asn Glu Leu Pro Glu Lys Lys Asn Ser
                325                 330                 335

Ala Gly Phe Ile Lys Leu Glu Asp Lys Gln Lys Leu Ile Val Glu Met
            340                 345                 350

Glu Lys Ser Val Leu Arg Glu Thr Ile Glu Ile Ile His Lys Ala Ala
        355                 360                 365

Pro Leu Met Glu Glu Val Ser Leu Leu Ile Asp Ala Val Ser Arg Ile
    370                 375                 380

Asp Glu Pro Phe Leu Met Val Ile Val Gly Glu Phe Asn Ser Gly Lys
385                 390                 395                 400

Ser Thr Val Ile Asn Ala Leu Leu Gly Lys Arg Tyr Leu Lys Glu Gly
                405                 410                 415

Val Val Pro Thr Thr Asn Glu Ile Thr Phe Leu Cys Tyr Ser Asp Leu
```

-continued

```
            420                 425                 430

Glu Ser Glu Glu Gln Gln Arg Cys Gln Thr His Pro Asp Gly Gln Tyr
        435                 440                 445

Ile Asn Ile Val Asp Thr Pro Gly Thr Asn Val Ile Leu Gln Arg Gln
    450                 455                 460

Gln Arg Leu Thr Glu Glu Phe Val Pro Arg Ala Asp Leu Leu Val Phe
465                 470                 475                 480

Val Leu Ser Ala Asp Arg Pro Leu Thr Glu Ser Glu Val Glu Val Thr
                485                 490                 495

Val Leu Leu Gly Met Glu Gly Lys Val Val Thr Arg Leu Asn Ala Tyr
            500                 505                 510

Ile Lys Val Ala Phe Leu Arg Tyr Thr Gln Gln Trp Lys Lys Lys Phe
        515                 520                 525

Val Phe Ile Leu Asn Lys Ser Asp Ile Tyr Arg Asp Ala Arg Glu Leu
    530                 535                 540

Glu Glu Ala Ile Ser Phe Val Lys Glu Asn Thr Arg Lys Leu Leu Asn
545                 550                 555                 560

Thr Glu Asn Val Ile Leu Tyr Pro Val Ser Ala Arg Ser Ala Leu Glu
                565                 570                 575

Ala Lys Leu Ser Thr Ala Ser Leu Val Gly Arg Asp Asp Leu Glu Ile
            580                 585                 590

Ala Asp Pro Gly Ser Asn Trp Arg Val Gln Ser Phe Asn Glu Leu Glu
        595                 600                 605

Lys Phe Leu Tyr Ser Phe Leu Asp Ser Ser Thr Ala Thr Gly Met Glu
    610                 615                 620

Arg Ile Arg Leu Lys Leu Glu Thr Pro Met Ala Ile Ala Glu Arg Leu
625                 630                 635                 640

Leu Ser Ser Val Glu Ala Leu Val Arg Gln Asp Cys Leu Ala Ala Arg
                645                 650                 655

Glu Asp Leu Ala Ser Ala Asp Lys Ile Ile Ser Arg Thr Lys Glu Tyr
            660                 665                 670

Ala Leu Lys Met Glu Tyr Glu Ser Ile Ser Trp Arg Arg Gln Ala Leu
        675                 680                 685

Ser Leu Ile Asp Asn Ala Arg Leu Gln Val Val Asp Leu Ile Gly Thr
    690                 695                 700

Thr Leu Arg Leu Ser Ser Leu Asp Leu Ala Ile Ser Tyr Val Phe Lys
705                 710                 715                 720

Gly Glu Lys Ser Ala Ser Val Ala Ala Thr Ser Lys Val Gln Gly Glu
                725                 730                 735

Ile Leu Ala Pro Ala Leu Thr Asn Ala Lys Glu Leu Leu Gly Lys Tyr
            740                 745                 750

Ala Glu Trp Leu Gln Ser Asn Thr Ala Arg Glu Gly Ser Leu Ser Leu
        755                 760                 765

Lys Ser Phe Glu Asn Lys Trp Pro Thr Tyr Val Asn Ser Lys Thr Gln
    770                 775                 780

Leu Gly Ile Asp Thr Tyr Asp Leu Leu Gln Lys Thr Asp Lys Val Ser
785                 790                 795                 800

Leu Lys Thr Ile Gln Asn Leu Ser Ala Gly Thr Thr Ser Lys Arg Leu
                805                 810                 815

Glu Gln Asp Ile Arg Glu Val
            820
```

<210> SEQ ID NO 25

<211> LENGTH: 2037
<212> TYPE: DNA
<213> ORGANISM: Arabidopsis thaliana

<400> SEQUENCE: 25

```
acaaagacca gttaaaaacg tgtgtagtat aacttactgg taagtaaagc tataagcaag     60
aatctgtacc ttattttctc tctctctagt gagccctgac catccgaatt tcgcattcgc    120
caatcgctgt gtttccgtgt gttttccccc tttttggttt tagatttgcc taaaccaatc    180
agaacaagag aaacctggaa acaagaacca aaaaaagtgg gctttctctg catcatcatt    240
ccacttctgg tccccaactg aaaaggacaa tccaaagcta gatcccttca aattttcctt    300
tttgttttcg aaattttcgc aatttttaat attattttgg aagtctatgt ttctttctga    360
tctttagcaa caaaggaagg tggaatctgt ttcacgttta cacaaaaaca tgtcaactgg    420
agattttctc tttccctaac ttttgaccat acagtatggt ccatacttaa tattctctct    480
ttgtttttaa taaaataaaa ggtttggtta tcaagcatat atgtcattag cttaaagcta    540
tgactttgtt tagaaaactt aggaggacca tatggcaagc ttttatacag tgttagactt    600
ctaacgttaa ttctaaacaa tctccagtat caagcattaa caaggtttat tctagcacct    660
ctggattttt aaaacttctc gaaccaatcc ttaactaaaa aagaaattca agcgttttat    720
ctttagaaat cacagctagc atatgctgag aattactctc catggaaact tatactaaga    780
ttgttttttt ccctcatatt taagccacta aagtcaaaag attagtacat tgacaactaa    840
gtttagatgc tctatgcgga gaatcaattt catatgaatg tatcaagcaa ttcatgaact    900
ctaggagacc ataaaatcca attgacagaa aaaatgagtc aactaacata tttacctgtg    960
atatgaggta catgtgcagg tcaaagatca gaagaaaatt ttctccatga gtctcttgag   1020
cttccaactc atccagcgat ttgtatcaca aacaatctga aaaagaagct aaaaaaacgtt   1080
ataccaaagt ttcacgccca taatgctatt gtttggttct ttcaagaacc tccccaatct   1140
tttgaattcg cattcaaaaa aaccatcagt gagtccattt caagtcggaa ctggcaggta   1200
ttattcatta tgacaaagta catacacttg ccccccactg aacaatgtca agaagggaaa   1260
acccgacatt gtgttggaat agctaaagtc tcatctcgtc tcgtgataca tgaaggttat   1320
caatatcaac ttgtagcaac tgtaatttac ttctaatatc tgataattct ttctggattc   1380
ctaaaagacg atcaagtctt agctgagctt cttctcgata aggcttggca acaatattca   1440
caaagttaac tagattactc gtcgcatctg aaagatcttt ttgcatagcg tcttcgagct   1500
gttgagccaa cgcatcagcc actttattca ccttaccaat tatagcctgt cttcgatatg   1560
ggaagtttgc tatagccaca tacctgtcac atagattatg ttatgcatac aaccagtctt   1620
tcttaaaagt cataaatatg cctctagttg caagaaaaaa atacactagg cgtgatctaa   1680
gaaggtggag taatgagaca ttgggaagag gggaaattta gagcagtgtt attaccctcc   1740
agcggagcaa aggccaagag caagaagatc ttccagtgtg gtcggtagca ctgaggttag   1800
aagtgatgca gacagtcctg cagctccaag cccaccaact gtcacaaaga actagaaaag   1860
gcaagcaaaa ctcaactatg tcaaaagtgt cacttagatt gattcttgaa tagcgagacg   1920
aagtatctgg gaaaatacgg tactgaatta acatctccgt cagatcatag gttcggattg   1980
aacagatgac acaattaaac aatgatgaag atcaagacac tttaatcgac tgaattc      2037
```

<210> SEQ ID NO 26
<211> LENGTH: 2097
<212> TYPE: DNA
<213> ORGANISM: Arabidopsis thaliana

<400> SEQUENCE: 26

```
aaaaactttt caaaacttca tgtgttgtga aaacaaaagt tttttggtaa tgaaaactcg     60
acaaagacca gttaaaaacg tgtgtagtat aacttactgg taagtaaagc tataagcaag    120
aatctgtacc ttattttctc tctctctagt gagccctgac catccgaatt tcgcattcgc    180
caatcgctgt gtttccgtgt gttttccccc tttttggttt tagatttgcc taaaccaatc    240
agaacaagag aaacctggaa acaagaacca aaaaaagtgg gctttctctg catcatcatt    300
ccacttctgg tccccaactg aaaaggacaa tccaaagcta gatcccttca aattttcctt    360
tttgttttcg aaattttcgc aatttttaat attattttgg aagtctatgt ttctttctga    420
tctttagcaa caaaggaagg tggaatctgt ttcacgttta cacaaaaaca tgtcaactgg    480
agattttctc tttccctaac ttttgaccat acagtatggt ccatacttaa tattctctct    540
ttgtttttaa taaaataaaa ggtttggtta tcaagcatat atgtcattag cttaaagcta    600
tgactttgtt tagaaaactt aggaggacca tatggcaagc ttttatacag tgttagactt    660
ctaacgttaa ttctaaacaa tctccagtat caagcattaa caaggtttat tctagcacct    720
ctggattttt aaaacttctc gaaccaatcc ttaactaaaa aagaaattca agcgttttat    780
ctttagaaat cacagctagc atatgctgag aattactctc catggaaact tatactaaga    840
ttgttttttt ccctcatatt taagccacta aagtcaaaag attagtacat tgacaactaa    900
gtttagatgc tctatgcgga gaatcaattt catatgaatg tatcaagcaa ttcatgaact    960
ctaggagacc ataaaatcca attgacagaa aaaatgagtc aactaacata tttacctgtg   1020
atatgaggta catgtgcagg tcaaagatca gaagaaaatt ttctccatga gtctcttgag   1080
cttccaactc atccagcgat ttgtatcaca aacaatctga aaaagaagct aaaaaaacgtt  1140
ataccaaagt ttcacgccca taatgctatt gtttggttct ttcaagaacc tccccaatct   1200
tttgaattcg cattcaaaaa aaccatcagt gagtccattt caagtcggaa ctggcaggta   1260
ttattcatta tgacaaagta catacacttg ccccccactg aacaatgtca agaagggaaa   1320
acccgacatt gtgttggaat agctaaagtc tcatctcgtc tcgtgataca tgaaggttat   1380
caatatcaac ttgtagcaac tgtaatttac ttctaatatc tgataattct ttctggattc   1440
ctaaaagacg atcaagtctt agctgagctt cttctcgata aggcttggca acaatattca   1500
caaagttaac tagattactc gtcgcatctg aaagatcttt ttgcatagcg tcttcgagct   1560
gttgagccaa cgcatcagcc actttattca ccttaccaat tatagcctgt cttcgatatg   1620
ggaagtttgc tatagccaca tacctgtcac atagattatg ttatgcatac aaccagtctt   1680
tcttaaaagt cataaatatg cctctagttg caagaaaaaa atacactagg cgtgatctaa   1740
gaaggtggag taatgagaca ttgggaagag gggaaattta gagcagtgtt attaccctcc   1800
agcggagcaa aggccaagag caagaagatc ttccagtgtg gtcggtagca ctgaggttag   1860
aagtgatgca gacagtcctg cagctccaag cccaccaact gtcacaaaga actagaaaag   1920
gcaagcaaaa ctcaactatg tcaaaagtgt cacttagatt gattcttgaa tagcgagacg   1980
aagtatctgg gaaaatacgg tactgaatta acatctccgt cagatcatag gttcggattg   2040
aacagatgac acaattaaac aatgatgaag atcaagacac tttaatcgac tgaattc      2097
```

<210> SEQ ID NO 27
<211> LENGTH: 6400
<212> TYPE: DNA
<213> ORGANISM: Arabidopsis thaliana

<400> SEQUENCE: 27

```
tagttagaac ttagactaaa agtatttaat acttgaagct caccacttct cgaatatctt     60
gttccaatcg ttttgatgtg gttccggcac tcaagttctg tattgttttc aagctgactt    120
tatcagtttt ctgaagtaag tcatatgtgt ctatgcccaa ttgcgttttt gaattgacat    180
atgttggcca tttgttttcg aatgatttca gagacagact cccttcacgg gcagtatttg    240
attgtagcca ttcagcatat tttccaagca attcctgcaa acagtgaaat gtaaagtcaa    300
tcaggtcaca acaagacatt gttagacaat atttactttc tgcatgaata gtgactatat    360
ctcagacctc atatatatga ccaacatgtc cccagttagg ccaatactca aagaataaag    420
catcacactt actttcgcat ttgtgagtgc tggagcgagt atttcacctt gaactttgga    480
tgtagctgct actgaggccg atttttcccc tttgaacacg tacgagatcg caagatcaag    540
gcttgatagt cgcagggtag ttcctatcag atcaacaact tgtaatctgg cattatcaat    600
ctgcgataaa agccagagta caaaacacaa aaaagccaag ttagaacaat ccaatttcct    660
ccttcgtgat tcaacaagat aatatctaat agaatttata ccaacgagag agcctgcctt    720
ctccaagaaa tgctctcata ttccatctta agcgcgtatt ctttagttcg actgataatc    780
ttgtctgctg aagccaagtc ttccctagca gctaggcaat cttgtctcac aagagcttcc    840
acagaagaaa ggagacgctc agcaatcgcc atgggtgtct ccaatttaag ccttattctc    900
tccatcccgg tagctgttga gctatccaag aagctataaa gaaatttctc aagttcattg    960
aagctctgga ctctccaatt agaaccagga tctgcgatct caagatcatc tctgccaacc   1020
aaagaagctg ttgaaagctt cgcctcaaga gcagaccgtg cggacaccgg atacaatatc   1080
acattttctg tattaagcaa cttccgtgta ttctctttaa caaatgaaat agcttcctca   1140
agctgcagca gtaaaattaa tctttagtca agaaaaatcc agcaattaca gagactatca   1200
aggaaaagac ataaatattg tttctgataa acctcacgag catcacgata gatatcagat   1260
ttattcagaa taaacacaaa tttctttttc cactgctgtg tgtaccggag aaacgcaacc   1320
tgacaaacgc aatgagatgt aaatcagcct acagtaaaat caagacagca ggaagctcca   1380
gaggtagaga tagaaatgac atgggtatga tgacattgag aagcttattc cttcttttga   1440
aactttttca gatttcaaa ataagaacca aatattcata aggttagtac ttcgtagatg   1500
atcatttaca tacaatttgc catggacgta aaatcagttt tgctgtacca ataacaactc   1560
acctctcaaa tgtattggcc taagctttac caaaatatgg accaacagga catactggtt   1620
ccagcaatag ctataacact cattactttg aaaataaatt agtctagttt aaatttataa   1680
tcaacaaaac cttgatatat gcattcaacc tagtgacaac tttcccttcc ctacacaagg   1740
tcttgatggt ctatacatga cttaactaac tactttcgtg aaaaatagat ctaacaagct   1800
acttaggcag atacatattg agcaaaaaca acaacaacta acatgccaag taaaacggta   1860
acttctacct cactttcagt taaagggcgg tcagcagaaa gaacaaaaac aagcaaatct   1920
gcacgtggaa caaattcttc tgtaagacgc tgttgccttt gaaggatcac attggtccca   1980
ggtgtgtcaa caatatttat ctgctcgaaa ggagaacaac ccaaatcaat tcctccaaat   2040
aattagtaaa aattcaggac tgcgatggta gaattttgaa ttactcacat ccttaagtat   2100
tggtgcagga agatagcata catattggcc atctggatgt gtttggcaac gttgttgctc   2160
ttcggattcc aagtcagagt agcacagaaa cgtgatttca ttggtagtgg ggactacccc   2220
ttctttcagg tatctcttcc caagaagtgc attgataacc gttgattttc cagagttaaa   2280
ttccccctag taccagcaaa ttgtggattc caattaatta tccatacaaa aactattttg   2340
```

-continued

```
aatcataaag gcaacttgtc ccacttaaaa catcttccaa gaacggcata ctcacaagtc   2400
acaagaaagc gaaaaaacta tgtacacaag cagatggtac agttaagaaa tatgcagttc   2460
ccttacaacc agatccataa gcaaattaag aagagaagca tagacagaac aaaagaagaa   2520
gcgaaacatc atagtcatag gcgacgaaag aagatattga gaagcactaa aggacaagtg   2580
actagaagca tgcccattgt atctcaagct atctagtgct ggcaaaagtg tgtaactaaa   2640
atgtttctgg aatgaatata gagctaatac caatgcaaat tcctggaatc acaatttgac   2700
ggagttgagt gcagaattac cactataacc atcagaaacg gctcatcgat ccgagaaaca   2760
gcatcaatta gaagggagac ttcctccatc tgttaatgaa aaatagtcga agaagtaaat   2820
gaaaccatat tataaccaca caaaaaccta cttagaacca tttcaaaaaa ttgacttcaa   2880
ctaccaaatg tttgaaataa aaatcaccag tggagccgcc ttgtggatga tttcaatcgt   2940
ctctctcaac acagatttct ccatttctac tattagtttc tgtttgtcct ctaattttat   3000
gaagccagca gaattctttt tctccggcag ttcattcata ttttgtgtct catgattatt   3060
tacaacataa gctccatcaa gactctggcg aagagctaca tccctagaag aacgcaaatc   3120
tttcaacgaa ataacaaaac cagaaacacc tgatttcagt aactgcaatt cttctttagc   3180
ttcttcattg cctctgcaag tcacatatat cggtattttc acgctcttca acaaagaatc   3240
cgccacttgc gtatcttctt caccagatcc aagtataagg aaatcagcac cctcggagct   3300
tgaggcaatt agagcagaat caacatcctt cacaatccga gctaccagtg gaagaagtac   3360
cgagtcgggg ttggatccca tcaatgtgtt tctcgccaca atcgccggaa gacctgtaca   3420
tagcattgag agacaaaact cactctatga gaaattaaat gctaaaactg aatgaaatca   3480
gttgttacct tcgtcggaga gagcaacacc actagcacca acggcggagg cgatatcaac   3540
acgttcagcg atcaagaggt aagcacggcc tttgacaagt gatttcagca aacaagccgc   3600
ctcgtagagc ttaccagcgg tggctccgcc atcaatcacg acgatttgaa ccgatttagc   3660
taaagcacgg tcgaccaaat caagagtctc ttcacgattc ccgctcataa cctcgtcggc   3720
gtctagccgg agaagtaaac cgggaacggc gagttcggga cgcttgtaac caccaggata   3780
aagagttcgc ggcctagaag aagaagtctg atcggcggat tcatgcgaaa tgtttctgat   3840
cgagagagaa gaaaaacgcc tatgacgtgg aggagtaaag gaggataact taaagcaccg   3900
gccaggaaac ggtggagatg cggcggagat aagaaacggt gacgtcacac attgccggtg   3960
agagattaga gttctcatgg agagagaaag agagagagtg agataccttc gtctgtgttt   4020
ctgattagtt ttcttatctc ttaaatatcc tattggccca tcccaaagct ataagacgga   4080
cggcgcgatt aattactttt caaacacatg aattaacgtt ttcacatatg tgttcatatc   4140
caaaaggtcc aaagtatacc acgaaaaggg agaaaaacag atttaaattc gtgaaatccc   4200
tctcccacaa ttaaatttac ttcttccaaa caaagacaaa cggcttgaac cagtcaagta   4260
agtgatacgg caccactaga tgttccagag cctccatctt ttttaatacg aagaagattt   4320
gtcctttgtg tgtatgaatt taacaagttt taattataga tttgtgtgtg tatgaattta   4380
aaaacctagt acgtagcatc agggaatgat atcatagcta ttttagttga gctttcaaat   4440
aagagatgat caaaatttag aacttctaag aacatgaacg aataaacaac tattttcttt   4500
tcaaaccaac taaggtagat ggtcactgaa agtatataca tcagataaaa gttgcttgtt   4560
attccagatg aagttggacc gagaaaaaaa aaagttactt gttattcaat atgtttggat   4620
ctttgtcttg cagattgcta tatagggttg ataatgggct tcgttgtaat gggtatacag   4680
```

-continued

```
tgtataagaa tcggccttgt gcaaccaatc ctaatatgtg tgtctcatta aggtaagtgc   4740
ttaagattag aagagtaaaa cacttgactt atcaactatg tcaactaagg gttctatatt   4800
tttattaaat aaaaaataat tgaatatttt ttagaatgat ttaataaatt taatgctatt   4860
gtttgattta aatgtataat tcaccgcgag aagaaatttt ataactcaaa ttttaaagtt   4920
ttaagttgta tttgtttatt ttgttaaatg tttaatattg tataattgta ttttgattgt   4980
tgtttctcgg atttcacccg tagtacatca tcccatatta atatcgaatc aaacccgtca   5040
attctaaaat ttcacccgtg gtagtattta attgtataat tatattttaa ttgtcattct   5100
aagatttcac tcctaattct atcgcaaatt attatcaacc caaaccagtc aattctaaaa   5160
tatcacccgt agtacaccat cccatattaa tatcgaatca agcccgtcaa ttctaggatt   5220
tcacccgtgg tagtatttaa ttgtataatt atattttaat tgtcattcta ggatttcact   5280
cctaattcta tcgcaaatta ttatcaaccc aaaccagtca attctaaaat atcacccgta   5340
gtacaccatc ccatattaat atcgattcaa actcgtcaat tctaggattt cgctcgtggt   5400
agtatttaat tgtataatta tattttaatt gtcattttaa ctcctagttc tatcgcaaat   5460
tcttatcaac ccaaacagtc aattctaaaa tttcacccgt agtataaagt ttaaatattt   5520
ataatattta aatttcttat aaaagaatca aaatgtgttt taaaaaaatt aaagttttaa   5580
gttttttttt tttaatattg ttaattttgt ttagtgttta agattatata attacattat   5640
gattgtcatt atatgttttt ctccatagca tactatccca tgttattatc cactcaaacc   5700
tgtcacacca tataaccccg tcccgtgaaa ttaaacacaa atttgtcatt ttattataaa   5760
tttcaaatat ttataaaatt agaaacttca aaaaagatta atattgaccc aaacttcatc   5820
attgaatttt gagtgttata tctaagattt ctctcgcaat atatcgtccc gtattaatat   5880
cttttatatt gtttaaattt cttgtaaaat ttaatttata attttttaaa ctttttaaag   5940
tttcaatttt ttaaaataaa taaccctagg aaacaaacca ttttaattta aagataaact   6000
ttataaaaag tttttaaaat tataatattt aacttttgat aaagttataa tatttataat   6060
ttcttgaaac attttaaagt ttcaattctt taaaataata aatccgagta aaatcagata   6120
actattttaa ttttggacgc ttgataaatc aagcttcctg ctcattcgta atcagaatca   6180
ttttggtcct tttataatat gggtctgaac cattgtccaa tttttctaag cgatgtggga   6240
cattgtacac atattatttc ttcataggtt gaataatata tgtccgttta aaaaactttg   6300
aattacatca tattcagaaa aaaatataat attttattaa ctatatatat tttatataaa   6360
ttcaaaataa ataaagtata agatcaaata aaaatgaaag                         6400
```

<210> SEQ ID NO 28
<211> LENGTH: 30
<212> TYPE: PRT
<213> ORGANISM: Arabidopsis thaliana

<400> SEQUENCE: 28

```
Met Glu Ala Leu Ser His Val Gly Ile Gly Leu Ser Pro Phe Gln Leu
1               5                   10                  15

Cys Arg Leu Pro Pro Ala Thr Thr Lys Leu Arg Arg Ser His
            20                  25                  30
```

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29
tgtccaaatt ttatgtgaca ctcc 24

<210> SEQ ID NO 30
<211> LENGTH: 23
<212> TYPE: DNA
<213> ORGANISM: Artificial Sequence
<220> FEATURE:
<223> OTHER INFORMATION: Synthetic

<400> SEQUENCE: 30
ttgtgaaagg cttgaatgta aga 23

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
ccgaattctc tgtgttggcg 20

<210> SEQ ID NO 32
<211> LENGTH: 24
<212> TYPE: DNA
<213> ORGANISM: Artificial Sequence
<220> FEATURE:
<223> OTHER INFORMATION: Synthetic

<400> SEQUENCE: 32
aagcttcgta cagaccctgc tgac 24

<210> SEQ ID NO 33
<211> LENGTH: 18
<212> TYPE: DNA
<213> ORGANISM: Artificial Sequence
<220> FEATURE:
<223> OTHER INFORMATION: Synthetic

<400> SEQUENCE: 33
ggtaagttga cggtcaag 18

<210> SEQ ID NO 34
<211> LENGTH: 19
<212> TYPE: DNA
<213> ORGANISM: Artificial Sequence
<220> FEATURE:
<223> OTHER INFORMATION: Synthetic

<400> SEQUENCE: 34
cgatagggcc gtagctgtc 19

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
ggttaacttg tgatcgaac 19

<210> SEQ ID NO 36

-continued

<211> LENGTH: 18
<212> TYPE: DNA
<213> ORGANISM: Artificial Sequence
<220> FEATURE:
<223> OTHER INFORMATION: Synthetic

<400> SEQUENCE: 36
gcagccagtc tgccctag 18

<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37
gcgcagtcct ttcttgagg 19

<210> SEQ ID NO 38
<211> LENGTH: 19
<212> TYPE: DNA
<213> ORGANISM: Artificial Sequence
<220> FEATURE:
<223> OTHER INFORMATION: Synthetic

<400> SEQUENCE: 38
ctgaccggtg aggttctgc 19

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
ccaggaatcg ctgaacattc 20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
gcgatcgcgg tagctttcgg 20

<210> SEQ ID NO 41
<211> LENGTH: 17
<212> TYPE: DNA
<213> ORGANISM: Artificial Sequence
<220> FEATURE:
<223> OTHER INFORMATION: Synthetic

<400> SEQUENCE: 41
ctaggcagtg tacgttc 17

<210> SEQ ID NO 42
<211> LENGTH: 28
<212> TYPE: DNA
<213> ORGANISM: Artificial Sequence
<220> FEATURE:
<223> OTHER INFORMATION: Synthetic

<400> SEQUENCE: 42
ccgaattcgt gacctctacc cgtactgc 28

<210> SEQ ID NO 43
<211> LENGTH: 28
<212> TYPE: DNA
<213> ORGANISM: Artificial Sequence
<220> FEATURE:
<223> OTHER INFORMATION: Synthetic

<400> SEQUENCE: 43
ccaagcttcg ttttataaag gcgctcag 28

<210> SEQ ID NO 44
<211> LENGTH: 19
<212> TYPE: DNA
<213> ORGANISM: Artificial Sequence
<220> FEATURE:
<223> OTHER INFORMATION: Synthetic

<400> SEQUENCE: 44
ctgctcgtga gcaatttgc 19

<210> SEQ ID NO 45
<211> LENGTH: 16
<212> TYPE: DNA
<213> ORGANISM: Artificial Sequence
<220> FEATURE:
<223> OTHER INFORMATION: Synthetic

<400> SEQUENCE: 45
ccgttctgaa aggctc 16

<210> SEQ ID NO 46
<211> LENGTH: 16
<212> TYPE: DNA
<213> ORGANISM: Artificial Sequence
<220> FEATURE:
<223> OTHER INFORMATION: Synthetic

<400> SEQUENCE: 46
cagtgaattg taatac 16

<210> SEQ ID NO 47
<211> LENGTH: 18
<212> TYPE: DNA
<213> ORGANISM: Artificial Sequence
<220> FEATURE:
<223> OTHER INFORMATION: Synthetic

<400> SEQUENCE: 47
gaaatagcca tcgcgagc 18

<210> SEQ ID NO 48
<211> LENGTH: 29
<212> TYPE: DNA
<213> ORGANISM: Artificial Sequence
<220> FEATURE:
<223> OTHER INFORMATION: Synthetic

<400> SEQUENCE: 48
ccgaattcgt ggcagtggaa aatcgtggg 29

<210> SEQ ID NO 49
<211> LENGTH: 27
<212> TYPE: DNA

<213> ORGANISM: Artificial Sequence
<220> FEATURE:
<223> OTHER INFORMATION: Synthetic

<400> SEQUENCE: 49
ccgaattcca cttgcacgat tgggatc 27

<210> SEQ ID NO 50
<211> LENGTH: 28
<212> TYPE: DNA
<213> ORGANISM: Artificial Sequence
<220> FEATURE:
<223> OTHER INFORMATION: Synthetic

<400> SEQUENCE: 50
ccgaattcgc cctactcatt aactatag 28

<210> SEQ ID NO 51
<211> LENGTH: 27
<212> TYPE: DNA
<213> ORGANISM: Artificial Sequence
<220> FEATURE:
<223> OTHER INFORMATION: Synthetic

<400> SEQUENCE: 51
ccgaattccg gagcgatcgc ttgtttg 27

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
gattaatgag actatatatg agag 24

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atctgcataa cttcaattga actg 24

<210> SEQ ID NO 54
<211> LENGTH: 22
<212> TYPE: DNA
<213> ORGANISM: Artificial Sequence
<220> FEATURE:
<223> OTHER INFORMATION: Synthetic

<400> SEQUENCE: 54
gaacccccag aatatcaaca tc 22

<210> SEQ ID NO 55
<211> LENGTH: 23
<212> TYPE: DNA
<213> ORGANISM: Artificial Sequence
<220> FEATURE:
<223> OTHER INFORMATION: Synthetic

<400> SEQUENCE: 55
gctctgatgg tgattctggt aac 23

<210> SEQ ID NO 56
<211> LENGTH: 26
<212> TYPE: DNA
<213> ORGANISM: Artificial Sequence
<220> FEATURE:
<223> OTHER INFORMATION: Synthetic

<400> SEQUENCE: 56
gtagcattct ttagagattg atctag 26

<210> SEQ ID NO 57
<211> LENGTH: 28
<212> TYPE: DNA
<213> ORGANISM: Artificial Sequence
<220> FEATURE:
<223> OTHER INFORMATION: Synthetic

<400> SEQUENCE: 57
tattcgagtt tgaaattatg atttatgc 28

<210> SEQ ID NO 58
<211> LENGTH: 24
<212> TYPE: DNA
<213> ORGANISM: Artificial Sequence
<220> FEATURE:
<223> OTHER INFORMATION: Synthetic

<400> SEQUENCE: 58
gctacagttc tcaaccggta aatc 24

<210> SEQ ID NO 59
<211> LENGTH: 29
<212> TYPE: DNA
<213> ORGANISM: Artificial Sequence
<220> FEATURE:
<223> OTHER INFORMATION: Synthetic

<400> SEQUENCE: 59
cataagcttt tatgctccaa aatagtctc 29

<210> SEQ ID NO 60
<211> LENGTH: 24
<212> TYPE: DNA
<213> ORGANISM: Artificial Sequence
<220> FEATURE:
<223> OTHER INFORMATION: Synthetic

<400> SEQUENCE: 60
cttgatcttg tgttctgaca tctc 24

<210> SEQ ID NO 61
<211> LENGTH: 27
<212> TYPE: DNA
<213> ORGANISM: Artificial Sequence
<220> FEATURE:
<223> OTHER INFORMATION: Synthetic

<400> SEQUENCE: 61
ctaaactatt cacaaatgcc atagacg 27

<210> SEQ ID NO 62
<211> LENGTH: 24
<212> TYPE: DNA
<213> ORGANISM: Artificial Sequence
<220> FEATURE:

-continued

<223> OTHER INFORMATION: Synthetic

<400> SEQUENCE: 62
agccgtcttg tcccatcatt aaag 24

<210> SEQ ID NO 63
<211> LENGTH: 26
<212> TYPE: DNA
<213> ORGANISM: Artificial Sequence
<220> FEATURE:
<223> OTHER INFORMATION: Synthetic

<400> SEQUENCE: 63
gcacaaacaa acagggtcaa tagtta 26

<210> SEQ ID NO 64
<211> LENGTH: 23
<212> TYPE: DNA
<213> ORGANISM: Artificial Sequence
<220> FEATURE:
<223> OTHER INFORMATION: Synthetic

<400> SEQUENCE: 64
ttaaagtgaa gcttaagcag agg 23

<210> SEQ ID NO 65
<211> LENGTH: 24
<212> TYPE: DNA
<213> ORGANISM: Artificial Sequence
<220> FEATURE:
<223> OTHER INFORMATION: Synthetic

<400> SEQUENCE: 65
cattgttaga aagtcaacac tttg 24

<210> SEQ ID NO 66
<211> LENGTH: 23
<212> TYPE: DNA
<213> ORGANISM: Artificial Sequence
<220> FEATURE:
<223> OTHER INFORMATION: Synthetic

<400> SEQUENCE: 66
gcaagacata accaatgaac aag 23

<210> SEQ ID NO 67
<211> LENGTH: 22
<212> TYPE: DNA
<213> ORGANISM: Artificial Sequence
<220> FEATURE:
<223> OTHER INFORMATION: Synthetic

<400> SEQUENCE: 67
gacacgtatg cgtttctaag ag 22

<210> SEQ ID NO 68
<211> LENGTH: 24
<212> TYPE: DNA
<213> ORGANISM: Artificial Sequence
<220> FEATURE:
<223> OTHER INFORMATION: Synthetic

<400> SEQUENCE: 68
ctccaacttc aagcaaaacg gatg 24

-continued

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
ctctgttttt tgggctagtg atgg 24

<210> SEQ ID NO 70
<211> LENGTH: 22
<212> TYPE: DNA
<213> ORGANISM: Artificial Sequence
<220> FEATURE:
<223> OTHER INFORMATION: Synthetic

<400> SEQUENCE: 70
gcatacccaa tatcctttgt gc 22

<210> SEQ ID NO 71
<211> LENGTH: 23
<212> TYPE: DNA
<213> ORGANISM: Artificial Sequence
<220> FEATURE:
<223> OTHER INFORMATION: Synthetic

<400> SEQUENCE: 71
gatagtataa ccagaggttg gag 23

<210> SEQ ID NO 72
<211> LENGTH: 25
<212> TYPE: DNA
<213> ORGANISM: Artificial Sequence
<220> FEATURE:
<223> OTHER INFORMATION: Synthetic

<400> SEQUENCE: 72
gaatcttctc aaactgaaat ccacc 25

<210> SEQ ID NO 73
<211> LENGTH: 22
<212> TYPE: DNA
<213> ORGANISM: Artificial Sequence
<220> FEATURE:
<223> OTHER INFORMATION: Synthetic

<400> SEQUENCE: 73
tcgaaaggaa gatcggtgaa cc 22

<210> SEQ ID NO 74
<211> LENGTH: 24
<212> TYPE: DNA
<213> ORGANISM: Artificial Sequence
<220> FEATURE:
<223> OTHER INFORMATION: Synthetic

<400> SEQUENCE: 74
gattgtgcta tggttcagga gttc 24

<210> SEQ ID NO 75
<211> LENGTH: 23
<212> TYPE: DNA
<213> ORGANISM: Artificial Sequence
<220> FEATURE:
<223> OTHER INFORMATION: Synthetic

<400> SEQUENCE: 75
catcagctat aacctcctca gtg 23

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76
actgactata aggacccctc aaac 24

<210> SEQ ID NO 77
<211> LENGTH: 28
<212> TYPE: DNA
<213> ORGANISM: Artificial Sequence
<220> FEATURE:
<223> OTHER INFORMATION: Synthetic

<400> SEQUENCE: 77
gttgaccata attcatccac cactatta 28

<210> SEQ ID NO 78
<211> LENGTH: 27
<212> TYPE: DNA
<213> ORGANISM: Artificial Sequence
<220> FEATURE:
<223> OTHER INFORMATION: Synthetic

<400> SEQUENCE: 78
ggaattccga gtcgagttgc tttgttg 27

<210> SEQ ID NO 79
<211> LENGTH: 30
<212> TYPE: DNA
<213> ORGANISM: Artificial Sequence
<220> FEATURE:
<223> OTHER INFORMATION: Synthetic

<400> SEQUENCE: 79
cgtctagagc ttacctcaaa ggtacatgga 30

<210> SEQ ID NO 80
<211> LENGTH: 28
<212> TYPE: DNA
<213> ORGANISM: Artificial Sequence
<220> FEATURE:
<223> OTHER INFORMATION: Synthetic

<400> SEQUENCE: 80
cgggatccat gagtaaagga gaagaact 28

<210> SEQ ID NO 81
<211> LENGTH: 27
<212> TYPE: DNA
<213> ORGANISM: Artificial Sequence
<220> FEATURE:
<223> OTHER INFORMATION: Synthetic

<400> SEQUENCE: 81
gctctagata gttcatccat gccatgt 27

<210> SEQ ID NO 82
<211> LENGTH: 28

```
<212> TYPE: DNA
<213> ORGANISM: Artificial Sequence
<220> FEATURE:
<223> OTHER INFORMATION: Synthetic

<400> SEQUENCE: 82

ggactagtac gatggcggaa gtatcagc                                        28


<210> SEQ ID NO 83
<211> LENGTH: 30
<212> TYPE: DNA
<213> ORGANISM: Artificial Sequence
<220> FEATURE:
<223> OTHER INFORMATION: Synthetic

<400> SEQUENCE: 83

cgggatccgc accgaaggag cctttagatt                                      30


<210> SEQ ID NO 84
<211> LENGTH: 27
<212> TYPE: DNA
<213> ORGANISM: Artificial Sequence
<220> FEATURE:
<223> OTHER INFORMATION: Synthetic

<400> SEQUENCE: 84

gactagttgg ctcaacgctt acctcaa                                         27


<210> SEQ ID NO 85
<211> LENGTH: 25
<212> TYPE: DNA
<213> ORGANISM: Artificial Sequence
<220> FEATURE:
<223> OTHER INFORMATION: Synthetic

<400> SEQUENCE: 85

cgggatccgc catcgtctct tacga                                           25


<210> SEQ ID NO 86
<211> LENGTH: 61
<212> TYPE: PRT
<213> ORGANISM: Arabidopsis thaliana

<400> SEQUENCE: 86

Asp Pro Tyr Lys Thr Leu Lys Ile Arg Pro Asp Ser Ser Glu Tyr Glu
1               5                   10                  15

Val Lys Lys Ala Phe Arg Gln Leu Ala Lys Lys Tyr His Pro Asp Val
            20                  25                  30

Cys Arg Gly Ser Asn Cys Gly Val Gln Phe Gln Thr Ile Asn Glu Ala
        35                  40                  45

Tyr Asp Ile Val Leu Lys Gln Ile Lys Asn Gln Met Glu
    50                  55                  60


<210> SEQ ID NO 87
<211> LENGTH: 68
<212> TYPE: PRT
<213> ORGANISM: Phaseolus vulgaris

<400> SEQUENCE: 87

Ser Leu Tyr Asp Ile Leu Gly Ile Pro Ala Gly Ala Ser Ser Gln Glu
1               5                   10                  15

Ile Lys Ala Ala Tyr Arg Arg Leu Ala Arg Val Cys His Pro Asp Val
            20                  25                  30
```

```
Ala Ala Ile Asp Arg Lys Asn Ser Ser Ala Asp Glu Phe Met Lys Ile
        35                  40                  45

His Ala Ala Tyr Ser Thr Leu Ser Asp Pro Asp Lys Arg Ala Asn Tyr
    50                  55                  60

Asp Arg Ser Leu
65


<210> SEQ ID NO 88
<211> LENGTH: 68
<212> TYPE: PRT
<213> ORGANISM: Arabidopsis thaliana

<400> SEQUENCE: 88

Ser Leu Tyr Glu Ile Leu Glu Ile Pro Val Gly Ser Thr Ser Gln Glu
1               5                   10                  15

Ile Lys Ser Ala Tyr Arg Arg Leu Ala Arg Ile Cys His Pro Asp Val
            20                  25                  30

Ala Arg Asn Ser Arg Asp Asn Ser Ser Ala Asp Asp Phe Met Lys Ile
        35                  40                  45

His Ala Ala Tyr Cys Thr Leu Ser Asp Pro Glu Lys Arg Ala Val Tyr
    50                  55                  60

Asp Arg Arg Thr
65


<210> SEQ ID NO 89
<211> LENGTH: 63
<212> TYPE: PRT
<213> ORGANISM: Mycoplasma pneumoniae

<400> SEQUENCE: 89

Thr Leu Tyr Asp Leu Leu Glu Leu Pro Gln Thr Ala Thr Leu Gln Glu
1               5                   10                  15

Ile Lys Thr Ala Tyr Lys Arg Leu Ala Lys Arg Tyr His Pro Asp Ile
            20                  25                  30

Asn Lys Gln Gly Ala Asp Thr Phe Val Lys Ile Asn Asn Ala Tyr Ala
        35                  40                  45

Val Leu Ser Asp Thr Thr Gln Lys Ala Glu Tyr Asp Ala Met Leu
    50                  55                  60


<210> SEQ ID NO 90
<211> LENGTH: 63
<212> TYPE: PRT
<213> ORGANISM: Mycoplasma genitalium

<400> SEQUENCE: 90

Asn Leu Tyr Asp Leu Leu Glu Leu Pro Thr Thr Ala Ser Ile Lys Glu
1               5                   10                  15

Ile Lys Ile Ala Tyr Lys Arg Leu Ala Lys Arg Tyr His Pro Asp Val
            20                  25                  30

Asn Lys Leu Gly Ser Gln Thr Phe Val Glu Ile Asn Asn Ala Tyr Ser
        35                  40                  45

Ile Leu Ser Asp Pro Asn Gln Lys Glu Lys Tyr Asp Ser Met Leu
    50                  55                  60


<210> SEQ ID NO 91
<211> LENGTH: 68
<212> TYPE: PRT
<213> ORGANISM: Arabidopsis thaliana

<400> SEQUENCE: 91
```

```
Ser Phe Tyr Asp Leu Leu Gly Val Thr Glu Ser Val Thr Leu Pro Glu
1               5                   10                  15

Ile Lys Gln Ala Tyr Lys Gln Leu Ala Arg Lys Tyr His Pro Asp Val
            20                  25                  30

Ser Pro Pro Asp Arg Val Glu Glu Tyr Thr Asp Arg Phe Ile Arg Val
        35                  40                  45

Gln Glu Ala Tyr Glu Thr Leu Ser Asp Pro Arg Arg Arg Val Leu Tyr
    50                  55                  60

Asp Arg Asp Leu
65


<210> SEQ ID NO 92
<211> LENGTH: 69
<212> TYPE: PRT
<213> ORGANISM: Drosophila melanogaster

<400> SEQUENCE: 92

Asn Cys Tyr Asp Val Leu Gly Val Thr Arg Glu Ser Ser Lys Ser Glu
1               5                   10                  15

Ile Gly Lys Ala Tyr Arg Gln Leu Ala Arg Arg Tyr His Pro Asp Leu
            20                  25                  30

His Arg Gly Ala Glu Ala Lys Ala Ala Ala Glu Thr Gln Phe Lys Leu
        35                  40                  45

Val Ala Thr Ala Tyr Glu Ile Leu Arg Asp Glu Glu Ser Arg Thr Asp
    50                  55                  60

Tyr Asp Tyr Met Leu
65


<210> SEQ ID NO 93
<211> LENGTH: 70
<212> TYPE: PRT
<213> ORGANISM: Caenorhabditis elegans

<400> SEQUENCE: 93

Asn Cys Tyr Asp Val Leu Glu Val Asn Arg Glu Glu Phe Asp Lys Gln
1               5                   10                  15

Lys Leu Ala Lys Ala Tyr Arg Ala Leu Ala Arg Lys His His Pro Asp
            20                  25                  30

Arg Val Lys Asn Lys Glu Glu Lys Leu Leu Ala Glu Glu Arg Phe Arg
        35                  40                  45

Val Ile Ala Thr Ala Tyr Glu Thr Leu Lys Asp Asp Glu Ala Lys Thr
    50                  55                  60

Asn Tyr Asp Tyr Tyr Leu
65                  70


<210> SEQ ID NO 94
<211> LENGTH: 72
<212> TYPE: PRT
<213> ORGANISM: Arabidopsis thaliana

<400> SEQUENCE: 94

Ser Pro Tyr Asp Thr Leu Glu Leu Asp Arg Asn Ala Glu Glu Glu Gln
1               5                   10                  15

Ile Lys Val Ala Tyr Arg Arg Leu Ala Lys Phe Tyr His Pro Asp Val
            20                  25                  30

Tyr Asp Gly Lys Gly Thr Leu Glu Glu Gly Glu Thr Ala Glu Ala Arg
        35                  40                  45
```

-continued

```
Phe Ile Lys Ile Gln Ala Ala Tyr Glu Leu Leu Met Asp Ser Glu Lys
    50                  55                  60

Lys Val Gln Tyr Asp Met Asp Asn
65                  70


<210> SEQ ID NO 95
<211> LENGTH: 68
<212> TYPE: PRT
<213> ORGANISM: Schizosaccharomyces pombe

<400> SEQUENCE: 95

Lys Leu Tyr Asp Ile Leu Glu Val His Phe Glu Ala Ser Ala Glu Glu
1               5                   10                  15

Ile Lys Lys Ser Tyr Lys Arg Leu Ala Leu Leu His His Pro Asp Lys
            20                  25                  30

Ala Pro Ile His Glu Lys Glu Glu Ala Ala Glu Arg Phe Arg Gly Val
        35                  40                  45

Gln Glu Ala Tyr Asp Ile Leu Lys Asp Pro Glu Ser Arg Glu Met Tyr
    50                  55                  60

Asp Met Tyr Gly
65


<210> SEQ ID NO 96
<211> LENGTH: 66
<212> TYPE: PRT
<213> ORGANISM: Unknown
<220> FEATURE:
<223> OTHER INFORMATION: Synthetic

<400> SEQUENCE: 96

Asp Phe Tyr Lys Ile Leu Gly Ala Glu Pro His Phe Leu Gly Asp Gly
1               5                   10                  15

Ile Arg Arg Ala Phe Glu Ser Arg Ile Ala Lys Pro Pro Gln Tyr Gly
            20                  25                  30

Tyr Ser Thr Glu Ala Leu Ala Gly Arg Arg Gln Met Leu Gln Ile Ala
        35                  40                  45

His Asp Thr Leu Thr Asn Gln Ser Ser Arg Thr Glu Tyr Asp Arg Ala
    50                  55                  60

Leu Ser
65


<210> SEQ ID NO 97
<211> LENGTH: 66
<212> TYPE: PRT
<213> ORGANISM: Oryza sativa

<400> SEQUENCE: 97

Asp Phe Tyr Lys Val Leu Gly Ala Glu Pro His Phe Leu Gly Asp Gly
1               5                   10                  15

Ile Arg Arg Ala Phe Glu Ala Arg Ile Ala Lys Pro Pro Gln Tyr Gly
            20                  25                  30

Tyr Ser Thr Asp Ala Leu Val Gly Arg Arg Gln Met Leu Gln Ile Ala
        35                  40                  45

His Asp Thr Leu Met Asn Gln Asn Ser Arg Thr Gln Tyr Asp Arg Ala
    50                  55                  60

Leu Ser
65


<210> SEQ ID NO 98
```

<211> LENGTH: 66
<212> TYPE: PRT
<213> ORGANISM: Solanum tuberosum

<400> SEQUENCE: 98

```
Asp Phe Tyr Arg Val Leu Gly Ala Glu Ala His Phe Leu Gly Asp Gly
1               5                   10                  15

Ile Arg Arg Cys Tyr Asp Ala Arg Ile Thr Lys Pro Pro Gln Tyr Gly
            20                  25                  30

Tyr Ser Gln Glu Ala Leu Ile Gly Arg Arg Gln Ile Leu Gln Ala Ala
        35                  40                  45

Cys Glu Thr Leu Ala Asp Ser Thr Ser Arg Arg Glu Tyr Asn Gln Gly
    50                  55                  60

Leu Ala
65
```

<210> SEQ ID NO 99
<211> LENGTH: 66
<212> TYPE: PRT
<213> ORGANISM: Artificial Sequence
<220> FEATURE:
<223> OTHER INFORMATION: Synthetic

<400> SEQUENCE: 99

```
Asp Leu Tyr Lys Ile Leu Gly Ala Glu Thr His Phe Leu Gly Asp Gly
1               5                   10                  15

Ile Arg Arg Ala Tyr Glu Ala Lys Phe Ser Lys Pro Pro Gln Tyr Ala
            20                  25                  30

Phe Ser Asn Glu Ala Leu Ile Ser Arg Arg Gln Ile Leu Gln Ala Ala
        35                  40                  45

Cys Glu Thr Leu Ala Asp Pro Ala Ser Arg Arg Glu Tyr Asn Gln Ser
    50                  55                  60

Leu Val
65
```

<210> SEQ ID NO 100
<211> LENGTH: 66
<212> TYPE: PRT
<213> ORGANISM: Arabidopsis thaliana

<400> SEQUENCE: 100

```
Asp Phe Tyr Gln Val Leu Gly Ala Gln Thr His Phe Leu Thr Asp Gly
1               5                   10                  15

Ile Arg Arg Ala Phe Glu Ala Arg Val Ser Lys Pro Pro Gln Phe Gly
            20                  25                  30

Phe Ser Asp Asp Ala Leu Ile Ser Arg Arg Gln Ile Leu Gln Ala Ala
        35                  40                  45

Cys Glu Thr Leu Ser Asn Pro Arg Ser Arg Arg Glu Tyr Asn Glu Gly
    50                  55                  60

Leu Leu
65
```

<210> SEQ ID NO 101
<211> LENGTH: 66
<212> TYPE: PRT
<213> ORGANISM: Protochlorococcus marinus MED4

<400> SEQUENCE: 101

```
Asp His Phe Arg Leu Ile Gly Val Ser Pro Ser Ala Thr Ser Glu Glu
1               5                   10                  15
```

```
Ile Leu Arg Ala Phe Gln Leu Arg Leu Asp Lys Thr Pro Asp Glu Gly
            20                  25                  30

Phe Thr Tyr Glu Val Leu Thr Gln Arg Ser Glu Leu Leu Arg Leu Thr
        35                  40                  45

Ala Asp Leu Leu Thr Asp Pro Asp Ser Arg Arg Asp Tyr Glu Asn Leu
    50                  55                  60

Leu Leu
65


<210> SEQ ID NO 102
<211> LENGTH: 66
<212> TYPE: PRT
<213> ORGANISM: Protochlorococcus marinus MT9313

<400> SEQUENCE: 102

Asp His Phe Arg Leu Leu Gly Val Ser Pro Ser Ala Asp Ser Glu Ala
1               5                   10                  15

Ile Leu Arg Ala Leu Glu Leu Arg Leu Asp Arg Cys Pro Asp Gln Gly
            20                  25                  30

Phe Thr His Glu Val Leu Ile Gln Arg Ala Glu Leu Leu Arg Leu Ser
        35                  40                  45

Ala Asp Leu Leu Thr Asp Pro Pro Arg Arg Gln Ala Tyr Glu Thr Ala
    50                  55                  60

Leu Leu
65


<210> SEQ ID NO 103
<211> LENGTH: 66
<212> TYPE: PRT
<213> ORGANISM: Synechocystis PCC6803

<400> SEQUENCE: 103

Asp His Phe Arg Leu Leu Gly Val Ser Pro Ser Ala Asp Pro Ala Ser
1               5                   10                  15

Ile Leu Arg Arg Leu Gln Thr Arg Ser Asp Ser Pro Pro Asp Asp Gly
            20                  25                  30

Phe Thr His Glu Gly Leu Leu Gln Arg Gln Ala Leu Leu His Arg Ser
        35                  40                  45

Ala Asp Leu Leu Thr Asp Pro Ser Glu Arg Ala Asp Tyr Glu Ala Ala
    50                  55                  60

Leu Leu
65


<210> SEQ ID NO 104
<211> LENGTH: 66
<212> TYPE: PRT
<213> ORGANISM: Synechocystis PCC6803

<400> SEQUENCE: 104

Asp Phe Tyr Arg Ile Leu Gly Ile Pro Pro Gln Ser Gly Gly Glu Thr
1               5                   10                  15

Ile Glu Gln Ala Tyr Gln Asp Arg Leu Leu Gln Leu Pro Arg Arg Glu
            20                  25                  30

Phe Ser Asp Ala Ala Val Thr Leu Arg Asn Gln Leu Leu Ala Ile Ala
        35                  40                  45

Tyr Glu Thr Leu Arg Asp Pro Glu Lys Arg Gln Ala Tyr Asp Gln Glu
    50                  55                  60
```

```
Trp Trp
65


<210> SEQ ID NO 105
<211> LENGTH: 66
<212> TYPE: PRT
<213> ORGANISM: Nostoc punctiforme

<400> SEQUENCE: 105

Asp Tyr Tyr Arg Ile Leu Gly Leu Pro Leu Ala Ala Ser Glu Glu Gln
1               5                   10                  15

Leu Arg Gln Ala Tyr Ser Asp Arg Ile Val Gln Leu Pro Arg Arg Glu
            20                  25                  30

Tyr Ser Gln Ala Ala Ile Ser Ser Arg Lys Gln Leu Ile Glu Glu Ala
        35                  40                  45

Tyr Val Val Leu Ser Asp Pro Lys Gln Arg Ser Thr Tyr Asp Gln Leu
    50                  55                  60

Tyr Leu
65


<210> SEQ ID NO 106
<211> LENGTH: 66
<212> TYPE: PRT
<213> ORGANISM: Anabaena PCC7120

<400> SEQUENCE: 106

Asp Tyr Tyr Arg Ile Leu Gly Leu Pro Leu Ala Ala Ser Asp Glu Gln
1               5                   10                  15

Leu Arg Gln Ala Tyr Ser Asp Arg Ile Val Gln Leu Pro Arg Arg Glu
            20                  25                  30

Tyr Ser Gln Ala Ala Ile Ala Ser Arg Lys Gln Leu Ile Glu Glu Ala
        35                  40                  45

Tyr Val Val Leu Ser Asp Pro Lys Glu Arg Ser Ser Tyr Asp Gln Leu
    50                  55                  60

Tyr Leu
65


<210> SEQ ID NO 107
<211> LENGTH: 66
<212> TYPE: PRT
<213> ORGANISM: Bombyx mori

<400> SEQUENCE: 107

Asp Tyr Tyr Ala Leu Leu Gly Cys Asp Glu Asn Ser Thr Val Glu Gln
1               5                   10                  15

Ile Thr Ala Glu Tyr Lys Ile Leu Ala Leu Gln His His Pro Asp Lys
            20                  25                  30

Asn Asp Gly Glu Lys Glu Ala Glu Met Lys Phe Gln Lys Leu Lys Glu
        35                  40                  45

Ala Lys Glu Ile Leu Cys Asp Pro Ser Lys Arg Ala Leu Tyr Asp Lys
    50                  55                  60

Trp Arg
65


<210> SEQ ID NO 108
<211> LENGTH: 66
<212> TYPE: PRT
<213> ORGANISM: Drosophila melanogaster

<400> SEQUENCE: 108
```

-continued

```
Asp Phe Tyr Gly Leu Leu His Cys Asp Glu Asn Ser Ser Pro Glu Gln
1               5                   10                  15

Ile Gln Ala Glu Tyr Lys Val Leu Ala Leu Gln Tyr His Pro Asp Lys
            20                  25                  30

Asn Ser Gly Asp Lys Glu Ala Glu Ala Lys Phe Gln Gln Leu Lys Glu
        35                  40                  45

Ala Lys Glu Thr Leu Cys Asp Pro Glu Lys Arg Ala Ile Tyr Asp Lys
    50                  55                  60

Trp Arg
65
```

<210> SEQ ID NO 109
<211> LENGTH: 66
<212> TYPE: PRT
<213> ORGANISM: Mus musculus

<400> SEQUENCE: 109

```
Asp Tyr Tyr Ala Leu Leu Gly Cys Asp Glu Leu Ser Ser Val Glu Gln
1               5                   10                  15

Ile Leu Ala Glu Phe Lys Ile Arg Ala Leu Glu Cys His Pro Asp Lys
            20                  25                  30

His Pro Glu Asn Ser Lys Ala Val Glu Thr Phe Gln Lys Leu Gln Lys
        35                  40                  45

Ala Lys Glu Ile Leu Cys Asn Ala Glu Ser Arg Ala Arg Tyr Asp His
    50                  55                  60

Trp Arg
65
```

<210> SEQ ID NO 110
<211> LENGTH: 65
<212> TYPE: PRT
<213> ORGANISM: Saccharomyces cerevisiae

<400> SEQUENCE: 110

```
Asp Ala Tyr Ser Ile Leu Gly Val Pro Pro Asp Ser Ser Gln Glu Gln
1               5                   10                  15

Ile Arg Lys His Tyr Lys Lys Ile Ala Val Leu Val His Pro Asp Lys
            20                  25                  30

Asn Lys Gln Ala Gly Ala Glu Glu Ala Phe Lys Val Leu Gln Arg Ala
        35                  40                  45

Phe Glu Leu Ile Gly Glu Pro Glu Asn Arg Leu Ile Tyr Asp Gln Ser
    50                  55                  60

Ile
65
```

<210> SEQ ID NO 111
<211> LENGTH: 64
<212> TYPE: PRT
<213> ORGANISM: Leishmania major

<400> SEQUENCE: 111

```
Glu Leu Tyr Gln Val Leu Glu Leu Asp Ala Gln Cys Thr Thr Ala Glu
1               5                   10                  15

Ile Ser Gln Gln Tyr Arg Arg Leu Ala Leu Arg Tyr His Pro Asp Arg
            20                  25                  30

Asn Ala Gly Ala Thr Val Glu Gln Phe Gln Arg Ile Glu Glu Ala His
        35                  40                  45
```

-continued

```
Arg Val Leu Ser Asp Leu Arg Gln Arg Gln Leu Tyr Asp Thr Val Gly
    50                  55                  60
```

<210> SEQ ID NO 112
<211> LENGTH: 67
<212> TYPE: PRT
<213> ORGANISM: Schizosaccharomyces pombe

<400> SEQUENCE: 112

```
Asp Tyr Tyr Thr Ile Leu Gly Ala Glu Ser Thr Ser Ser Tyr Val Glu
1               5                   10                  15

Ile Arg Gln Gln Tyr Leu Lys Leu Val Leu Arg Tyr His Pro Asp Arg
            20                  25                  30

Asn Pro Gly Arg Glu Ala Glu Val Leu Pro Gln Phe Gln Leu Ile Gln
        35                  40                  45

Lys Ala His Glu Val Leu Lys Asp Pro Lys Leu Arg Glu Leu Phe Asp
    50                  55                  60

Gln Arg Arg
65
```

<210> SEQ ID NO 113
<211> LENGTH: 67
<212> TYPE: PRT
<213> ORGANISM: Schizosaccharomyces pombe

<400> SEQUENCE: 113

```
Asp Tyr Tyr Ala Ile Leu Lys Leu Gln Lys Asn Ala Thr Phe Gln Gln
1               5                   10                  15

Ile Arg Lys Gln Tyr Leu Phe Leu Ala Leu Gln Tyr His Pro Asp Arg
            20                  25                  30

Asn Pro Gly Asp Glu Glu Arg Ala Val Lys Arg Phe Gln Arg Leu Gln
        35                  40                  45

Leu Ala His Glu Val Leu Ser Asp Ala Thr Lys Arg Leu Ile Tyr Asp
    50                  55                  60

Gln Leu Phe
65
```

<210> SEQ ID NO 114
<211> LENGTH: 68
<212> TYPE: PRT
<213> ORGANISM: Schizosaccharomyces pombe

<400> SEQUENCE: 114

```
Asn His Tyr Ser Val Leu Asn Leu Lys Asp Gly Lys Thr Tyr Thr Asp
1               5                   10                  15

Asp Glu Ile Lys Glu Ala Tyr Arg Lys Ala Leu Leu Leu Phe His Pro
            20                  25                  30

Asp Lys Cys Lys Glu Lys Pro Ser Val Val Tyr Thr Ile Asp Gln Val
        35                  40                  45

Lys Glu Ala Tyr Gln Val Leu Ser Ser Glu Lys Asp Arg Gln Gln Tyr
    50                  55                  60

Gln Ile Lys Gln
65
```

<210> SEQ ID NO 115
<211> LENGTH: 652
<212> TYPE: PRT
<213> ORGANISM: Anabaena PCC7120

<400> SEQUENCE: 115

-continued

```
Gln Gly Lys Tyr Ala Val Arg Ile Pro Leu Asp Tyr Tyr Arg Ile Leu
1               5                   10                  15

Gly Leu Pro Leu Ala Ala Ser Asp Glu Gln Leu Arg Gln Ala Tyr Ser
            20                  25                  30

Asp Arg Ile Val Gln Leu Pro Arg Arg Glu Tyr Ser Gln Ala Ala Ile
        35                  40                  45

Ala Ser Arg Lys Gln Leu Ile Glu Glu Ala Tyr Val Val Leu Ser Asp
    50                  55                  60

Pro Lys Glu Arg Ser Ser Tyr Asp Gln Leu Tyr Leu Ala His Ala Tyr
65                  70                  75                  80

Asp Pro Asp Asn Ala Ala Thr Thr Lys Val Ala Val Glu Asn Arg Gly
                85                  90                  95

Asp Ser Asn Asn Gly His Phe Asp Val Gln Ser Leu Ser Ile Glu Val
            100                 105                 110

Ser Ser Glu Glu Leu Ile Gly Ala Leu Leu Ile Leu Gln Glu Leu Gly
        115                 120                 125

Glu Tyr Glu Leu Val Leu Lys Leu Gly Arg Asn Tyr Leu Gly Asn Gln
    130                 135                 140

Asn Gly Thr Ala Ser Thr Arg Asn Gly Asn His Arg Thr Pro Glu Glu
145                 150                 155                 160

Phe Leu Asp Ser Ser Glu Arg Pro Asp Ile Leu Leu Thr Val Ala Leu
                165                 170                 175

Ala Ser Leu Glu Leu Gly Arg Glu Gln Trp Gln Gln Gly His Tyr Glu
            180                 185                 190

Asn Ala Ala Leu Ser Leu Glu Thr Gly Gln Glu Val Leu Phe Ser Glu
        195                 200                 205

Gly Ile Phe Pro Ser Val Gln Ala Glu Ile Gln Ala Asp Leu Tyr Lys
    210                 215                 220

Leu Arg Pro Tyr Arg Ile Leu Glu Leu Leu Ala Leu Pro Gln Glu Lys
225                 230                 235                 240

Thr Ile Glu Arg His Gln Gly Leu Asp Leu Leu Gln Ser Ile Leu Asp
                245                 250                 255

Asp Arg Gly Gly Ile Asp Gly Thr Gly Asn Asp Gln Ser Gly Leu Asn
            260                 265                 270

Ile Asp Asp Phe Leu Arg Phe Ile Gln Gln Leu Arg His His Leu Thr
        275                 280                 285

Val Ala Glu Gln His Lys Leu Phe Asp Gly Glu Ser Lys Arg Pro Ser
    290                 295                 300

Ala Val Ala Thr Tyr Leu Ala Val Tyr Ala Ser Ile Ala Arg Gly Phe
305                 310                 315                 320

Thr Gln Arg Gln Pro Ala Leu Ile Arg His Ala Lys Gln Ile Leu Met
                325                 330                 335

Arg Leu Ser Lys Arg Gln Asp Val His Leu Glu Gln Ser Leu Cys Ala
            340                 345                 350

Leu Leu Leu Gly Gln Thr Glu Glu Ala Thr Arg Val Leu Glu Leu Ser
        355                 360                 365

Gln Glu Tyr Glu Ala Leu Ala Leu Ile Arg Glu Lys Ser Gln Asp Ser
    370                 375                 380

Pro Asp Leu Leu Pro Gly Leu Cys Leu Tyr Ala Glu Gln Trp Leu Gln
385                 390                 395                 400

Asn Glu Val Phe Pro His Phe Arg Asp Leu Ser Arg Gln Gln Ala Ser
                405                 410                 415
```

-continued

```
Leu Lys Asp Tyr Phe Ala Asn Gln Gln Val Gln Ala Tyr Leu Glu Ala
            420                 425                 430

Leu Pro Asn Asp Ala Glu Thr Thr Asn Glu Trp Ala Val Ile Asn Arg
        435                 440                 445

Gln Ser Phe Ser Gln Pro Arg Gly Asn Ser Tyr Ser Gly Gly Thr Pro
    450                 455                 460

Val Ala Lys Arg Pro Val Gly Lys Ala Asn Arg Pro Gly Glu Ala Ser
465                 470                 475                 480

Thr Arg Pro Val Pro Gln Arg Ser His Pro Ser Glu Val Asn Arg Gln
                485                 490                 495

Phe His Gln Asn Arg Thr Pro Asp Pro Glu Leu Pro Glu Thr Ser Asn
            500                 505                 510

His Arg Arg Pro Glu Ser Ser Asn Phe Thr Thr Ala Arg Glu Asn Ile
        515                 520                 525

Ser Thr Thr Asp Ala Tyr Thr Asp Asn Tyr Pro Pro Glu Ile Pro Val
    530                 535                 540

Glu Arg Ala Ser Arg Pro Val Gln Pro Gly Val Ser Gly Tyr Thr Gln
545                 550                 555                 560

Ser Thr Pro Pro Arg Gln Thr Pro Lys Arg Arg Arg Arg Lys Lys Pro
                565                 570                 575

Gln Ala Val Val Asn Arg Gly His Ser Ile His Gln Gln Arg Gln Pro
            580                 585                 590

Ser Pro Ser Thr Leu Gly Arg Lys Thr Arg Leu Leu Trp Ile Val Leu
        595                 600                 605

Gly Ser Leu Gly Gly Ile Leu Leu Phe Trp Leu Ile Val Ser Thr Thr
    610                 615                 620

Phe Gly Trp Leu Lys Asn Val Phe Phe Pro Ala Pro Ser Leu Gln Gly
625                 630                 635                 640

Glu Gln Leu Ser Ile Gln Ile Ser Gln Pro Pro Leu
                645                 650


<210> SEQ ID NO 116
<211> LENGTH: 624
<212> TYPE: PRT
<213> ORGANISM: Nostoc punctiforme

<400> SEQUENCE: 116

Met Arg Ile Pro Leu Asp Tyr Tyr Arg Ile Leu Gly Leu Pro Leu Ala
1               5                   10                  15

Ala Ser Glu Glu Gln Leu Arg Gln Ala Tyr Ser Asp Arg Ile Val Gln
            20                  25                  30

Leu Pro Arg Arg Glu Tyr Ser Gln Ala Ala Ile Ser Ser Arg Lys Gln
        35                  40                  45

Leu Ile Glu Glu Ala Tyr Val Val Leu Ser Asp Pro Lys Gln Arg Ser
    50                  55                  60

Thr Tyr Asp Gln Leu Tyr Leu Ala His Ala Tyr Asp Pro Asp Asn Leu
65                  70                  75                  80

Ala Ala Ala Ala Val Ala Gln Glu Asn Arg Thr Glu Ser Thr Lys Arg
                85                  90                  95

Gly Ser Asp Thr Gln Ser Leu Gly Ile Glu Ile Thr Gln Asp Glu Leu
            100                 105                 110

Val Gly Ala Leu Leu Ile Leu Gln Glu Leu Gly Glu Tyr Glu Leu Val
        115                 120                 125

Leu Lys Leu Gly Arg Pro Tyr Leu Val Asn Lys Asn Ser Ala Thr Ser
    130                 135                 140
```

```
Ser Arg Lys Ser Asn Asn Leu Ala Asp Glu Glu Ile Tyr Glu Ser Ala
145                 150                 155                 160

Glu His Pro Asp Val Val Leu Thr Val Ala Leu Ala Cys Leu Glu Leu
                165                 170                 175

Gly Arg Glu Gln Trp Gln Gln Gly His Tyr Glu Asn Ala Ala Ile Ser
            180                 185                 190

Leu Glu Thr Gly Gln Glu Leu Leu Val Arg Glu Gly Leu Phe Ser Ser
        195                 200                 205

Ile Gln Ala Glu Ile Gln Ala Asp Leu Tyr Lys Leu Arg Pro Tyr Arg
    210                 215                 220

Ile Leu Glu Leu Leu Ala Leu Pro Gln Glu Lys Thr Ala Glu Arg Ser
225                 230                 235                 240

Gln Gly Leu Glu Leu Leu Gln Asn Leu Leu Glu Asp Arg Gly Gly Ile
                245                 250                 255

Asp Gly Thr Asn Asn Asp Glu Ser Gly Leu Asn Ile Asp Asp Phe Leu
            260                 265                 270

Arg Phe Ile Gln Gln Leu Arg Asn His Leu Thr Val Ala Glu Gln His
        275                 280                 285

Lys Leu Phe Glu Ala Gln Ser Lys Arg Ser Ser Ala Val Ala Thr Tyr
    290                 295                 300

Leu Ala Val Tyr Ala Leu Ile Ala Arg Gly Phe Ala Gln Arg Gln Pro
305                 310                 315                 320

Ala Leu Ile Arg Gln Ala Arg Gln Met Leu Val Arg Leu Gly Lys Arg
                325                 330                 335

Gln Asp Val His Leu Glu Gln Ser Leu Cys Ala Leu Leu Leu Gly Gln
            340                 345                 350

Thr Glu Glu Ala Thr Arg Val Leu Glu Leu Ser Gln Glu Tyr Glu Ala
        355                 360                 365

Leu Ala Phe Ile Arg Glu Lys Ser Gln Asp Ser Pro Asp Leu Leu Pro
    370                 375                 380

Gly Leu Cys Leu Tyr Ala Glu Gln Trp Leu Gln His Glu Val Phe Pro
385                 390                 395                 400

His Phe Arg Asp Leu Ala Asn Gln Gln Ala Phe Leu Lys Asp Tyr Phe
                405                 410                 415

Ala Asn Gln Gln Val Gln Ala Tyr Leu Glu Ala Leu Pro Thr Asp Ala
            420                 425                 430

Gln Thr Thr Asn Glu Trp Ala Val Ile Asn Pro Gln Tyr Phe Pro Gln
        435                 440                 445

Ala Lys Ala Lys Asn Thr His Phe His Asn Asn Ser Thr Lys Thr Ser
    450                 455                 460

Ala Ser Phe Asn His Ser Arg Val Pro Asn Pro Asp Leu Pro Glu Thr
465                 470                 475                 480

Pro Thr Lys Glu Thr Ser Glu Tyr Pro Asn Phe Ser Pro Pro Met Trp
                485                 490                 495

Ser Ser Ser Gly Ser Ile Lys Ser Glu Val Pro Ala Ala Glu Arg Met
            500                 505                 510

Ser Arg Gly Thr Asn Gln His Leu Asn Gly Ser Ala Lys Ser Ala Ala
        515                 520                 525

Ser Gly His Asn Gln Lys Arg Arg Arg Arg Lys Pro Thr Pro Ser Ala
    530                 535                 540

Ser Arg Glu Arg Ile Pro Asp Asn Arg Pro His Ser Arg Arg Pro Arg
545                 550                 555                 560
```

-continued

```
Arg Arg Arg Thr Phe Ala Asn Thr Ile Glu Gly Lys Thr Arg Leu Val
                565                 570                 575

Trp Arg Val Phe Ile Ser Leu Val Ser Ile Leu Val Phe Trp Val Leu
            580                 585                 590

Ala Thr Thr Thr Phe Gly Trp Leu Lys Asn Leu Phe Phe Pro Gln Pro
        595                 600                 605

Ser Pro Pro Asp Leu Gln Leu Phe Val Gln Ile Asn Gln Pro Pro Leu
    610                 615                 620


<210> SEQ ID NO 117
<211> LENGTH: 557
<212> TYPE: PRT
<213> ORGANISM: Protochlorococcus marinus MED4

<400> SEQUENCE: 117

Met Glu Leu Pro Leu Asp His Phe Arg Leu Ile Gly Val Ser Pro Ser
1               5                   10                  15

Ala Thr Ser Glu Glu Ile Leu Arg Ala Phe Gln Leu Arg Leu Asp Lys
            20                  25                  30

Thr Pro Asp Glu Gly Phe Thr Tyr Glu Val Leu Thr Gln Arg Ser Glu
        35                  40                  45

Leu Leu Arg Leu Thr Ala Asp Leu Leu Thr Asp Pro Asp Ser Arg Arg
    50                  55                  60

Asp Tyr Glu Asn Leu Leu Leu Asn Gly Ala Ser Gly Leu Asp Leu Ser
65                  70                  75                  80

Ser Asn Arg Glu Val Ala Gly Leu Ile Leu Leu Trp Glu Ser Gly Ser
                85                  90                  95

Ser Lys Glu Ala Phe Lys Ile Thr Arg Lys Ala Leu Gln Pro Pro Gln
            100                 105                 110

Thr Pro Ala Leu Gly Ser Ser Arg Glu Ala Asp Leu Thr Leu Leu Ala
        115                 120                 125

Ala Leu Thr Ser Arg Asp Ala Ala Ile Gln Glu Gln Asp Gln Arg Ser
    130                 135                 140

Tyr Ser Asn Ala Ala Asp Phe Leu Gln Glu Gly Ile Gln Leu Leu Gln
145                 150                 155                 160

Arg Met Gly Lys Leu Gly Glu Leu Arg Lys Thr Leu Glu Glu Asp Leu
                165                 170                 175

Val Ser Leu Leu Pro Tyr Arg Ile Leu Asp Leu Leu Ser Arg Asp Leu
            180                 185                 190

Asn Asp Tyr Asp Ser His Lys Lys Gly Leu Ser Met Leu Glu Asn Leu
        195                 200                 205

Ile Ile Lys Arg Gly Gly Leu Glu Gly Lys Asn Lys Ser Glu Tyr Asn
    210                 215                 220

Asp Phe Leu Asn Gln Gln Glu Phe Glu Ser Phe Phe Gln Gln Ile Lys
225                 230                 235                 240

Pro Phe Leu Thr Val Gln Asp Gln Ile Asp Leu Phe Leu Glu Leu Gln
                245                 250                 255

Lys Arg Gly Ser Ser Glu Ala Gly Phe Leu Ala Phe Leu Ser Leu Thr
            260                 265                 270

Ala Ile Gly Phe Ala Arg Arg Lys Pro Ala Lys Leu Phe Glu Ala Arg
        275                 280                 285

Lys Ile Leu Lys Lys Leu Asn Leu Ser Gly Leu Asp Ser Met Pro Leu
    290                 295                 300

Ile Gly Cys Leu Asp Leu Leu Leu Ala Asp Val Glu Gln Ser Ser Ala
305                 310                 315                 320
```

```
Arg Phe Leu Ser Ser Ser Asp Glu Lys Leu Arg Asp Trp Leu Asn Asn
                325                 330                 335

Tyr Pro Gly Glu Lys Leu Glu Ala Ile Cys Ile Phe Cys Lys Asn Trp
            340                 345                 350

Leu Glu Asn Asp Val Leu Val Gly Tyr Arg Asp Ile Asp Leu Lys Glu
        355                 360                 365

Ile Asp Leu Asp Ser Trp Phe Glu Asp Arg Glu Ile Gln Glu Phe Ile
    370                 375                 380

Glu Gln Ile Glu Lys Lys Ser Asn Arg Thr Val Phe Lys Ser Gly Pro
385                 390                 395                 400

Gln Asn Lys Pro Ile Phe Gln Ala Gln Glu Ser Leu Lys Asp Ser Ser
                405                 410                 415

Thr Gly Pro Asp Leu Asn Ser Asp Asn Phe Glu Glu Gly Arg Leu Pro
            420                 425                 430

Leu Pro Gly Gly Val Arg Glu Asp Gly Gln Glu Val Ile Glu Glu Asn
        435                 440                 445

Ile Tyr Thr Asp Glu Ile Ile Lys Asn Lys Ser Ile Glu Phe Tyr Lys
    450                 455                 460

Tyr Ala Ile Glu Lys Ile Ala Glu Leu Lys Phe Val Phe Gly Glu Ala
465                 470                 475                 480

Leu Glu Asn Tyr Arg Ile Phe Asn Lys Ser Ser Tyr Leu Thr Tyr Leu
                485                 490                 495

Tyr Ala Phe Leu Ile Leu Phe Ala Phe Gly Leu Gly Val Gly Phe Val
            500                 505                 510

Arg Asn Asn Leu Lys Lys Pro Val Gln Glu Lys Glu Ile Ile Asp Asn
        515                 520                 525

Ser Leu Ser Ile Asn Glu Asn Lys Asn Val Phe Tyr Glu Gly Leu Asn
    530                 535                 540

Gln Asp Asp Lys Lys Lys Val Leu Asp Asn Ser Lys Ile
545                 550                 555


<210> SEQ ID NO 118
<211> LENGTH: 524
<212> TYPE: PRT
<213> ORGANISM: Protochlorococcus marinus MT9313

<400> SEQUENCE: 118

Met Ala Ala Gln Leu Val Asp Leu Pro Ile Asp His Phe Arg Leu Leu
1               5                   10                  15

Gly Val Ser Pro Ser Ala Asp Ser Glu Ala Ile Leu Arg Ala Leu Glu
            20                  25                  30

Leu Arg Leu Asp Arg Cys Pro Asp Gln Gly Phe Thr His Glu Val Leu
        35                  40                  45

Ile Gln Arg Ala Glu Leu Leu Arg Leu Ser Ala Asp Leu Leu Thr Asp
    50                  55                  60

Pro Pro Arg Arg Gln Ala Tyr Glu Thr Ala Leu Leu Glu Leu Ser Arg
65                  70                  75                  80

Asp His Pro Gly Glu Thr Ala Gly Leu Asp Val Ser Pro Ser Arg Glu
                85                  90                  95

Val Ala Gly Leu Ile Leu Leu Phe Glu Ala Asn Ser Ser His Glu Val
            100                 105                 110

Phe His Leu Ala Ser Gln Gly Leu Gln Pro Pro Gln Ser Pro Thr Leu
        115                 120                 125

Gly Ser Glu Arg Glu Ala Asp Leu Ala Leu Leu Leu Ala Leu Ala Cys
```

-continued

```
    130                 135                 140

Arg Ala Ala Ala Ala Glu Glu Gln Glu Gln Arg Arg Tyr Glu Ala Ala
145                 150                 155                 160

Ala Ser Leu Leu His Asp Gly Ile Gln Leu Leu Gln Arg Met Gly Lys
                165                 170                 175

Leu Ser Glu Glu Cys His Lys Leu Glu Asn Asp Leu Asp Ala Leu Leu
            180                 185                 190

Pro Tyr Arg Ile Leu Asp Leu Leu Ser Arg Asp Leu Gly Asp Gln Val
        195                 200                 205

Ser His Gln Glu Gly Leu Arg Leu Leu Asp Asn Phe Val Ser Gln Arg
    210                 215                 220

Gly Gly Leu Glu Gly Thr Ala Pro Ser Pro Ala Pro Gly Gly Leu Asp
225                 230                 235                 240

Gln Ser Glu Phe Asp Asn Phe Phe Lys Gln Ile Arg Lys Phe Leu Thr
                245                 250                 255

Val Gln Glu Gln Val Asp Leu Phe Leu Arg Trp Gln Gln Ala Gly Ser
            260                 265                 270

Ala Asp Ala Gly Phe Leu Gly Gly Leu Ala Leu Ala Ala Val Gly Phe
        275                 280                 285

Ser Arg Arg Lys Pro Glu Arg Val Gln Glu Ala Arg Gln His Leu Glu
    290                 295                 300

Arg Leu Gln Leu Asp Gly Cys Asp Pro Leu Pro Met Leu Gly Cys Leu
305                 310                 315                 320

Asp Leu Leu Leu Gly Asp Val Gly Arg Ala Gln Glu Arg Phe Leu Arg
                325                 330                 335

Ser Thr Asp Pro Arg Val Lys Asp Cys Leu Asn Ser His Pro Gly Asp
            340                 345                 350

Glu Leu Ala Ala Phe Cys Glu Tyr Cys Arg Ser Trp Leu Arg Gly Asp
        355                 360                 365

Val Leu Pro Gly Tyr Arg Asp Val Asp Ala Glu Ala Val Asp Leu Glu
    370                 375                 380

Ala Trp Phe Ala Asp Arg Asp Val Gln Ala Tyr Val Glu Arg Leu Glu
385                 390                 395                 400

Arg Ser Glu Asn Arg Ala Ser Ser Leu Gly Lys Ala Phe Ser Gly Ser
                405                 410                 415

Ser Val Lys Gln Pro Phe Pro Trp Ala Pro Leu Asp Pro Asp Gly Ile
            420                 425                 430

Leu Pro Leu Ser Leu Gly Gly Pro Asp Val Gly Gln Pro Ala Ala Asp
        435                 440                 445

Gln Ser Ser Asp Glu Phe Ala Ser Asp Gly Met Ala Trp Ile Asp Arg
    450                 455                 460

Leu Ala Asp Leu Pro Arg Pro Thr Arg Pro Val Leu Ile Gly Ser Val
465                 470                 475                 480

Val Phe Ala Ala Leu Ile Ala Ala Phe Ala Gly Phe Ser Leu Phe Gly
                485                 490                 495

Gln Arg Pro Arg Thr Ser Val Ser Thr Ala Ala Asp Gln Pro Gln Val
            500                 505                 510

Thr Ala Pro Pro Thr Ala Thr Leu Gln Glu Glu Val
        515                 520
```

<210> SEQ ID NO 119
<211> LENGTH: 566
<212> TYPE: PRT
<213> ORGANISM: Synechocystis PCC6803

<400> SEQUENCE: 119

```
Met Phe Ile Pro Leu Asp Phe Tyr Arg Ile Leu Gly Ile Pro Pro Gln
1               5                   10                  15

Ser Gly Gly Glu Thr Ile Glu Gln Ala Tyr Gln Asp Arg Leu Leu Gln
            20                  25                  30

Leu Pro Arg Arg Glu Phe Ser Asp Ala Ala Val Thr Leu Arg Asn Gln
        35                  40                  45

Leu Leu Ala Ile Ala Tyr Glu Thr Leu Arg Asp Pro Glu Lys Arg Gln
    50                  55                  60

Ala Tyr Asp Gln Glu Trp Trp Gly Ala Met Asp Glu Ala Leu Gly Glu
65                  70                  75                  80

Ala Leu Pro Leu Thr Thr Pro Glu Leu Glu Cys Ser Pro Glu Gln Glu
                85                  90                  95

Ile Gly Ala Leu Leu Ile Leu Leu Asp Leu Gly Glu Tyr Glu Leu Val
            100                 105                 110

Val Lys Tyr Gly Glu Pro Val Leu His Asp Pro Asn Pro Pro Ala Gly
        115                 120                 125

Gly Leu Pro Gln Asp Tyr Leu Leu Ser Val Ile Leu Ala His Trp Glu
    130                 135                 140

Leu Ser Arg Glu Arg Trp Gln Gln Gln Gln Tyr Glu Phe Ala Ala Thr
145                 150                 155                 160

Ala Ser Leu Lys Ala Leu Ala Arg Leu Gln Gln Asp Asn Asp Phe Pro
                165                 170                 175

Ala Leu Glu Ala Glu Ile Arg Gln Glu Leu Tyr Arg Leu Arg Pro Tyr
            180                 185                 190

Arg Ile Leu Glu Leu Leu Ala Lys Glu Gly Gln Gly Glu Glu Gln Arg
        195                 200                 205

Gln Gln Gly Leu Ala Leu Leu Gln Ala Met Val Gln Asp Arg Gly Gly
    210                 215                 220

Ile Glu Gly Lys Gly Glu Asp Tyr Ser Gly Leu Gly Asn Asp Asp Phe
225                 230                 235                 240

Leu Lys Phe Ile His Gln Leu Arg Cys His Leu Thr Val Ala Glu Gln
                245                 250                 255

Asn Ala Leu Phe Leu Pro Glu Ser Gln Arg Pro Ser Leu Val Ala Ser
            260                 265                 270

Tyr Leu Ala Val His Ser Leu Met Ala Glu Gly Val Lys Glu Gln Asp
        275                 280                 285

Pro Met Ala Ile Val Glu Ala Lys Ser Leu Ile Ile Gln Leu Glu Asn
    290                 295                 300

Cys Gln Asp Leu Ala Leu Glu Lys Val Ile Cys Glu Leu Leu Leu Gly
305                 310                 315                 320

Gln Thr Glu Val Val Leu Ala Ala Ile Asp Gln Gly Asp Pro Lys Ile
                325                 330                 335

Val Ala Gly Leu Glu Ser Lys Leu Ala Thr Gly Glu Asp Pro Leu Thr
            340                 345                 350

Ala Phe Tyr Thr Phe Thr Glu Gln Trp Leu Glu Glu Glu Ile Val Pro
        355                 360                 365

Tyr Phe Arg Asp Leu Ser Pro Glu Thr Leu Ser Pro Lys Ala Tyr Phe
    370                 375                 380

Asn Asn Pro Ser Val Gln Gln Tyr Leu Glu Gln Leu Glu Pro Asp Ser
385                 390                 395                 400

Phe Thr Thr Asp Asn Ser Phe Ala Ser Pro Ala Leu Leu Ser Thr Ala
```

-continued

```
            405                 410                 415

Thr Glu Ser Glu Thr Pro Met Val His Ser Ser Ala Ala Leu Pro Asp
            420                 425                 430

Arg Pro Leu Thr Ser Thr Val Pro Ser Arg Arg Gly Arg Ser Pro Arg
        435                 440                 445

Arg Ser Arg Asp Asp Val Phe Pro Ser Ala Asp Asn Ser Ser Gly Leu
    450                 455                 460

Ala Val Thr Thr Leu Ser Pro Ala Ile Ala Tyr Asp Thr His Ser Leu
465                 470                 475                 480

Gly Thr Asn Gly Ile Gly Gly Asp Ser Thr Ser Asn Gly Phe Ser Ser
                485                 490                 495

Asn Ser Ala Pro Glu Ser Thr Ser Lys His Lys Ser Pro Arg Arg Arg
            500                 505                 510

Lys Lys Arg Val Thr Ile Lys Pro Val Arg Phe Gly Ile Phe Leu Leu
        515                 520                 525

Cys Leu Ala Gly Ile Val Gly Gly Ala Thr Ala Leu Ile Ile Asn Arg
    530                 535                 540

Thr Gly Asp Pro Leu Gly Gly Leu Leu Glu Asp Pro Leu Asp Val Phe
545                 550                 555                 560

Leu Asp Gln Pro Ser Glu
                565


<210> SEQ ID NO 120
<211> LENGTH: 573
<212> TYPE: PRT
<213> ORGANISM: Synechococcus PCC7002

<400> SEQUENCE: 120

Thr Val Arg Ile Pro Leu Asp Tyr Tyr Arg Ile Leu Cys Val Pro Ala
1               5                   10                  15

Lys Ala Thr Thr Ala Gln Ile Thr Gln Ala Tyr Arg Asp Arg Leu Ser
            20                  25                  30

Gln Phe Pro Arg Arg Glu His Asn Ala Leu Ala Ile Glu Ala Arg Asn
        35                  40                  45

Arg Ile Ile Glu Gln Ala Phe Glu Val Leu Ser Gln Thr Glu Thr Arg
    50                  55                  60

Ala Val Tyr Asp His Glu Leu Ser Gly Asn Met Phe Arg Ser Leu Val
65                  70                  75                  80

Pro Ser Arg Pro Lys Leu Pro Phe Pro Asp Arg Pro Ser Ser Asp Thr
                85                  90                  95

Glu Leu Glu Ala Leu Thr Ala His Gln Pro Thr Ile Asp Ile Ala Glu
            100                 105                 110

Lys Asp Leu Leu Gly Gly Leu Leu Leu Leu Leu Asp Leu Gly Glu Tyr
        115                 120                 125

Glu Leu Val Leu Lys Trp Ala Ala Pro Tyr Leu Lys Gly Lys Gly Lys
    130                 135                 140

Leu Val Lys Glu Gly Lys Phe Gly Ala Val Glu Ile Val Glu Gln Glu
145                 150                 155                 160

Leu Arg Leu Cys Leu Ala Leu Ala His Trp Glu Leu Ser Arg Glu Gln
                165                 170                 175

Trp Leu Gln Gln His Tyr Glu Gln Ala Ala Leu Ser Gly Gln Lys Ser
            180                 185                 190

Gln Glu Leu Leu Val Asp Val Ala Gln Phe Ala Asp Leu Gln Gln Glu
        195                 200                 205
```

-continued

```
Ile Gln Gly Asp Leu Asn Arg Leu Arg Pro Tyr Gln Val Leu Glu Leu
    210                 215                 220

Leu Ala Leu Pro Glu Ser Glu Thr Gln Glu Arg Gln Arg Gly Leu Gln
225                 230                 235                 240

Leu Leu Gln Glu Met Leu Ser Ala Arg Val Gly Ile Asp Gly Gln Gly
                245                 250                 255

Asp Asp Gln Ser Gly Leu Ser Ile Asp Asp Phe Leu Arg Phe Ile Gln
            260                 265                 270

Gln Leu Arg Ser Tyr Leu Thr Val Gln Glu Gln Leu Asp Leu Phe Val
        275                 280                 285

Ala Glu Ser Lys Arg Pro Ser Ala Ala Ala Ala Tyr Leu Ala Val Tyr
    290                 295                 300

Ala Leu Leu Ala Ala Gly Phe Ser Gln Arg Lys Pro Asp Leu Val Val
305                 310                 315                 320

Gln Ala Gln Thr Leu Leu Lys Arg Leu Gly Lys Arg Gln Asp Val Phe
                325                 330                 335

Leu Glu Gln Ser Ile Cys Ala Leu Leu Leu Gly Gln Pro Ser Glu Ala
            340                 345                 350

Asn Gln Leu Leu Glu Gln Ser Gln Glu Gln Glu Ala Ile Ala Tyr Ile
        355                 360                 365

Gln Glu Gln Ser Glu Gly Ala Pro Asp Leu Leu Pro Gly Leu Cys Leu
    370                 375                 380

Tyr Gly Glu Gln Trp Leu Lys Thr Glu Val Phe Ser His Phe Arg Asp
385                 390                 395                 400

Leu Arg Gln Arg Leu Glu Asp Gly Ser Val Ser Leu Thr Ala Tyr Phe
                405                 410                 415

Ala Asp Pro Glu Val Gln Gln Tyr Leu Asp Asp Leu Leu Thr Glu Ala
            420                 425                 430

Val Pro Thr Pro Thr Pro His Pro Asp Thr Glu Ser Thr Ala Ala Pro
        435                 440                 445

Ser Glu Lys Pro Pro Glu Thr Leu Gln Ser Glu Thr Gly Val Ser Pro
    450                 455                 460

His Pro Ser Arg Pro Ala Lys Val Asp Ser Phe Glu Asp Leu Val Thr
465                 470                 475                 480

Gln Thr Pro Ala Thr Val Pro Pro Ala Pro Pro Ser Pro Gly Val Ala
                485                 490                 495

Pro Val Thr Ala Ala Leu Asn Pro Asp Pro Glu Ala Ser Ser Ala Ser
            500                 505                 510

Ser Lys Ser Val Ser Ser Lys Lys Ser Ile Gly Pro Trp Gly Ala Ile
        515                 520                 525

Ala Ala Ile Val Gly Ser Val Leu Leu Val Val Gly Leu Val Arg Ile
    530                 535                 540

Leu Ser Gly Leu Thr Thr Gln Glu Pro Leu Gln Val Thr Leu Asn Gly
545                 550                 555                 560

Glu Pro Pro Leu Thr Ile Pro Ser Leu Asp Thr Ala Glu
                565                 570


<210> SEQ ID NO 121
<211> LENGTH: 515
<212> TYPE: PRT
<213> ORGANISM: Synechococcus WH8102

<400> SEQUENCE: 121

Gly Asp Leu Trp Thr Leu Asp Leu Pro Ile Asp His Phe Arg Leu Leu
1               5                   10                  15
```

-continued

```
Gly Val Ser Pro Ser Ala Asp Pro Ala Ser Ile Leu Arg Arg Leu Gln
            20                  25                  30

Thr Arg Ser Asp Ser Pro Pro Asp Asp Gly Phe Thr His Glu Gly Leu
        35                  40                  45

Leu Gln Arg Gln Ala Leu Leu His Arg Ser Ala Asp Leu Leu Thr Asp
    50                  55                  60

Pro Ser Glu Arg Ala Asp Tyr Glu Ala Ala Leu Leu Ser Leu Ser Ala
65                  70                  75                  80

Thr His Pro Asn Glu Thr Val Gly Leu Asp Leu Ala Ala Ser Ser Glu
                85                  90                  95

Val Ala Gly Leu Ile Leu Leu Trp Glu Ala Gly Ala Ala Leu Glu Ala
            100                 105                 110

Phe Gln Leu Ala Arg Gln Gly Leu Gln Pro Pro Gln Ala Pro Ala Leu
        115                 120                 125

Gly Ser Gly Arg Glu Ala Asp Leu Thr Leu Leu Ala Ala Leu Ala Cys
    130                 135                 140

Arg Asp Ala Ala Arg Asp Glu Gln Gln Gln Arg Arg Tyr Glu Ser Ala
145                 150                 155                 160

Ala Gln Leu Leu Arg Asp Gly Ile Glu Leu Gln Gln Arg Met Gly Lys
                165                 170                 175

Leu Pro Asp Gln Gln Ala Arg Leu Gln Gln Glu Leu Asp Asp Leu Leu
            180                 185                 190

Pro Tyr Arg Val Leu Asp Leu Leu Ser Arg Asp Leu Ser Asp Ala Asp
        195                 200                 205

Ala Arg Gln Gln Gly Ile Ser Leu Leu Asp Gln Leu Val Arg Asp Arg
    210                 215                 220

Gly Gly Leu Asp Pro Glu Gly Leu Asp Ser Glu Thr Pro Ala Ala Met
225                 230                 235                 240

Gly Gln Ala Asp Phe Glu Ser Phe Phe Gln Gln Ile Arg Arg Phe Leu
                245                 250                 255

Thr Val Gln Glu Gln Val Asp Leu Phe Arg Gly Trp Phe Ala Glu Gly
            260                 265                 270

Ser Ile Glu Ala Gly Cys Leu Ala Val Phe Ala Leu Ala Ala Ala Gly
        275                 280                 285

Tyr Ser Arg Arg Lys Pro Glu Phe Leu Glu Gln Ala Arg Glu Gln Leu
    290                 295                 300

Gln Arg Leu Val Ala Ser Asp Leu Asp Pro Met Pro Leu Leu Gly Cys
305                 310                 315                 320

Leu Asp Leu Leu Leu Gly Asn Val Ala Glu Ala Ser Leu His Phe Ser
                325                 330                 335

Ala Ile Arg Asp Glu Glu Leu Leu Ser Trp Leu Ala Glu His Pro Gly
            340                 345                 350

Asp His Leu Ala Ala Gln Cys Glu Tyr Cys Arg Val Trp Leu Glu Arg
        355                 360                 365

Asp Val Leu Pro Gly Tyr Arg Asp Val Asp Ala Ala Gly Val Asp Leu
    370                 375                 380

Asp Ala Trp Phe Ala Asp Arg Asp Val Gln Ala Tyr Val Asp Arg Ile
385                 390                 395                 400

Asp Arg Gln Ser Ala Arg Leu Gly Ser Ala Ala Thr Val Thr Gly Ala
                405                 410                 415

Gly Leu Ser Ser Ala Pro Ser Ala Asp Ala Ser Ser Pro His Glu Ala
            420                 425                 430
```

```
Ala Leu Asp Asp Asp His Leu Pro Ala Glu Glu Ala Pro Ser Ser Asp
        435                 440                 445

Pro Ala Asn Gln Arg Leu Ser Asn Arg Leu Arg Trp Leu Ala Ala Ser
    450                 455                 460

Leu Val Val Gly Leu Val Ala Ala Leu Ala Ala Ala Val Met Leu Arg
465                 470                 475                 480

Pro Arg Glu Thr Ala Pro Val Val Leu Gln Pro Glu Pro Asp Arg Gln
                485                 490                 495

Asp Ala Val Glu Pro Lys Pro Ser Ala Gln Asp Ser Ala Thr Leu Lys
            500                 505                 510

Pro Gln Ala
        515


<210> SEQ ID NO 122
<211> LENGTH: 525
<212> TYPE: PRT
<213> ORGANISM: Oryza sativa

<400> SEQUENCE: 122

Ala Ala Glu Arg Ser Leu Pro Leu Gln Val Asp Phe Tyr Lys Val Leu
1               5                   10                  15

Gly Ala Glu Pro His Phe Leu Gly Asp Gly Ile Arg Arg Ala Phe Glu
            20                  25                  30

Ala Arg Ile Ala Lys Pro Pro Gln Tyr Gly Tyr Ser Thr Asp Ala Leu
        35                  40                  45

Val Gly Arg Arg Gln Met Leu Gln Ile Ala His Asp Thr Leu Met Asn
    50                  55                  60

Gln Asn Ser Arg Thr Gln Tyr Asp Arg Ala Leu Ser Glu Asn Arg Glu
65                  70                  75                  80

Glu Ala Leu Thr Met Asp Ile Ala Trp Asp Lys Glu Ala Gly Glu Ala
                85                  90                  95

Leu Ala Val Leu Val Thr Gly Glu Gln Leu Leu Leu Asp Arg Pro Pro
            100                 105                 110

Lys Arg Phe Lys Gln Asp Val Val Leu Ala Met Ala Leu Ala Tyr Val
        115                 120                 125

Asp Leu Ser Arg Asp Ala Met Ala Ala Ser Pro Pro Asp Val Ile Gly
    130                 135                 140

Cys Cys Glu Val Leu Glu Arg Ala Leu Lys Leu Leu Gln Glu Asp Gly
145                 150                 155                 160

Ala Ser Asn Leu Ala Pro Asp Leu Leu Ser Gln Ile Asp Glu Thr Leu
                165                 170                 175

Glu Glu Ile Thr Pro Arg Cys Val Leu Glu Leu Leu Ser Leu Pro Ile
            180                 185                 190

Asp Thr Glu His His Lys Lys Arg Gln Glu Gly Leu Gln Gly Ala Arg
        195                 200                 205

Asn Ile Leu Trp Ser Val Gly Arg Gly Gly Ile Ala Thr Val Gly Gly
    210                 215                 220

Gly Phe Ser Arg Glu Ala Phe Met Asn Glu Ala Phe Leu Arg Met Thr
225                 230                 235                 240

Ser Ile Glu Gln Met Asp Phe Phe Ser Lys Thr Pro Asn Ser Ile Pro
                245                 250                 255

Pro Glu Trp Phe Glu Ile Tyr Asn Val Ala Leu Ala His Val Ala Gln
            260                 265                 270

Ala Ile Ile Ser Lys Arg Pro Gln Phe Ile Met Met Ala Asp Asp Leu
        275                 280                 285
```

```
Phe Glu Gln Leu Gln Lys Phe Asn Ile Gly Ser His Tyr Ala Tyr Asp
    290                 295                 300

Asn Glu Met Asp Leu Ala Leu Glu Arg Ala Phe Cys Ser Leu Leu Val
305                 310                 315                 320

Gly Asp Val Ser Lys Cys Arg Met Trp Leu Gly Ile Asp Asn Glu Ser
                325                 330                 335

Ser Pro Tyr Arg Asp Pro Lys Ile Leu Glu Phe Ile Val Thr Asn Ser
            340                 345                 350

Ser Ile Ser Glu Glu Asn Asp Leu Leu Pro Gly Leu Cys Lys Leu Leu
        355                 360                 365

Glu Thr Trp Leu Ile Phe Glu Val Phe Pro Arg Ser Arg Asp Thr Arg
    370                 375                 380

Gly Met Gln Phe Arg Leu Gly Asp Tyr Tyr Asp Asp Pro Glu Val Leu
385                 390                 395                 400

Ser Tyr Leu Glu Arg Met Glu Gly Gly Gly Ala Ser His Leu Ala Ala
                405                 410                 415

Ala Ala Ala Ile Ala Lys Leu Gly Ala Gln Ala Thr Ala Ala Leu Gly
            420                 425                 430

Thr Val Lys Ser Asn Ala Ile Gln Ala Phe Asn Lys Val Phe Pro Leu
        435                 440                 445

Ile Glu Gln Leu Asp Arg Ser Ala Met Glu Asn Thr Lys Asp Gly Pro
    450                 455                 460

Gly Gly Tyr Leu Glu Asn Phe Asp Gln Glu Asn Ala Pro Ala His Asp
465                 470                 475                 480

Ser Arg Asn Ala Ala Leu Lys Ile Ile Ser Ala Gly Ala Leu Phe Ala
                485                 490                 495

Leu Leu Ala Val Ile Gly Ala Lys Tyr Leu Pro Arg Lys Arg Pro Leu
            500                 505                 510

Ser Ala Ile Arg Ser Glu His Gly Ser Val Ala Val Ala
        515                 520                 525


<210> SEQ ID NO 123
<211> LENGTH: 578
<212> TYPE: PRT
<213> ORGANISM: Arabidopsis thaliana

<400> SEQUENCE: 123

Arg Pro Glu Arg His Val Pro Ile Pro Ile Asp Phe Tyr Gln Val Leu
1               5                   10                  15

Gly Ala Gln Thr His Phe Leu Thr Asp Gly Ile Arg Arg Ala Phe Glu
            20                  25                  30

Ala Arg Val Ser Lys Pro Pro Gln Phe Gly Phe Ser Asp Asp Ala Leu
        35                  40                  45

Ile Ser Arg Arg Gln Ile Leu Gln Ala Ala Cys Glu Thr Leu Ser Asn
    50                  55                  60

Pro Arg Ser Arg Arg Glu Tyr Asn Glu Gly Leu Leu Asp Asp Glu Glu
65                  70                  75                  80

Ala Thr Val Ile Thr Asp Val Pro Trp Asp Lys Val Pro Gly Ala Leu
                85                  90                  95

Cys Val Leu Gln Glu Gly Gly Glu Thr Glu Ile Val Leu Arg Val Gly
            100                 105                 110

Glu Ala Leu Leu Lys Glu Arg Leu Pro Lys Ser Phe Lys Gln Asp Val
        115                 120                 125

Val Leu Val Met Ala Leu Ala Phe Leu Asp Val Ser Arg Asp Ala Met
```

-continued

```
    130                 135                 140

Ala Leu Asp Pro Pro Asp Phe Ile Thr Gly Tyr Glu Phe Val Glu Glu
145                 150                 155                 160

Ala Leu Lys Leu Leu Gln Glu Glu Gly Ala Ser Ser Leu Ala Pro Asp
                165                 170                 175

Leu Arg Ala Gln Ile Asp Glu Thr Leu Glu Glu Ile Thr Pro Arg Tyr
            180                 185                 190

Val Leu Glu Leu Leu Gly Leu Pro Leu Gly Asp Asp Tyr Ala Ala Lys
        195                 200                 205

Arg Leu Asn Gly Leu Ser Gly Val Arg Asn Ile Leu Trp Ser Val Gly
    210                 215                 220

Gly Gly Gly Ala Ser Ala Leu Val Gly Gly Leu Thr Arg Glu Lys Phe
225                 230                 235                 240

Met Asn Glu Ala Phe Leu Arg Met Thr Ala Ala Glu Gln Val Asp Leu
                245                 250                 255

Phe Val Ala Thr Pro Ser Asn Ile Pro Ala Glu Ser Phe Glu Val Tyr
            260                 265                 270

Glu Val Ala Leu Ala Leu Val Ala Gln Ala Phe Ile Gly Lys Lys Pro
        275                 280                 285

His Leu Leu Gln Asp Ala Asp Lys Gln Phe Gln Gln Leu Gln Gln Ala
    290                 295                 300

Lys Val Met Ala Met Glu Ile Pro Ala Met Leu Tyr Asp Thr Arg Asn
305                 310                 315                 320

Asn Trp Glu Ile Asp Phe Gly Leu Glu Arg Gly Leu Cys Ala Leu Leu
                325                 330                 335

Ile Gly Lys Val Asp Glu Cys Arg Met Trp Leu Gly Leu Asp Ser Glu
            340                 345                 350

Asp Ser Gln Tyr Arg Asn Pro Ala Ile Val Glu Phe Val Leu Glu Asn
        355                 360                 365

Ser Asn Arg Asp Asp Asn Asp Asp Leu Pro Gly Leu Cys Lys Leu Leu
    370                 375                 380

Glu Thr Trp Leu Ala Gly Val Val Phe Pro Arg Phe Arg Asp Thr Lys
385                 390                 395                 400

Asp Lys Lys Phe Lys Leu Gly Asp Tyr Tyr Asp Asp Pro Met Val Leu
                405                 410                 415

Ser Tyr Leu Glu Arg Val Glu Val Val Gln Gly Ser Pro Leu Ala Ala
            420                 425                 430

Ala Ala Ala Met Ala Arg Ile Gly Ala Glu His Val Lys Ala Ser Ala
        435                 440                 445

Met Gln Ala Leu Gln Lys Val Phe Pro Ser Arg Tyr Thr Asp Arg Asn
    450                 455                 460

Ser Ala Glu Pro Lys Asp Val Gln Glu Thr Val Phe Ser Val Asp Pro
465                 470                 475                 480

Val Gly Asn Asn Val Gly Arg Asp Gly Glu Pro Gly Val Phe Ile Ala
                485                 490                 495

Glu Ala Val Arg Pro Ser Glu Asn Phe Glu Thr Asn Asp Tyr Ala Ile
            500                 505                 510

Arg Ala Gly Val Ser Glu Ser Ser Val Asp Glu Thr Thr Val Glu Met
        515                 520                 525

Ser Val Ala Asp Met Leu Lys Glu Ala Ser Val Lys Ile Leu Ala Ala
    530                 535                 540

Gly Val Ala Ile Gly Leu Ile Ser Leu Phe Ser Gln Lys Tyr Phe Leu
545                 550                 555                 560
```

```
Lys Ser Ser Ser Ser Phe Gln Arg Lys Asp Met Val Ser Ser Met Glu
                565                 570                 575

Ser Asp


<210> SEQ ID NO 124
<211> LENGTH: 99
<212> TYPE: PRT
<213> ORGANISM: Solanum tuberosum

<400> SEQUENCE: 124

Pro Ser Asp His His Ile Ser Met Pro Ile Asp Phe Tyr Arg Val Leu
1               5                   10                  15

Gly Ala Glu Ala His Phe Leu Gly Asp Gly Ile Arg Arg Cys Tyr Asp
            20                  25                  30

Ala Arg Ile Thr Lys Pro Pro Gln Tyr Gly Tyr Ser Gln Glu Ala Leu
        35                  40                  45

Ile Gly Arg Arg Gln Ile Leu Gln Ala Ala Cys Glu Thr Leu Ala Asp
    50                  55                  60

Ser Thr Ser Arg Arg Glu Tyr Asn Gln Gly Leu Ala Gln His Glu Phe
65                  70                  75                  80

Asp Thr Ile Leu Thr Pro Val Pro Trp Asp Lys Val Pro Gly Ala Met
                85                  90                  95

Cys Val Leu


<210> SEQ ID NO 125
<211> LENGTH: 760
<212> TYPE: PRT
<213> ORGANISM: Oryza sativa

<400> SEQUENCE: 125

Met Glu Gly Phe His Asn Leu Leu Ala Arg Pro Asn Ser Ala Pro Phe
1               5                   10                  15

Ala Phe Ser Leu Pro Arg Pro Arg Pro Arg Pro Arg Arg Arg Pro Pro
            20                  25                  30

Pro His Pro Ser Ala Ala Cys Arg Ala Ala Ser Arg Trp Ala Glu Arg
        35                  40                  45

Leu Phe Ala Asp Phe His Leu Leu Pro Thr Ala Ala Pro Ser Asp Pro
    50                  55                  60

Pro Ser Pro Ala Pro Ala Pro Ala Ala Ala Pro Ser Ala Ser Pro Phe
65                  70                  75                  80

Val Pro Leu Phe Pro Asp Ala Ala Glu Arg Ser Leu Pro Leu Gln Val
                85                  90                  95

Asp Phe Tyr Lys Val Leu Gly Ala Glu Pro His Phe Leu Gly Asp Gly
            100                 105                 110

Ile Arg Arg Ala Phe Glu Ala Arg Ile Ala Lys Pro Pro Gln Tyr Gly
        115                 120                 125

Tyr Ser Thr Asp Ala Leu Val Gly Arg Arg Gln Met Leu Gln Ile Ala
    130                 135                 140

His Asp Thr Leu Met Asn Gln Asn Ser Arg Thr Gln Tyr Asp Arg Ala
145                 150                 155                 160

Leu Ser Glu Asn Arg Glu Glu Ala Leu Thr Met Asp Ile Ala Trp Asp
                165                 170                 175

Lys Glu Ala Gly Glu Ala Leu Ala Val Leu Val Thr Gly Glu Gln Leu
            180                 185                 190

Leu Leu Asp Arg Pro Pro Lys Arg Phe Lys Gln Asp Val Val Leu Ala
```

-continued

```
        195                 200                 205

Met Ala Leu Ala Tyr Val Asp Leu Ser Arg Asp Ala Met Ala Ala Ser
    210                 215                 220

Pro Pro Asp Val Ile Gly Cys Cys Glu Val Leu Glu Arg Ala Leu Lys
225                 230                 235                 240

Leu Leu Gln Glu Asp Gly Ala Ser Asn Leu Ala Pro Asp Leu Leu Ser
                245                 250                 255

Gln Ile Asp Glu Thr Leu Glu Glu Ile Thr Pro Arg Cys Val Leu Glu
            260                 265                 270

Leu Leu Ser Leu Pro Ile Asp Thr Glu His His Lys Lys Arg Gln Glu
        275                 280                 285

Gly Leu Gln Gly Ala Arg Asn Ile Leu Trp Ser Val Gly Arg Gly Gly
    290                 295                 300

Ile Ala Thr Val Gly Gly Gly Phe Ser Arg Glu Ala Phe Met Asn Glu
305                 310                 315                 320

Ala Phe Leu Arg Met Thr Ser Ile Glu Gln Met Asp Phe Phe Ser Lys
                325                 330                 335

Thr Pro Asn Ser Ile Pro Pro Glu Trp Phe Glu Ile Tyr Asn Val Ala
            340                 345                 350

Leu Ala His Val Ala Gln Ala Ile Ile Ser Lys Arg Pro Gln Phe Ile
        355                 360                 365

Met Met Ala Asp Asp Leu Phe Glu Gln Leu Gln Lys Phe Asn Ile Gly
    370                 375                 380

Ser His Tyr Ala Tyr Asp Asn Glu Met Asp Leu Ala Leu Glu Arg Ala
385                 390                 395                 400

Phe Cys Ser Leu Leu Val Gly Asp Val Ser Lys Cys Arg Met Trp Leu
                405                 410                 415

Gly Ile Asp Asn Glu Ser Ser Pro Tyr Arg Asp Pro Lys Ile Leu Glu
            420                 425                 430

Phe Ile Val Thr Asn Ser Ser Ile Ser Glu Glu Asn Asp Leu Leu Pro
        435                 440                 445

Gly Leu Cys Lys Leu Leu Glu Thr Trp Leu Ile Phe Glu Val Phe Pro
    450                 455                 460

Arg Ser Arg Asp Thr Arg Gly Met Gln Phe Arg Leu Gly Asp Tyr Tyr
465                 470                 475                 480

Asp Asp Pro Glu Val Leu Ser Tyr Leu Glu Arg Met Glu Gly Gly Gly
                485                 490                 495

Ala Ser His Leu Ala Ala Ala Ala Ala Ile Ala Lys Leu Gly Ala Gln
            500                 505                 510

Ala Thr Ala Ala Leu Gly Thr Val Lys Ser Asn Ala Ile Gln Ala Phe
        515                 520                 525

Asn Lys Val Phe Pro Leu Ile Glu Gln Leu Asp Arg Ser Ala Met Glu
    530                 535                 540

Asn Thr Lys Asp Gly Pro Gly Gly Tyr Leu Glu Asn Phe Asp Gln Glu
545                 550                 555                 560

Asn Ala Pro Ala His Asp Ser Arg Asn Ala Ala Leu Lys Ile Ile Ser
                565                 570                 575

Ala Gly Ala Leu Phe Ala Leu Leu Ala Val Ile Gly Ala Lys Tyr Leu
            580                 585                 590

Pro Arg Lys Arg Pro Leu Ser Ala Ile Arg Ser Glu His Gly Ser Val
        595                 600                 605

Ala Val Ala Asn Ser Val Asp Ser Thr Asp Asp Pro Ala Leu Asp Glu
    610                 615                 620
```

```
Asp Pro Val His Ile Pro Arg Met Asp Ala Lys Leu Ala Glu Asp Ile
625                 630                 635                 640

Val Arg Lys Trp Gln Ser Ile Lys Ser Lys Ala Leu Gly Pro Glu His
                645                 650                 655

Ser Val Ala Ser Leu Gln Glu Val Leu Asp Gly Asn Met Leu Lys Val
            660                 665                 670

Trp Thr Asp Arg Ala Ala Glu Ile Glu Arg His Gly Trp Phe Trp Glu
        675                 680                 685

Tyr Thr Leu Ser Asp Val Thr Ile Asp Ser Ile Thr Ile Ser Leu Asp
    690                 695                 700

Gly Arg Arg Ala Thr Val Glu Ala Thr Ile Asp Glu Ala Gly Gln Leu
705                 710                 715                 720

Thr Asp Val Thr Glu Pro Arg Asn Asn Asp Ser Tyr Asp Thr Lys Tyr
                725                 730                 735

Thr Thr Arg Tyr Glu Met Ala Phe Ser Lys Leu Gly Gly Trp Lys Ile
            740                 745                 750

Thr Glu Gly Ala Val Leu Lys Ser
        755                 760
```

<210> SEQ ID NO 126
<211> LENGTH: 2283
<212> TYPE: DNA
<213> ORGANISM: Oryza sativa

<400> SEQUENCE: 126

```
atggagggct tccacaacct cctcgcccgc cccaactcgg cgccattcgc cttctccctc      60
cctcgcccgc gcccgcgccc gcgccgcagg ccgccgcctc accccctccgc tgcctgccgc    120
gccgcgagcc gctgggccga acgcctcttc gccgacttcc acctcctccc caccgccgcg    180
ccctccgacc cgccgtcccc ggccccggcc ccggccgccg cgccctccgc ctccccccttc    240
gtcccgctct tccccgacgc cgccgaacgc tccctcccgc tccaagtcga tttctacaag    300
gttctagggg cagagccaca tttccttggc gatggcatca ggagggcgtt cgaggcacgg    360
atagccaagc caccgcagta tggctacagc acggatgctc ttgttggtcg tcgacaaatg    420
ctgcagattg cccatgacac tctcatgaac cagaactccc gcactcagta tgatcgtgcg    480
ctttctgaga accgtgaaga agctctcacc atggatattg cttgggacaa ggaggctggg    540
gaggcacttg ctgtgcttgt aactggagaa cagttgcttc tggatcggcc acccaagcgc    600
ttcaagcagg acgtggtgct agcgatggct ctggcttatg tggatctatc aagggatgct    660
atggcagcaa gccctccaga tgtaattggc tgctgcgagg tgctcgagag ggctctcaag    720
ctcttgcagg aagatggagc aagcaatctc gcacctgatc tgctttcaca gattgatgaa    780
actctcgagg agattacacc tcgctgtgta ttggagcttc tctcccttcc tattgacaca    840
gagcatcata agaagcgcca agaagggctt caaggtgcga gaaacatttt gtggagcgtt    900
ggcagaggag gtattgctac cgttggagga ggattttctc gtgaagcctt catgaacgag    960
gctttttga ggatgacatc aattgaacag atggatttct tttcaaaaac accgaatagc    1020
attcctcctg aatggtttga aatttacaat gtagcacttg cacatgtcgc tcaagcaatt   1080
ataagtaaaa ggccacaatt catcatgatg gcggatgatc tttttgaaca actccagaag   1140
ttcaacatag gttctcatta tgcttatgat aatgagatgg accttgcatt ggaaagggca   1200
ttctgctcat tgctagtcgg agatgttagc aagtgcagaa tgtggcttgg aattgataat   1260
gagtcttcac catacagaga ccccaaaatt ctagagttta ttgtgaccaa ctctagcatc   1320
```

```
agtgaagaga atgatcttct tccagggctg tgcaagcttt tggagacttg gcttatcttt   1380

gaggtttttc ctaggagcag agatactcgg ggcatgcagt tcagacttgg agattactac   1440

gatgatccag aagttttaag ctacctagaa aggatggagg gtggtggtgc ttctcatttg   1500

gctgctgctg ctgctattgc aaaacttggt gctcaagcta cagctgcact tggtactgtg   1560

aaatcaaatg ctattcaagc gttcaacaag gtttttccat tgatagaaca gttagacagg   1620

tcagccatgg aaaatactaa agatggccct gggggatatc ttgaaaattt tgaccaggaa   1680

aatgcacctg ctcatgattc gagaaatgcc gccttgaaga ttatctctgc tggcgcactg   1740

tttgcactgt tggcagtaat tggggccaaa tatttgcctc gtaagaggcc cctttctgct   1800

attaggagtg agcatggatc tgtggcagtt gctaatagtg tcgactctac tgatgatcct   1860

gcactagatg aagatccagt acatattcct agaatggatg cgaagctggc agaagatatt   1920

gttcgcaagt ggcagagtat caaatctaag gccttgggac cagaacattc ggttgcatca   1980

ttgcaagagg ttcttgatgg caacatgcta aaggtgtgga ctgaccgagc agcggagatt   2040

gagcgtcatg ggtggttctg ggagtataca ctatccgatg tgacgattga tagcatcact   2100

atctccctag atggtcgacg agcgactgtg gaggctacga ttgatgaggc aggccaactt   2160

actgatgtta ctgagcccag aaacaatgat tcatatgaca caaaatacac tacccggtat   2220

gagatggcct tctccaagct aggagggtgg aagataacgg aaggagcagt cctcaagtcg   2280

tag                                                                 2283
```

```
<210> SEQ ID NO 127
<211> LENGTH: 801
<212> TYPE: PRT
<213> ORGANISM: Arabidopsis thaliana

<400> SEQUENCE: 127

Met Glu Ala Leu Ser His Val Gly Ile Gly Leu Ser Pro Phe Gln Leu
1               5                   10                  15

Cys Arg Leu Pro Pro Ala Thr Thr Lys Leu Arg Arg Ser His Asn Thr
            20                  25                  30

Ser Thr Thr Ile Cys Ser Ala Ser Lys Trp Ala Asp Arg Leu Leu Ser
        35                  40                  45

Asp Phe Asn Phe Thr Ser Asp Ser Ser Ser Ser Ser Phe Ala Thr Ala
    50                  55                  60

Thr Thr Thr Ala Thr Leu Val Ser Pro Pro Pro Ser Ile Asp Arg Pro
65                  70                  75                  80

Glu Arg His Val Pro Ile Pro Ile Asp Phe Tyr Gln Val Leu Gly Ala
                85                  90                  95

Gln Thr His Phe Leu Thr Asp Gly Ile Arg Arg Ala Phe Glu Ala Arg
            100                 105                 110

Val Ser Lys Pro Pro Gln Phe Gly Phe Ser Asp Asp Ala Leu Ile Ser
        115                 120                 125

Arg Arg Gln Ile Leu Gln Ala Ala Cys Glu Thr Leu Ser Asn Pro Arg
    130                 135                 140

Ser Arg Arg Glu Tyr Asn Glu Gly Leu Leu Asp Asp Glu Glu Ala Thr
145                 150                 155                 160

Val Ile Thr Asp Val Pro Trp Asp Lys Val Pro Gly Ala Leu Cys Val
                165                 170                 175

Leu Gln Glu Gly Gly Glu Thr Glu Ile Val Leu Arg Val Gly Glu Ala
            180                 185                 190
```

-continued

```
Leu Leu Lys Glu Arg Leu Pro Lys Ser Phe Lys Gln Asp Val Val Leu
        195                 200                 205

Val Met Ala Leu Ala Phe Leu Asp Val Ser Arg Asp Ala Met Ala Leu
    210                 215                 220

Asp Pro Pro Asp Phe Ile Thr Gly Tyr Glu Phe Val Glu Glu Ala Leu
225                 230                 235                 240

Lys Leu Leu Gln Glu Glu Gly Ala Ser Ser Leu Ala Pro Asp Leu Arg
                245                 250                 255

Ala Gln Ile Asp Glu Thr Leu Glu Glu Ile Thr Pro Arg Tyr Val Leu
            260                 265                 270

Glu Leu Leu Gly Leu Pro Leu Gly Asp Asp Tyr Ala Ala Lys Arg Leu
        275                 280                 285

Asn Gly Leu Ser Gly Val Arg Asn Ile Leu Trp Ser Val Gly Gly Gly
    290                 295                 300

Gly Ala Ser Ala Leu Val Gly Gly Leu Thr Arg Glu Lys Phe Met Asn
305                 310                 315                 320

Glu Ala Phe Leu Arg Met Thr Ala Ala Glu Gln Val Asp Leu Phe Val
                325                 330                 335

Ala Thr Pro Ser Asn Ile Pro Ala Glu Ser Phe Glu Val Tyr Glu Val
            340                 345                 350

Ala Leu Ala Leu Val Ala Gln Ala Phe Ile Gly Lys Lys Pro His Leu
        355                 360                 365

Leu Gln Asp Ala Asp Lys Gln Phe Gln Gln Leu Gln Gln Ala Lys Val
    370                 375                 380

Met Ala Met Glu Ile Pro Ala Met Leu Tyr Asp Thr Arg Asn Asn Trp
385                 390                 395                 400

Glu Ile Asp Phe Gly Leu Glu Arg Gly Leu Cys Ala Leu Leu Ile Gly
                405                 410                 415

Lys Val Asp Glu Cys Arg Met Trp Leu Gly Leu Asp Ser Glu Asp Ser
            420                 425                 430

Gln Tyr Arg Asn Pro Ala Ile Val Glu Phe Val Leu Glu Asn Ser Asn
        435                 440                 445

Arg Asp Asp Asn Asp Asp Leu Pro Gly Leu Cys Lys Leu Leu Glu Thr
    450                 455                 460

Trp Leu Ala Gly Val Val Phe Pro Arg Phe Arg Asp Thr Lys Asp Lys
465                 470                 475                 480

Lys Phe Lys Leu Gly Asp Tyr Tyr Asp Asp Pro Met Val Leu Ser Tyr
                485                 490                 495

Leu Glu Arg Val Glu Val Val Gln Gly Ser Pro Leu Ala Ala Ala Ala
            500                 505                 510

Ala Met Ala Arg Ile Gly Ala Glu His Val Lys Ala Ser Ala Met Gln
        515                 520                 525

Ala Leu Gln Lys Val Phe Pro Ser Arg Tyr Thr Asp Arg Asn Ser Ala
    530                 535                 540

Glu Pro Lys Asp Val Gln Glu Thr Val Phe Ser Val Asp Pro Val Gly
545                 550                 555                 560

Asn Asn Val Gly Arg Asp Gly Glu Pro Gly Val Phe Ile Ala Glu Ala
                565                 570                 575

Val Arg Pro Ser Glu Asn Phe Glu Thr Asn Asp Tyr Ala Ile Arg Ala
            580                 585                 590

Gly Val Ser Glu Ser Ser Val Asp Glu Thr Thr Val Glu Met Ser Val
        595                 600                 605

Ala Asp Met Leu Lys Glu Ala Ser Val Lys Ile Leu Ala Ala Gly Val
```

-continued

```
    610                 615                 620

Ala Ile Gly Leu Ile Ser Leu Phe Ser Gln Lys Tyr Phe Leu Lys Ser
625                 630                 635                 640

Ser Ser Ser Phe Gln Arg Lys Asp Met Val Ser Ser Met Glu Ser Asp
                645                 650                 655

Val Ala Thr Ile Gly Ser Val Arg Ala Asp Asp Ser Glu Ala Leu Pro
            660                 665                 670

Arg Met Asp Ala Arg Thr Ala Glu Asn Ile Val Ser Lys Trp Gln Lys
        675                 680                 685

Ile Lys Ser Leu Ala Phe Gly Pro Asp His Arg Ile Glu Met Leu Pro
    690                 695                 700

Glu Val Leu Asp Gly Arg Met Leu Lys Ile Trp Thr Asp Arg Ala Ala
705                 710                 715                 720

Glu Thr Ala Gln Leu Gly Leu Val Tyr Asp Tyr Thr Leu Leu Lys Leu
                725                 730                 735

Ser Val Asp Ser Val Thr Val Ser Ala Asp Gly Thr Arg Ala Leu Val
            740                 745                 750

Glu Ala Thr Leu Glu Glu Ser Ala Cys Leu Ser Asp Leu Val His Pro
        755                 760                 765

Glu Asn Asn Ala Thr Asp Val Arg Thr Tyr Thr Thr Arg Tyr Glu Val
    770                 775                 780

Phe Trp Ser Lys Ser Gly Trp Lys Ile Thr Glu Gly Ser Val Leu Ala
785                 790                 795                 800

Ser
```

<210> SEQ ID NO 128
<211> LENGTH: 2406
<212> TYPE: DNA
<213> ORGANISM: Arabidopsis thaliana

<400> SEQUENCE: 128

```
atggaagctc tgagtcacgt cggcattggt ctctccccat tccaattatg ccgattacca      60

ccggcgacga caaagctccg acgtagccac aacacctcta caactatctg ctccgccagc     120

aaatgggccg accgtcttct ctccgacttc aatttcacct ccgattcctc ctcctcctcc     180

ttcgccaccg ccaccaccac cgccactctc gtctctccgc caccatctat tgatcgtccc     240

gaacgccacg tccccatccc cattgatttc taccaggtat taggagctca aacacatttc     300

ttaaccgatg gaatcagaag agcattcgaa gctagggttt cgaaaccgcc gcaattcggt     360

ttcagcgacg acgctttaat cagccggaga cagattcttc aagctgcttg cgaaactctg     420

tctaatcctc ggtctagaag agagtacaat gaaggtcttc ttgatgatga agaagctaca     480

gtcatcactg atgttccttg ggataaggtt cctggtgctc tctgtgtatt gcaagaaggt     540

ggtgagactg agatagttct tcgggttggt gaggctctgc ttaaggagag gttgcctaag     600

tcgtttaagc aagatgtggt tttagttatg gcgcttgcgt ttctcgatgt ctcgagggat     660

gctatggcat tggatccacc tgattttata actggttatg agtttgttga ggaagctttg     720

aagcttttac aggaggaagg agcaagtagc cttgcaccgg atttacgtgc acaaattgat     780

gagactttgg aagagatcac tccgcgttat gtcttggagc tacttggctt accgcttggt     840

gatgattacg ctgcgaaaag actaaatggt ttaagcggtg tgcggaatat tttgtggtct     900

gttggaggag gtggagcatc agctcttgtt gggggtttga cccgtgagaa gtttatgaat     960

gaggcgtttt tacgaatgac agctgctgag caggttgatc tttttgtagc taccccaagc    1020
```

-continued

```
aatattccag cagagtcatt tgaagtttac gaagttgcac ttgctcttgt ggctcaagct   1080

tttattggta agaagccaca ccttttacag gatgctgata agcaattcca gcaacttcag   1140

caggctaagg taatggctat ggagattcct gcgatgttgt atgatacacg gaataattgg   1200

gagatagact tcggtctaga aaggggactc tgtgcactgc ttataggcaa agttgatgaa   1260

tgccgtatgt ggttgggctt agacagtgag gattcacaat ataggaatcc agctattgtg   1320

gagtttgttt tggagaattc aaatcgtgat gacaatgatg atctccctgg actatgcaaa   1380

ttgttggaaa cctggttggc aggggttgtc tttcctaggt tcagagacac caaagataaa   1440

aaatttaaac tcggggacta ctatgatgat cctatggttt tgagttactt ggaaagagtg   1500

gaggtagttc agggttctcc tttagctgct gctgcagcta tggcaaggat tggagccgag   1560

catgtgaaag ctagtgctat gcaggcactg cagaaagttt ttccttcccg ctatacagat   1620

agaaactcgg ctgaacccaa ggatgtgcaa gagacagtgt ttagtgtaga tcctgttggt   1680

aacaatgtag gccgtgatgg tgagcctggt gtctttattg cagaagctgt aagaccctct   1740

gaaaactttg aaactaatga ttatgcaatt cgagctgggg tctcagagag tagcgttgat   1800

gaaactactg ttgaaatgtc cgttgctgat atgttaaagg aggcaagtgt gaagatccta   1860

gctgctggtg tggcaattgg actgatttca ctgttcagcc agaagtattt tcttaaaagc   1920

agctcatctt ttcaacgcaa ggatatggtt tcttctatgg aatctgatgt cgctaccata   1980

gggtcagtca gagctgacga ttcagaagca cttcccagaa tggatgctag gactgcagag   2040

aatatagtat ccaagtggca gaagattaag tctctggctt ttgggcctga tcaccgcata   2100

gaaatgttac cagaggtttt ggatgggcga atgctgaaga tttggactga cagagcagct   2160

gaaactgcgc agcttgggtt ggtttatgat tatacactgt tgaaactatc tgttgacagt   2220

gtgacagtct cagcagatgg aacccgtgct ctggtggaag caactctgga ggagtctgct   2280

tgtctatctg atttggttca tccagaaaac aatgctactg atgtcagaac ctacacaaca   2340

agatacgaag ttttctggtc caagtcaggg tggaaaatca ctgaaggctc tgttcttgca   2400

tcataa                                                              2406
```

```
<210> SEQ ID NO 129
<211> LENGTH: 801
<212> TYPE: PRT
<213> ORGANISM: Arabidopsis thaliana

<400> SEQUENCE: 129

Met Glu Ala Leu Ser His Val Gly Ile Gly Leu Ser Pro Phe Gln Leu
1               5                   10                  15

Cys Arg Leu Pro Pro Ala Thr Thr Lys Leu Arg Arg Ser His Asn Thr
            20                  25                  30

Ser Thr Thr Ile Cys Ser Ala Ser Lys Trp Ala Asp Arg Leu Leu Ser
        35                  40                  45

Asp Phe Asn Phe Thr Ser Asp Ser Ser Ser Ser Ser Phe Ala Thr Ala
    50                  55                  60

Thr Thr Thr Ala Thr Leu Val Ser Pro Pro Pro Ser Ile Asp Arg Pro
65                  70                  75                  80

Glu Arg His Val Pro Ile Pro Ile Asp Phe Tyr Gln Val Leu Gly Ala
                85                  90                  95

Gln Thr His Phe Leu Thr Asp Gly Ile Arg Arg Ala Phe Glu Ala Arg
            100                 105                 110

Val Ser Lys Pro Pro Gln Phe Gly Phe Ser Asp Asp Ala Leu Ile Ser
        115                 120                 125
```

```
Arg Arg Gln Ile Leu Gln Ala Ala Cys Glu Thr Leu Ser Asn Pro Arg
    130                 135                 140

Ser Arg Arg Glu Tyr Asn Glu Gly Leu Leu Asp Asp Glu Glu Ala Thr
145                 150                 155                 160

Val Ile Thr Asp Val Pro Trp Asp Lys Val Pro Gly Ala Leu Cys Val
                165                 170                 175

Leu Gln Glu Gly Gly Glu Thr Glu Ile Val Leu Arg Val Gly Glu Ala
            180                 185                 190

Leu Leu Lys Glu Arg Leu Pro Lys Ser Phe Lys Gln Asp Val Val Leu
        195                 200                 205

Val Met Ala Leu Ala Phe Leu Asp Val Ser Arg Asp Ala Met Ala Leu
    210                 215                 220

Asp Pro Pro Asp Phe Ile Thr Gly Tyr Glu Phe Val Glu Glu Ala Leu
225                 230                 235                 240

Lys Leu Leu Gln Glu Glu Gly Ala Ser Ser Leu Ala Pro Asp Leu Arg
                245                 250                 255

Ala Gln Ile Asp Glu Thr Leu Glu Glu Ile Thr Pro Arg Tyr Val Leu
            260                 265                 270

Glu Leu Leu Gly Leu Pro Leu Gly Asp Asp Tyr Ala Ala Lys Arg Leu
        275                 280                 285

Asn Gly Leu Ser Gly Val Arg Asn Ile Leu Trp Ser Val Gly Gly Gly
    290                 295                 300

Gly Ala Ser Ala Leu Val Gly Gly Leu Thr Arg Glu Lys Phe Met Asn
305                 310                 315                 320

Glu Ala Phe Leu Arg Met Thr Ala Ala Glu Gln Val Asp Leu Phe Val
                325                 330                 335

Ala Thr Pro Ser Asn Ile Pro Ala Glu Ser Phe Glu Val Tyr Glu Val
            340                 345                 350

Ala Leu Ala Leu Val Ala Gln Ala Phe Ile Gly Lys Lys Pro His Leu
        355                 360                 365

Leu Gln Asp Ala Asp Lys Gln Phe Gln Gln Leu Gln Gln Ala Lys Val
    370                 375                 380

Met Ala Met Glu Ile Pro Ala Met Leu Tyr Asp Thr Arg Asn Asn Trp
385                 390                 395                 400

Glu Ile Asp Phe Gly Leu Glu Arg Gly Leu Cys Ala Leu Leu Ile Gly
                405                 410                 415

Lys Val Asp Glu Cys Arg Met Trp Leu Gly Leu Asp Ser Glu Asp Ser
            420                 425                 430

Gln Tyr Arg Asn Pro Ala Ile Val Glu Phe Val Leu Glu Asn Ser Asn
        435                 440                 445

Arg Asp Asp Asn Asp Asp Leu Pro Gly Leu Cys Lys Leu Leu Glu Thr
    450                 455                 460

Trp Leu Ala Gly Val Val Phe Pro Arg Phe Arg Asp Thr Lys Asp Lys
465                 470                 475                 480

Lys Phe Lys Leu Gly Asp Tyr Tyr Asp Asp Pro Met Val Leu Ser Tyr
                485                 490                 495

Leu Glu Arg Val Glu Val Val Gln Gly Ser Pro Leu Ala Ala Ala Ala
            500                 505                 510

Ala Met Ala Arg Ile Gly Ala Glu His Val Lys Ala Ser Ala Met Gln
        515                 520                 525

Ala Leu Gln Lys Val Phe Pro Ser Arg Tyr Thr Asp Arg Asn Ser Ala
    530                 535                 540
```

-continued

```
Glu Pro Lys Asp Val Gln Glu Thr Val Phe Ser Val Asp Pro Val Gly
545                 550                 555                 560

Asn Asn Val Gly Arg Asp Gly Glu Pro Gly Val Phe Ile Ala Glu Ala
                565                 570                 575

Val Arg Pro Ser Glu Asn Phe Glu Thr Asn Asp Tyr Ala Ile Arg Ala
            580                 585                 590

Gly Val Ser Glu Ser Ser Val Asp Glu Thr Thr Val Glu Met Ser Val
        595                 600                 605

Ala Asp Met Leu Lys Glu Ala Ser Val Lys Ile Leu Ala Ala Gly Val
    610                 615                 620

Ala Ile Gly Leu Ile Ser Leu Phe Ser Gln Lys Tyr Phe Leu Lys Ser
625                 630                 635                 640

Ser Ser Ser Phe Gln Arg Lys Asp Met Val Ser Ser Met Glu Ser Asp
                645                 650                 655

Val Ala Thr Ile Gly Ser Val Arg Ala Asp Asp Ser Glu Ala Leu Pro
            660                 665                 670

Arg Met Asp Ala Arg Thr Ala Glu Asn Ile Val Ser Lys Trp Gln Lys
        675                 680                 685

Ile Lys Ser Leu Ala Phe Gly Pro Asp His Arg Ile Glu Met Leu Pro
    690                 695                 700

Glu Val Leu Asp Gly Arg Met Leu Lys Ile Trp Thr Asp Arg Ala Ala
705                 710                 715                 720

Glu Thr Ala Gln Leu Gly Leu Val Tyr Asp Tyr Thr Leu Leu Lys Leu
                725                 730                 735

Ser Val Asp Ser Val Thr Val Ser Ala Asp Gly Thr Arg Ala Leu Val
            740                 745                 750

Glu Ala Thr Leu Glu Glu Ser Ala Cys Leu Ser Asp Leu Val His Pro
        755                 760                 765

Glu Asn Asn Ala Thr Asp Val Arg Thr Tyr Thr Thr Arg Tyr Glu Val
    770                 775                 780

Phe Trp Ser Lys Ser Gly Trp Lys Ile Thr Glu Gly Ser Val Leu Ala
785                 790                 795                 800

Ser
```

<210> SEQ ID NO 130
<211> LENGTH: 2637
<212> TYPE: DNA
<213> ORGANISM: Arabidopsis thaliana

<400> SEQUENCE: 130

```
gatttaactt atactactca aaatcaaaat tccataaacc ctagacgacc aaacagtctc      60

ttcaatatgt aaaacagaac aaagtttttg tagtagccta aaaagacact cccatggaag     120

ctctgagtca cgtcggcatt ggtctctccc cattccaatt atgccgatta ccaccggcga     180

cgacaaagct ccgacgtagc cacaacacct ctacaactat ctgctccgcc agcaaatggg     240

ccgaccgtct tctctccgac ttcaatttca cctccgattc ctcctcctcc tccttcgcca     300

ccgccaccac caccgccact ctcgtctctc cgccaccatc tattgatcgt cccgaacgcc     360

acgtccccat ccccattgat ttctaccagg tattaggagc tcaaacacat ttcttaaccg     420

atggaatcag aagagcattc gaagctaggg tttcgaaacc gccgcaattc ggtttcagcg     480

acgacgcttt aatcagccgg agacagattc ttcaagctgc ttgcgaaact ctgtctaatc     540

ctcggtctag aagagagtac aatgaaggtc ttcttgatga tgaagaagct acagtcatca     600

ctgatgttcc ttgggataag gttcctggtg ctctctgtgt attgcaagaa ggtggtgaga     660
```

-continued

```
ctgagatagt tcttcgggtt ggtgaggctc tgcttaagga gaggttgcct aagtcgttta    720
agcaagatgt ggttttagtt atggcgcttg cgtttctcga tgtctcgagg gatgctatgg    780
cattggatcc acctgatttt ataactggtt atgagtttgt tgaggaagct ttgaagcttt    840
tacaggagga aggagcaagt agccttgcac cggatttacg tgcacaaatt gatgagactt    900
tggaagagat cactccgcgt tatgtcttgg agctacttgg cttaccgctt ggtgatgatt    960
acgctgcgaa aagactaaat ggtttaagcg gtgtgcggaa tattttgtgg tctgttggag   1020
gaggtggagc atcagctctt gttgggggtt tgacccgtga gaagtttatg aatgaggcgt   1080
ttttacgaat gacagctgct gagcaggttg atctttttgt agctacccca agcaatattc   1140
cagcagagtc atttgaagtt tacgaagttg cacttgctct tgtggctcaa gcttttattg   1200
gtaagaagcc acacctttta caggatgctg ataagcaatt ccagcaactt cagcaggcta   1260
aggtaatggc tatggagatt cctgcgatgt tgtatgatac acggaataat tgggagatag   1320
acttcggtct agaaagggga ctctgtgcac tgcttatagg caaagttgat gaatgccgta   1380
tgtggttggg cttagacagt gaggattcac aatataggaa tccagctatt gtggagtttg   1440
ttttggagaa ttcaaatcgt gatgacaatg atgatctccc tggactatgc aaattgttgg   1500
aaacctggtt ggcaggggtt gtctttccta ggttcagaga caccaaagat aaaaaattta   1560
aactcgggga ctactatgat gatcctatgg ttttgagtta cttggaaaga gtggaggtag   1620
ttcagggttc tcctttagct gctgctgcag ctatggcaag gattggagcc gagcatgtga   1680
aagctagtgc tatgcaggca ctgcagaaag tttttccttc ccgctataca gatagaaact   1740
cggctgaacc caaggatgtg caagagacag tgtttagtgt agatcctgtt ggtaacaatg   1800
taggccgtga tggtgagcct ggtgtcttta ttgcagaagc tgtaagaccc tctgaaaact   1860
ttgaaactaa tgattatgca attcgagctg gggtctcaga gagtagcgtt gatgaaacta   1920
ctgttgaaat gtccgttgct gatatgttaa aggaggcaag tgtgaagatc ctagctgctg   1980
gtgtggcaat tggactgatt tcactgttca gccagaagta ttttcttaaa agcagctcat   2040
cttttcaacg caaggatatg gtttcttcta tggaatctga tgtcgctacc atagggtcag   2100
tcagagctga cgattcagaa gcacttccca gaatggatgc taggactgca gagaatatag   2160
tatccaagtg gcagaagatt aagtctctgg cttttgggcc tgatcaccgc atagaaatgt   2220
taccagaggt tttggatggg cgaatgctga agatttggac tgacagagca gctgaaactg   2280
cgcagcttgg gttggtttat gattatacac tgttgaaact atctgttgac agtgtgacag   2340
tctcagcaga tggaacccgt gctctggtgg aagcaactct ggaggagtct gcttgtctat   2400
ctgatttggt tcatccagaa aacaatgcta ctgatgtcag aacctacaca acaagatacg   2460
aagttttctg gtccaagtca gggtggaaaa tcactgaagg ctctgttctt gcatcataat   2520
atactcatat gtagcatgtc tgagcttgcg agattctctt tgttttgtaa attctctctc   2580
taagttagtg tttataaatg aacacaaaaa aattaacgtt caaaaaaaaa aaaaaaa      2637
```

<210> SEQ ID NO 131
<211> LENGTH: 801
<212> TYPE: PRT
<213> ORGANISM: Arabidopsis thaliana

<400> SEQUENCE: 131

```
Met Glu Ala Leu Ser His Val Gly Ile Gly Leu Ser Pro Phe Gln Leu
1               5                   10                  15

Cys Arg Leu Pro Pro Ala Thr Thr Lys Leu Arg Arg Ser His Asn Thr
```

-continued

```
            20                  25                  30

Ser Thr Thr Ile Cys Ser Ala Ser Lys Trp Ala Asp Arg Leu Leu Ser
        35                  40                  45

Asp Phe Asn Phe Thr Ser Asp Ser Ser Ser Ser Ser Phe Ala Thr Ala
    50                  55                  60

Thr Thr Thr Ala Thr Leu Val Ser Pro Pro Pro Ser Ile Asp Arg Pro
65                  70                  75                  80

Glu Arg His Val Pro Ile Pro Ile Asp Phe Tyr Gln Val Leu Gly Ala
                85                  90                  95

Gln Thr His Phe Leu Thr Asp Gly Ile Arg Arg Ala Phe Glu Ala Arg
            100                 105                 110

Val Ser Lys Pro Pro Gln Phe Gly Phe Ser Asp Asp Ala Leu Ile Ser
        115                 120                 125

Arg Arg Gln Ile Leu Gln Ala Ala Cys Glu Thr Leu Ser Asn Pro Arg
    130                 135                 140

Ser Arg Arg Glu Tyr Asn Glu Gly Leu Leu Asp Asp Glu Glu Ala Thr
145                 150                 155                 160

Val Ile Thr Asp Val Pro Trp Asp Lys Val Pro Gly Ala Leu Cys Val
                165                 170                 175

Leu Gln Glu Gly Gly Glu Thr Glu Ile Val Leu Arg Val Gly Glu Ala
            180                 185                 190

Leu Leu Lys Glu Arg Leu Pro Lys Ser Phe Lys Gln Asp Val Val Leu
        195                 200                 205

Val Met Ala Leu Ala Phe Leu Asp Val Ser Arg Asp Ala Met Ala Leu
    210                 215                 220

Asp Pro Pro Asp Phe Ile Thr Gly Tyr Glu Phe Val Glu Glu Ala Leu
225                 230                 235                 240

Lys Leu Leu Gln Glu Glu Gly Ala Ser Ser Leu Ala Pro Asp Leu Arg
                245                 250                 255

Ala Gln Ile Asp Glu Thr Leu Glu Glu Ile Thr Pro Arg Tyr Val Leu
            260                 265                 270

Glu Leu Leu Gly Leu Pro Leu Gly Asp Asp Tyr Ala Ala Lys Arg Leu
        275                 280                 285

Asn Gly Leu Ser Gly Val Arg Asn Ile Leu Trp Ser Val Gly Gly Gly
    290                 295                 300

Gly Ala Ser Ala Leu Val Gly Gly Leu Thr Arg Glu Lys Phe Met Asn
305                 310                 315                 320

Glu Ala Phe Leu Arg Met Thr Ala Ala Glu Gln Val Asp Leu Phe Val
                325                 330                 335

Ala Thr Pro Ser Asn Ile Pro Ala Glu Ser Phe Glu Val Tyr Glu Val
            340                 345                 350

Ala Leu Ala Leu Val Ala Gln Ala Phe Ile Gly Lys Lys Pro His Leu
        355                 360                 365

Leu Gln Asp Ala Asp Lys Gln Phe Gln Gln Leu Gln Gln Ala Lys Val
    370                 375                 380

Met Ala Met Glu Ile Pro Ala Met Leu Tyr Asp Thr Arg Asn Asn Trp
385                 390                 395                 400

Glu Ile Asp Phe Gly Leu Glu Arg Gly Leu Cys Ala Leu Leu Ile Gly
                405                 410                 415

Lys Val Asp Glu Cys Arg Met Trp Leu Gly Leu Asp Ser Glu Asp Ser
            420                 425                 430

Gln Tyr Arg Asn Pro Ala Ile Val Glu Phe Val Leu Glu Asn Ser Asn
        435                 440                 445
```

```
Arg Asp Asp Asn Asp Asp Leu Pro Gly Leu Cys Lys Leu Leu Glu Thr
    450                 455                 460

Trp Leu Ala Gly Val Val Phe Pro Arg Phe Arg Asp Thr Lys Asp Lys
465                 470                 475                 480

Lys Phe Lys Leu Gly Asp Tyr Tyr Asp Asp Pro Met Val Leu Ser Tyr
                485                 490                 495

Leu Glu Arg Val Glu Val Val Gln Gly Ser Pro Leu Ala Ala Ala Ala
            500                 505                 510

Ala Met Ala Arg Ile Gly Ala Glu His Val Lys Ala Ser Ala Met Gln
        515                 520                 525

Ala Leu Gln Lys Val Phe Pro Ser Arg Tyr Thr Asp Arg Asn Ser Ala
    530                 535                 540

Glu Pro Lys Asp Val Gln Glu Thr Val Phe Ser Val Asp Pro Val Gly
545                 550                 555                 560

Asn Asn Val Gly Arg Asp Gly Glu Pro Gly Val Phe Ile Ala Glu Ala
                565                 570                 575

Val Arg Pro Ser Glu Asn Phe Glu Thr Asn Asp Tyr Ala Ile Arg Ala
            580                 585                 590

Gly Val Ser Glu Ser Ser Val Asp Glu Thr Thr Val Glu Met Ser Val
        595                 600                 605

Ala Asp Met Leu Lys Glu Ala Ser Val Lys Ile Leu Ala Ala Gly Val
    610                 615                 620

Ala Ile Gly Leu Ile Ser Leu Phe Ser Gln Lys Tyr Phe Leu Lys Ser
625                 630                 635                 640

Ser Ser Ser Phe Gln Arg Lys Asp Met Val Ser Ser Met Glu Ser Asp
                645                 650                 655

Val Ala Thr Ile Gly Ser Val Arg Ala Asp Asp Ser Glu Ala Leu Pro
            660                 665                 670

Arg Met Asp Ala Arg Thr Ala Glu Asn Ile Val Ser Lys Trp Gln Lys
        675                 680                 685

Ile Lys Ser Leu Ala Phe Gly Pro Asp His Arg Ile Glu Met Leu Pro
    690                 695                 700

Glu Val Leu Asp Gly Arg Met Leu Lys Ile Trp Thr Asp Arg Ala Ala
705                 710                 715                 720

Glu Thr Ala Gln Leu Gly Leu Val Tyr Asp Tyr Thr Leu Leu Lys Leu
                725                 730                 735

Ser Val Asp Ser Val Thr Val Ser Ala Asp Gly Thr Arg Ala Leu Val
            740                 745                 750

Glu Ala Thr Leu Glu Glu Ser Ala Cys Leu Ser Asp Leu Val His Pro
        755                 760                 765

Glu Asn Asn Ala Thr Asp Val Arg Thr Tyr Thr Thr Arg Tyr Glu Val
    770                 775                 780

Phe Trp Ser Lys Ser Gly Trp Lys Ile Thr Glu Gly Ser Val Leu Ala
785                 790                 795                 800

Ser
```

```
<210> SEQ ID NO 132
<211> LENGTH: 561
<212> TYPE: DNA
<213> ORGANISM: Arabidopsis thaliana
<220> FEATURE:
<221> NAME/KEY: misc_feature
<222> LOCATION: (127)..(127)
<223> OTHER INFORMATION: n is a, c, g, or t
<220> FEATURE:
```

```
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t

<400> SEQUENCE: 132

ataaacacta acttagagag agaatttaca aaacaaagag aatctcgcaa gctcagacat     60

gctacatatg agtatattat gatgcaagaa cagagccttc agtgattttc caccctgact    120

tggaccngaa aacttcgtat cttgttgtgt aggttctgac atcagtagca ttgttttctg    180

gatgaaccaa atcagataga caagcagact cctccagagt tgcttccacc agagcacggg    240

ttccatctgc tgagactgtc acactgtcaa cagatagttt caacagtgta taatcataaa    300

ccaacccaag ctgcgcagtt tcagctgctc tgtcagtcca aatcttcagc attcgcccat    360

ccaaaacctc tggtaacatt tctatgcggt gatcaggccc aaaagccaga gacttaatct    420

tctgccactt ggatactata ttctctgcag tcctagcatc cattctggga agtgcttctg    480

aatcgtcagc tctgactgac cctatggtag cgacatcagn ttccatagaa gaaaccatat    540

ncttgcgttg aaaagatgag c                                             561


<210> SEQ ID NO 133
<211> LENGTH: 295
<212> TYPE: DNA
<213> ORGANISM: Medicago truncatula

<400> SEQUENCE: 133

ctggtgtagc aattggactc ataactttag ctggtttgaa gattttacct tctaaaaatg     60

gctcgcccgt tcttcacaaa gtgactggtt cagcaattgc gtcagatact atcaatttag    120

gtcctgtagg agatgaagaa ttaggagagc aactaccaaa aatgagtgca atggttgcag    180

aagctctagt ccgcaagtgg caatatatca catcccaagc ttttggacct gaccattgcc    240

taggaagatt gcaagaggtg ttggacggcc aaatgttgaa gatatggact gatcg         295


<210> SEQ ID NO 134
<211> LENGTH: 527
<212> TYPE: DNA
<213> ORGANISM: Medicago truncatula

<400> SEQUENCE: 134

cccaagcttt tggacctgac cattgcctag gaagattgca agaggtgttg gacggcgaaa     60

tgttgaagat atggactgat cgagcagctg agattgcaga gcttggttgg tcatatgact    120

acaacttgga ggatctcaac atcgacagtg tgaccatatc acagaatggg cggcgtgcag    180

tagtggaaac aactctcaaa gagtctaccc acctcactgc tgttggtcat ccacagcatg    240

ctacttccaa cagcagaacc tacacaacaa gatatgaaat gtctttttca gattcagggt    300

ggaaaattat tgaaggagct gtccttgagt cgtaattagg ttttgtaata tgtaatatat    360

gtcaggttag tacacttcaa tattaacccc ctcgagccta tgcccactgt cttgtatgta    420

cctgttgttt tgtgcatttt tcaagcattt atgtagtcag gctgtaaata cttggagggt    480

atttgatcaa ataattatcc ggttaaaaaa aaaaaaaaaa aaaaaaa                  527


<210> SEQ ID NO 135
<211> LENGTH: 660
<212> TYPE: DNA
<213> ORGANISM: Medicago truncatula
```

<400> SEQUENCE: 135
cacgcttctc caaaaaacct aaccgtctcc attcctccgc cgtctccgcc accagtaaat 60
gggcggagcg actcatttcc gatttccaat tcctcggcga cacctcctct tcctcctcca 120
ccaccacctc cgccacagtc actctcactc cttcttaccc tcctccgata gaacgccacg 180
tgtcactccc tctcgacctg tacaaaatcc tcggcgccga aacgcatttt ctcggtgatg 240
gtattcggag agcttatgaa gcgaaattct cgaagcctcc tcagtatgct ttcagtaatg 300
aagctttgat tagtcgtcgt cagattcttc aagctgcttg tgaaacccta gctgatcctg 360
cttctagaag agagtataat caaagcctcg tcgacgatga agacgaagat gaggaatctt 420
ccattctcac tgaaatccct ttcgacaaag ttcctggagc tctgtgcgtg ttgcaagaag 480
ctggagagac ggagttggtg cttcggattg gagggggttt actgagagag aggttaccga 540
agatgtttaa gcaagatgtt gtgttggcta tggcgcttgc atatgttgac gtttctaggg 600
atgctatggc tttgtccccg ccagatttca ttgttgcttg tgagatgctg gaaagggcat 660

<210> SEQ ID NO 136
<211> LENGTH: 187
<212> TYPE: DNA
<213> ORGANISM: Glycine max

<400> SEQUENCE: 136
agcgttgtgt gtgttgcagg aagctggaga gacggagctt gtgcttgaga ttgggcaggg 60
tttgcttagg gagaggttgc cgaagacgtt taagcaggat gttgtgttgg ctatggcact 120
cgcatttgtt gacgtgtcaa gggatgcttg gcttgttcac cggatttcat tgcggctgtg 180
agatgct 187

<210> SEQ ID NO 137
<211> LENGTH: 608
<212> TYPE: DNA
<213> ORGANISM: Solanum tuberosum

<400> SEQUENCE: 137
ggaaagcttc cttaacaatg gaggcattaa cacagctaag ctttggcatt tgtactccac 60
gcctttcatc accatttcaa ctagccgccg ccggtggtaa gaagccgccg agactcaatg 120
ccgttaacgg aggagctagt agtgttaccg gtggaacaag tagtttacct actaacttct 180
ccgctagtaa atgggcggat cgtcttctcg ccgatttcca attccttcct tccaccacca 240
cctccgactc atcggatttc cagaattcaa cttctacaac ctccgttacg actattcctc 300
ctcctgttgc tccttcagac caccacattt caatgcctat agacttttat agagtgcttg 360
gtgctgaagc tcacttcctc ggtgacggta ttaggagatg ctacgatgct agaattacaa 420
agcctccgca gtacggatac agtcaggaag cattgattgg ccgacggcag attcttcaag 480
ctgcttgtga aacccttgct gactctacct ctcgtagaga gtacaatcaa ggcctcgctc 540
agcatgagtt cgatactatt ctaactcctg tcccctggga taaagttccg ggagcaatgt 600
gtgttttg 608

<210> SEQ ID NO 138
<211> LENGTH: 307
<212> TYPE: DNA
<213> ORGANISM: Populus balsamifera

<400> SEQUENCE: 138

```
gaagatttca tgaatgaggc cttcttacgt atgacagcag ctgagcaggt tgatctgttc     60

gtcaccacgc caagtaatat cccggctcaa aattttgaag tttatggagt ggcacttgcc    120

cttgttgccc aagctttcat tggtaaaaag cctcatctca tcacagatgc tgataaccta    180

ttcggacagc ttcagcagat taaggtaaca aatcaaggga gtcttgttcc tgtctttggt    240

tccatggaaa accgtgatat tgactttggg ttggagaggg gctttgttca ctgcttgtag    300

gccagct                                                              307


<210> SEQ ID NO 139
<211> LENGTH: 416
<212> TYPE: DNA
<213> ORGANISM: Mesembryanthemum crystallinum

<400> SEQUENCE: 139

gggaaacgtg ccttggtgga agcaactctt caagaatcag cgcagttaac tgacgttaac     60

caacctgagc ataacgattc ttacagcaga acatacacaa caaggtacga gatgtttcac    120

tccaatgctg ggtggaagat catagaggga gctgtcctcc aatcttaagc tgctggaaat    180

ccagtcttga atgtacatat tttcacatca tctgcacatt atgaatgaag gatggtatgt    240

gttttctgga cagtggtatt tgatcatgtt gtgtttattt tggtaacaag ttttgatcat    300

tatcaaaaag atcactcttg taagttagtt ttttccacaa taaatcaact atttatatga    360

aagtttttat atcaggacta cttgccttta cttatataaa ctttgagaaa tttttt        416


<210> SEQ ID NO 140
<211> LENGTH: 465
<212> TYPE: DNA
<213> ORGANISM: Oryza sativa
<220> FEATURE:
<221> NAME/KEY: misc_feature
<222> LOCATION: (113)..(113)
<223> OTHER INFORMATION: n is a, c, g, or t

<400> SEQUENCE: 140

tggtgcttct catttgggct gctgctgctg ctattgcaaa acttggtgct caagctacag     60

ctgcacttgg tactgtgaaa tcaaatgcta ttcaagcgtt caacaaggtt ttnccattga    120

tagaacagtt agacaggtca gccatggaaa atactaaaga tggccctggg ggatatcttg    180

aaaattttga ccaggaaaat gcacctgctc atgattcgag aaatgccgcc ttgaagatta    240

tctctctggc gcactgtttg cactgttggc agtaattggg gccaaatatt tgcctcgtaa    300

gaggcccctt tctgctatta ggagtgagca tggatctgtg gcagttgcta atagtgtcga    360

ctctactgat gatcctgcac tagatgaaga tccagtacat attcctagaa tggatgcgaa    420

gctggcagaa gatattgttc gcaagtggca gagtatcaaa tctaa                    465


<210> SEQ ID NO 141
<211> LENGTH: 309
<212> TYPE: DNA
<213> ORGANISM: Oryza sativa

<400> SEQUENCE: 141

atcataagaa gcgccaagaa gggcttcaag gtgcgagaaa cattttgtgg agcgttggca     60

gaggaggtat tgctaccgtt ggaggaggat tttctcgtga agccttcatg aacgaggctt    120

ttttgaggat gacatcaatt gaacagatgg atttcttttc aaaaacaccg aatagcattc    180

ctcctgaatg gtttgaaatt tacaatgtag cacttgcaca tgtcgctcaa gcaattataa    240

gtaaaaggcc acaattcatc atgatggcgg atgatctttt tgaacaactc cagaagttcc    300
```

-continued

```
acataggtc                                                            309

<210> SEQ ID NO 142
<211> LENGTH: 336
<212> TYPE: DNA
<213> ORGANISM: Oryza sativa

<400> SEQUENCE: 142

atcataagaa gcgccaagaa gggcttcaag gtgcgagaaa cattttgtgg agcgttggca     60

gaggaggtat tgctaccgtt ggaggaggat tttctcgtga agccttcatg aacgaggctt    120

ttttgaggat gacatcaatt gaacagatgg atttcttttc aaaaacaccg aatagcattc    180

ctcctgaatg gtttgaaatt tacaatgtag cacttgcaca tgtcgctcaa gcaattataa    240

gtaaaaggcc acaattcatc atgatggcgg atgatctttt tgaacaactc cagaagttca    300

acataggttc tcattatgct tatgataatg agatgg                              336

<210> SEQ ID NO 143
<211> LENGTH: 537
<212> TYPE: DNA
<213> ORGANISM: Triticum aestivum

<400> SEQUENCE: 143

cagtgcttgc aattggaggg cacttactgg aggaccgccc gcccaagcgg ttcaagcagg     60

atgtggtgct ggcaatggcg ctcgcttatg tggatctatc aagggacgca atggcggcta    120

gccctccaga tgtaatccgc tgctgtgagg tgcttgaaag ggctctcaag cttttgcagg    180

aggatggggc aatcaatctc gcacctggtt tgctctcaca aattgatgaa actctggagg    240

atatcacacc tcgttgtgtt ttggagcttc ttgcccttcc tcttgatgaa aaacatcaga    300

atgaacacca agaaggtctt cgtggtgtga gaaacatttt gtggagtgtt ggcagaggag    360

gtattggtac tgttggagga ggattttcgc gtgaagccta catgaatgaa gccttcctgc    420

agatgacatc ggcggagcag atggatttct tctcaaaaac accgaatagc ataccgcctg    480

aatggtttga aatctatagc gtggcacttg caaatgttgc tcaagcaatt gtaagta       537

<210> SEQ ID NO 144
<211> LENGTH: 418
<212> TYPE: DNA
<213> ORGANISM: Triticum monococcum
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t

<400> SEQUENCE: 144

acacctcgtt gtgttttgga gcttcttgcc cttcctcttg atgaaaagca ccagagtaaa     60

cgccaagaag gtcttcgtgg tgtgagaaac attttgtgga gtgttggtag aggaggtatt    120

gctactgttg gaggaggatt ttcncgtgaa gcctacatga atgaggcctt tttgcagatg    180

acatcagcgg agcagatgga tttcttttca aaaacgccaa atagcatacc acctgaatgg    240

tttgaaatct atagtgtggc actcgcaaat gttgctcaag caattgtaag taaaaggcca    300

nagctcatca tggtggcaga tgatcttttc gaacagctcc agaagttcaa tataggttct    360

caatatgctt atgataatga attggatctt gtgttggaaa gggcactttg ctcattgc      418
```

```
<210> SEQ ID NO 145
<211> LENGTH: 480
<212> TYPE: DNA
<213> ORGANISM: Hordeum vulgare

<400> SEQUENCE: 145

gcgagcatga gtccgtggca gttgctaatg ttgttgactc aggtgatgat gacgaaccag      60

atgagcccat acagattcct aaaatggatg cgaagctggc agaagatatt gttcgcaagt     120

ggcagagcat caaatccaag gccttgggat cagatcattc tgttgcatca ttgcaagagg     180

ttcttgatgg caacatgctg aaggtatgga cggaccgagc agcagagatc gagcgcaaag     240

gctggttctg ggactacacg ctgtccaacg tggcgatcga cagcatcacc gtctccctgg     300

acggacggcg ggcgaccgtg gaggcgacaa ttgaggaggc gggtcagctc accgacgcaa     360

ccgaccccag gaacgatgat ttgtacgaca ctaagtacac cacccggtac gagatggcct     420

tcaccggacc aggagggtgg aagataaccg aaggcgcagt cctcaagtcg tcatagggcg     480


<210> SEQ ID NO 146
<211> LENGTH: 622
<212> TYPE: DNA
<213> ORGANISM: Hordeum vulgare
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t

<400> SEQUENCE: 146

gaaactctgg nngnagatca cccctcgttg tgttttagag cttcttgccc ttcctcttga      60

cgagnaagca ccagagtaaa cgccaagnaa ggtcttcgtg gtgtgagaaa cattttgtgg     120

agtgttggta gaggaggtat tgctactgtt ggtggaggat tttcacggga agcctacatg     180

aatgaggcct tttgcagat gacatcagct gagcagatgg atttcttttc aaaaacgccg     240

aatagcatac cacctgaatg gtttgaaatc tatagcgtgg cactcgcaaa tgttgctcaa     300

gcaattgtaa gtaaaaggcc agagctcatc atggtggcag atgatctttt cgaacagctc     360

cagaagttca atatcggttc tcaatatgct tatggtaacg agatggatct tgcgttggaa     420

agggcacttt gctcattgct tgtgggagac attagcaact gcagaacttg gcttgcgatt     480

gataatgaat cttcaccaca tagagacccg aaaattgtag agtttattgt gaacaactct     540

agcattgacc accaggagaa tgatcttctt ccaggcctgt gtaagctttt ggagacttgg     600

cttgtctcag aggttttccc ta                                              622


<210> SEQ ID NO 147
<211> LENGTH: 604
<212> TYPE: DNA
<213> ORGANISM: Hordeum vulgare
<220> FEATURE:
<221> NAME/KEY: misc_feature
<222> LOCATION: (13)..(13)
<223> OTHER INFORMATION: n is a, c, g, or t
```

<220> FEATURE:
<221> NAME/KEY: misc_feature
<222> LOCATION: (516)..(516)
<223> OTHER INFORMATION: n is a, c, g, or t

<400> SEQUENCE: 147

```
tggcttcacc tgnaaatcca gcactaagtt tctcttatca ccaacccaag gatctcttct      60

agcctagcaa taatccgaat agaacacacc gaaaaacaaa gctcatcgct gactaactga     120

ctaaccaaac tatctccgtc ttccaaactg acaagagcct agactagact gcttatttac     180

acaccagaaa aacacgggag gaatcaatca acaaggttta ctgcacgctg aacgccctat     240

gacgacttga ggactgcgcc ttcggttatc ttccaccctc ctggtccggt gaaggccatc     300

tcgtaccggg tggtgtactt agtgtcgtac aaatcatcgt tcctggggtc ggttgcgtcg     360

gtgagctgac ccgcctcctc aattgtcgcc tccacggtcg cccgccgtcc gtccagggag     420

acggtgatgc tgtcgatcgc cacgttgaac agcgtgtagt cccagaacca gcctttgcgc     480

tcaatctctg ctgctcggtc tgtccatacc ttcagnatgt tgccatcaag aacctcttgc     540

aatgatgcaa cagaatgatc tgatcccaag gccttggatt tgatgctctg ccacttgcga     600

acaa                                                                  604
```

<210> SEQ ID NO 148
<211> LENGTH: 653
<212> TYPE: DNA
<213> ORGANISM: Sorghum bicolor

<400> SEQUENCE: 148

```
tatgggtctg tggcagttgc tgactctgtt gatggtctgg gagcagatga agagccacta      60

gaaattccta gaatggatgc aaagttggct gaagatattg ttcgcaagtg gcaaagtatc     120

aagtccaagg ctttggggcc agaacacact gtcacggcat tgcaagagat cctcgatggc     180

aacatgctga aggtatggat ggaccgagcc acagagattg agcgtcacgg ttggttctgg     240

gaatacacac tctccgacgt gacgatcgac agtatcaccg tctccatgga cggtcgacgg     300

gcaactgtgg aggcgacgat tgaggagatg ggccaactta ccgacgtagc agacccaaag     360

aacaacgacg cctacgacac aaagtacacc gctcggtacg agatgagcta ctccaagtcc     420

ggagggtgga ggatcaccga aggagcagtc ctcaagtcgt agaacggtcg tgcagcagga     480

gtaggcgagt aggggttgct caactcccat tctttttct tttgcaccag tgtatgtaaa     540

taaacagtgt gagcacaggt tcttttctct cctggagaga gtttggttag gttgattagt     600

gatgagttcc tgaggccgag agaatttgtc atctagtttg tattgataga gat            653
```

<210> SEQ ID NO 149
<211> LENGTH: 535
<212> TYPE: DNA
<213> ORGANISM: Sorghum bicolor

<400> SEQUENCE: 149

```
gcacgaggat agaacagcta gacagatcag gcaaggatac cccaggtgat gatcttgaga      60

aatctcttga aaaacttgcc caagaaatgt tgctggagat gctatccatg attccaaaaa     120

tgccgctttg aagattatct ctgctggtgc actgtttgca ctatttgcag taataggtct     180

gaagtgcttg cctcgtaaga agtcacttcc tgctcttaag agcgaatatg ggtctgtggc     240

agttgctgac tctgttgatg gtctgggagc agatgaagag ccactagaaa ttcctagaat     300

ggatgcaaag ttggctgaag atattgttcg caagtggcaa agtatcaagt ccaaggcttt     360
```

-continued

```
ggggccagaa cacactgtca cggcattgca agagatcctc gatggcaaca tgctgaaggt    420

atggatggac cgagccacag agattgagcg tcacggttgg ttctgggaat acacactctc    480

cgacgtgacg atcgacagta tcaccgtctc catggacggt cgacgggcaa ctgtg         535


<210> SEQ ID NO 150
<211> LENGTH: 479
<212> TYPE: DNA
<213> ORGANISM: Zea mays

<400> SEQUENCE: 150

gccacaggcc gccaccgcct ggcccctcca cctgccgctc cgccagccgc tgggccgacc     60

gcctcttcgc cgacttccac ctcctccccg ccgccgccga cccgccagcc gcggcctcct    120

cttcctcctc gtccccgttc gtcccgatct tccccgaagc cgccgaccgc gccttgcccc    180

tcccggtcga cttctacaag attcttggtg cggagccaca tttcctaggc gatggcattc    240

ggagggcgtt cgagtcgcgg atagctaagc cacctcagta tgggtacagc acagaagctc    300

ttgctgggcg acggcaaatg ctgcagattg cccatgatac tctcacaaac cagagctcgc    360

gcaccgagta cgaccgtgcg ctttccgagg accgtgatgc ggcactcacc atggatgttg    420

cctgggataa ggttccaggt gtgctgcgtg tgcttcagga ggctggggag gcacaactg     479


<210> SEQ ID NO 151
<211> LENGTH: 446
<212> TYPE: DNA
<213> ORGANISM: Zea mays

<400> SEQUENCE: 151

agcaatgtgg gcaagtgcga cactatagat ctcaaaccat tcaggtggta tgctattcgg     60

tgttttagag aagaaatcca tctgctcagc tgatgtcatc tgcaagaaag cctcattcat    120

gaaggcctca cgagaaaatc ctcctccaac agtagcaata ccacccctgc caacactcca    180

caatatgttt tttgcacctt gcagaccttc ttggcgttta tttttatgtt tttcatcagt    240

aggaagagca agaagctcca atacacaacg aggtgtaatc tcctccaaag tttcatcaat    300

ctgtgcaagc agttcaggtg caagattgct tgcaccatcc tcctgcagga gcttcagtgc    360

cctctcaagc acctcacaac agcagattac atctggaggg cttgctgcca tagcatccct    420

tgatatgtcc acataagcca atgcca                                         446


<210> SEQ ID NO 152
<211> LENGTH: 657
<212> TYPE: DNA
<213> ORGANISM: Zea mays

<400> SEQUENCE: 152

cgcgtcgacg tatagagtct gcatccatgt tgccttgaat gaagcgtctg caaaagaagg     60

ctcttttatc accagtcgtg tcaggaagca ttttgaaaat atatcaaaat ttctttggct    120

gagtgatagg cctaattcaa atagcaaagg aagtgataaa cacccagcgg ttaatgatat    180

tactgctgca gtttgcaagc aaaagatgga tattcaagaa gcagaaacac ttgtaaaaca    240

gtggcaagac ataaaatctg aagctcttgg ccctgactat caaactgaca tgctacctga    300

gattcttgat ggttcaatgc tctctaagtg ggaagactta gcgttattag caaaggacca    360

gtcttgctat tggagatttg tgctgctaaa tcttaatgtt gttcgagccg agataatctt    420

ggatgaaata ggtgctggtg aggcagcaga aattgatgct gtacttgagg aagcggctga    480

gcttgttgac gattcccagc ccaagaaacc gagttattac agcacatatg aagttcagta    540
```

-continued

```
cgtattgagg aggcagaatc atggatcttg gaaaatctcc gaggctgctg tccgggacct    600

gacgtgattt ctgccaactc ggcaaacggg ctacacaacc attggcgtat aggcggc       657


<210> SEQ ID NO 153
<211> LENGTH: 871
<212> TYPE: DNA
<213> ORGANISM: Ceratopteris richardii

<400> SEQUENCE: 153

gtggtgtctt tgctcgtgtt cctggataca caagggatga gtatatgaag gcagcttttt     60

ctcgaatgac agctgctgag caagtagctt tgttcacaaa tacacccagt aatatcccag    120

cagagagttc tgaggtttac acagttgcgc ttgctcacat agcagaggga tttgttgcaa    180

agaagccgca attgattcag gaagctgatt cactctttct tcagcttcag cgaacaaatg    240

cctcatcatc tagtttgcta gttactggtg gtctacggcc attatcaagt ctgcagcttg    300

attttgcttt tgaacgagcc atgtgcaaac tgctcctagg agaactggat ggttgtcgtg    360

catggctagg tttggatgat acaaactctc catatagaga ccctgcagtg actgattttg    420

ttatagctaa ttcttttgga agtgaggaag gtgattattt accaggcctt tgcaagttgt    480

tggaaagttg gttgagggaa gcggtgtttt tccccaaccc gtcaacagaa aagtggaggt    540

acaagttgag ggagtatttt ttatgatgca aggagaaaaa aagccgccgt gaatttttc     600

gcggggggcg ctatgaaaaa atatattcaa cctttttttg ttggggcgtc gtctacaaag    660

aatgatggag tgtcattgtt gcttttgagg tgacgaaggg gcggcgctcc tctttaaggg    720

atcgtccgtg gggcgcgcg ctcccatatc gccatcttcg ggacaccttg ttcgtgggtc     780

aaatggtgat gtcttttta ccacgaacgt cacattattc ttataatata agcgtgcggc     840

agcactctca gcttcgacga aacagcctaa a                                   871


<210> SEQ ID NO 154
<211> LENGTH: 541
<212> TYPE: DNA
<213> ORGANISM: Physcomitrella patens

<400> SEQUENCE: 154

gagaacggaa gctttagaag tggaggttgt ccccaaaatg gatgctaggt tggcggaaat     60

tatggttcga agatggcaag cagctaaagc tcgagcactt ggttctgctc atgatatggc    120

ggctcttcct gaggtgctgg agggcgagat gctgaagagc tggacagacc gtgttagtga    180

cgtcaagaga aatggttggt tttgggaata cactctcctt ggtcttcaca ttgatagtgt    240

aacagtaagt gacgatggga ggcgagcaac tgcggaagcc actttgcaag aggcagcccg    300

cttggtggac cgcaacaacc ctgaccacaa tgattcttat agaagcactt acactacgcg    360

atatgacctc cggcatggca tagatggttg gcgaatcaat ggaggagctg tgctgcgtac    420

ttgattctga gattttcatc tccggatcat gttgacttgt aggcagatcg actagttgca    480

acccttgcat gctacgaatg agtagtcttt ttggatattt tgatccatca tgcagctttg    540

a                                                                    541


<210> SEQ ID NO 155
<211> LENGTH: 2109
<212> TYPE: DNA
<213> ORGANISM: Protochlorococcus marinus MED4

<400> SEQUENCE: 155
```

-continued

```
ttggaacttc cattagatca ctttcgttta ataggcgtaa gcccctcagc aacatctgag     60

gaaatattaa gggctttcca attacgcttg gataaaactc ctgatgaagg attcacgtac    120

gaggttttaa ctcaaaggtc ggaattgctt cgccttactg cagatttgct tacagatcca    180

gatagtagaa gagattacga aaatttatta ctaaatggag catcaggttt agatttatct    240

tccaatagag aggttgcagg attaattctc ctttgggaat cgggctcttc taaagaagcc    300

tttaaaataa caagaaaagc attgcaaccc ccccaaactc ctgcattggg tagcagtaga    360

gaagctgatc ttaccttgtt agcggcttta acatctagag atgctgcaat acaagagcaa    420

gatcaaagat cttactcaaa tgctgcagat tttttacaag aaggcataca gcttcttcaa    480

agaatgggca aactagggga attacggaaa actcttgagg aggacttagt gtcgcttctt    540

ccgtatcgaa ttcttgattt gttaagtaga gatctaaatg attatgactc gcataaaaaa    600

ggtttaagta tgctggaaaa tttaataatc aaaagaggtg gattagaagg aaaaaataaa    660

tctgaatata atgattttct aaatcagcaa gaatttgaat ctttctttca acaaataaag    720

ccattcttga ctgttcagga tcagatagat ttatttttag aattacaaaa aaggggttca    780

agtgaagcag gatttttagc ttttttatct ttaacagcaa ttggttttgc aagaagaaaa    840

cctgcaaaat tattcgaagc tcgaaaaata ttaaaaaaac taaatttatc aggacttgac    900

tcaatgccat taataggttg ccttgatttg cttttagcag atgttgagca atcctcagca    960

aggtttttaa gtagttccga tgagaagtta agagattggt tgaataatta tcctggagaa   1020

aaattagaag caatatgtat tttttgtaaa aattggttag aaaatgatgt tttggttggt   1080

tatagggata ttgatttaaa agaaatcgat ttagactctt ggtttgaaga tagagaaatc   1140

caagaattta ttgagcaaat agaaaagaag tcaaatagaa ctgtgtttaa gtctgggcct   1200

caaaataaac ctatttttca agcccaagaa tctttaaaag attcaagtac gggccctgat   1260

ttaaattcgg ataattttga agaaggccga ttacctttgc ctggaggagt aagagaagat   1320

ggtcaagaag ttattgaaga aaatatttat acagatgaga ttattaaaaa caaatcaata   1380

gaattttata agtacgcaat agaaaaaatt gctgaattaa aatttgtatt tggagaagcc   1440

ttagagaact acagaatatt taataaatct tcctacctaa catatctgta tgcttttttg   1500

attttatttg cttttggcct aggtgttgga tttgtaagaa ataatctcaa aaaacccgtg   1560

caggaaaaag aaataattga taactcgtta tcgataaatg aaaataagaa tgtcttttat   1620

gaaggtttaa atcaagatga taaaaagaaa gttctcgata actcaaaaat tattctctca   1680

gataatgcag aaaaagttat tttttcaggt gaagaaataa aaactgcttc tccctcctta   1740

gaaaaaatag aaaatttaat taatacatgg cttgttaaca aaagtaaatt tctagcagga   1800

aaaggtgaaa ttaatttatc aaagatagtt caagatgatt tgattgatag attaaagaag   1860

gaaagagaac ttgatattca aaaaggtatc tacaaaaata tcaatgctaa tatcgaaaat   1920

attgtacttt taactcaaac ggcatcaaga atatcagtat cagttgactt aaagtattca   1980

gaaaaaatat taaaaataga tggggaattg ataaatgaaa caactttcac tccttttttg   2040

aaagttaaat atattttagg tttctcaaat aactcctgga aattagttga ctacattagt   2100

ggtgtttag                                                            2109
```

<210> SEQ ID NO 156
<211> LENGTH: 702
<212> TYPE: PRT
<213> ORGANISM: Protochlorococcus marinus MED4

<400> SEQUENCE: 156

```
Leu Glu Leu Pro Leu Asp His Phe Arg Leu Ile Gly Val Ser Pro Ser
1               5                   10                  15

Ala Thr Ser Glu Glu Ile Leu Arg Ala Phe Gln Leu Arg Leu Asp Lys
            20                  25                  30

Thr Pro Asp Glu Gly Phe Thr Tyr Glu Val Leu Thr Gln Arg Ser Glu
        35                  40                  45

Leu Leu Arg Leu Thr Ala Asp Leu Leu Thr Asp Pro Asp Ser Arg Arg
    50                  55                  60

Asp Tyr Glu Asn Leu Leu Leu Asn Gly Ala Ser Gly Leu Asp Leu Ser
65                  70                  75                  80

Ser Asn Arg Glu Val Ala Gly Leu Ile Leu Leu Trp Glu Ser Gly Ser
                85                  90                  95

Ser Lys Glu Ala Phe Lys Ile Thr Arg Lys Ala Leu Gln Pro Pro Gln
            100                 105                 110

Thr Pro Ala Leu Gly Ser Ser Arg Glu Ala Asp Leu Thr Leu Leu Ala
        115                 120                 125

Ala Leu Thr Ser Arg Asp Ala Ala Ile Gln Glu Gln Asp Gln Arg Ser
    130                 135                 140

Tyr Ser Asn Ala Ala Asp Phe Leu Gln Glu Gly Ile Gln Leu Leu Gln
145                 150                 155                 160

Arg Met Gly Lys Leu Gly Glu Leu Arg Lys Thr Leu Glu Glu Asp Leu
                165                 170                 175

Val Ser Leu Leu Pro Tyr Arg Ile Leu Asp Leu Leu Ser Arg Asp Leu
            180                 185                 190

Asn Asp Tyr Asp Ser His Lys Lys Gly Leu Ser Met Leu Glu Asn Leu
        195                 200                 205

Ile Ile Lys Arg Gly Gly Leu Glu Gly Lys Asn Lys Ser Glu Tyr Asn
    210                 215                 220

Asp Phe Leu Asn Gln Gln Glu Phe Glu Ser Phe Phe Gln Gln Ile Lys
225                 230                 235                 240

Pro Phe Leu Thr Val Gln Asp Gln Ile Asp Leu Phe Leu Glu Leu Gln
                245                 250                 255

Lys Arg Gly Ser Ser Glu Ala Gly Phe Leu Ala Phe Leu Ser Leu Thr
            260                 265                 270

Ala Ile Gly Phe Ala Arg Arg Lys Pro Ala Lys Leu Phe Glu Ala Arg
        275                 280                 285

Lys Ile Leu Lys Lys Leu Asn Leu Ser Gly Leu Asp Ser Met Pro Leu
    290                 295                 300

Ile Gly Cys Leu Asp Leu Leu Leu Ala Asp Val Glu Gln Ser Ser Ala
305                 310                 315                 320

Arg Phe Leu Ser Ser Ser Asp Glu Lys Leu Arg Asp Trp Leu Asn Asn
                325                 330                 335

Tyr Pro Gly Glu Lys Leu Glu Ala Ile Cys Ile Phe Cys Lys Asn Trp
            340                 345                 350

Leu Glu Asn Asp Val Leu Val Gly Tyr Arg Asp Ile Asp Leu Lys Glu
        355                 360                 365

Ile Asp Leu Asp Ser Trp Phe Glu Asp Arg Glu Ile Gln Glu Phe Ile
    370                 375                 380

Glu Gln Ile Glu Lys Lys Ser Asn Arg Thr Val Phe Lys Ser Gly Pro
385                 390                 395                 400

Gln Asn Lys Pro Ile Phe Gln Ala Gln Glu Ser Leu Lys Asp Ser Ser
                405                 410                 415
```

-continued

```
Thr Gly Pro Asp Leu Asn Ser Asp Asn Phe Glu Glu Gly Arg Leu Pro
            420                 425                 430

Leu Pro Gly Gly Val Arg Glu Asp Gly Gln Glu Val Ile Glu Glu Asn
        435                 440                 445

Ile Tyr Thr Asp Glu Ile Ile Lys Asn Lys Ser Ile Glu Phe Tyr Lys
    450                 455                 460

Tyr Ala Ile Glu Lys Ile Ala Glu Leu Lys Phe Val Phe Gly Glu Ala
465                 470                 475                 480

Leu Glu Asn Tyr Arg Ile Phe Asn Lys Ser Ser Tyr Leu Thr Tyr Leu
                485                 490                 495

Tyr Ala Phe Leu Ile Leu Phe Ala Phe Gly Leu Gly Val Gly Phe Val
            500                 505                 510

Arg Asn Asn Leu Lys Lys Pro Val Gln Glu Lys Glu Ile Ile Asp Asn
        515                 520                 525

Ser Leu Ser Ile Asn Glu Asn Lys Asn Val Phe Tyr Glu Gly Leu Asn
    530                 535                 540

Gln Asp Asp Lys Lys Lys Val Leu Asp Asn Ser Lys Ile Ile Leu Ser
545                 550                 555                 560

Asp Asn Ala Glu Lys Val Ile Phe Ser Gly Glu Glu Ile Lys Thr Ala
                565                 570                 575

Ser Pro Ser Leu Glu Lys Ile Glu Asn Leu Ile Asn Thr Trp Leu Val
            580                 585                 590

Asn Lys Ser Lys Phe Leu Ala Gly Lys Gly Glu Ile Asn Leu Ser Lys
        595                 600                 605

Ile Val Gln Asp Asp Leu Ile Asp Arg Leu Lys Lys Glu Arg Glu Leu
    610                 615                 620

Asp Ile Gln Lys Gly Ile Tyr Lys Asn Ile Asn Ala Asn Ile Glu Asn
625                 630                 635                 640

Ile Val Leu Leu Thr Gln Thr Ala Ser Arg Ile Ser Val Ser Val Asp
                645                 650                 655

Leu Lys Tyr Ser Glu Lys Ile Leu Lys Ile Asp Gly Glu Leu Ile Asn
            660                 665                 670

Glu Thr Thr Phe Thr Pro Phe Leu Lys Val Lys Tyr Ile Leu Gly Phe
        675                 680                 685

Ser Asn Asn Ser Trp Lys Leu Val Asp Tyr Ile Ser Gly Val
    690                 695                 700
```

<210> SEQ ID NO 157
<211> LENGTH: 1986
<212> TYPE: DNA
<213> ORGANISM: Protochlorococcus marinus MT9313

<400> SEQUENCE: 157

```
gtggacctgc caatagatca tttccgcttg ctgggtgtca gtccttcggc agacagtgag      60

gcgattttgc gggccttgga gttgaggttg gatcgctgcc ctgaccaagg tttcacccat     120

gaggtcttaa ttcagcgggc agaattgttg cggctttcag cagatttgct gactgatccg     180

ccacggcgtc aggcctatga gactgccttg ttggagctca gtcgtgatca tccaggtgag     240

accgccggtc ttgatgtgtc acctagtaga gaggtggcag ggctgatctt gctgtttgaa     300

gcgaattctt ctcatgaggt tttcatctc gcctctcagg gattgcaacc gccccagtcc     360

ccgacgctag gtagcgaacg agaagctgac ctcgctttgt tgttggcact ggcctgtcgg     420

gctgcagccg ctgaggaaca ggaacaacgg cgttatgaag cagcagcgtc tcttctgcat     480

gacgggatcc agttgctgca gcggatgggc aagctctccg aagagtgcca caagcttgag     540
```

-continued

```
aacgatttag atgcccttct gccctatcgc attctcgact tattgagtcg ggatcttggt    600
gatcaggttt ctcaccagga aggactgcgc ctacttgaca actttgtgag ccagagagga    660
ggtcttgagg gaacggcccc atcgcctgca cctggtggtc ttgatcagtc cgaatttgac    720
aacttcttca agcagatcag aaagttttta actgttcagg aacaggttga tcttttcctg    780
cgctggcagc aagccggatc agcagatgcg ggtttcctgg gtgggttggc tcttgctgct    840
gttggatttt cgcgtcggaa gcctgaacgg gtgcaggaag ctcggcagca cttagagagg    900
cttcaactgg atggatgcga cccgttgccg atgctgggtt gcttggacct cttgctcgga    960
gatgtgggcc gcgctcagga gcgttttctg cgcagtacag atcctcgagt gaaggactgt   1020
cttaacagcc accctggcga tgaattggct gctttttgtg agtactgccg ctcttggctg   1080
cgaggggacg tgcttcccgg ttatagggat gtggatgctg aggccgttga tctagaggct   1140
tggtttgctg atcgggatgt tcaggcttat gtggagcgcc tggaacgcag cgaaaatcgt   1200
gcttcttctt taggtaaggc cttctcagga tcgtctgtga agcaaccctt cccttgggcg   1260
cctcttgatc ccgatgggat tttgcccctc tctcttggtg ggcctgatgt tggtcaacct   1320
gcagctgatc agagctctga tgagtttgcc agcgatggta tggcatggat tgatcgttta   1380
gcagatctgc cacgcccgac gcggccggtg ctgatcggtt cggttgtctt tgcggccctg   1440
attgcagcct ttgcaggctt cagtttgttt ggccaacgtc ctcgtacgtc agttagtacg   1500
gctgctgatc agcctcaagt cacagcacct cctacagcca cactgcaaga ggaggtcctc   1560
atgcctcaag tccctgtcag cgctgtggtt gagccgctta ctttggagca gccgaatgag   1620
gcacagctca aggcctgctt tcaggcctgg ctcagcaaca aggcagtcgt gcttgccggt   1680
ggcaagagtg atgcactgcc tgaggtcgca agagatccat tggtgcagcg cgtggcgcaa   1740
gagcgtgcca gggatgctgc tttagctcag acccagaagg ttgtggccag catcagctct   1800
gtagaggtgg tgagtcgaac gccgcagcgt attgagctga atgccgttgt gacctatcgc   1860
gatcaacgcg ttgatgctgc cggcaaggtt gttgaccaaa cgccccaaaa agatctctcg   1920
gtgacttaca tccttggtcg tgatcccgat cgttggcgcc tgcatgaata catcagcggc   1980
aaataa                                                              1986
```

<210> SEQ ID NO 158
<211> LENGTH: 661
<212> TYPE: PRT
<213> ORGANISM: Protochlorococcus marinus MT9313

<400> SEQUENCE: 158

```
Val Asp Leu Pro Ile Asp His Phe Arg Leu Leu Gly Val Ser Pro Ser
1               5                   10                  15

Ala Asp Ser Glu Ala Ile Leu Arg Ala Leu Glu Leu Arg Leu Asp Arg
            20                  25                  30

Cys Pro Asp Gln Gly Phe Thr His Glu Val Leu Ile Gln Arg Ala Glu
        35                  40                  45

Leu Leu Arg Leu Ser Ala Asp Leu Leu Thr Asp Pro Pro Arg Arg Gln
    50                  55                  60

Ala Tyr Glu Thr Ala Leu Leu Glu Leu Ser Arg Asp His Pro Gly Glu
65                  70                  75                  80

Thr Ala Gly Leu Asp Val Ser Pro Ser Arg Glu Val Ala Gly Leu Ile
                85                  90                  95

Leu Leu Phe Glu Ala Asn Ser Ser His Glu Val Phe His Leu Ala Ser
            100                 105                 110
```

-continued

```
Gln Gly Leu Gln Pro Pro Gln Ser Pro Thr Leu Gly Ser Glu Arg Glu
        115                 120                 125

Ala Asp Leu Ala Leu Leu Leu Ala Leu Ala Cys Arg Ala Ala Ala Ala
    130                 135                 140

Glu Glu Gln Glu Gln Arg Arg Tyr Glu Ala Ala Ala Ser Leu Leu His
145                 150                 155                 160

Asp Gly Ile Gln Leu Leu Gln Arg Met Gly Lys Leu Ser Glu Glu Cys
                165                 170                 175

His Lys Leu Glu Asn Asp Leu Asp Ala Leu Leu Pro Tyr Arg Ile Leu
            180                 185                 190

Asp Leu Leu Ser Arg Asp Leu Gly Asp Gln Val Ser His Gln Glu Gly
        195                 200                 205

Leu Arg Leu Leu Asp Asn Phe Val Ser Gln Arg Gly Gly Leu Glu Gly
    210                 215                 220

Thr Ala Pro Ser Pro Ala Pro Gly Gly Leu Asp Gln Ser Glu Phe Asp
225                 230                 235                 240

Asn Phe Phe Lys Gln Ile Arg Lys Phe Leu Thr Val Gln Glu Gln Val
                245                 250                 255

Asp Leu Phe Leu Arg Trp Gln Gln Ala Gly Ser Ala Asp Ala Gly Phe
            260                 265                 270

Leu Gly Gly Leu Ala Leu Ala Ala Val Gly Phe Ser Arg Arg Lys Pro
        275                 280                 285

Glu Arg Val Gln Glu Ala Arg Gln His Leu Glu Arg Leu Gln Leu Asp
    290                 295                 300

Gly Cys Asp Pro Leu Pro Met Leu Gly Cys Leu Asp Leu Leu Leu Gly
305                 310                 315                 320

Asp Val Gly Arg Ala Gln Glu Arg Phe Leu Arg Ser Thr Asp Pro Arg
                325                 330                 335

Val Lys Asp Cys Leu Asn Ser His Pro Gly Asp Glu Leu Ala Ala Phe
            340                 345                 350

Cys Glu Tyr Cys Arg Ser Trp Leu Arg Gly Asp Val Leu Pro Gly Tyr
        355                 360                 365

Arg Asp Val Asp Ala Glu Ala Val Asp Leu Glu Ala Trp Phe Ala Asp
    370                 375                 380

Arg Asp Val Gln Ala Tyr Val Glu Arg Leu Glu Arg Ser Glu Asn Arg
385                 390                 395                 400

Ala Ser Ser Leu Gly Lys Ala Phe Ser Gly Ser Ser Val Lys Gln Pro
                405                 410                 415

Phe Pro Trp Ala Pro Leu Asp Pro Asp Gly Ile Leu Pro Leu Ser Leu
            420                 425                 430

Gly Gly Pro Asp Val Gly Gln Pro Ala Ala Asp Gln Ser Ser Asp Glu
        435                 440                 445

Phe Ala Ser Asp Gly Met Ala Trp Ile Asp Arg Leu Ala Asp Leu Pro
    450                 455                 460

Arg Pro Thr Arg Pro Val Leu Ile Gly Ser Val Val Phe Ala Ala Leu
465                 470                 475                 480

Ile Ala Ala Phe Ala Gly Phe Ser Leu Phe Gly Gln Arg Pro Arg Thr
                485                 490                 495

Ser Val Ser Thr Ala Ala Asp Gln Pro Gln Val Thr Ala Pro Pro Thr
            500                 505                 510

Ala Thr Leu Gln Glu Glu Val Leu Met Pro Gln Val Pro Val Ser Ala
        515                 520                 525
```

```
Val Val Glu Pro Leu Thr Leu Glu Gln Pro Asn Glu Ala Gln Leu Lys
    530                 535                 540

Gly Leu Leu Gln Ala Trp Leu Ser Asn Lys Ala Val Val Leu Ala Gly
545                 550                 555                 560

Gly Lys Ser Asp Ala Leu Pro Glu Val Ala Arg Asp Pro Leu Val Gln
                565                 570                 575

Arg Val Ala Gln Glu Arg Ala Arg Asp Ala Ala Leu Ala Gln Thr Gln
            580                 585                 590

Lys Val Val Ala Ser Ile Ser Ser Val Glu Val Val Ser Arg Thr Pro
        595                 600                 605

Gln Arg Ile Glu Leu Asn Ala Val Val Thr Tyr Arg Asp Gln Arg Val
    610                 615                 620

Asp Ala Ala Gly Lys Val Val Asp Gln Thr Pro Gln Lys Asp Leu Ser
625                 630                 635                 640

Val Thr Tyr Ile Leu Gly Arg Asp Pro Asp Arg Trp Arg Leu His Glu
                645                 650                 655

Tyr Ile Ser Gly Lys
            660


<210> SEQ ID NO 159
<211> LENGTH: 2151
<212> TYPE: DNA
<213> ORGANISM: Synechococcus PCC7002

<400> SEQUENCE: 159

gtgcgcattc cgctcgacta ttaccgcatc ctatgcgtcc ccgccaaggc aaccactgcc      60

caaattaccc aagcctatcg cgatcgcctc tcccaatttc cccgtcgcga acataatgcc     120

ttggccattg aggcccgcaa ccggattatc gagcaagcct ttgaggtgtt atcccaaaca     180

gaaacccgcg ccgtctacga ccatgagctg tcgggcaata tgtttcgttc cctcgtcccc     240

agccgtccga aactgccttt tcccgatcgc ccctccagtg acacagagtt agaagccctg     300

acagcccacc aaccaaccat tgacatcgcg gaaaaagatt tactgggggg actgctgtta     360

ctcctcgacc tgggggagta cgaattagtg ctgaagtggg ctgcccccta cctcaagggc     420

aaaggcaagc tggtcaagga agggaaattt ggggccgtcg aaatcgtcga gcaagaacta     480

cggctttgtt tggccctggc ccactgggaa ttgagccggg aacagtggct ccaacaacat     540

tatgaacagg cggctctctc cggtcagaag agtcaagagc tattggtaga tgtggcacaa     600

tttgcagacc tccaacagga aattcaaggg gatctcaatc gcctcagacc ctatcaagtt     660

ctagaacttc tggccctacc cgaatcagaa acccaagagc gacaacgggg cttacaactg     720

ctccaggaaa tgttgagtgc tcgcgtgggg attgatggcc agggggacga tcagtcgggt     780

ctaagtattg atgatttttt gcgctttatc cagcagttac gcagttatct aacggtgcaa     840

gaacagttgg atctctttgt ggcagaatca aagcgacctt cggcggcagc ggcctaccta     900

gcggtgtatg ctctcttggc tgctgggttt tcgcaacgga aacctgacct ggtcgtgcaa     960

gcccagaccc tattaaaacg cctcggcaaa cgccaggatg ttttcttgga gcaatcaatc    1020

tgcgccttac ttttaggtca gccgtcggaa gccaatcaac tgttagaaca aagtcaggaa    1080

caggaggcga tcgcctacat tcaagagcag tctgaggggg caccggatct actcccaggc    1140

ctatgtctct acggggaaca gtggctgaag acagaggttt tttcccattt ccgcgatctc    1200

cggcaacggc ttgaagatgg ctctgtttcg ttgacggctt acttcgccga tcctgaagtg    1260

cagcaatatc ttgacgatct cctcacggag gctgtcccca cacccacacc acatccagac    1320
```

-continued

```
acagaaagta cagcggcccc gtcggaaaag ccaccggaaa cattacagtc agaaaccggt   1380

gtttcgccgc atcccagtcg tcccgccaag gttgattcct ttgaggatct cgtcactcaa   1440

actcccgcta cagttccccc ggcaccgcct tctcctggtg tagcacctgt aactgcggca   1500

ttaaacccag acccggaagc gtcttctgct tcgtcaaaat cagtttcgtc aaaaaagtct   1560

atcgggcctt ggggggcgat cgccgctatc gtggggagtg ttttgctggt cgtgggcctg   1620

gtgcgaattt tgtctggcct aactacccag gaacccttac aggtcaccct caacggtgag   1680

ccacccctaa cgatccccag cttagacacc gccgaggcaa ataataatcc ggagaatgga   1740

gcgaccgata caacgacaac gcctgcgctc aatgaggcga tcgccgctga ggtgattcaa   1800

acttggtttg agagtaaagc tagagccttt ggccaagacc gtgatttggc ggctctagaa   1860

aatattttgg cagaaccgtc cctgtcccgc tggcgcagta gtgcccaggc cgtccgcagc   1920

gctggtacct accgcaccta tgaccacagt ttgaccattg aaacggtgag cttcaaccca   1980

gaccaaccca atgtggcgac cgttgaggcc caggtgcagg aaaaggcaga ttattaccgg   2040

gcgaatgggg aacgcgatcc cggccagtcc tatgattctg acctgcgtgt ccgctacagc   2100

ttggtgcgcc aaggcgatcg ctggttgatt cgttcttccc aaaccctgta a             2151
```

<210> SEQ ID NO 160
<211> LENGTH: 716
<212> TYPE: PRT
<213> ORGANISM: Synechococcus PCC7002

<400> SEQUENCE: 160

```
Met Arg Ile Pro Leu Asp Tyr Tyr Arg Ile Leu Cys Val Pro Ala Lys
1               5                   10                  15

Ala Thr Thr Ala Gln Ile Thr Gln Ala Tyr Arg Asp Arg Leu Ser Gln
            20                  25                  30

Phe Pro Arg Arg Glu His Asn Ala Leu Ala Ile Glu Ala Arg Asn Arg
        35                  40                  45

Ile Ile Glu Gln Ala Phe Glu Val Leu Ser Gln Thr Glu Thr Arg Ala
    50                  55                  60

Val Tyr Asp His Glu Leu Ser Gly Asn Met Phe Arg Ser Leu Val Pro
65                  70                  75                  80

Ser Arg Pro Lys Leu Pro Phe Pro Asp Arg Pro Ser Ser Asp Thr Glu
                85                  90                  95

Leu Glu Ala Leu Thr Ala His Gln Pro Thr Ile Asp Ile Ala Glu Lys
            100                 105                 110

Asp Leu Leu Gly Gly Leu Leu Leu Leu Leu Asp Leu Gly Glu Tyr Glu
        115                 120                 125

Leu Val Leu Lys Trp Ala Ala Pro Tyr Leu Lys Gly Lys Gly Lys Leu
    130                 135                 140

Val Lys Glu Gly Lys Phe Gly Ala Val Glu Ile Val Glu Gln Glu Leu
145                 150                 155                 160

Arg Leu Cys Leu Ala Leu Ala His Trp Glu Leu Ser Arg Glu Gln Trp
                165                 170                 175

Leu Gln Gln His Tyr Glu Gln Ala Ala Leu Ser Gly Gln Lys Ser Gln
            180                 185                 190

Glu Leu Leu Val Asp Val Ala Gln Phe Ala Asp Leu Gln Gln Glu Ile
        195                 200                 205

Gln Gly Asp Leu Asn Arg Leu Arg Pro Tyr Gln Val Leu Glu Leu Leu
    210                 215                 220

Ala Leu Pro Glu Ser Glu Thr Gln Glu Arg Gln Arg Gly Leu Gln Leu
```

-continued

```
225                 230                 235                 240

Leu Gln Glu Met Leu Ser Ala Arg Val Gly Ile Asp Gly Gln Gly Asp
                245                 250                 255

Asp Gln Ser Gly Leu Ser Ile Asp Asp Phe Leu Arg Phe Ile Gln Gln
            260                 265                 270

Leu Arg Ser Tyr Leu Thr Val Gln Glu Gln Leu Asp Leu Phe Val Ala
        275                 280                 285

Glu Ser Lys Arg Pro Ser Ala Ala Ala Ala Tyr Leu Ala Val Tyr Ala
    290                 295                 300

Leu Leu Ala Ala Gly Phe Ser Gln Arg Lys Pro Asp Leu Val Val Gln
305                 310                 315                 320

Ala Gln Thr Leu Leu Lys Arg Leu Gly Lys Arg Gln Asp Val Phe Leu
                325                 330                 335

Glu Gln Ser Ile Cys Ala Leu Leu Leu Gly Gln Pro Ser Glu Ala Asn
            340                 345                 350

Gln Leu Leu Glu Gln Ser Gln Glu Gln Glu Ala Ile Ala Tyr Ile Gln
        355                 360                 365

Glu Gln Ser Glu Gly Ala Pro Asp Leu Leu Pro Gly Leu Cys Leu Tyr
    370                 375                 380

Gly Glu Gln Trp Leu Lys Thr Glu Val Phe Ser His Phe Arg Asp Leu
385                 390                 395                 400

Arg Gln Arg Leu Glu Asp Gly Ser Val Ser Leu Thr Ala Tyr Phe Ala
                405                 410                 415

Asp Pro Glu Val Gln Gln Tyr Leu Asp Asp Leu Leu Thr Glu Ala Val
            420                 425                 430

Pro Thr Pro Thr Pro His Pro Asp Thr Glu Ser Thr Ala Ala Pro Ser
        435                 440                 445

Glu Lys Pro Pro Glu Thr Leu Gln Ser Glu Thr Gly Val Ser Pro His
    450                 455                 460

Pro Ser Arg Pro Ala Lys Val Asp Ser Phe Glu Asp Leu Val Thr Gln
465                 470                 475                 480

Thr Pro Ala Thr Val Pro Pro Ala Pro Pro Ser Pro Gly Val Ala Pro
                485                 490                 495

Val Thr Ala Ala Leu Asn Pro Asp Pro Glu Ala Ser Ser Ala Ser Ser
            500                 505                 510

Lys Ser Val Ser Ser Lys Lys Ser Ile Gly Pro Trp Gly Ala Ile Ala
        515                 520                 525

Ala Ile Val Gly Ser Val Leu Leu Val Val Gly Leu Val Arg Ile Leu
    530                 535                 540

Ser Gly Leu Thr Thr Gln Glu Pro Leu Gln Val Thr Leu Asn Gly Glu
545                 550                 555                 560

Pro Pro Leu Thr Ile Pro Ser Leu Asp Thr Ala Glu Ala Asn Asn Asn
                565                 570                 575

Pro Glu Asn Gly Ala Thr Asp Thr Thr Thr Thr Pro Ala Leu Asn Glu
            580                 585                 590

Ala Ile Ala Ala Glu Val Ile Gln Thr Trp Phe Glu Ser Lys Ala Arg
        595                 600                 605

Ala Phe Gly Gln Asp Arg Asp Leu Ala Ala Leu Glu Asn Ile Leu Ala
    610                 615                 620

Glu Pro Ser Leu Ser Arg Trp Arg Ser Ser Ala Gln Ala Val Arg Ser
625                 630                 635                 640

Ala Gly Thr Tyr Arg Thr Tyr Asp His Ser Leu Thr Ile Glu Thr Val
                645                 650                 655
```

```
Ser Phe Asn Pro Asp Gln Pro Asn Val Ala Thr Val Glu Ala Gln Val
            660                 665                 670

Gln Glu Lys Ala Asp Tyr Tyr Arg Ala Asn Gly Glu Arg Asp Pro Gly
        675                 680                 685

Gln Ser Tyr Asp Ser Asp Leu Arg Val Arg Tyr Ser Leu Val Arg Gln
    690                 695                 700

Gly Asp Arg Trp Leu Ile Arg Ser Ser Gln Thr Leu
705                 710                 715


<210> SEQ ID NO 161
<211> LENGTH: 2469
<212> TYPE: DNA
<213> ORGANISM: Synechococcus PCC7942

<400> SEQUENCE: 161

cttgccgact aaaggctaag catcgccatt ccttagatta aagcagtctg tcggcggcgc      60

tgtgccggtt aacaccagtc tgtcgctgac agcggtgcct ttctggggct tgcctgtggg     120

gcgagtaacc gatcgctggg ataagagttg gtgcttctgg ctctcaagaa tagggttttc     180

cgtcgcgtat tcccgatcac atccccctgt gtctgctacg gagataacgc cgatcactca     240

acagaattgg taagttgacg gtcaagttgg gatgatgaag tcggctcaag ctggcgatcc     300

ggatctggtg ggtgttctgt gcgtattcct ctcgattact accgaattct ctgtgttggc     360

gtgcaagcct cggcagacaa acttgccgaa agctaccgcg atcgcctcaa ccaatcgccc     420

tcccatgagt tttcagagct ggcattgcag gcgcggcggc aactcctcga agcagcgatt     480

gctgagctga gtgatcccga acagcgcgat cgctacgatc gccgcttttt tcagggcggt     540

ctggaagcga ttgaaccaag cctagaactc gaagactggc agcgaattgg agccctgctg     600

atcctgctgg aattggggga atacgatcgc gtttcgcaac tggctgagga actcctgcca     660

gactacgacg cgagcgcaga agtacgcgat cagttcgcgc ggggtgatat cgccttggcg     720

atcgcactat cccagcaatc cctcggtcga gaatgccgtc agcagggtct gtacgaacag     780

gccgcccagc actttggccg cagccagtct gccctagccg atcatcagcg ctttcctgaa     840

ctgagtcgaa ccctgcacca agaacaagga cagctacggc cctatcgcat tttggagcgg     900

ttggcccagc ccttgactgc cgatagcgat cgccagcagg gtttgctgtt gttgcaggcg     960

atgttggacg accggcaggg cattgaaggc cctggggatg atggctcggg gctgacccct    1020

gataactttt tgatgtttct ccagcaaatt cgcggctatc tgaccctggc tgaacagcag    1080

ttgctgtttg aatcggaagc gcgtcggccc tcgccggctg cgagcttttt tgcctgctac    1140

accctgattg cgcggggctt ttgcgatcac caaccctcgt tgatccatcg cgccagcttg    1200

ctcttgcatg aactcaagag ccgcatggat gtgcacatcg aacaggcgat cgccagccta    1260

ttgctcggac agcccgaaga agctgaggcg ctactcgtcc agagccaaga tgaggaaacc    1320

ctcagccaaa tccgtgccct agcccaaggg gaagccctga tcgtcggttt gtgccgattc    1380

acggaaacct ggctagcgac caaggtattt ccggatttcc gcgacctcaa ggaaaggact    1440

gcgccgctgc agccctactt tgacgacccc gatgtccaga cctatctgga tgcgatcgtg    1500

gagttgccgt ccgatttgat gccaacgccg ctacccgttg agccgcttga ggtgcgatcg    1560

tcgttgctgg ccaaggaact gccgacccca gcaacgcctg gtgtagctcc accccctcgc    1620

cgccgtcgcc gcgatcgctc cgaacgtcct gctcgcacgg ccaaacgctt gcccttgccc    1680

tggattggtt tgggggttgt ggtggttctc ggcggtggaa caggggtttg ggcttggcga    1740
```

-continued

```
tcgcgttcca attccacccc gccgaccccg ccccccgtgg ttcaaacgct gcctgaggcg   1800

gtacctgccc cttcgcccgc gccagttacc gttgccctcg atcgggctca ggctgaaact   1860

gtgttgcaaa actggttggc cgctaaagct gcagccttgg ggcctcaata cgatcgcgat   1920

cgcttagcga cggtgctgac cggtgaggtt ctgcagactt ggcagggttt ttctagccag   1980

caggccaaca cccagctcac atcacagttc gatcacaagt taaccgtcga ctcagttcag   2040

ctcagtgacg gtgatcaacg agcagtagtc caagccaagg tcgatgaagt tgagcaggtc   2100

tatcgaggcg accagctgct cgaaacgcgc cgagatttgg gcttggtgat ccgctaccag   2160

ctcgtgcgcg agaacaacat ctggaaaatt gcttcgatta gtttggtgcg ctaggaattc   2220

gcaaggggtg aaccccctgc ggtcttttct gtagatcccc tagagcgatc gcagaatgtt   2280

cagcgattcc tggatgtgcg cttgggcatt caagagtgaa tcaaaaatgt ggcgcacctt   2340

gccctctttg tcgatcacat aagtgacgcg acccggaatc acaaacaggg ttttgggcac   2400

gccataggtt tgacggaggc gatcgcctgc atcgctcagc agttggaagg gcaagttgta   2460

tttctgggc                                                           2469
```

<210> SEQ ID NO 162
<211> LENGTH: 631
<212> TYPE: PRT
<213> ORGANISM: Synechococcus PCC7942

<400> SEQUENCE: 162

```
Met Arg Ile Pro Leu Asp Tyr Tyr Arg Ile Leu Cys Val Gly Val Gln
1               5                   10                  15

Ala Ser Ala Asp Lys Leu Ala Glu Ser Tyr Arg Asp Arg Leu Asn Gln
            20                  25                  30

Ser Pro Ser His Glu Phe Ser Glu Leu Ala Leu Gln Ala Arg Arg Gln
        35                  40                  45

Leu Leu Glu Ala Ala Ile Ala Glu Leu Ser Asp Pro Glu Gln Arg Asp
    50                  55                  60

Arg Tyr Asp Arg Arg Phe Phe Gln Gly Gly Leu Glu Ala Ile Glu Pro
65                  70                  75                  80

Ser Leu Glu Leu Glu Asp Trp Gln Arg Ile Gly Ala Leu Leu Ile Leu
                85                  90                  95

Leu Glu Leu Gly Glu Tyr Asp Arg Val Ser Gln Leu Ala Glu Glu Leu
            100                 105                 110

Leu Pro Asp Tyr Asp Ala Ser Ala Glu Val Arg Asp Gln Phe Ala Arg
        115                 120                 125

Gly Asp Ile Ala Leu Ala Ile Ala Leu Ser Gln Gln Ser Leu Gly Arg
    130                 135                 140

Glu Cys Arg Gln Gln Gly Leu Tyr Glu Gln Ala Ala Gln His Phe Gly
145                 150                 155                 160

Arg Ser Gln Ser Ala Leu Ala Asp His Gln Arg Phe Pro Glu Leu Ser
                165                 170                 175

Arg Thr Leu His Gln Glu Gln Gly Gln Leu Arg Pro Tyr Arg Ile Leu
            180                 185                 190

Glu Arg Leu Ala Gln Pro Leu Thr Ala Asp Ser Asp Arg Gln Gln Gly
        195                 200                 205

Leu Leu Leu Leu Gln Ala Met Leu Asp Asp Arg Gln Gly Ile Glu Gly
    210                 215                 220

Pro Gly Asp Asp Gly Ser Gly Leu Thr Leu Asp Asn Phe Leu Met Phe
225                 230                 235                 240
```

-continued

```
Leu Gln Gln Ile Arg Gly Tyr Leu Thr Leu Ala Glu Gln Gln Leu Leu
                245                 250                 255

Phe Glu Ser Glu Ala Arg Arg Pro Ser Pro Ala Ala Ser Phe Phe Ala
            260                 265                 270

Cys Tyr Thr Leu Ile Ala Arg Gly Phe Cys Asp His Gln Pro Ser Leu
        275                 280                 285

Ile His Arg Ala Ser Leu Leu Leu His Glu Leu Lys Ser Arg Met Asp
    290                 295                 300

Val His Ile Glu Gln Ala Ile Ala Ser Leu Leu Leu Gly Gln Pro Glu
305                 310                 315                 320

Glu Ala Glu Ala Leu Leu Val Gln Ser Gln Asp Glu Glu Thr Leu Ser
                325                 330                 335

Gln Ile Arg Ala Leu Ala Gln Gly Glu Ala Leu Ile Val Gly Leu Cys
            340                 345                 350

Arg Phe Thr Glu Thr Trp Leu Ala Thr Lys Val Phe Pro Asp Phe Arg
        355                 360                 365

Asp Leu Lys Glu Arg Thr Ala Pro Leu Gln Pro Tyr Phe Asp Asp Pro
    370                 375                 380

Asp Val Gln Thr Tyr Leu Asp Ala Ile Val Glu Leu Pro Ser Asp Leu
385                 390                 395                 400

Met Pro Thr Pro Leu Pro Val Glu Pro Leu Glu Val Arg Ser Ser Leu
                405                 410                 415

Leu Ala Lys Glu Leu Pro Thr Pro Ala Thr Pro Gly Val Ala Pro Pro
            420                 425                 430

Pro Arg Arg Arg Arg Arg Asp Arg Ser Glu Arg Pro Ala Arg Thr Ala
        435                 440                 445

Lys Arg Leu Pro Leu Pro Trp Ile Gly Leu Gly Val Val Val Val Leu
    450                 455                 460

Gly Gly Gly Thr Gly Val Trp Ala Trp Arg Ser Arg Ser Asn Ser Thr
465                 470                 475                 480

Pro Pro Thr Pro Pro Pro Val Val Gln Thr Leu Pro Glu Ala Val Pro
                485                 490                 495

Ala Pro Ser Pro Ala Pro Val Thr Val Ala Leu Asp Arg Ala Gln Ala
            500                 505                 510

Glu Thr Val Leu Gln Asn Trp Leu Ala Ala Lys Ala Ala Ala Leu Gly
        515                 520                 525

Pro Gln Tyr Asp Arg Asp Arg Leu Ala Thr Val Leu Thr Gly Glu Val
    530                 535                 540

Leu Gln Thr Trp Gln Gly Phe Ser Ser Gln Gln Ala Asn Thr Gln Leu
545                 550                 555                 560

Thr Ser Gln Phe Asp His Lys Leu Thr Val Asp Ser Val Gln Leu Ser
                565                 570                 575

Asp Gly Asp Gln Arg Ala Val Val Gln Ala Lys Val Asp Glu Val Glu
            580                 585                 590

Gln Val Tyr Arg Gly Asp Gln Leu Leu Glu Thr Arg Arg Asp Leu Gly
        595                 600                 605

Leu Val Ile Arg Tyr Gln Leu Val Arg Glu Asn Asn Ile Trp Lys Ile
    610                 615                 620

Ala Ser Ile Ser Leu Val Arg
625                 630
```

<210> SEQ ID NO 163
<211> LENGTH: 2400
<212> TYPE: DNA

-continued

<213> ORGANISM: Anabaena PCC7120

<400> SEQUENCE: 163

```
attatgttga tcacggtgca ggggaagtac gctgtgcgaa ttccgctaga ttactaccga     60
attttagggc taccgttagc ggcaagtgat gaacaactgc gacaagcata cagcgatcgc    120
attgtccaat tgccgcgacg ggagtattct caagcagcaa ttgcttcccg taaacaactt    180
atagaagaag cttacgtggt tttatcagat ccaaaggaac gcagcagtta tgaccagctg    240
tatcttgctc acgcctacga cccagacaac gcggctacaa ccaaagtggc agtggaaaat    300
cgtggggaca gcaacaatgg tcatttcgat gtccaaagcc tgagcatcga agtttcctcc    360
gaggaattaa ttggtgcttt attaattttg caagagttgg gagagtatga actcgtactc    420
aagttaggtc gtaattactt aggtaatcaa aacggcacag catccaccag aaatggcaat    480
catcgcacgc ctgaagaatt tctcgatagt tctgaacgtc cagatattct cttgactgtt    540
gctttggcct cattagaatt agggcgggaa caatggcaac aaggccacta tgaaaacgct    600
gctttgtctt tagagactgg gcaagaagtg ctgtttagtg aaggcatctt ccccagcgtc    660
caggcagaaa ttcaggctga tctttacaaa ttacgccctt atagaatttt agaattactt    720
gccttacccc aggaaaaaac cattgaacgc caccaagggc tggatctatt acaaagcatc    780
ttagacgatc gcggtggcat tgatggtaca ggcaatgatc aatcaggctt aaacattgat    840
gacttcctcc gattcatcca gcaattacgc caccacttaa cagtggctga acaacataag    900
ttgtttgatg gtgaaagcaa acgcccttcg gctgtggcta catacttagc tgtttatgct    960
tccatcgcca gaggattcac ccaacgccag cccgctttaa ttcgtcatgc caagcaaatt   1020
ctgatgcgtt tgtctaagcg gcaagatgtg catttagagc agtccctgtg tgcgctatta   1080
ctagggcaaa ctgaagaagc cacgcgagtt ttagaactga gccaagaata cgaagcttta   1140
gccttaattc gagaaaaatc tcaagattca cccgatttac tgccaggttt gtgcttatat   1200
gccgaacaat ggctgcaaaa tgaagttttc cccccatttcc gcgatttgtc cagacagcaa   1260
gcttccctga aagattactt tgctaatcaa caagtacaag cgtatttaga agccttgccc   1320
aacgacgcgg aaaccactaa tgaatgggct gtaattaacc gccaatcgtt ttctcaaccc   1380
aggggcaatt cttactctgg aggaacgcca gtcgccaaac gtcccgtagg gaaggcgaac   1440
aggccaggag aagcgtccac aagaccagtt ccccaacgta gtcatccatc agaagtaaat   1500
cggcagtttc atcaaaacag aacccctgat cccgaattac cagaaacatc aaaccacaga   1560
agaccagagt cttcaaattt tacaactgct agagaaaata tatcgaccac agatgcttac   1620
actgacaatt atccaccaga gatccctgta gaacgcgcca gcagacctgt tcagccgggg   1680
gtaagtggtt atacccaatc gacccctcca cggcaaactc ctaaacgcag gagacgcaag   1740
aagccacagg cagttgtcaa cagaggacac agtattcatc agcaacgcca accctcacct   1800
agcactctag gccggaaaac aagattactt tggatagttt tgggttcttt gggtgggata   1860
ttattgttct ggctgatagt ctcaacgact tttgggtggt taaagaatgt attcttccca   1920
gcaccatctt tacaaggtga gcaattatcg attcagatta gtcaaccacc tttagagatt   1980
cctgacaaaa atgcccagat acaatcccca gaggtgagtc tcacagaaga aacggcaagg   2040
aaaataattg aaaattggtt ggctaccaaa gctagtgctt taggcgctga acataaaatt   2100
gagagtttaa acgagatttt aactggttca gcgttatctc aatggcggct aattgccttg   2160
caagataaag cagacaatcg tcatcgagaa tacagtcata gtgtcaaggt agactccatc   2220
agtaaatctg acatagatcc caatcgtgca agtgtggggg ctacagtcag agagttaacc   2280
```

-continued

```
caattttatg agaatgggca aaaagggaag tcttctgacg aaagattacg tgtacgctat   2340

gaattgattc gacaagatga tatttggcgg attcagagga tgtcagccgc tataaattaa   2400


<210> SEQ ID NO 164
<211> LENGTH: 798
<212> TYPE: PRT
<213> ORGANISM: Anabaena PCC7120

<400> SEQUENCE: 164

Met Leu Ile Thr Val Gln Gly Lys Tyr Ala Val Arg Ile Pro Leu Asp
1               5                   10                  15

Tyr Tyr Arg Ile Leu Gly Leu Pro Leu Ala Ala Ser Asp Glu Gln Leu
            20                  25                  30

Arg Gln Ala Tyr Ser Asp Arg Ile Val Gln Leu Pro Arg Arg Glu Tyr
        35                  40                  45

Ser Gln Ala Ala Ile Ala Ser Arg Lys Gln Leu Ile Glu Glu Ala Tyr
    50                  55                  60

Val Val Leu Ser Asp Pro Lys Glu Arg Ser Ser Tyr Asp Gln Leu Tyr
65                  70                  75                  80

Leu Ala His Ala Tyr Asp Pro Asp Asn Ala Ala Thr Thr Lys Val Ala
                85                  90                  95

Val Glu Asn Arg Gly Asp Ser Asn Asn Gly His Phe Asp Val Gln Ser
            100                 105                 110

Leu Ser Ile Glu Val Ser Ser Glu Glu Leu Ile Gly Ala Leu Leu Ile
        115                 120                 125

Leu Gln Glu Leu Gly Glu Tyr Glu Leu Val Leu Lys Leu Gly Arg Asn
    130                 135                 140

Tyr Leu Gly Asn Gln Asn Gly Thr Ala Ser Thr Arg Asn Gly Asn His
145                 150                 155                 160

Arg Thr Pro Glu Glu Phe Leu Asp Ser Ser Glu Arg Pro Asp Ile Leu
                165                 170                 175

Leu Thr Val Ala Leu Ala Ser Leu Glu Leu Gly Arg Glu Gln Trp Gln
            180                 185                 190

Gln Gly His Tyr Glu Asn Ala Ala Leu Ser Leu Glu Thr Gly Gln Glu
        195                 200                 205

Val Leu Phe Ser Glu Gly Ile Phe Pro Ser Val Gln Ala Glu Ile Gln
    210                 215                 220

Ala Asp Leu Tyr Lys Leu Arg Pro Tyr Arg Ile Leu Glu Leu Leu Ala
225                 230                 235                 240

Leu Pro Gln Glu Lys Thr Ile Glu Arg His Gln Gly Leu Asp Leu Leu
                245                 250                 255

Gln Ser Ile Leu Asp Asp Arg Gly Gly Ile Asp Gly Thr Gly Asn Asp
            260                 265                 270

Gln Ser Gly Leu Asn Ile Asp Asp Phe Leu Arg Phe Ile Gln Gln Leu
        275                 280                 285

Arg His His Leu Thr Val Ala Glu Gln His Lys Leu Phe Asp Gly Glu
    290                 295                 300

Ser Lys Arg Pro Ser Ala Val Ala Thr Tyr Leu Ala Val Tyr Ala Ser
305                 310                 315                 320

Ile Ala Arg Gly Phe Thr Gln Arg Gln Pro Ala Leu Ile Arg His Ala
                325                 330                 335

Lys Gln Ile Leu Met Arg Leu Ser Lys Arg Gln Asp Val His Leu Glu
            340                 345                 350
```

-continued

```
Gln Ser Leu Cys Ala Leu Leu Leu Gly Gln Thr Glu Glu Ala Thr Arg
        355                 360                 365

Val Leu Glu Leu Ser Gln Glu Tyr Glu Ala Leu Ala Leu Ile Arg Glu
    370                 375                 380

Lys Ser Gln Asp Ser Pro Asp Leu Leu Pro Gly Leu Cys Leu Tyr Ala
385                 390                 395                 400

Glu Gln Trp Leu Gln Asn Glu Val Phe Pro His Phe Arg Asp Leu Ser
                405                 410                 415

Arg Gln Gln Ala Ser Leu Lys Asp Tyr Phe Ala Asn Gln Gln Val Gln
            420                 425                 430

Ala Tyr Leu Glu Ala Leu Pro Asn Asp Ala Glu Thr Thr Asn Glu Trp
        435                 440                 445

Ala Val Ile Asn Arg Gln Ser Phe Ser Gln Pro Arg Gly Asn Ser Tyr
    450                 455                 460

Ser Gly Gly Thr Pro Val Ala Lys Arg Pro Val Gly Lys Ala Asn Arg
465                 470                 475                 480

Pro Gly Glu Ala Ser Thr Arg Pro Val Pro Gln Arg Ser His Pro Ser
                485                 490                 495

Glu Val Asn Arg Gln Phe His Gln Asn Arg Thr Pro Asp Pro Glu Leu
            500                 505                 510

Pro Glu Thr Ser Asn His Arg Arg Pro Glu Ser Ser Asn Phe Thr Thr
        515                 520                 525

Ala Arg Glu Asn Ile Ser Thr Thr Asp Ala Tyr Thr Asp Asn Tyr Pro
    530                 535                 540

Pro Glu Ile Pro Val Glu Arg Ala Ser Arg Pro Val Gln Pro Gly Val
545                 550                 555                 560

Ser Gly Tyr Thr Gln Ser Thr Pro Pro Arg Gln Thr Pro Lys Arg Arg
                565                 570                 575

Arg Arg Lys Lys Pro Gln Ala Val Val Asn Arg Gly His Ser Ile His
            580                 585                 590

Gln Gln Arg Gln Pro Ser Pro Ser Thr Leu Gly Arg Lys Thr Arg Leu
        595                 600                 605

Leu Trp Ile Val Leu Gly Ser Leu Gly Gly Ile Leu Leu Phe Trp Leu
    610                 615                 620

Ile Val Ser Thr Thr Phe Gly Trp Leu Lys Asn Val Phe Phe Pro Ala
625                 630                 635                 640

Pro Ser Leu Gln Gly Glu Gln Leu Ser Ile Gln Ile Ser Gln Pro Pro
                645                 650                 655

Leu Glu Ile Pro Asp Lys Asn Ala Gln Ile Gln Ser Pro Glu Val Ser
            660                 665                 670

Leu Thr Glu Glu Thr Ala Arg Lys Ile Ile Glu Asn Trp Leu Ala Thr
        675                 680                 685

Lys Ala Ser Ala Leu Gly Ala Glu His Lys Ile Glu Ser Leu Asn Glu
    690                 695                 700

Ile Leu Thr Gly Ser Ala Leu Ser Gln Trp Arg Leu Ile Ala Leu Gln
705                 710                 715                 720

Asp Lys Ala Asp Asn Arg His Arg Glu Tyr Ser His Ser Val Lys Val
                725                 730                 735

Asp Ser Ile Ser Lys Ser Asp Ile Asp Pro Asn Arg Ala Ser Val Gly
            740                 745                 750

Ala Thr Val Arg Glu Leu Thr Gln Phe Tyr Glu Asn Gly Gln Lys Gly
        755                 760                 765

Lys Ser Ser Asp Glu Arg Leu Arg Val Arg Tyr Glu Leu Ile Arg Gln
```

```
    770                 775                 780

Asp Asp Ile Trp Arg Ile Gln Arg Met Ser Ala Ala Ile Asn
785                 790                 795


<210> SEQ ID NO 165
<211> LENGTH: 798
<212> TYPE: PRT
<213> ORGANISM: Anabaena PCC7120

<400> SEQUENCE: 165

Met Leu Ile Thr Val Gln Gly Lys Tyr Ala Val Arg Ile Pro Leu Asp
1               5                   10                  15

Tyr Tyr Arg Ile Leu Gly Leu Pro Leu Ala Ala Ser Asp Glu Gln Leu
            20                  25                  30

Arg Gln Ala Tyr Ser Asp Arg Ile Val Gln Leu Pro Arg Arg Glu Tyr
        35                  40                  45

Ser Gln Ala Ala Ile Ala Ser Arg Lys Gln Leu Ile Glu Glu Ala Tyr
    50                  55                  60

Val Val Leu Ser Asp Pro Lys Glu Arg Ser Ser Tyr Asp Gln Leu Tyr
65                  70                  75                  80

Leu Ala His Ala Tyr Asp Pro Asp Asn Ala Ala Thr Thr Lys Val Ala
                85                  90                  95

Val Glu Asn Arg Gly Asp Ser Asn Asn Gly His Phe Asp Val Gln Ser
            100                 105                 110

Leu Ser Ile Glu Val Ser Ser Glu Glu Leu Ile Gly Ala Leu Leu Ile
        115                 120                 125

Leu Gln Glu Leu Gly Glu Tyr Glu Leu Val Leu Lys Leu Gly Arg Asn
    130                 135                 140

Tyr Leu Gly Asn Gln Asn Gly Thr Ala Ser Thr Arg Asn Gly Asn His
145                 150                 155                 160

Arg Thr Pro Glu Glu Phe Leu Asp Ser Ser Glu Arg Pro Asp Ile Leu
                165                 170                 175

Leu Thr Val Ala Leu Ala Ser Leu Glu Leu Gly Arg Glu Gln Trp Gln
            180                 185                 190

Gln Gly His Tyr Glu Asn Ala Ala Leu Ser Leu Glu Thr Gly Gln Glu
        195                 200                 205

Val Leu Phe Ser Glu Gly Ile Phe Pro Ser Val Gln Ala Glu Ile Gln
    210                 215                 220

Ala Asp Leu Tyr Lys Leu Arg Pro Tyr Arg Ile Leu Glu Leu Leu Ala
225                 230                 235                 240

Leu Pro Gln Glu Lys Thr Ile Glu Arg His Gln Gly Leu Asp Leu Leu
                245                 250                 255

Gln Ser Ile Leu Asp Asp Arg Gly Gly Ile Asp Gly Thr Gly Asn Asp
            260                 265                 270

Gln Ser Gly Leu Asn Ile Asp Asp Phe Leu Arg Phe Ile Gln Gln Leu
        275                 280                 285

Arg His His Leu Thr Val Ala Glu Gln His Lys Leu Phe Asp Gly Glu
    290                 295                 300

Ser Lys Arg Pro Ser Ala Val Ala Thr Tyr Leu Ala Val Tyr Ala Ser
305                 310                 315                 320

Ile Ala Arg Gly Phe Thr Gln Arg Gln Pro Ala Leu Ile Arg His Ala
                325                 330                 335

Lys Gln Ile Leu Met Arg Leu Ser Lys Arg Gln Asp Val His Leu Glu
            340                 345                 350
```

-continued

```
Gln Ser Leu Cys Ala Leu Leu Leu Gly Gln Thr Glu Glu Ala Thr Arg
        355                 360                 365

Val Leu Glu Leu Ser Gln Glu Tyr Glu Ala Leu Ala Leu Ile Arg Glu
    370                 375                 380

Lys Ser Gln Asp Ser Pro Asp Leu Leu Pro Gly Leu Cys Leu Tyr Ala
385                 390                 395                 400

Glu Gln Trp Leu Gln Asn Glu Val Phe Pro His Phe Arg Asp Leu Ser
                405                 410                 415

Arg Gln Gln Ala Ser Leu Lys Asp Tyr Phe Ala Asn Gln Gln Val Gln
            420                 425                 430

Ala Tyr Leu Glu Ala Leu Pro Asn Asp Ala Glu Thr Thr Asn Glu Trp
        435                 440                 445

Ala Val Ile Asn Arg Gln Ser Phe Ser Gln Pro Arg Gly Asn Ser Tyr
    450                 455                 460

Ser Gly Gly Thr Pro Val Ala Lys Arg Pro Val Gly Lys Ala Asn Arg
465                 470                 475                 480

Pro Gly Glu Ala Ser Thr Arg Pro Val Pro Gln Arg Ser His Pro Ser
                485                 490                 495

Glu Val Asn Arg Gln Phe His Gln Asn Arg Thr Pro Asp Pro Glu Leu
            500                 505                 510

Pro Glu Thr Ser Asn His Arg Arg Pro Glu Ser Ser Asn Phe Thr Thr
        515                 520                 525

Ala Arg Glu Asn Ile Ser Thr Thr Asp Ala Tyr Thr Asp Asn Tyr Pro
    530                 535                 540

Pro Glu Ile Pro Val Glu Arg Ala Ser Arg Pro Val Gln Pro Gly Val
545                 550                 555                 560

Ser Gly Tyr Thr Gln Ser Thr Pro Pro Arg Gln Thr Pro Lys Arg Arg
                565                 570                 575

Arg Arg Lys Lys Pro Gln Ala Val Val Asn Arg Gly His Ser Ile His
            580                 585                 590

Gln Gln Arg Gln Pro Ser Pro Ser Thr Leu Gly Arg Lys Thr Arg Leu
        595                 600                 605

Leu Trp Ile Val Leu Gly Ser Leu Gly Gly Ile Leu Leu Phe Trp Leu
    610                 615                 620

Ile Val Ser Thr Thr Phe Gly Trp Leu Lys Asn Val Phe Phe Pro Ala
625                 630                 635                 640

Pro Ser Leu Gln Gly Glu Gln Leu Ser Ile Gln Ile Ser Gln Pro Pro
                645                 650                 655

Leu Glu Ile Pro Asp Lys Asn Ala Gln Ile Gln Ser Pro Glu Val Ser
            660                 665                 670

Leu Thr Glu Glu Thr Ala Arg Lys Ile Ile Glu Asn Trp Leu Ala Thr
        675                 680                 685

Lys Ala Ser Ala Leu Gly Ala Glu His Lys Ile Glu Ser Leu Asn Glu
    690                 695                 700

Ile Leu Thr Gly Ser Ala Leu Ser Gln Trp Arg Leu Ile Ala Leu Gln
705                 710                 715                 720

Asp Lys Ala Asp Asn Arg His Arg Glu Tyr Ser His Ser Val Lys Val
                725                 730                 735

Asp Ser Ile Ser Lys Ser Asp Ile Asp Pro Asn Arg Ala Ser Val Gly
            740                 745                 750

Ala Thr Val Arg Glu Leu Thr Gln Phe Tyr Glu Asn Gly Gln Lys Gly
        755                 760                 765

Lys Ser Ser Asp Glu Arg Leu Arg Val Arg Tyr Glu Leu Ile Arg Gln
```

```
    770                 775                 780

Asp Asp Ile Trp Arg Ile Gln Arg Met Ser Ala Ala Ile Asn
785                 790                 795


<210> SEQ ID NO 166
<211> LENGTH: 2307
<212> TYPE: DNA
<213> ORGANISM: Nostoc punctiforme

<400> SEQUENCE: 166

gtgcgaattc cgctagatta ctaccgaatt ttaggactac cgttagcggc aagtgaagaa      60

caattgcgac aggcatacag cgatcgcatt gtacaattgc cacgacgtga gtattctcag     120

gcagcaattt cttctcgtaa acaactcata gaagaagctt acgtggtttt atcagatcca     180

aaacaacgca gtacctacga tcagctttat cttgcccacg cctatgaccc tgataacctt     240

gctgctgccg cagtagcaca ggaaaatcgt acagaaagca ccaaaagggg tagtgatacc     300

cagagtcttg gtatagaaat tacccaagac gaattagttg gcgctttatt aattttgcaa     360

gagttgggtg aatacgaact tgtattgaaa ctaggtcgtc cgtacctagt aaataaaaat     420

agtgctacaa gttcaagaaa aagcaataac ttagcagatg aagaaattta tgaaagtgct     480

gaacacccag atgtcgttct cactgttgct cttgcctgtc tagaattagg tcgggaacag     540

tggcagcaag gtcactacga aaatgccgcc atatccctag aaactggtca agagctgcta     600

gtacgtgaag gtttgttctc cagtatccag gcagaaattc aggctgatct ttacaaattg     660

cggccatatc gaattttgga gttgctcgca ttacctcaag aaaagactgc cgaacgaagc     720

caaggcttag aattattgca aaatctctta gaagatcgtg gcgggattga tggcacgaac     780

aatgatgaat cgggtttaaa catagatgac tttctgcgat ttatccagca gttacgcaac     840

cacttaacag ttgcagaaca gcacaagtta tttgaagctc aaagcaaacg ttcttctgct     900

gttgccactt acttagctgt ttatgccttg atagcgcgag gatttgctca acggcaacct     960

gctttaattc gtcaagcaag acaaatgctc gtgcgtctgg gcaagcgcca agatgtacat    1020

ttagaacagt cgctatgtgc cttacttttg ggcaaactg aagaagcaac tcgtgtttta    1080

gaacttagtc aggagtacga agctttagct tttattcggg aaaaatctca ggactctcca    1140

gatttgttac cgggtctgtg tttatatgca gaacagtggc tgcaacacga agtctttccc    1200

cattttcgag atttagcaaa ccagcaagct ttcctaaaag attactttgc taaccaacag    1260

gtgcaagctt atttagaagc actgccaact gatgcccaaa caactaatga atgggctgta    1320

attaaccccc agtattttcc ccaggccaag gcaaagaata ctcattttca taacaattca    1380

actaaaactt cagcgtcatt taatcacagc agagtaccta acccagattt gccagaaaca    1440

ccaacaaaag aaacctctga atatccaaac ttctcaccac ctatgtggag ttcatctgga    1500

agtataaaat cagaggttcc tgctgctgaa aggatgagca gaggtactaa tcagcatttg    1560

aacggttcag ctaagagtgc tgcatctggt cataaccaaa agcgtaggcg gagaaaacct    1620

actccatctg ctagccgaga gcgtatacca gataatcgtc ctcattctcg tcgtccccga    1680

aggcggcgaa cttttgcgaa caccatagaa ggtaaaacac ggctggtatg gagagtgttt    1740

atttctttgg tgagcatatt agttttttgg gtattagcca caacaacttt tggatggtta    1800

aaaaatctgt tttttcctca accttctccg cctgatctac agttgtttgt acaaataaac    1860

caaccaccgt tacctattcc cgatccaaat agaaaaccag aatcagaaga aggccccttta   1920

acaaatgcag aggcagaaga agttattcac acttggttat ctaccaaagc cgcagcttta    1980
```

-continued

```
gggcccaatc atgagattaa taatttagag caaattttaa ctggttcagc tttatctcaa   2040

tggcgactga ttgctcaaca gaataagtta gacaatcgct accgcaagtt cgaccatagt   2100

ttgaagatag aatctgttga gaaaattggt ttatttgcag atcgtgccgc agtagaagct   2160

acggtcaaag aagtgacgca gttatatgaa aataatcagt ttaaaaactc ttctaacgat   2220

aaattaagag ttcggtatga cttgattcga gaacgaggta aatggcgtat tcagagtaca   2280

tctgttgtaa atcaattcac cagataa                                       2307
```

<210> SEQ ID NO 167
<211> LENGTH: 768
<212> TYPE: PRT
<213> ORGANISM: Nostoc punctiforme

<400> SEQUENCE: 167

```
Val Arg Ile Pro Leu Asp Tyr Tyr Arg Ile Leu Gly Leu Pro Leu Ala
1               5                   10                  15

Ala Ser Glu Glu Gln Leu Arg Gln Ala Tyr Ser Asp Arg Ile Val Gln
            20                  25                  30

Leu Pro Arg Arg Glu Tyr Ser Gln Ala Ala Ile Ser Ser Arg Lys Gln
        35                  40                  45

Leu Ile Glu Glu Ala Tyr Val Val Leu Ser Asp Pro Lys Gln Arg Ser
    50                  55                  60

Thr Tyr Asp Gln Leu Tyr Leu Ala His Ala Tyr Asp Pro Asp Asn Leu
65                  70                  75                  80

Ala Ala Ala Ala Val Ala Gln Glu Asn Arg Thr Glu Ser Thr Lys Arg
                85                  90                  95

Gly Ser Asp Thr Gln Ser Leu Gly Ile Glu Ile Thr Gln Asp Glu Leu
            100                 105                 110

Val Gly Ala Leu Leu Ile Leu Gln Glu Leu Gly Glu Tyr Glu Leu Val
        115                 120                 125

Leu Lys Leu Gly Arg Pro Tyr Leu Val Asn Lys Asn Ser Ala Thr Ser
    130                 135                 140

Ser Arg Lys Ser Asn Asn Leu Ala Asp Glu Glu Ile Tyr Glu Ser Ala
145                 150                 155                 160

Glu His Pro Asp Val Val Leu Thr Val Ala Leu Ala Cys Leu Glu Leu
                165                 170                 175

Gly Arg Glu Gln Trp Gln Gln Gly His Tyr Glu Asn Ala Ala Ile Ser
            180                 185                 190

Leu Glu Thr Gly Gln Glu Leu Leu Val Arg Glu Gly Leu Phe Ser Ser
        195                 200                 205

Ile Gln Ala Glu Ile Gln Ala Asp Leu Tyr Lys Leu Arg Pro Tyr Arg
    210                 215                 220

Ile Leu Glu Leu Leu Ala Leu Pro Gln Glu Lys Thr Ala Glu Arg Ser
225                 230                 235                 240

Gln Gly Leu Glu Leu Leu Gln Asn Leu Leu Glu Asp Arg Gly Gly Ile
                245                 250                 255

Asp Gly Thr Asn Asn Asp Glu Ser Gly Leu Asn Ile Asp Asp Phe Leu
            260                 265                 270

Arg Phe Ile Gln Gln Leu Arg Asn His Leu Thr Val Ala Glu Gln His
        275                 280                 285

Lys Leu Phe Glu Ala Gln Ser Lys Arg Ser Ser Ala Val Ala Thr Tyr
    290                 295                 300

Leu Ala Val Tyr Ala Leu Ile Ala Arg Gly Phe Ala Gln Arg Gln Pro
305                 310                 315                 320
```

-continued

```
Ala Leu Ile Arg Gln Ala Arg Gln Met Leu Val Arg Leu Gly Lys Arg
                325                 330                 335

Gln Asp Val His Leu Glu Gln Ser Leu Cys Ala Leu Leu Leu Gly Gln
            340                 345                 350

Thr Glu Glu Ala Thr Arg Val Leu Glu Leu Ser Gln Glu Tyr Glu Ala
        355                 360                 365

Leu Ala Phe Ile Arg Glu Lys Ser Gln Asp Ser Pro Asp Leu Leu Pro
    370                 375                 380

Gly Leu Cys Leu Tyr Ala Glu Gln Trp Leu Gln His Glu Val Phe Pro
385                 390                 395                 400

His Phe Arg Asp Leu Ala Asn Gln Gln Ala Phe Leu Lys Asp Tyr Phe
                405                 410                 415

Ala Asn Gln Gln Val Gln Ala Tyr Leu Glu Ala Leu Pro Thr Asp Ala
            420                 425                 430

Gln Thr Thr Asn Glu Trp Ala Val Ile Asn Pro Gln Tyr Phe Pro Gln
        435                 440                 445

Ala Lys Ala Lys Asn Thr His Phe His Asn Asn Ser Thr Lys Thr Ser
    450                 455                 460

Ala Ser Phe Asn His Ser Arg Val Pro Asn Pro Asp Leu Pro Glu Thr
465                 470                 475                 480

Pro Thr Lys Glu Thr Ser Glu Tyr Pro Asn Phe Ser Pro Pro Met Trp
                485                 490                 495

Ser Ser Ser Gly Ser Ile Lys Ser Glu Val Pro Ala Ala Glu Arg Met
            500                 505                 510

Ser Arg Gly Thr Asn Gln His Leu Asn Gly Ser Ala Lys Ser Ala Ala
        515                 520                 525

Ser Gly His Asn Gln Lys Arg Arg Arg Arg Lys Pro Thr Pro Ser Ala
    530                 535                 540

Ser Arg Glu Arg Ile Pro Asp Asn Arg Pro His Ser Arg Arg Pro Arg
545                 550                 555                 560

Arg Arg Arg Thr Phe Ala Asn Thr Ile Glu Gly Lys Thr Arg Leu Val
                565                 570                 575

Trp Arg Val Phe Ile Ser Leu Val Ser Ile Leu Val Phe Trp Val Leu
            580                 585                 590

Ala Thr Thr Thr Phe Gly Trp Leu Lys Asn Leu Phe Phe Pro Gln Pro
        595                 600                 605

Ser Pro Pro Asp Leu Gln Leu Phe Val Gln Ile Asn Gln Pro Pro Leu
    610                 615                 620

Pro Ile Pro Asp Pro Asn Arg Lys Pro Glu Ser Glu Glu Gly Pro Leu
625                 630                 635                 640

Thr Asn Ala Glu Ala Glu Glu Val Ile His Thr Trp Leu Ser Thr Lys
                645                 650                 655

Ala Ala Ala Leu Gly Pro Asn His Glu Ile Asn Asn Leu Glu Gln Ile
            660                 665                 670

Leu Thr Gly Ser Ala Leu Ser Gln Trp Arg Leu Ile Ala Gln Gln Asn
        675                 680                 685

Lys Leu Asp Asn Arg Tyr Arg Lys Phe Asp His Ser Leu Lys Ile Glu
    690                 695                 700

Ser Val Glu Lys Ile Gly Leu Phe Ala Asp Arg Ala Ala Val Glu Ala
705                 710                 715                 720

Thr Val Lys Glu Val Thr Gln Leu Tyr Glu Asn Asn Gln Phe Lys Asn
                725                 730                 735
```

-continued

```
Ser Ser Asn Asp Lys Leu Arg Val Arg Tyr Asp Leu Ile Arg Glu Arg
            740                 745                 750

Gly Lys Trp Arg Ile Gln Ser Thr Ser Val Val Asn Gln Phe Thr Arg
        755                 760                 765
```

<210> SEQ ID NO 168
<211> LENGTH: 2145
<212> TYPE: DNA
<213> ORGANISM: Synechocystis PCC6803

<400> SEQUENCE: 168

```
gtgtttatcc ccctcgactt ttatcgtatt ttaggcattc ctccccagag tggtggggaa     60

accattgagc aggcctacca agatcgcctt ttacaattac cccggcgaga atttagtgac    120

gccgcagtta ctctccgcaa tcaattactg gcgatcgcct atgaaaccct gagggatccg    180

gaaaaacgtc aggcatacga ccaagaatgg tggggagcca tggatgaagc cctgggggag    240

gccttacccc tcactacccc ggagttggaa tgtagcccag agcaagaaat tggagccctg    300

ttgatcctgt tggatttggg ggaatacgaa ctcgtggtta agtatggtga gccagtactc    360

cacgatccca accctccggc gggaggcctg ccccaggact atttgctttc ggtaattttg    420

gcccactggg aactgagccg ggaacgttgg caacaacagc agtatgaatt tgccgccacc    480

gccagtctta aggccctagc tcggttgcaa caggataatg acttccccgc cttggaagca    540

gaaattcgtc aggaactata ccgtctgcga ccctaccgta tcctcgaact tttggctaag    600

gaggggcaag gggaggagca acgtcagcag ggtctagctc tgttgcaagc gatggtgcag    660

gaccggggcg gcattgaagg taagggggaa gattattccg gattgggaaa tgatgacttt    720

ctaaaattca tccaccaact acgctgtcac ctcacagtgg ccgagcaaaa cgccctattt    780

ttgcccgaaa gtcaacggcc atctttagta gcaagctatt tggcagtaca tagtctgatg    840

gctgagggag tgaaggaaca ggaccccatg gccattgtcg aagcaaaatc tttgattata    900

cagttggaaa attgtcaaga tttggcccta gaaaaggtaa tttgtgaatt attattgggt    960

caaacggaag ttgttctggc ggcgatcgac cagggagatc cgaaaatagt agctggcctc   1020

gaatctaagt tagcgacggg ggaagacccc ttaactgctt tttatacttt cactgagcag   1080

tggctagagg aagaaattgt cccctacttt agggatcttt ctccggagac cctttccccc   1140

aaggcctatt tcaataatcc ctccgttcag cagtatctag aacaactaga gccggattcc   1200

ttcaccactg acaattcttt tgcctcccct gccctcctta gcaccgcaac ggaatcggaa   1260

actcccatgg tacatagttc cgccgccctt cccgatcgcc ctttgacctc caccgttccc   1320

tcacgacggg gacgcagtcc aagacgttcc cgagacgatg ttttccccag cgccgacaat   1380

tccagtggtt tggccgtcac caccctatct ccggcgatcg cctacgacac ccactccttg   1440

ggcaccaacg gtattggcgg ggatagcact agcaacggtt tttccagtaa ctccgcccca   1500

gaatccacca gtaaacataa atctccccgg cgacgcaaaa aacgggtgac catcaagccg   1560

gtgcgcttcg gcatttttct gctttgccta gcaggcattg tgggggggc aactgcccta    1620

attatcaatc gtactggcga tcccctaggt gggttgctag aagacccccct agatgttttc  1680

ctggaccaac cttcagaatt tatccccgat gaagccacga gccggaattt gattctcagt   1740

caacccaact tcaatcagca agtgggtcag atggtagtac aaggctggct tgatagtaaa   1800

aagttagcct ttggccaaaa ctacgatgtc ggggcattgc agagtgtttt agccccccaat  1860

ctccttgccc aacaacgggg tcgggcccaa cgggatcaag cccaaaaggt ctatcaccaa   1920

tacgaacaca agttgcagat tttagcctat caagttaacc cccaagaccc caaccgagcc   1980
```

```
accgttactg cccgggtaga agaaattagc cagcccttta ccctaggtaa tcaacagcag   2040

aagggctccg ccaccaaaga tgacttgact gtgcgctatc agctagtacg acaccaaggg   2100

gtttggaaaa ttgaccaaat acaagtggta aatggccccc gttag                   2145


<210> SEQ ID NO 169
<211> LENGTH: 714
<212> TYPE: PRT
<213> ORGANISM: Synechocystis PCC6803

<400> SEQUENCE: 169

Met Phe Ile Pro Leu Asp Phe Tyr Arg Ile Leu Gly Ile Pro Pro Gln
1               5                   10                  15

Ser Gly Gly Glu Thr Ile Glu Gln Ala Tyr Gln Asp Arg Leu Leu Gln
            20                  25                  30

Leu Pro Arg Arg Glu Phe Ser Asp Ala Ala Val Thr Leu Arg Asn Gln
        35                  40                  45

Leu Leu Ala Ile Ala Tyr Glu Thr Leu Arg Asp Pro Glu Lys Arg Gln
    50                  55                  60

Ala Tyr Asp Gln Glu Trp Trp Gly Ala Met Asp Glu Ala Leu Gly Glu
65                  70                  75                  80

Ala Leu Pro Leu Thr Thr Pro Glu Leu Glu Cys Ser Pro Glu Gln Glu
                85                  90                  95

Ile Gly Ala Leu Leu Ile Leu Leu Asp Leu Gly Glu Tyr Glu Leu Val
            100                 105                 110

Val Lys Tyr Gly Glu Pro Val Leu His Asp Pro Asn Pro Pro Ala Gly
        115                 120                 125

Gly Leu Pro Gln Asp Tyr Leu Leu Ser Val Ile Leu Ala His Trp Glu
    130                 135                 140

Leu Ser Arg Glu Arg Trp Gln Gln Gln Gln Tyr Glu Phe Ala Ala Thr
145                 150                 155                 160

Ala Ser Leu Lys Ala Leu Ala Arg Leu Gln Gln Asp Asn Asp Phe Pro
                165                 170                 175

Ala Leu Glu Ala Glu Ile Arg Gln Glu Leu Tyr Arg Leu Arg Pro Tyr
            180                 185                 190

Arg Ile Leu Glu Leu Leu Ala Lys Glu Gly Gln Gly Glu Glu Gln Arg
        195                 200                 205

Gln Gln Gly Leu Ala Leu Leu Gln Ala Met Val Gln Asp Arg Gly Gly
    210                 215                 220

Ile Glu Gly Lys Gly Glu Asp Tyr Ser Gly Leu Gly Asn Asp Asp Phe
225                 230                 235                 240

Leu Lys Phe Ile His Gln Leu Arg Cys His Leu Thr Val Ala Glu Gln
                245                 250                 255

Asn Ala Leu Phe Leu Pro Glu Ser Gln Arg Pro Ser Leu Val Ala Ser
            260                 265                 270

Tyr Leu Ala Val His Ser Leu Met Ala Glu Gly Val Lys Glu Gln Asp
        275                 280                 285

Pro Met Ala Ile Val Glu Ala Lys Ser Leu Ile Ile Gln Leu Glu Asn
    290                 295                 300

Cys Gln Asp Leu Ala Leu Glu Lys Val Ile Cys Glu Leu Leu Leu Gly
305                 310                 315                 320

Gln Thr Glu Val Val Leu Ala Ala Ile Asp Gln Gly Asp Pro Lys Ile
                325                 330                 335

Val Ala Gly Leu Glu Ser Lys Leu Ala Thr Gly Glu Asp Pro Leu Thr
```

-continued

```
            340                 345                 350

Ala Phe Tyr Thr Phe Thr Glu Gln Trp Leu Glu Glu Glu Ile Val Pro
        355                 360                 365

Tyr Phe Arg Asp Leu Ser Pro Glu Thr Leu Ser Pro Lys Ala Tyr Phe
    370                 375                 380

Asn Asn Pro Ser Val Gln Gln Tyr Leu Glu Gln Leu Glu Pro Asp Ser
385                 390                 395                 400

Phe Thr Thr Asp Asn Ser Phe Ala Ser Pro Ala Leu Leu Ser Thr Ala
                405                 410                 415

Thr Glu Ser Glu Thr Pro Met Val His Ser Ser Ala Ala Leu Pro Asp
            420                 425                 430

Arg Pro Leu Thr Ser Thr Val Pro Ser Arg Arg Gly Arg Ser Pro Arg
        435                 440                 445

Arg Ser Arg Asp Asp Val Phe Pro Ser Ala Asp Asn Ser Ser Gly Leu
    450                 455                 460

Ala Val Thr Thr Leu Ser Pro Ala Ile Ala Tyr Asp Thr His Ser Leu
465                 470                 475                 480

Gly Thr Asn Gly Ile Gly Gly Asp Ser Thr Ser Asn Gly Phe Ser Ser
                485                 490                 495

Asn Ser Ala Pro Glu Ser Thr Ser Lys His Lys Ser Pro Arg Arg Arg
            500                 505                 510

Lys Lys Arg Val Thr Ile Lys Pro Val Arg Phe Gly Ile Phe Leu Leu
        515                 520                 525

Cys Leu Ala Gly Ile Val Gly Gly Ala Thr Ala Leu Ile Ile Asn Arg
    530                 535                 540

Thr Gly Asp Pro Leu Gly Gly Leu Leu Glu Asp Pro Leu Asp Val Phe
545                 550                 555                 560

Leu Asp Gln Pro Ser Glu Phe Ile Pro Asp Glu Ala Thr Ser Arg Asn
                565                 570                 575

Leu Ile Leu Ser Gln Pro Asn Phe Asn Gln Gln Val Gly Gln Met Val
            580                 585                 590

Val Gln Gly Trp Leu Asp Ser Lys Lys Leu Ala Phe Gly Gln Asn Tyr
        595                 600                 605

Asp Val Gly Ala Leu Gln Ser Val Leu Ala Pro Asn Leu Leu Ala Gln
    610                 615                 620

Gln Arg Gly Arg Ala Gln Arg Asp Gln Ala Gln Lys Val Tyr His Gln
625                 630                 635                 640

Tyr Glu His Lys Leu Gln Ile Leu Ala Tyr Gln Val Asn Pro Gln Asp
                645                 650                 655

Pro Asn Arg Ala Thr Val Thr Ala Arg Val Glu Glu Ile Ser Gln Pro
            660                 665                 670

Phe Thr Leu Gly Asn Gln Gln Gln Lys Gly Ser Ala Thr Lys Asp Asp
        675                 680                 685

Leu Thr Val Arg Tyr Gln Leu Val Arg His Gln Gly Val Trp Lys Ile
    690                 695                 700

Asp Gln Ile Gln Val Val Asn Gly Pro Arg
705                 710
```

<210> SEQ ID NO 170
<211> LENGTH: 714
<212> TYPE: PRT
<213> ORGANISM: Synechocystis PCC6803

<400> SEQUENCE: 170

-continued

```
Met Phe Ile Pro Leu Asp Phe Tyr Arg Ile Leu Gly Ile Pro Pro Gln
1               5                   10                  15

Ser Gly Gly Glu Thr Ile Glu Gln Ala Tyr Gln Asp Arg Leu Leu Gln
            20                  25                  30

Leu Pro Arg Arg Glu Phe Ser Asp Ala Ala Val Thr Leu Arg Asn Gln
        35                  40                  45

Leu Leu Ala Ile Ala Tyr Glu Thr Leu Arg Asp Pro Glu Lys Arg Gln
    50                  55                  60

Ala Tyr Asp Gln Glu Trp Trp Gly Ala Met Asp Glu Ala Leu Gly Glu
65                  70                  75                  80

Ala Leu Pro Leu Thr Thr Pro Glu Leu Glu Cys Ser Pro Glu Gln Glu
                85                  90                  95

Ile Gly Ala Leu Leu Ile Leu Leu Asp Leu Gly Glu Tyr Glu Leu Val
            100                 105                 110

Val Lys Tyr Gly Glu Pro Val Leu His Asp Pro Asn Pro Pro Ala Gly
        115                 120                 125

Gly Leu Pro Gln Asp Tyr Leu Leu Ser Val Ile Leu Ala His Trp Glu
    130                 135                 140

Leu Ser Arg Glu Arg Trp Gln Gln Gln Gln Tyr Glu Phe Ala Ala Thr
145                 150                 155                 160

Ala Ser Leu Lys Ala Leu Ala Arg Leu Gln Gln Asp Asn Asp Phe Pro
                165                 170                 175

Ala Leu Glu Ala Glu Ile Arg Gln Glu Leu Tyr Arg Leu Arg Pro Tyr
            180                 185                 190

Arg Ile Leu Glu Leu Leu Ala Lys Glu Gly Gln Gly Glu Glu Gln Arg
        195                 200                 205

Gln Gln Gly Leu Ala Leu Leu Gln Ala Met Val Gln Asp Arg Gly Gly
    210                 215                 220

Ile Glu Gly Lys Gly Glu Asp Tyr Ser Gly Leu Gly Asn Asp Asp Phe
225                 230                 235                 240

Leu Lys Phe Ile His Gln Leu Arg Cys His Leu Thr Val Ala Glu Gln
                245                 250                 255

Asn Ala Leu Phe Leu Pro Glu Ser Gln Arg Pro Ser Leu Val Ala Ser
            260                 265                 270

Tyr Leu Ala Val His Ser Leu Met Ala Glu Gly Val Lys Glu Gln Asp
        275                 280                 285

Pro Met Ala Ile Val Glu Ala Lys Ser Leu Ile Ile Gln Leu Glu Asn
    290                 295                 300

Cys Gln Asp Leu Ala Leu Glu Lys Val Ile Cys Glu Leu Leu Leu Gly
305                 310                 315                 320

Gln Thr Glu Val Val Leu Ala Ala Ile Asp Gln Gly Asp Pro Lys Ile
                325                 330                 335

Val Ala Gly Leu Glu Ser Lys Leu Ala Thr Gly Glu Asp Pro Leu Thr
            340                 345                 350

Ala Phe Tyr Thr Phe Thr Glu Gln Trp Leu Glu Glu Glu Ile Val Pro
        355                 360                 365

Tyr Phe Arg Asp Leu Ser Pro Glu Thr Leu Ser Pro Lys Ala Tyr Phe
    370                 375                 380

Asn Asn Pro Ser Val Gln Gln Tyr Leu Glu Gln Leu Glu Pro Asp Ser
385                 390                 395                 400

Phe Thr Thr Asp Asn Ser Phe Ala Ser Pro Ala Leu Leu Ser Thr Ala
                405                 410                 415

Thr Glu Ser Glu Thr Pro Met Val His Ser Ser Ala Ala Leu Pro Asp
```

```
            420                 425                 430

Arg Pro Leu Thr Ser Thr Val Pro Ser Arg Arg Gly Arg Ser Pro Arg
        435                 440                 445

Arg Ser Arg Asp Asp Val Phe Pro Ser Ala Asp Asn Ser Ser Gly Leu
    450                 455                 460

Ala Val Thr Thr Leu Ser Pro Ala Ile Ala Tyr Asp Thr His Ser Leu
465                 470                 475                 480

Gly Thr Asn Gly Ile Gly Gly Asp Ser Thr Ser Asn Gly Phe Ser Ser
                485                 490                 495

Asn Ser Ala Pro Glu Ser Thr Ser Lys His Lys Ser Pro Arg Arg Arg
            500                 505                 510

Lys Lys Arg Val Thr Ile Lys Pro Val Arg Phe Gly Ile Phe Leu Leu
        515                 520                 525

Cys Leu Ala Gly Ile Val Gly Gly Ala Thr Ala Leu Ile Ile Asn Arg
    530                 535                 540

Thr Gly Asp Pro Leu Gly Gly Leu Leu Glu Asp Pro Leu Asp Val Phe
545                 550                 555                 560

Leu Asp Gln Pro Ser Glu Phe Ile Pro Asp Glu Ala Thr Ser Arg Asn
                565                 570                 575

Leu Ile Leu Ser Gln Pro Asn Phe Asn Gln Gln Val Gly Gln Met Val
            580                 585                 590

Val Gln Gly Trp Leu Asp Ser Lys Lys Leu Ala Phe Gly Gln Asn Tyr
        595                 600                 605

Asp Val Gly Ala Leu Gln Ser Val Leu Ala Pro Asn Leu Leu Ala Gln
    610                 615                 620

Gln Arg Gly Arg Ala Gln Arg Asp Gln Ala Gln Lys Val Tyr His Gln
625                 630                 635                 640

Tyr Glu His Lys Leu Gln Ile Leu Ala Tyr Gln Val Asn Pro Gln Asp
                645                 650                 655

Pro Asn Arg Ala Thr Val Thr Ala Arg Val Glu Glu Ile Ser Gln Pro
            660                 665                 670

Phe Thr Leu Gly Asn Gln Gln Gln Lys Gly Ser Ala Thr Lys Asp Asp
        675                 680                 685

Leu Thr Val Arg Tyr Gln Leu Val Arg His Gln Gly Val Trp Lys Ile
    690                 695                 700

Asp Gln Ile Gln Val Val Asn Gly Pro Arg
705                 710


<210> SEQ ID NO 171
<211> LENGTH: 819
<212> TYPE: PRT
<213> ORGANISM: Arabidopsis thaliana

<400> SEQUENCE: 171

Met Pro Val Ala Tyr Thr Phe Pro Val Leu Pro Ser Ser Cys Leu Leu
1               5                   10                  15

Cys Gly Ile Ser Asn Arg Ser Thr Ser Phe Val Val Asp Arg Pro Glu
            20                  25                  30

Leu Gln Ile Ser Gly Leu Leu Val Val Arg Ser Glu Ser Gly Glu Phe
        35                  40                  45

Phe Gly Ser Gly Leu Ser Leu Arg Arg Phe Gln Arg Glu Gly Arg Arg
    50                  55                  60

Arg Leu Asn Ala Ala Gly Gly Gly Ile His Val Val Asp Asn Ala Pro
65                  70                  75                  80
```

-continued

```
Ser Arg Thr Ser Ser Leu Ala Ala Ser Thr Ser Thr Ile Glu Leu Pro
                85                  90                  95

Val Thr Cys Tyr Gln Leu Ile Gly Val Ser Glu Gln Ala Glu Lys Asp
            100                 105                 110

Glu Val Val Lys Ser Val Ile Asn Leu Lys Lys Thr Asp Ala Glu Glu
        115                 120                 125

Gly Tyr Thr Met Glu Ala Ala Ala Ala Arg Gln Asp Leu Leu Met Asp
    130                 135                 140

Val Arg Asp Lys Leu Leu Phe Glu Ser Glu Tyr Ala Gly Asn Leu Lys
145                 150                 155                 160

Glu Lys Ile Ala Pro Lys Ser Pro Leu Arg Ile Pro Trp Ala Trp Leu
                165                 170                 175

Pro Gly Ala Leu Cys Leu Leu Gln Glu Val Gly Gln Glu Lys Leu Val
            180                 185                 190

Leu Asp Ile Gly Arg Ala Ala Leu Arg Asn Leu Asp Ser Lys Pro Tyr
        195                 200                 205

Ile His Asp Ile Phe Leu Ser Met Ala Leu Ala Glu Cys Ala Ile Ala
    210                 215                 220

Lys Ala Ala Phe Glu Val Asn Lys Val Ser Gln Gly Phe Glu Ala Leu
225                 230                 235                 240

Ala Arg Ala Gln Ser Phe Leu Lys Ser Lys Val Thr Leu Gly Lys Leu
                245                 250                 255

Ala Leu Leu Thr Gln Ile Glu Glu Ser Leu Glu Gly Leu Ala Pro Pro
            260                 265                 270

Cys Thr Leu Asp Leu Leu Gly Leu Pro Arg Thr Pro Glu Asn Ala Glu
        275                 280                 285

Arg Arg Arg Gly Ala Ile Ala Ala Leu Arg Glu Leu Leu Arg Gln Gly
    290                 295                 300

Leu Ser Val Glu Ala Ser Cys Gln Ile Gln Asp Trp Pro Cys Phe Leu
305                 310                 315                 320

Ser Gln Ala Ile Ser Arg Leu Leu Ala Thr Glu Ile Val Asp Leu Leu
                325                 330                 335

Pro Trp Asp Asp Leu Ala Ile Thr Arg Lys Asn Lys Lys Ser Leu Glu
            340                 345                 350

Ser His Asn Gln Arg Val Val Ile Asp Phe Asn Cys Phe Tyr Met Val
        355                 360                 365

Leu Leu Gly His Ile Ala Val Gly Phe Ser Gly Lys Gln Asn Glu Thr
    370                 375                 380

Ile Asn Lys Ala Lys Thr Ile Cys Glu Cys Leu Ile Ala Ser Glu Gly
385                 390                 395                 400

Val Asp Leu Lys Phe Glu Glu Ala Phe Cys Ser Phe Leu Leu Lys Gln
                405                 410                 415

Gly Ser Glu Ala Glu Ala Leu Glu Lys Leu Lys Gln Leu Glu Ser Asn
            420                 425                 430

Ser Asp Ser Ala Val Arg Asn Ser Ile Leu Gly Lys Glu Ser Arg Ser
        435                 440                 445

Thr Ser Ala Thr Pro Ser Leu Glu Ala Trp Leu Met Glu Ser Val Leu
    450                 455                 460

Ala Asn Phe Pro Asp Thr Arg Gly Cys Ser Pro Ser Leu Ala Asn Phe
465                 470                 475                 480

Phe Arg Ala Glu Lys Lys Tyr Pro Glu Asn Lys Lys Met Gly Ser Pro
                485                 490                 495

Ser Ile Met Asn His Lys Thr Asn Gln Arg Pro Leu Ser Thr Thr Gln
```

-continued

```
            500                 505                 510

Phe Val Asn Ser Ser Gln His Leu Tyr Thr Ala Val Glu Gln Leu Thr
        515                 520                 525

Pro Thr Asp Leu Gln Ser Pro Val Val Ser Ala Lys Asn Asn Asp Glu
    530                 535                 540

Thr Ser Ala Ser Met Pro Ser Val Gln Leu Lys Arg Asn Leu Gly Val
545                 550                 555                 560

His Lys Asn Lys Ile Trp Asp Glu Trp Leu Ser Gln Ser Ser Leu Ile
                565                 570                 575

Gly Arg Val Ser Val Val Ala Leu Leu Gly Cys Thr Val Phe Phe Ser
            580                 585                 590

Leu Lys Leu Ser Gly Ile Arg Ser Gly Arg Leu Gln Ser Met Pro Ile
        595                 600                 605

Ser Val Ser Ala Arg Pro His Ser Glu Ser Asp Ser Phe Leu Trp Lys
    610                 615                 620

Thr Glu Ser Gly Asn Phe Arg Lys Asn Leu Asp Ser Val Asn Arg Asn
625                 630                 635                 640

Gly Ile Val Gly Asn Ile Lys Val Leu Ile Asp Met Leu Lys Met His
                645                 650                 655

Cys Gly Glu His Pro Asp Ala Leu Tyr Leu Lys Ser Ser Gly Gln Ser
            660                 665                 670

Ala Thr Ser Leu Ser His Ser Ala Ser Glu Leu His Lys Arg Pro Met
        675                 680                 685

Asp Thr Glu Glu Ala Glu Glu Leu Val Arg Gln Trp Glu Asn Val Lys
    690                 695                 700

Ala Glu Ala Leu Gly Pro Thr His Gln Val Tyr Ser Leu Ser Glu Val
705                 710                 715                 720

Leu Asp Glu Ser Met Leu Val Gln Trp Gln Thr Leu Ala Gln Thr Ala
                725                 730                 735

Glu Ala Lys Ser Cys Tyr Trp Arg Phe Val Leu Leu His Leu Glu Val
            740                 745                 750

Leu Gln Ala His Ile Phe Glu Asp Gly Ile Ala Gly Glu Ala Ala Glu
        755                 760                 765

Ile Glu Ala Leu Leu Glu Glu Ala Ala Glu Leu Val Asp Glu Ser Gln
    770                 775                 780

Pro Lys Asn Ala Lys Tyr Tyr Ser Thr Tyr Lys Ile Arg Tyr Ile Leu
785                 790                 795                 800

Lys Lys Gln Glu Asp Gly Leu Trp Lys Phe Cys Gln Ser Asp Ile Gln
                805                 810                 815

Ile Gln Lys


<210> SEQ ID NO 172
<211> LENGTH: 2857
<212> TYPE: DNA
<213> ORGANISM: Arabidopsis thaliana

<400> SEQUENCE: 172

actgtcaaaa ctcaaaagcc ttgagaccaa atttccgatt ttttctcctc tgaagaaatc      60

caacaaattg taccatgatt ccagcttcac tctacttctt ctagggttcg ttcgttttct     120

ggagctgttg cgcaatgcca gtagcttaca catttccagt tctcccttct tcttgtctgc     180

tttgcggaat ctccaatcgc agcaccagct tcgtcgtaga tcgcccggag cttcagatct     240

caggtctcct cgtcgttcgt tctgaatccg gtgaattctt cggttctggt ttatctttgc     300
```

-continued

```
ggcggtttca gcgagaagga cggaggaggt tgaatgctgc tggtggtggt atccatgtcg    360
tcgacaatgc gccgtctcgt acttcttctc tcgctgcatc tacctctaca atcgaactcc    420
cggttacgtg ttaccagctt atcggagttt ctgagcaagc tgagaaagac gaggtcgtta    480
agtcggttat aaatttgaaa aaaactgatg ctgaagaggg ttatacaatg gaagctgctg    540
cagctcgcca ggatcttctc atggatgtta gggataaact tctttttgaa tcagaatatg    600
ctggtaacct aaaagaaaag attgctccta aatctcctct cagaattccg tgggcatggt    660
tgcctggtgc tctatgcctt cttcaagagg ttggacaaga aaaacttgtg ctggatattg    720
gccgggctgc tctcaggaac cttgattcaa agccatatat tcatgatata ttcttatcta    780
tggcacttgc tgagtgtgca attgccaagg ctgctttcga ggttaacaag gtctctcaag    840
gatttgaagc tcttgctcgt gctcaaagtt ttctgaagag taaagttact cttgggaaac    900
ttgcattgtt aactcagatt gaggagtcac tagaggggct tgcaccacct tgcacattgg    960
atctactggg cctgccacgc acgccagaaa atgcagagag gaggcgaggt gcaattgccg   1020
cgctacgcga actgctcaga cagggcctta gtgttgaagc ttcatgtcaa attcaagact   1080
ggccatgctt tttgagccag gcaattagca ggttattggc cacagagatt gtcgatcttc   1140
ttccatggga tgatttagcc attacacgga aaaataaaaa atcactggaa tcccacaatc   1200
aaagagttgt tattgatttt aattgtttct acatggtgtt acttggtcac atcgctgttg   1260
gattttcagg caagcaaaat gaaacgatta ataaagcaaa aacgatatgc gaatgtctca   1320
tagcatcaga aggtgttgat ctgaaatttg aggaagcttt ttgctcattt cttctaaaac   1380
agggttccga ggcagaggcc ctggaaaaac ttaagcagct ggaatcaaat tcagactctg   1440
ccgttcgtaa ttcgatcttg ggaaaagagt cgagaagtac ttctgctact ccctcactgg   1500
aagcgtggct aatggagtcc gtgcttgcta actttccaga cacaaggggt tgttctccat   1560
ctttggccaa tttttccgg gctgaaaaga aatatccaga aaacaagaaa atggggtcac   1620
cttcgatcat gaatcataag acgaaccaaa gaccactttc cacaacacag ttcgtgaact   1680
cgtcacaaca tctttataca gctgtcgagc agttgacacc aacagatttg cagagcccag   1740
tggtatcagc caagaataat gatgaaacca gtgccagtat gccatctgtt caactgaaga   1800
ggaaccttgg tgtacacaaa aataaaatat gggatgagtg gctctctcaa agcagtttga   1860
tcggaagggt atctgttgtt gctttactgg gttgcaccgt gttcttctct ctgaagctat   1920
caggcattag gtctggtaga ctacagagta tgcctatatc ggtttctgct aggccgcatt   1980
cagaatcaga ttcttttctg tggaaaacag agtctgggaa tttcagaaaa aaccttgatt   2040
ctgtgaatag aaatggtatc gtgggaaaca tcaaagtgct cattgacatg ttaaagatgc   2100
attgtggcga acatccggat gccctgtatc tgaaaagctc tggtcaatca gctacatcat   2160
tgtctcattc tgcgtcagaa ctgcataaga gaccaatgga tacagaagaa gcggaagagc   2220
ttgtgagaca gtgggaaaat gttaaggctg aagctcttgg accaacacat caagtttata   2280
gcctttccga agtccttgat gaatccatgc ttgtccagtg gcaaacattg gcacaaacag   2340
cagaggcgaa atcctgttat tggaggttcg ttctgcttca tcttgaggtt ttgcaagcac   2400
atatattcga agatggtatt gctggtgagg ctgcagaaat cgaagctctt ctggaggaag   2460
cagcagaatt agttgatgaa tctcagccca aaaacgcaaa atattatagc acttacaaga   2520
tccgatatat tctgaagaag caagaagatg gattgtggaa attctgccaa agcgatattc   2580
aaatacagaa gtgaaaatcc cccagaaaaa aaagctcatc atctaactaa aggttgtagc   2640
atcaacagta gaacatggga tcatttagct aacggttgtt cttgtttacc taacggtgta   2700
```

ggaaagtctc aggtttgttt ctttattcct tagtaaccca caggatttgt ctttgtagat 2760
tcttttgatt tcaatgtgtt tatggataaa caaacttctt gagtattttt tttattatta 2820
ttgtaaagcg ttactgatca caaaaaaaaa aaaaaaa 2857

<210> SEQ ID NO 173
<211> LENGTH: 819
<212> TYPE: PRT
<213> ORGANISM: Arabidopsis thaliana

<400> SEQUENCE: 173

Met Pro Val Ala Tyr Thr Phe Pro Val Leu Pro Ser Ser Cys Leu Leu
1 5 10 15

Cys Gly Ile Ser Asn Arg Ser Thr Ser Phe Val Val Asp Arg Pro Glu
20 25 30

Leu Gln Ile Ser Gly Leu Leu Val Val Arg Ser Glu Ser Gly Glu Phe
35 40 45

Phe Gly Ser Gly Leu Ser Leu Arg Arg Phe Gln Arg Glu Gly Arg Arg
50 55 60

Arg Leu Asn Ala Ala Gly Gly Gly Ile His Val Val Asp Asn Ala Pro
65 70 75 80

Ser Arg Thr Ser Ser Leu Ala Ala Ser Thr Ser Thr Ile Glu Leu Pro
85 90 95

Val Thr Cys Tyr Gln Leu Ile Gly Val Ser Glu Gln Ala Glu Lys Asp
100 105 110

Glu Val Val Lys Ser Val Ile Asn Leu Lys Lys Thr Asp Ala Glu Glu
115 120 125

Gly Tyr Thr Met Glu Ala Ala Ala Ala Arg Gln Asp Leu Leu Met Asp
130 135 140

Val Arg Asp Lys Leu Leu Phe Glu Ser Glu Tyr Ala Gly Asn Leu Lys
145 150 155 160

Glu Lys Ile Ala Pro Lys Ser Pro Leu Arg Ile Pro Trp Ala Trp Leu
165 170 175

Pro Gly Ala Leu Cys Leu Leu Gln Glu Val Gly Gln Glu Lys Leu Val
180 185 190

Leu Asp Ile Gly Arg Ala Ala Leu Arg Asn Leu Asp Ser Lys Pro Tyr
195 200 205

Ile His Asp Ile Phe Leu Ser Met Ala Leu Ala Glu Cys Ala Ile Ala
210 215 220

Lys Ala Ala Phe Glu Val Asn Lys Val Ser Gln Gly Phe Glu Ala Leu
225 230 235 240

Ala Arg Ala Gln Ser Phe Leu Lys Ser Lys Val Thr Leu Gly Lys Leu
245 250 255

Ala Leu Leu Thr Gln Ile Glu Glu Ser Leu Glu Gly Leu Ala Pro Pro
260 265 270

Cys Thr Leu Asp Leu Leu Gly Leu Pro Arg Thr Pro Glu Asn Ala Glu
275 280 285

Arg Arg Arg Gly Ala Ile Ala Ala Leu Arg Glu Leu Leu Arg Gln Gly
290 295 300

Leu Ser Val Glu Ala Ser Cys Gln Ile Gln Asp Trp Pro Cys Phe Leu
305 310 315 320

Ser Gln Ala Ile Ser Arg Leu Leu Ala Thr Glu Ile Val Asp Leu Leu
325 330 335

Pro Trp Asp Asp Leu Ala Ile Thr Arg Lys Asn Lys Lys Ser Leu Glu

-continued

```
            340                 345                 350

Ser His Asn Gln Arg Val Val Ile Asp Phe Asn Cys Phe Tyr Met Val
        355                 360                 365

Leu Leu Gly His Ile Ala Val Gly Phe Ser Gly Lys Gln Asn Glu Thr
    370                 375                 380

Ile Asn Lys Ala Lys Thr Ile Cys Glu Cys Leu Ile Ala Ser Glu Gly
385                 390                 395                 400

Val Asp Leu Lys Phe Glu Glu Ala Phe Cys Ser Phe Leu Leu Lys Gln
                405                 410                 415

Gly Ser Glu Ala Glu Ala Leu Glu Lys Leu Lys Gln Leu Glu Ser Asn
            420                 425                 430

Ser Asp Ser Ala Val Arg Asn Ser Ile Leu Gly Lys Glu Ser Arg Ser
        435                 440                 445

Thr Ser Ala Thr Pro Ser Leu Glu Ala Trp Leu Met Glu Ser Val Leu
    450                 455                 460

Ala Asn Phe Pro Asp Thr Arg Gly Cys Ser Pro Ser Leu Ala Asn Phe
465                 470                 475                 480

Phe Arg Ala Glu Lys Lys Tyr Pro Glu Asn Lys Lys Met Gly Ser Pro
                485                 490                 495

Ser Ile Met Asn His Lys Thr Asn Gln Arg Pro Leu Ser Thr Thr Gln
            500                 505                 510

Phe Val Asn Ser Ser Gln His Leu Tyr Thr Ala Val Glu Gln Leu Thr
        515                 520                 525

Pro Thr Asp Leu Gln Ser Pro Val Val Ser Ala Lys Asn Asn Asp Glu
    530                 535                 540

Thr Ser Ala Ser Met Pro Ser Val Gln Leu Lys Arg Asn Leu Gly Val
545                 550                 555                 560

His Lys Asn Lys Ile Trp Asp Glu Trp Leu Ser Gln Ser Ser Leu Ile
                565                 570                 575

Gly Arg Val Ser Val Val Ala Leu Leu Gly Cys Thr Val Phe Phe Ser
            580                 585                 590

Leu Lys Leu Ser Gly Ile Arg Ser Gly Arg Leu Gln Ser Met Pro Ile
        595                 600                 605

Ser Val Ser Ala Arg Pro His Ser Glu Ser Asp Ser Phe Leu Trp Lys
    610                 615                 620

Thr Glu Ser Gly Asn Phe Arg Lys Asn Leu Asp Ser Val Asn Arg Asn
625                 630                 635                 640

Gly Ile Val Gly Asn Ile Lys Val Leu Ile Asp Met Leu Lys Met His
                645                 650                 655

Cys Gly Glu His Pro Asp Ala Leu Tyr Leu Lys Ser Ser Gly Gln Ser
            660                 665                 670

Ala Thr Ser Leu Ser His Ser Ala Ser Glu Leu His Lys Arg Pro Met
        675                 680                 685

Asp Thr Glu Glu Ala Glu Glu Leu Val Arg Gln Trp Glu Asn Val Lys
    690                 695                 700

Ala Glu Ala Leu Gly Pro Thr His Gln Val Tyr Ser Leu Ser Glu Val
705                 710                 715                 720

Leu Asp Glu Ser Met Leu Val Gln Trp Gln Thr Leu Ala Gln Thr Ala
                725                 730                 735

Glu Ala Lys Ser Cys Tyr Trp Arg Phe Val Leu Leu His Leu Glu Val
            740                 745                 750

Leu Gln Ala His Ile Phe Glu Asp Gly Ile Ala Gly Glu Ala Ala Glu
        755                 760                 765
```

```
Ile Glu Ala Leu Leu Glu Glu Ala Ala Glu Leu Val Asp Glu Ser Gln
    770                 775                 780

Pro Lys Asn Ala Lys Tyr Tyr Ser Thr Tyr Lys Ile Arg Tyr Ile Leu
785                 790                 795                 800

Lys Lys Gln Glu Asp Gly Leu Trp Lys Phe Cys Gln Ser Asp Ile Gln
                805                 810                 815

Ile Gln Lys


<210> SEQ ID NO 174
<211> LENGTH: 491
<212> TYPE: DNA
<213> ORGANISM: Triticum aestivum
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (483)..(484)
<223> OTHER INFORMATION: n is a, c, g, or t
<220> FEATURE:
<221> NAME/KEY: misc_feature
<222> LOCATION: (487)..(487)
<223> OTHER INFORMATION: n is a, c, g, or t
<220> FEATURE:
<221> NAME/KEY: misc_feature
<222> LOCATION: (489)..(490)
<223> OTHER INFORMATION: n is a, c, g, or t

<400> SEQUENCE: 174

ggccgtcggc aaatactgca gnttgcacat gatactctca caaaccagag ctcccgcacc     60

gagtatgacc gcgcgctctc tgaggaccgt gacgcggcgc tcacactgga tgttgcttgg    120

gacaaggttc cgggtgtgct atgtgccctt caggaggctg gggaggcaca ggcagtgctt    180

gcaattggag agcacttact ggaggaccgc ccgcccaagc ggttcaagca ggatgtggtg    240

ctggcaatgg cgctcgctta tgtggacata tcaagggatg caatggcggc tagccctcca    300

gatgtaatcc gctgctgtga ggtgcttgaa agggctctca agctcttgca ggaggatggg    360

gcaatcaacc ttgcacctgg tctgctttca caaattgatg aaactctgga ggagatcaca    420

cctcgttgtg ttttggagct tcttgccctt nctcttgatg aaaaacatca nattgaacgc    480

cannaangnn t                                                         491


<210> SEQ ID NO 175
<211> LENGTH: 545
<212> TYPE: DNA
<213> ORGANISM: Gossypium arboreum
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
```

<400> SEQUENCE: 175
aattgcagaa ggcattgttc gcaagtggca gaacattaaa tctgaggcgt ttggacctga 60
tcaccgcctt gataaattgc cagaggttct ggatggtcaa atgttgaaga catggacaga 120
tcgtgcagcc gaaatcgctc agcttggttg ggtatatgaa tatagtctac tgaacatggc 180
cattgacagt gttacccttt cactagatgg ccagcgagct gtagtcgaag ctactctgga 240
agaatccacc tgcttgactg atgttcatca tccggagaac aatgcctcta atgtaaactc 300
ctacaccacg agatatgaga tgtcttgttc caactcaggc tggaaaatca ctgaaggatc 360
tgtctacaaa tcttaactat gatgtataaa gcataaaaag cctgaaagct ccaatgtggt 420
taccagcttt gcctttttac gtagctatat ttgttatatt gtttgagaaa acaagagtta 480
gcgttttcca gtcatgcaag cagttcaaat taaaagaggc aatgcttntc atggganaacn 540 aaatg 545

<210> SEQ ID NO 176
<211> LENGTH: 420
<212> TYPE: DNA
<213> ORGANISM: Hordeum vulgare

<400> SEQUENCE: 176
gatgagccca tacagattcc taaaatggat gcgaagctgg cagaagatat tgttcgcaag 60
tggcagagca tcaaatccaa ggccttggga tcagatcatt ctgttgcatc attgcaagag 120
gttcttgatg gcaacatgct gaaggtatgg acagaccgag cagcagagat tgagcgcaaa 180
ggctggttct gggactacac gctgttcaac gtggcgatcg acagcatcac cgtctccctg 240
gacggacggc gggcgaccgt ggaggcgaca attgaggagg cgggtcagct caccgacgca 300
accgacccca ggaacgatga tttgtacgac actaagtaca ccacccggta cgagatggcc 360
ttcaccggac caggagggtg gaagataacc gaaggcgcag tcctcaagtc gtcatagggc 420

<210> SEQ ID NO 177
<211> LENGTH: 606
<212> TYPE: DNA
<213> ORGANISM: Triticum aestivum

<400> SEQUENCE: 177
ctgcaaatct agcactatgt ttctctttat ctccaggatc tagcctagca ccaacaatcc 60
aaatacaaca caagaaaaat aaagctcttc gtcgatcaca tcagactaac gcaactatcg 120
gtcttccaaa ctaaaaaggg cctagactgc ctgcttattt acacaccccc aaaagaaaac 180
tggaaggaat taacaaactt aatgaggtta ccgcacacca actaccctaa gacgacttga 240
ggaccgcgcc ttccattatc ttccaccctc ctagtccggt gaaggtcatc tcataccggg 300
tggtgtactt cgtgtcgtac gagtcgttgt tcttggggtc ggttgcgtcg atgagctggc 360
ctgcctcctc gatcgttgcc tccacggtcg cccgccgtcc gtccagggag accgtgatgc 420
tgtcgatcgc cacgtcagac agtgtgtagt cccagaacca gcctttgcgc ccgatctccg 480
ctgctcggtc cgtccatacc ttcagcatgt tgccatcaag aacctcttgc aatgattcca 540
cagaatgatc tgatcccaag gccttggttt tgatactctg ccacttgcga acaatatctt 600
ctgcca 606

<210> SEQ ID NO 178
<211> LENGTH: 563
<212> TYPE: DNA

<213> ORGANISM: Gossypium arboreum

<400> SEQUENCE: 178

```
tttttttttt tttttttttt tttttttttt ttttttttaa cttgcctctt ttaatttgaa     60
ctgcttgcct gactggaaaa ccctaactct tgttttctca aacaatttaa caaatatagc    120
tccctaaaaa ggcaaagctg gtaaccacat tggagctttc aggcttttta tgctttatac    180
atcatagtta aaatttgtag acagatcctt cagtgatttt ccaacctgag ttggaacaaa    240
acatctcata tttcgtgggg taggagttta cattacaggc attgttctcc ggatgatgaa    300
cattactcaa gccggggggt tcttccaaaa taacttcgac tacagctcgc tggccattta    360
atgaaagggt aacactgtca atggccctgt tcagtcaact ttattcatat acccaaccca    420
gctgaccgat ttcggctgca ccaactgtcc atgttttcaa catttgacca tccaaaacct    480
ttggcaattt atcaaggggg ggatcaagtc caaacgcctc agatttaatg ttctgccact    540
tgcgaacaat gccttttgca att                                            563
```

<210> SEQ ID NO 179
<211> LENGTH: 360
<212> TYPE: DNA
<213> ORGANISM: Hordeum vulgare

<400> SEQUENCE: 179

```
gatgagccca tacagattcc taaaatggat gcgaagctgg cagaagatat tgttcgcaag     60
tggcagagca tcaaatccaa ggccttggga tcagatcatt ctgttgcatc attgcaagag    120
gttcttgatg gcaacatgct gaaggtatgg acagaccgag cagcagagat tgagcgcaaa    180
ggctggttct gggactacac gctgttcaac gtggcgatcg acagcatcac cgtctccctg    240
gacggacggc gggcgaccgt ggaggcgaca attgaggagg cgggtcagct caccgacgca    300
accgacccca ggaacgatga tttgtacgac actaagtaca ccacccggta cgagatggcc    360
```

<210> SEQ ID NO 180
<211> LENGTH: 300
<212> TYPE: DNA
<213> ORGANISM: Hordeum vulgare

<400> SEQUENCE: 180

```
tgatggcaac atgctgaagg tatggacaga ccgagcagca gagattgagc gcaaaggctg     60
gttctgggac tacacgctgt tcaacgtggc gatcgacagc atcaccgtct ccctggacgg    120
acggcgggcg accgtggagg cgacaattga ggaggcgggt cagctcaccg acgcaaccga    180
ccccaggaac gatgatttgt acgacactaa gtacaccacc cggtacgaga tggccttcac    240
cggaccagga gggtggaaga taaccgaagg cgcagtcctc aagtcgtcat agggcgttca    300
```

<210> SEQ ID NO 181
<211> LENGTH: 549
<212> TYPE: DNA
<213> ORGANISM: Triticum monococcum

<400> SEQUENCE: 181

```
tttttttttt tttttttttt ttttttttca gcggcaaatt cagcactatg tttctcttat     60
ccccaactca aagatcttct aagctagcaa taatccgaaa acgacacagg gaaaaacaaa    120
gctcatcgct gattgcacat cagactaacc aaactatctc caacttccaa actgagaagg    180
gcctagactg cttatttaca caccaaaaag aacacgggag gaatcaatca acaaaggtct    240
actgcacacc gaacgcccta tgacgacttg aggaccgcac cttctgttat cttccaccct    300
```

```
cctggtccag tgaaggtcat ctcgtaccgg gtggtgtact tagtgtcgta caaatcgttg    360

ttcctggggt cggttgcatc ggtaagctgg cctgcctcct caattgtcgc ctccacagtc    420

gcccgtcgtc cgtccaggga gacggtgatg ctgtcaatcg ccacgtcgga cagcgtgtag    480

tcccagaacc agcctttgcg ctcgatctct gctgctcggt ccctccatac cttcagcatg    540

ttgccatca                                                            549


<210> SEQ ID NO 182
<211> LENGTH: 573
<212> TYPE: DNA
<213> ORGANISM: Hordeum vulgare
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 182

gcgagnaagg acgagnatcg tcaagtcggc catcgagctg aggaaatcgg agatcgaaga     60

tgggtacacg gaggaggtgt ccacctgcag acaggctctg ctgctggacg tgagagacaa    120

gcttctcttt gaacaggagt acgcaggaag caccagggcc aaggttccgc ccagatcctc    180

tcttcatata ccctggagct ggttgcctgc tgccttgtgt gtcttgcagg aggttgggga    240

agagaagctg gtcttggaca ttggtcaggc agctctacga cgccctgatt ctaagccata    300

tgctcacgat gtacttcttg caatggcact agctgaatgc tccattgcaa aagctagctt    360

tgaaaaaagt aaagtatctc ttggctttga ggctctagca cgtgctcaat atcttttgag    420

gaaaaaacca tctttagaga agatgcctct tcttgagcag atcgaagaat cacttgaaga    480

gcttgcacca gcttgcactc tagaggtttt aagcctgccc cgtacacctg aaaattctga    540

acgcaggcgt ggtgctattg cagctctctg tga                                 573


<210> SEQ ID NO 183
<211> LENGTH: 400
<212> TYPE: DNA
<213> ORGANISM: Beta vulgaris

<400> SEQUENCE: 183

gcataacacg gcaagaagat gttgcagtta atggctttgg aaatgaggat gttacaatgg     60

agcttggccg tgataacact ttagattatg tgaatttagc cagttcaaat tttactgaag    120

ataatatcga gcaagaatcg gttactgaga agataaaaga tttaggtgtg aaggttatgt    180

gtgccggtgt ggtgattgga ctgacaactt tggctggcat gaaacttttg cctggcagaa    240

gtgggtctgc cattccacac aggcatcttg gttctgctgt ggcttctgat gtctccagtg    300

tggggctctc agtaaatgaa actactgagg agaaagtacc aaaaatggat gcaagacttg    360

cagaagttct agttagaaga tggcagaacg ttaaatcaca                          400


<210> SEQ ID NO 184
<211> LENGTH: 631
<212> TYPE: DNA
<213> ORGANISM: Prunus persica
<220> FEATURE:
<221> NAME/KEY: misc_feature
<222> LOCATION: (21)..(21)
<223> OTHER INFORMATION: n is a, c, g, or t
```

<400> SEQUENCE: 184
gcagttgcaa ttgctggggg ngattcacta cgtgaaaatt tcatgaacga ggccttcttg 60
catatgactg cagctgagca ggttgattta tttgtagcta cccccagtaa tatcccggca 120
gaaagctttg aagtttatgg ggtggctctt gcgcttgttg ctcaagcctt tgttggtaaa 180
aaacctcatc acattcaaga tgctgaaaac ctattccaga aacttcagca gtctaaggta 240
acagctgtag gacattctct tgacaactat ataaccaaag aaagcagtga gatagacttt 300
gctttggaga ggggactctg ttcacttctt ctaggggacc ttgatgacag tcgttcgtgg 360
ttgggcctag acagtaatga ttcaccatat agaaatccat ctgttgtaga ctttgtcttg 420
gagaactcaa aggatgacga tgacaatgac aatgacaatg atcttcctgg actttgcaag 480
ctattggaga cgtggttgat ggaggtggta ttccccaggt ttagagacac caaagacata 540
gagttcagac tgggagacta ctatgatgat cctacagtct tgagatactt agaaaggctg 600
gatggcacta atggttcacc cttagctgct g 631

<210> SEQ ID NO 185
<211> LENGTH: 647
<212> TYPE: DNA
<213> ORGANISM: Helianthus annuus

<400> SEQUENCE: 185
cagaaagagg tggctggatt gatgactttg gctggcttga aatttatacc gtcttaaaca 60
ggctctacta gtactactgc tcgtaaagaa gttgattcgg ctctggcttc agacgtcacc 120
aatgtggagg attctagggt tgaggatgct gaagacattc ctaaaatgga tgcaagatta 180
gccgaaggtc tagttcgtaa gtggcagagc ataaaatccc aagcccttgg acctgagcat 240
tgccactcaa aattatcata ggtattagat ggtgaaatgc acaagatctg gcttcaacgg 300
gcaaccgaaa ttgctcaacg tggttggttt tgggactaca cgcttttaaa cattaccatt 360
gacagtgtta ccgtttcact cgatgggcgc ttagctgttg tggaagcaac ccttgaagag 420
tctgccaagt tgattgattt gacccacccg gaaaacaatg actcctataa tttaacttac 480
accacacgtt atgagatgtc gtgtgccaag tcatcatgga aaatcacaaa gggggctgtc 540
ctcaaatcat aacagatgta attctttctc accttttctg tatttatctg ttattagatt 600
actcagcagt tgaatgatat gtttctccac catttcgatc atgagcg 647

<210> SEQ ID NO 186
<211> LENGTH: 652
<212> TYPE: DNA
<213> ORGANISM: Helianthus annuus

<400> SEQUENCE: 186
tgtggtggtt ggattgatga ctttggctgg cttgaaattt acaccgtcca aaagaggctc 60
tactagtact actgctcgta aagaagttga ttcggctctg gcttcagacg tcaccaatag 120
gattctaggg ttgaggatgc tgaagacatt cctaaaatgg atgcaagatt agccgagggt 180
ctagttcgta agtggcagag cataaaatcc caagcccttg gacctgagca ttgccactca 240
aaattatcag aggtattaga tggtgaaatg cacaagatct ggcttcaacg ggcaaccgaa 300
attgctcaac gtggttggtt ttgggactac acgcttttaa acattaccat tgacagtgtt 360
accgtctcac tcgatgggcg cttagctgtt gtggaagcaa cccttgaaga gtctgccaag 420
ttgattgatt tgacccaccc ggaaaacaat gactcctata atttaactta caccacacgt 480
tatgagatgt cgtgtgccaa gtcttcatgg aaaatcacaa agggggctgt cctcaaatca 540

-continued taacagatgt aattctttct caccttttct gtatttaact gttattagat tactcagcag 600
ttgaatgata tgtttctcca ccatatcgat catgagtgta tttggtgctg cc 652

<210> SEQ ID NO 187
<211> LENGTH: 460
<212> TYPE: DNA
<213> ORGANISM: Populus tremula

<400> SEQUENCE: 187
gactgaaaaa ataaaagatg ccagtatcaa aatatgtgtg ctggtgtggc aattggactg 60
ctgactttag ctggcctgaa gtgttttcct cctaggactg gctccttcat tcgacagaaa 120
gaaattggtt cggcaatggc atctgacacc atcaatttga attcagcagt agatgaacaa 180
atttccgagg acttacccag aatggatgca aggggtgcag aggatatagt tcgcaagtgg 240
caaaacatta aatctcaggc ttttggaact gatcactgcc tggcaaaatt gccagaggtt 300
ttggatagtc agatgttgaa aatatggaca gatcgtgcgg ccgaaattgc acatcttggt 360
tgggtatacg agtatatgct gttggacctg actattgaca gtgtgactgt atctgtagat 420
ggcctaaatg ctgtagtaga agcaacactc aaagagtcaa 460

<210> SEQ ID NO 188
<211> LENGTH: 3933
<212> TYPE: DNA
<213> ORGANISM: Chlamydomonas reinhardtii

<400> SEQUENCE: 188
atgaactcgg cggagcacgt ctctgttgcc gtggactatt accgaatgct gcacgttccc 60
cgcgtaagcc gccctgacgc cattcgcaag gcgtatgaga acctggtgaa gcaaccccc 120 gctgccgcgt actctgcgga caccctcttc gcacgcgcgg tgctactcaa ggcagccgcg 180
gagtcgctga ccgacccgga cctgcgccgc tcatatgacg ccaagctggc cgctggtcac 240
acagccctgc gcgtcagcca gcaggaccta cccggagccc ttgtcgtgct gcaggaggtg 300
agccgtgctc tggcgaccgc tcaacccctt gcgaccgcta aaaccatcag cacatatagc 360
acatataaat tcccatgggt tctgtactac cgcccacccc tctgaagggg gcgagtattc 420
attcttcacg catgagcgca gacttttacc ctatcaagtc ccgccctcgc ccgccttctc 480
ttcccacaga tcggcgagca ccagttggtt ctggatctgg gtctgcgctg gctagaggta 540
aacggcggcc agcccgacgc cggcgacgtg gccgctgccg tggccctggc ctactgtgac 600
cgcgctggtg agcgcctcac ctcccagctg cagccgccgc cggcctcagc gctgccaggc 660
cccgatggcg cggcggtgcc gcacgcgcac gtgggcgcgg tgctgcccgc atgcgacgac 720
ctggacgcag cgctgagcaa gctccggcgg tacggcatgg cgcagcagct gcagcagcag 780
atcgtgggcg cgctgcgggt gaggctggag caggggctgg accggcaacc ggtcatagat 840
gtagacacag ggatgtaggc gtcgatgcga ggggatggaa gtatggggtc ctgtgagtgt 900
gagccgatgg aaggtataga tgctgggagc tggcgcaccc gacccatgtc atccaaggac 960
ttggctgatg catcgctcac cccccgcctc caacccgaat gccctcagga cctggcgcca 1020
gagtacgcgt gcgagctggc cgccctgccg ctgggcgccg agaccgccgc ccggcgcgcc 1080
aagggcgtgg cgctcatgcg cggtgtgctg cgcgccgccg ccaccgtggc cgccgccaca 1140
gccaagtagg tgacaagcac gcaggaaatc gtgtgctata ttgcattgcg gtaccttgcc 1200
ttgcatcgcg gaggcagtgc tcgagaatgc gtttcgtgcg cgtgatccgt ttgctcgtcg 1260

-continued

```
tgccttatcc gccaccccag gcccgaggct gctgctgacg acagcgacga cgacgaggtg   1320
gacccgcgca gtgtgctggc ggccgcccgc cgcatgctga cccgcagccg cgacgtgctc   1380
acctgcagcg agcaggtaca gcgctgcaac cgggcagtta tagatggatg caagtgcgtg   1440
gacgccgaac gtacagtttt tgctgtgttc cccgcgtgca ccttagccgc tcctcctgca   1500
accctcactt gcgacctcaa tgcgtgcacc ttagccgctc ctcctgcaac cctcagttgc   1560
gacctcacga cacaccgtct ggcttacccc tgccccccacc ccaggtggcc ctgctgccgg   1620
acgcgctgcg cggcagcggt gtgtcgccca ccccggacgc gctgtacgac ggcgccctgg   1680
cgcacctggt ggacggcttc cgcaacggct ggccgcactc cgtgcaccag gtgggggagc   1740
gcggtgcctg gatgtctgga tggtcactgg ccgcaaggct gtgcgcacca tcgggtagag   1800
tgtaaccaaa tgatgtgcgc gcaatgaagg gtgagcagat tccagcctcc ctctgtcggc   1860
tggcgtccaa ctgtgccaac tgcgcacaca cctgcgcacg ccccaggccg accagctgct   1920
ggccaagctg gaggcgcagc aggcccgcgc agccgccatg cgccgcgagc agtccgagct   1980
ggccgccgcc gccgcagccc gccgtgccat gtacagcggt cccgccgccg cccacggtcc   2040
caccctgtac accaactaca acaaccctgc cggcagcggc aatggcgcgc cgccgccgcc   2100
gccccgcccc atgcccatgg tgcccagggg cgacggccag cacgccatgg cggcgtctgt   2160
ggcggcgcat gtgcactcca cggcgatggc ggagcacgcg gcgcgcagcg cggctggcgg   2220
cgccgccggc gcctccgatg gcggcgcgca cgccaacggc gtggctctag agcgggccgt   2280
gtgcgccgtc ctgctgggtg actacaccgc ggcggtggag cggctggggc tagacacgaa   2340
cgcggcggtg gagcaggagc agctgcgcga gttcgtcctg gtgcgccggg gagggcctac   2400
tgcaaaacgt gttgctcagg gtcttgagat accgaacaca atgttttcgt atacatctcc   2460
cgtcgagaga gctatgcctc caccgtcggc ccggctccac tgcacccgat gcggttgcag   2520
gcccactcgc ccaacggccg cggcgacctg cgcccgggcc tgagggcgct ggccacccgc   2580
tggctggagg gcgtggcgct ggcgtccttc cgcgacactg ccggcagccc cgtgccgccg   2640
ctggaggcca gctggttcgc ggacctgcgt gtcgccttct atctgcaggt gaggggcggc   2700
agaagagagg ggggaaaggg aggcgagaag gcgcttccgc cgctggcgca acgggccatc   2760
ctggtggagc acggcgctac atcgcatctg gtccaccgtc tctggatgta taattcgtgc   2820
actcttaacc ggccgcgcag gtatggcggc tgtgccgcgt ggagcaggtg ctggccgccg   2880
cccacttcct ggccaacctg ctgcccaaca tgctcaaggc catcgccggc actgccgtca   2940
aggtcgcagc caacaccgcc gtggcagcct cccgcgcgca gcgcctcagc gccaccgtcg   3000
cggccagcac cgccaccgcc tcgtcatctt cctctgccgc ccgcggcgct cgtgccggtg   3060
ccctgagcgc tgccaccgcc gccgcacacg ccgcgcgccg ccagcaggcg aacgcggtcg   3120
gtgccagcat cgtcggtgct gacgtgctgc cccccacagc agtggccgcg gctgccgcgg   3180
ctggcacagc ggccgccgcc gcagtcaccg gccccgccct cggccgtggc gctgcagctt   3240
ccgcctcttc ctttgaggag ggcgccgctg aggccgctga cctgcgtcgt cgctttgtcg   3300
ccaccagccg cggcgccagc gcggccgtcg gtgcgcccac agcaccagcc gctatgactg   3360
ggccccagca cggcgccgcc tctgctgcgc agtcgcaccg ggaggaggat gaggattcgc   3420
acggcggcca ggaggggggc gtgccgcggc gcatgagcga ggcggacctg cgtgcgcacc   3480
tggcgggcct ggagaaggcc atgtgggact cggagctgcc gccgccgccg ccatcccgcg   3540
cgcagaaggc gctcacctac gccgcaggac tggtgagttg ctgcgcagcc tgacggccat   3600
agttgccgta gtgccatagt gaccgagcac cgtgatgttt aggacatggg cggagaagtg   3660
```

-continued ttaggacatg aattgcatca acgctgcaaa tctggtgtat ggtacgcgcg ttccctgtca 3720
ccaacaaggc tgttgaccaa gctgctgctg cccttgcact ctttcaacgc ccgtctgcag 3780
ctggccgtgg tggtggcctt cctggtgtcc agcttcttcc gccgcaacga cggcgccgcc 3840
tccgccctgg cacccgccgc cgtcaccacc gcctccgtgg ccgttagcgc gcagcccgcc 3900
aagccgggca aggccacccg ctccgcgcac tga 3933

<210> SEQ ID NO 189
<211> LENGTH: 2511
<212> TYPE: DNA
<213> ORGANISM: Chlamydomonas reinhardtii

<400> SEQUENCE: 189
atgaactcgg cggagcacgt ctctgttgcc gtggactatt accgaatgct gcacgttccc 60
cgcgtaagcc gccctgacgc cattcgcaag gcgtatgaga acctggtgaa gcaacccccc 120
gctgccgcgt actctgcgga caccctcttc gcacgcgcgg tgctactcaa ggcagccgcg 180
gagtcgctga ccgacccgga cctgcgccgc tcatatgacg ccaagctggc cgctggtcac 240
acagccctgc gcgtcagcca gcaggaccta cccggagccc ttgtcgtgct gcaggagatc 300
ggcgagcacc agttggttct ggatctgggt ctgcgctggc tagaggtaaa cggcggccag 360
cccgacgccg gcgacgtggc cgctgccgtg gccctggcct actgtgaccg cgctggtgag 420
cgcctcacct cccagctgca gccgccgccg gcctcagcgc tgccaggccc cgatggcgcg 480
gcggtgccgc acgcgcacgt gggcgcggtg ctgcccgcat gcgacgacct ggacgcagcg 540
ctgagcaagc tccggcggta cggcatggcg cagcagctgc agcagcagat cgtgggcgcg 600
ctgcgggacc tggcgccaga gtacgcgtgc gagctggccg ccctgccgct gggcgccgag 660
accgccgccc ggcgcgccaa gggcgtggcg ctcatgcgcg gtgtgctgcg cgccgccgcc 720
accgtggccg ccgccacagc caagcccgag gctgctgctg acgacagcga cgacgacgag 780
gtggacccgc gcagtgtgct ggcggccgcc cgccgcatgc tgacccgcag ccgcgacgtg 840
ctcacctgca gcgagcaggt ggccctgctg ccggacgcgc tgcgcggcag cggtgtgtcg 900
cccaccccgg acgcgctgta cgacggcgcc ctggcgcacc tggtggacgg cttccgcaac 960
ggctggccgc actccgtgca ccaggccgac cagctgctgg ccaagctgga ggcgcagcag 1020
gcccgcgcag ccgccatgcg ccgcgagcag tccgagctgg ccgccgccgc cgcagcccgc 1080
cgtgccatgt acagcggtcc cgccgccgcc cacggtccca ccctgtacac caactacaac 1140
aaccctgccg gcagcggcaa tggcgcgccg ccgccgccgc cccgccccat gcccatggtg 1200
cccaggggcg acggccagca cgccatggcg gcgtctgtgg cggcgcatgt gcactccacg 1260
gcgatggcgg agcacgcggc gcgcagcgcg gctggcggcg ccgccggcgc ctccgatggc 1320
ggcgcgcacg ccaacggcgt ggctctagag cgggccgtgt gcgccgtcct gctgggtgac 1380
tacaccgcgg cggtggagcg gctggggcta gacacgaacg cggcggtgga gcaggagcag 1440
ctgcgcgagt tcgtcctggc ccactcgccc aacggccgcg gcgacctgcg cccgggcctg 1500
agggcgctgg ccacccgctg gctggagggc gtggcgctgg cgtccttccg cgacactgcc 1560
ggcagccccg tgccgccgct ggaggccagc tggttcgcgg acctgcgtgt cgccttctat 1620
ctgcaggtat ggcggctgtg ccgcgtggag caggtgctgg ccgccgccca cttcctggcc 1680
aacctgctgc ccaacatgct caaggccatc gccggcactg ccgtcaaggt cgcagccaac 1740
accgccgtgg cagcctcccg cgcgcagcgc ctcagcgcca ccgtcgcggc cagcaccgcc 1800

```
accgcctcgt catcttcctc tgccgcccgc ggcgctcgtg ccggtgccct gagcgctgcc   1860

accgccgccg cacacgccgc gcgccgccag caggcgaacg cggtcggtgc cagcatcgtc   1920

ggtgctgacg tgctgccccc cacagcagtg gccgcggctg ccgcggctgg cacagcggcc   1980

gccgccgcag tcaccggccc cgccctcggc cgtggcgctg cagcttccgc ctcttccttt   2040

gaggagggcg ccgctgaggc cgctgacctg cgtcgtcgct ttgtcgccac cagccgcggc   2100

gccagcgcgg ccgtcggtgc gcccacagca ccagccgcta tgactgggcc ccagcacggc   2160

gccgcctctg ctgcgcagtc gcaccgggag gaggatgagg attcgcacgg cggccaggag   2220

gggggcgtgc cgcggcgcat gagcgaggcg gacctgcgtg cgcacctggc gggcctggag   2280

aaggccatgt gggactcgga gctgccgccg ccgccgccat cccgcgcgca gaaggcgctc   2340

acctacgccg caggactgct ggccgtggtg gtggccttcc tggtgtccag cttcttccgc   2400

cgcaacgacg gcgccgcctc cgccctggca cccgccgccg tcaccaccgc ctccgtggcc   2460

gttagcgcgc agcccgccaa gccgggcaag gccacccgct ccgcgcactg a            2511


<210> SEQ ID NO 190
<211> LENGTH: 836
<212> TYPE: PRT
<213> ORGANISM: Chlamydomonas reinhardtii

<400> SEQUENCE: 190

Met Asn Ser Ala Glu His Val Ser Val Ala Val Asp Tyr Tyr Arg Met
1               5                   10                  15

Leu His Val Pro Arg Val Ser Arg Pro Asp Ala Ile Arg Lys Ala Tyr
            20                  25                  30

Glu Asn Leu Val Lys Gln Pro Pro Ala Ala Ala Tyr Ser Ala Asp Thr
        35                  40                  45

Leu Phe Ala Arg Ala Val Leu Leu Lys Ala Ala Ala Glu Ser Leu Thr
    50                  55                  60

Asp Pro Asp Leu Arg Arg Ser Tyr Asp Ala Lys Leu Ala Ala Gly His
65                  70                  75                  80

Thr Ala Leu Arg Val Ser Gln Gln Asp Leu Pro Gly Ala Leu Val Val
                85                  90                  95

Leu Gln Glu Ile Gly Glu His Gln Leu Val Leu Asp Leu Gly Leu Arg
            100                 105                 110

Trp Leu Glu Val Asn Gly Gly Gln Pro Asp Ala Gly Asp Val Ala Ala
        115                 120                 125

Ala Val Ala Leu Ala Tyr Cys Asp Arg Ala Gly Glu Arg Leu Thr Ser
    130                 135                 140

Gln Leu Gln Pro Pro Pro Ala Ser Ala Leu Pro Gly Pro Asp Gly Ala
145                 150                 155                 160

Ala Val Pro His Ala His Val Gly Ala Val Leu Pro Ala Cys Asp Asp
                165                 170                 175

Leu Asp Ala Ala Leu Ser Lys Leu Arg Arg Tyr Gly Met Ala Gln Gln
            180                 185                 190

Leu Gln Gln Gln Ile Val Gly Ala Leu Arg Asp Leu Ala Pro Glu Tyr
        195                 200                 205

Ala Cys Glu Leu Ala Ala Leu Pro Leu Gly Ala Glu Thr Ala Ala Arg
    210                 215                 220

Arg Ala Lys Gly Val Ala Leu Met Arg Gly Val Leu Arg Ala Ala Ala
225                 230                 235                 240

Thr Val Ala Ala Ala Thr Ala Lys Pro Glu Ala Ala Ala Asp Asp Ser
                245                 250                 255
```

```
Asp Asp Asp Glu Val Asp Pro Arg Ser Val Leu Ala Ala Ala Arg Arg
            260                 265                 270

Met Leu Thr Arg Ser Arg Asp Val Leu Thr Cys Ser Glu Gln Val Ala
        275                 280                 285

Leu Leu Pro Asp Ala Leu Arg Gly Ser Gly Val Ser Pro Thr Pro Asp
    290                 295                 300

Ala Leu Tyr Asp Gly Ala Leu Ala His Leu Val Asp Gly Phe Arg Asn
305                 310                 315                 320

Gly Trp Pro His Ser Val His Gln Ala Asp Gln Leu Leu Ala Lys Leu
                325                 330                 335

Glu Ala Gln Gln Ala Arg Ala Ala Ala Met Arg Arg Glu Gln Ser Glu
            340                 345                 350

Leu Ala Ala Ala Ala Ala Ala Arg Arg Ala Met Tyr Ser Gly Pro Ala
        355                 360                 365

Ala Ala His Gly Pro Thr Leu Tyr Thr Asn Tyr Asn Asn Pro Ala Gly
    370                 375                 380

Ser Gly Asn Gly Ala Pro Pro Pro Pro Pro Arg Pro Met Pro Met Val
385                 390                 395                 400

Pro Arg Gly Asp Gly Gln His Ala Met Ala Ala Ser Val Ala Ala His
                405                 410                 415

Val His Ser Thr Ala Met Ala Glu His Ala Ala Arg Ser Ala Ala Gly
            420                 425                 430

Gly Ala Ala Gly Ala Ser Asp Gly Gly Ala His Ala Asn Gly Val Ala
        435                 440                 445

Leu Glu Arg Ala Val Cys Ala Val Leu Leu Gly Asp Tyr Thr Ala Ala
    450                 455                 460

Val Glu Arg Leu Gly Leu Asp Thr Asn Ala Ala Val Glu Gln Glu Gln
465                 470                 475                 480

Leu Arg Glu Phe Val Leu Ala His Ser Pro Asn Gly Arg Gly Asp Leu
                485                 490                 495

Arg Pro Gly Leu Arg Ala Leu Ala Thr Arg Trp Leu Glu Gly Val Ala
            500                 505                 510

Leu Ala Ser Phe Arg Asp Thr Ala Gly Ser Pro Val Pro Pro Leu Glu
        515                 520                 525

Ala Ser Trp Phe Ala Asp Leu Arg Val Ala Phe Tyr Leu Gln Val Trp
    530                 535                 540

Arg Leu Cys Arg Val Glu Gln Val Leu Ala Ala Ala His Phe Leu Ala
545                 550                 555                 560

Asn Leu Leu Pro Asn Met Leu Lys Ala Ile Ala Gly Thr Ala Val Lys
                565                 570                 575

Val Ala Ala Asn Thr Ala Val Ala Ala Ser Arg Ala Gln Arg Leu Ser
            580                 585                 590

Ala Thr Val Ala Ala Ser Thr Ala Thr Ala Ser Ser Ser Ser Ser Ala
        595                 600                 605

Ala Arg Gly Ala Arg Ala Gly Ala Leu Ser Ala Ala Thr Ala Ala Ala
    610                 615                 620

His Ala Ala Arg Arg Gln Gln Ala Asn Ala Val Gly Ala Ser Ile Val
625                 630                 635                 640

Gly Ala Asp Val Leu Pro Pro Thr Ala Val Ala Ala Ala Ala Ala Ala
                645                 650                 655

Gly Thr Ala Ala Ala Ala Ala Val Thr Gly Pro Ala Leu Gly Arg Gly
            660                 665                 670
```

-continued

```
Ala Ala Ala Ser Ala Ser Ser Phe Glu Glu Gly Ala Ala Glu Ala Ala
        675                 680                 685

Asp Leu Arg Arg Arg Phe Val Ala Thr Ser Arg Gly Ala Ser Ala Ala
    690                 695                 700

Val Gly Ala Pro Thr Ala Pro Ala Ala Met Thr Gly Pro Gln His Gly
705                 710                 715                 720

Ala Ala Ser Ala Ala Gln Ser His Arg Glu Glu Asp Glu Asp Ser His
                725                 730                 735

Gly Gly Gln Glu Gly Gly Val Pro Arg Arg Met Ser Glu Ala Asp Leu
            740                 745                 750

Arg Ala His Leu Ala Gly Leu Glu Lys Ala Met Trp Asp Ser Glu Leu
        755                 760                 765

Pro Pro Pro Pro Pro Ser Arg Ala Gln Lys Ala Leu Thr Tyr Ala Ala
    770                 775                 780

Gly Leu Leu Ala Val Val Val Ala Phe Leu Val Ser Ser Phe Phe Arg
785                 790                 795                 800

Arg Asn Asp Gly Ala Ala Ser Ala Leu Ala Pro Ala Ala Val Thr Thr
                805                 810                 815

Ala Ser Val Ala Val Ser Ala Gln Pro Ala Lys Pro Gly Lys Ala Thr
            820                 825                 830

Arg Ser Ala His
        835


<210> SEQ ID NO 191
<211> LENGTH: 2022
<212> TYPE: DNA
<213> ORGANISM: Thermosynechococcus elongatus

<400> SEQUENCE: 191

gtgcgcattc ccctcgatta ttaccaagtg ttgggtgtgc ctattcaggc aacgccggag     60

caaattgagc aggcctttcg ggaccggctg ttgcagctcc ctacccatca gcactccccc    120

accacagttg ccacccgtcg cgaactcatt gagcaggcct atgcagtttt gcgagaaccg    180

gagcagcgcg atgcctacga tcgccactgc cgtaccgttg atcccgatga tttgattgcc    240

cagttggatc ccgatgccac cactccccac attgaaatta gtgatgagca attgtcgggg    300

gcactcctac tgctgtatga actaggaaat tatgcccaag ttgtcaacct gggagacgcc    360

tttcttaaaa aggatgtttt tgagcgcaat cgcccctaca cttcccctgc cgccgttgcc    420

gacattaccc tcactgtggc tttggcctat ctggaattgg gacgggagga atggcagcgg    480

cagtcctatg aatcagccgc ctctcagcta gaagccggtc tccaggtact tcagcgggta    540

aatttgtttc ccgagctcca ggagcagttt cagacggaac tgaatcggct gcgtccctac    600

cgcattctgg aattactggc actgcctttg tccgatagtg cgaatcggca gcggggtatt    660

ttattgctgc ggcaaatgct gagtgagcgc gggggcattg aggggcgcgg tgacgatcgc    720

tcaggactaa cagttgagga ttttctgaaa tttattttgc aactgcgcag ccatcttacc    780

gtggcagaac aacaggaact ctttgaacgg gaatcgcggc gtccctcagc ggtggccacc    840

taccttgcgg tacatgcctt ggtagcacgg ggagtgcatg aactgcagcc gagctatatt    900

tgtcgggcca aggatttatt gcagcagctg ctcccccatc aagacgtcta tcttgaactt    960

gccagttgct tgctgctttt gggacagccc accgaggcct tggcagctct tgaccacagc   1020

caagatcaac cgactctgga ctttatccgc cgtcatgccg gtgaggctgg cgatcgactg   1080

ccggggcttt attactacac cacacaatgg ctcacggagg aaatttatcc tgcatttcgg   1140
```

-continued

```
gacttggggg aaacacccgt ggccttggag gcttactttg ctgatgccaa tgtccaaacc   1200

tatctagagg ctctcagtga ggactccatt gcccctgaac cccctgcgac cactgcctct   1260

gcgctccctg aagtgatcag accaacggtg gccgtgcccc ctcccctctc cttcacagcg   1320

gaaacgttac cgttgcagga tcagagtcgg ctgggtcagg gcctttcggc atcggctttt   1380

accccttctg caactgcaac ggggacatcg atgccccaac catcgcctcg caaacggcgc   1440

agccctcgaa accgttgcgc ccaaaaacgt cagacttggt tttggatggg tgcaggagtg   1500

gttcttgtgg gtttaggggc gttggcaaaa gtctattggc ccgccaaaac cgctgaagcc   1560

cccccgccgc cggtgacacc ggcaccaact cctgtggcaa cgccgacccc aacgccacaa   1620

ccgacgacct tagccatcac tttaacacca gagatggcgc gcgatcgcct ccacacttgg   1680

cagcaaatta aagcccaagc ccttgggcga ccatttgagg tggacaaact aacaacgatt   1740

ttggcggagc cagaactcag ccgctggcga tcgcgggcac agggcttaaa gtccgagggc   1800

agctattggg tttataccct aaagaactta gaagtgaagg aagtccgcct ccaaaggagc   1860

gatcgtgtgg aggtgttggc agaagtcaac gaggatgccc gtttctatga acagggaacc   1920

ctgcgcactg atatttccta tagcgatccc taccgggtca tttatacctt tatccgtcgc   1980

ggcaatcaat ggttgattca aggcatgcag gtggttagtt aa                      2022
```

<210> SEQ ID NO 192
<211> LENGTH: 673
<212> TYPE: PRT
<213> ORGANISM: Thermosynechococcus elongatus

<400> SEQUENCE: 192

```
Met Arg Ile Pro Leu Asp Tyr Tyr Gln Val Leu Gly Val Pro Ile Gln
1               5                   10                  15

Ala Thr Pro Glu Gln Ile Glu Gln Ala Phe Arg Asp Arg Leu Leu Gln
            20                  25                  30

Leu Pro Thr His Gln His Ser Pro Thr Thr Val Ala Thr Arg Arg Glu
        35                  40                  45

Leu Ile Glu Gln Ala Tyr Ala Val Leu Arg Glu Pro Glu Gln Arg Asp
    50                  55                  60

Ala Tyr Asp Arg His Cys Arg Thr Val Asp Pro Asp Asp Leu Ile Ala
65                  70                  75                  80

Gln Leu Asp Pro Asp Ala Thr Thr Pro His Ile Glu Ile Ser Asp Glu
                85                  90                  95

Gln Leu Ser Gly Ala Leu Leu Leu Leu Tyr Glu Leu Gly Asn Tyr Ala
            100                 105                 110

Gln Val Val Asn Leu Gly Asp Ala Phe Leu Lys Lys Asp Val Phe Glu
        115                 120                 125

Arg Asn Arg Pro Tyr Thr Ser Pro Ala Ala Val Ala Asp Ile Thr Leu
    130                 135                 140

Thr Val Ala Leu Ala Tyr Leu Glu Leu Gly Arg Glu Glu Trp Gln Arg
145                 150                 155                 160

Gln Ser Tyr Glu Ser Ala Ala Ser Gln Leu Glu Ala Gly Leu Gln Val
                165                 170                 175

Leu Gln Arg Val Asn Leu Phe Pro Glu Leu Gln Glu Gln Phe Gln Thr
            180                 185                 190

Glu Leu Asn Arg Leu Arg Pro Tyr Arg Ile Leu Glu Leu Leu Ala Leu
        195                 200                 205

Pro Leu Ser Asp Ser Ala Asn Arg Gln Arg Gly Ile Leu Leu Leu Arg
    210                 215                 220
```

-continued

```
Gln Met Leu Ser Glu Arg Gly Gly Ile Glu Gly Arg Gly Asp Asp Arg
225                 230                 235                 240

Ser Gly Leu Thr Val Glu Asp Phe Leu Lys Phe Ile Leu Gln Leu Arg
                245                 250                 255

Ser His Leu Thr Val Ala Glu Gln Gln Glu Leu Phe Glu Arg Glu Ser
            260                 265                 270

Arg Arg Pro Ser Ala Val Ala Thr Tyr Leu Ala Val His Ala Leu Val
        275                 280                 285

Ala Arg Gly Val His Glu Leu Gln Pro Ser Tyr Ile Cys Arg Ala Lys
    290                 295                 300

Asp Leu Leu Gln Gln Leu Leu Pro His Gln Asp Val Tyr Leu Glu Leu
305                 310                 315                 320

Ala Ser Cys Leu Leu Leu Leu Gly Gln Pro Thr Glu Ala Leu Ala Ala
                325                 330                 335

Leu Asp His Ser Gln Asp Gln Pro Thr Leu Asp Phe Ile Arg Arg His
            340                 345                 350

Ala Gly Glu Ala Gly Asp Arg Leu Pro Gly Leu Tyr Tyr Tyr Thr Thr
        355                 360                 365

Gln Trp Leu Thr Glu Glu Ile Tyr Pro Ala Phe Arg Asp Leu Gly Glu
    370                 375                 380

Thr Pro Val Ala Leu Glu Ala Tyr Phe Ala Asp Ala Asn Val Gln Thr
385                 390                 395                 400

Tyr Leu Glu Ala Leu Ser Glu Asp Ser Ile Ala Pro Glu Pro Pro Ala
                405                 410                 415

Thr Thr Ala Ser Ala Leu Pro Glu Val Ile Arg Pro Thr Val Ala Val
            420                 425                 430

Pro Pro Pro Leu Ser Phe Thr Ala Glu Thr Leu Pro Leu Gln Asp Gln
        435                 440                 445

Ser Arg Leu Gly Gln Gly Leu Ser Ala Ser Ala Phe Thr Pro Ser Ala
    450                 455                 460

Thr Ala Thr Gly Thr Ser Met Pro Gln Pro Ser Pro Arg Lys Arg Arg
465                 470                 475                 480

Ser Pro Arg Asn Arg Cys Ala Gln Lys Arg Gln Thr Trp Phe Trp Met
                485                 490                 495

Gly Ala Gly Val Val Leu Val Gly Leu Gly Ala Leu Ala Lys Val Tyr
            500                 505                 510

Trp Pro Ala Lys Thr Ala Glu Ala Pro Pro Pro Pro Val Thr Pro Ala
        515                 520                 525

Pro Thr Pro Val Ala Thr Pro Thr Pro Thr Pro Gln Pro Thr Thr Leu
    530                 535                 540

Ala Ile Thr Leu Thr Pro Glu Met Ala Arg Asp Arg Leu His Thr Trp
545                 550                 555                 560

Gln Gln Ile Lys Ala Gln Ala Leu Gly Arg Pro Phe Glu Val Asp Lys
                565                 570                 575

Leu Thr Thr Ile Leu Ala Glu Pro Glu Leu Ser Arg Trp Arg Ser Arg
            580                 585                 590

Ala Gln Gly Leu Lys Ser Glu Gly Ser Tyr Trp Val Tyr Thr Leu Lys
        595                 600                 605

Asn Leu Glu Val Lys Glu Val Arg Leu Gln Arg Ser Asp Arg Val Glu
    610                 615                 620

Val Leu Ala Glu Val Asn Glu Asp Ala Arg Phe Tyr Glu Gln Gly Thr
625                 630                 635                 640
```

-continued

```
Leu Arg Thr Asp Ile Ser Tyr Ser Asp Pro Tyr Arg Val Ile Tyr Thr
                645                 650                 655

Phe Ile Arg Arg Gly Asn Gln Trp Leu Ile Gln Gly Met Gln Val Val
            660                 665                 670

Ser


<210> SEQ ID NO 193
<211> LENGTH: 2370
<212> TYPE: DNA
<213> ORGANISM: Trichodesmium erythraeum

<400> SEQUENCE: 193

gtgcggattc cattagatta ttatcgaatt ttaggtttac caattcaggc tactgctgaa     60

cagttgcggc aggcacatca agaccgcact cagcagtttc ctagaaggga gtattctgaa    120

gccacaatag ttgctcgtaa acagcttata gatgaggctt atgctgttct ttgcgatcct    180

gaacaacgtc aaacctatga tggtaacttt ttagctaaaa cctacgagcc aatagtagaa    240

gaactcaatc caagttctca gataaatttt gatcaagcac aagaaaaaga aaccacactt    300

aaggagacta gagaagttct tccggaaata gcttctaaac agttaaaaaa aaggacaagt    360

tatcaaaaca gagagactaa agctgcctct gattttcatt ctaatacccc tagtatagaa    420

atagaatatc cacaatttgt gggagccatc ctaattttac atgagctagg agaatatgag    480

ctagtattaa aaataactca cccttatctt cttaacaata gtataactat taaagatgga    540

cgttttggag acccagcatt agttttgcca gatgttgtcc ttacagttgc tctagcaaat    600

ttagaattgg gcagagagga atggcaacaa ggacaatacg aaagtgcagc tacagcttta    660

gaggctggcc tagggttatt gctacgagaa aacctatttg tccaaatacg aggagagata    720

caagctgacc tttataagct acgtccttat agaataatgg agctaatagc actaccagag    780

gaaatagctc tagaccgtag ccgtggacta gaaattcttc aagatatgct caatgaacgg    840

ggaggaattg atggtcaagg tgaagatagc tctggacttg ggatagaaga ttttctaaag    900

tttgttcagc agctacgtca atacttaact acagcagagc aaaagaagtt atttgaggca    960

gaagcccttc gcccttccgc agttggtgca tatctagcgg tttatacttt tttagctcaa   1020

gggtttgctc aaaaacaacc agcctttatt cgtaaagcta agttgatgtt aatgcaattg   1080

ggtcggagtc aagatgtaaa tttagagaaa tctgtctgtg ctttactttt agggcaaact   1140

gaagaagcta gtcgttcatt agaacttagc catgaaaatg aacctctatc ctttattaaa   1200

gaaaattctc aacaatctcc agatttattg ccaggtctat gtctctatgc tgaacattgg   1260

ttgacagagg aggtttttcc acatttccgt gatttgtctg acaagtcagc ttctttgaaa   1320

gattattttg cagatcaaca tgttcaagct tatctagaag ctttacctac agaagcagag   1380

gtagctaatc aatgggtagt cgttcagcct cgtcgtagta atcacaataa aaaacaaatg   1440

ttcgacccca aggaacttga gaagttgaat gtatcagatt tggaggataa agatatttct   1500

cgggtagatg ctactgctac tggtattgtt gcttctggaa gtcaaggaag ttctaattta   1560

ctaggggcta gttctgatgg gttgcttcaa gaattagaaa aatcatcatc tactagaggt   1620

gggccaaaac aagtaactac taagagttct agtcactatt taggaaaaat tagggaaaag   1680

agtataagtg gtttacctga gtttaatgaa agtacatcta ttgagagtgg ggggttaccc   1740

caatctatcc aagagcatag ttcacgtaga acttctgcta gaagagaacc tgttaagttt   1800

ggtcgtttaa tattaatcgc aattgtggga tttttgttaa taggatttat tgggttgtta   1860

acaattaaaa ctatcggctg gttagtaaat gctttaggat gggaaagaga aaaactgatg   1920
```

```
atacaattgg ataggcctcc tatagaaatc ccagaacctg atcgggttaa cctcgcagca   1980

tcaggaccga taacaaaaga agtagcaagg cgaacaattc aaagttggtt agatatcaag   2040

gcttctgctc ttggtcctaa tcataaaatt gaacaattac caaatatttt agtagaaccg   2100

gcactttctc gttggttacc tacagctaat gccctgaagc aagaaaagtc ataccgtagg   2160

tatgagcatg atttagaaat aagtaatata aagatgagta atacaaattc taatctcgct   2220

caagtagatg ctaaagtgat agaaaaggta gagttttatt ctgacaatgg tagattaact   2280

aatactaaca atgaaaactt atttgttcgt tatgatttag ttcgtaaaag tcaaaaatgg   2340

caaattagta attggaaggt attgagataa                                    2370
```

<210> SEQ ID NO 194
<211> LENGTH: 789
<212> TYPE: PRT
<213> ORGANISM: Trichodesmium erythraeum

<400> SEQUENCE: 194

```
Val Arg Ile Pro Leu Asp Tyr Tyr Arg Ile Leu Gly Leu Pro Ile Gln
1               5                   10                  15

Ala Thr Ala Glu Gln Leu Arg Gln Ala His Gln Asp Arg Thr Gln Gln
            20                  25                  30

Phe Pro Arg Arg Glu Tyr Ser Glu Ala Thr Ile Val Ala Arg Lys Gln
        35                  40                  45

Leu Ile Asp Glu Ala Tyr Ala Val Leu Cys Asp Pro Glu Gln Arg Gln
    50                  55                  60

Thr Tyr Asp Gly Asn Phe Leu Ala Lys Thr Tyr Glu Pro Ile Val Glu
65                  70                  75                  80

Glu Leu Asn Pro Ser Ser Gln Ile Asn Phe Asp Gln Ala Gln Glu Lys
                85                  90                  95

Glu Thr Thr Leu Lys Glu Thr Arg Glu Val Leu Pro Glu Ile Ala Ser
            100                 105                 110

Lys Gln Leu Lys Lys Arg Thr Ser Tyr Gln Asn Arg Glu Thr Lys Ala
        115                 120                 125

Ala Ser Asp Phe His Ser Asn Thr Pro Ser Ile Glu Ile Glu Tyr Pro
    130                 135                 140

Gln Phe Val Gly Ala Ile Leu Ile Leu His Glu Leu Gly Glu Tyr Glu
145                 150                 155                 160

Leu Val Leu Lys Ile Thr His Pro Tyr Leu Leu Asn Asn Ser Ile Thr
                165                 170                 175

Ile Lys Asp Gly Arg Phe Gly Asp Pro Ala Leu Val Leu Pro Asp Val
            180                 185                 190

Val Leu Thr Val Ala Leu Ala Asn Leu Glu Leu Gly Arg Glu Glu Trp
        195                 200                 205

Gln Gln Gly Gln Tyr Glu Ser Ala Ala Thr Ala Leu Glu Ala Gly Leu
    210                 215                 220

Gly Leu Leu Leu Arg Glu Asn Leu Phe Val Gln Ile Arg Gly Glu Ile
225                 230                 235                 240

Gln Ala Asp Leu Tyr Lys Leu Arg Pro Tyr Arg Ile Met Glu Leu Ile
                245                 250                 255

Ala Leu Pro Glu Glu Ile Ala Leu Asp Arg Ser Arg Gly Leu Glu Ile
            260                 265                 270

Leu Gln Asp Met Leu Asn Glu Arg Gly Gly Ile Asp Gly Gln Gly Glu
        275                 280                 285
```

-continued

```
Asp Ser Ser Gly Leu Gly Ile Glu Asp Phe Leu Lys Phe Val Gln Gln
    290                 295                 300

Leu Arg Gln Tyr Leu Thr Thr Ala Glu Gln Lys Lys Leu Phe Glu Ala
305                 310                 315                 320

Glu Ala Leu Arg Pro Ser Ala Val Gly Ala Tyr Leu Ala Val Tyr Thr
                325                 330                 335

Phe Leu Ala Gln Gly Phe Ala Gln Lys Gln Pro Ala Phe Ile Arg Lys
            340                 345                 350

Ala Lys Leu Met Leu Met Gln Leu Gly Arg Ser Gln Asp Val Asn Leu
        355                 360                 365

Glu Lys Ser Val Cys Ala Leu Leu Leu Gly Gln Thr Glu Glu Ala Ser
    370                 375                 380

Arg Ser Leu Glu Leu Ser His Glu Asn Glu Pro Leu Ser Phe Ile Lys
385                 390                 395                 400

Glu Asn Ser Gln Gln Ser Pro Asp Leu Leu Pro Gly Leu Cys Leu Tyr
                405                 410                 415

Ala Glu His Trp Leu Thr Glu Glu Val Phe Pro His Phe Arg Asp Leu
            420                 425                 430

Ser Asp Lys Ser Ala Ser Leu Lys Asp Tyr Phe Ala Asp Gln His Val
        435                 440                 445

Gln Ala Tyr Leu Glu Ala Leu Pro Thr Glu Ala Glu Val Ala Asn Gln
    450                 455                 460

Trp Val Val Val Gln Pro Arg Arg Ser Asn His Asn Lys Lys Gln Met
465                 470                 475                 480

Phe Asp Pro Lys Glu Leu Glu Lys Leu Asn Val Ser Asp Leu Glu Asp
                485                 490                 495

Lys Asp Ile Ser Arg Val Asp Ala Thr Ala Thr Gly Ile Val Ala Ser
            500                 505                 510

Gly Ser Gln Gly Ser Ser Asn Leu Leu Gly Ala Ser Ser Asp Gly Leu
        515                 520                 525

Leu Gln Glu Leu Glu Lys Ser Ser Ser Thr Arg Gly Gly Pro Lys Gln
    530                 535                 540

Val Thr Thr Lys Ser Ser Ser His Tyr Leu Gly Lys Ile Arg Glu Lys
545                 550                 555                 560

Ser Ile Ser Gly Leu Pro Glu Phe Asn Glu Ser Thr Ser Ile Glu Ser
                565                 570                 575

Gly Gly Leu Pro Gln Ser Ile Gln Glu His Ser Ser Arg Arg Thr Ser
            580                 585                 590

Ala Arg Arg Glu Pro Val Lys Phe Gly Arg Leu Ile Leu Ile Ala Ile
        595                 600                 605

Val Gly Phe Leu Leu Ile Gly Phe Ile Gly Leu Leu Thr Ile Lys Thr
    610                 615                 620

Ile Gly Trp Leu Val Asn Ala Leu Gly Trp Glu Arg Glu Lys Leu Met
625                 630                 635                 640

Ile Gln Leu Asp Arg Pro Pro Ile Glu Ile Pro Glu Pro Asp Arg Val
                645                 650                 655

Asn Leu Ala Ala Ser Gly Pro Ile Thr Lys Glu Val Ala Arg Arg Thr
            660                 665                 670

Ile Gln Ser Trp Leu Asp Ile Lys Ala Ser Ala Leu Gly Pro Asn His
        675                 680                 685

Lys Ile Glu Gln Leu Pro Asn Ile Leu Val Glu Pro Ala Leu Ser Arg
    690                 695                 700

Trp Leu Pro Thr Ala Asn Ala Leu Lys Gln Glu Lys Ser Tyr Arg Arg
```

-continued

```
705                 710                 715                 720

Tyr Glu His Asp Leu Glu Ile Ser Asn Ile Lys Met Ser Asn Thr Asn
                725                 730                 735

Ser Asn Leu Ala Gln Val Asp Ala Lys Val Ile Glu Lys Val Glu Phe
            740                 745                 750

Tyr Ser Asp Asn Gly Arg Leu Thr Asn Thr Asn Asn Glu Asn Leu Phe
        755                 760                 765

Val Arg Tyr Asp Leu Val Arg Lys Ser Gln Lys Trp Gln Ile Ser Asn
    770                 775                 780

Trp Lys Val Leu Arg
785


<210> SEQ ID NO 195
<211> LENGTH: 765
<212> TYPE: PRT
<213> ORGANISM: Homo sapiens

<400> SEQUENCE: 195

Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Val Thr Arg Arg Pro Leu Val Leu Gln Leu
    50                  55                  60

Val Asn Ala Thr Thr Glu Tyr Ala Glu Phe Leu His Cys Lys Gly Lys
65                  70                  75                  80

Lys Phe Thr Glu Ala Glu Thr Asp Arg Val Thr Gly Thr Asn Lys Gly
                85                  90                  95

Ile Ser Pro Val Pro Ile Asn Leu Arg Val Tyr Ser Pro His Val Leu
            100                 105                 110

Asn Leu Thr Leu Val Asp Leu Pro Gly Met Thr Lys Val Pro Val Gly
        115                 120                 125

Asp Gln Pro Pro Asp Ile Glu Phe Gln Ile Arg Asp Met Leu Met Gln
    130                 135                 140

Phe Val Thr Lys Glu Asn Cys Ser Asp Leu Ala Asn Ser Asp Ala Leu
145                 150                 155                 160

Lys Val Ala Lys Glu Val Asp Pro Gln Gly Gln Arg Thr Ile Gly Val
                165                 170                 175

Ile Thr Lys Leu Asp Leu Met Asp Glu Gly Thr Asp Ala Arg Asp Val
            180                 185                 190

Leu Glu Asn Lys Leu Leu Pro Leu Arg Arg Gly Tyr Ile Gly Val Val
        195                 200                 205

Asn Arg Ser Gln Lys Asp Ile Asp Gly Lys Lys Asp Ile Thr Phe Leu
    210                 215                 220

Ser His Pro Ser Tyr Arg His Leu Ala Asp Arg Met Gly Thr Pro Tyr
225                 230                 235                 240

Leu Gln Lys Val Leu Asn Gln Gln Leu Thr Asn His Ile Arg Asp Thr
                245                 250                 255

Leu Pro Gly Leu Arg Asn Lys Leu Gln Ser Gln Leu Leu Ser Ile Glu
            260                 265                 270

Lys Glu Val Glu Glu Tyr Lys Asn Phe Arg Pro Asp Asp Pro Ala Arg
        275                 280                 285
```

-continued

```
Lys Thr Lys Ala Leu Asp Phe Glu Lys Arg Ile Glu Gly Ser Gly Asp
    290                 295                 300

Gln Ile Asp Thr Tyr Glu Leu Ser Gly Gly Ala Arg Ile Asn Arg Ile
305                 310                 315                 320

Phe His Glu Arg Phe Pro Phe Glu Leu Val Lys Met Glu Phe Asp Glu
                325                 330                 335

Lys Glu Leu Arg Arg Glu Ile Ser Tyr Ala Ile Lys Asn Ile His Gly
            340                 345                 350

Ile Arg Thr Gly Leu Phe Thr Pro Asp Met Ala Lys Lys Ile Arg Glu
        355                 360                 365

Pro Cys Leu Lys Cys Val Asp Met Val Ile Ser Glu Leu Ile Ser Thr
    370                 375                 380

Val Arg Gln Cys Thr Lys Lys Leu Gln Gln Tyr Pro Arg Leu Arg Glu
385                 390                 395                 400

Glu Met Glu Arg Ile Val Thr Thr His Ile Arg Glu Arg Glu Gly Arg
                405                 410                 415

Thr Lys Glu Gln Val Met Met Asn Thr Asn His Glu Asp Phe Ile Gly
            420                 425                 430

Phe Ala Asn Ala Gln Gln Arg Ser Asn Gln Met Asn Lys Lys Lys Thr
        435                 440                 445

Ser Gly Asn Gln Asp Glu Ile Leu Val Ile Arg Lys Gly Trp Leu Thr
    450                 455                 460

Ile Asn Asn Ile Gly Ile Met Lys Gly Gly Ser Lys Glu Tyr Trp Phe
465                 470                 475                 480

Val Leu Thr Ala Glu Asn Leu Ser Trp Tyr Lys Asp Asp Ser Val Asp
                485                 490                 495

Asn Leu Lys Leu Arg Asp Val Glu Lys Gly Phe Met Ser Ser Lys His
            500                 505                 510

Ile Phe Ala Leu Phe Asn Thr Glu Gln Arg Asn Val Tyr Lys Asp Tyr
        515                 520                 525

Arg Gln Leu Glu Leu Ala Cys Glu Thr Gln Glu Glu Val Asp Ser Trp
    530                 535                 540

Lys Ala Ser Phe Leu Arg Ala Gly Val Tyr Pro Glu Arg Val Gly Asp
545                 550                 555                 560

Lys Glu Lys Asp Ser Phe Met His Ser Met Asp Pro Gln Leu Glu Arg
                565                 570                 575

Gln Val Glu Thr Ile Arg Asn Leu Val Asp Ser Tyr Met Ala Ile Val
            580                 585                 590

Asn Lys Thr Val Arg Asp Leu Met Pro Lys Thr Ile Met His Leu Met
        595                 600                 605

Ile Asn Asn Thr Lys Glu Phe Ile Phe Ser Glu Leu Leu Ala Asn Leu
    610                 615                 620

Tyr Ser Cys Gly Asp Gln Asn Thr Leu Met Arg Asp Glu Met Leu Arg
625                 630                 635                 640

Met Tyr His Ala Leu Lys Glu Ala Leu Ser Ile Ile Gly Asn Ile Asn
                645                 650                 655

Thr Thr Thr Val Ser Thr Pro Met Pro Pro Pro Val Asp Asp Ser Trp
            660                 665                 670

Leu Gln Val Gln Ser Val Pro Ala Gly Arg Arg Ser Pro Thr Ser Ser
        675                 680                 685

Pro Thr Pro Gln Arg Arg Ala Pro Ala Val Pro Pro Ala Arg Pro Gly
    690                 695                 700

Ser Ala Gly Ser Ala Leu Gly Gly Ala Pro Pro Val Pro Ser Arg Pro
```

```
705                 710                 715                 720

Gly Ala Ser Pro Asp Pro Phe Gly Pro Pro Pro Gln Val Pro Ser Arg
                725                 730                 735

Pro Asn Arg Ala Pro Pro Gly Val Pro Ser Arg Ser Gly Gln Ala Ser
            740                 745                 750

Pro Ser Arg Pro Glu Ser Pro Arg Pro Pro Phe Asp Leu
        755                 760                 765


<210> SEQ ID NO 196
<211> LENGTH: 670
<212> TYPE: PRT
<213> ORGANISM: Saccharomyces cerevisiae

<400> SEQUENCE: 196

Met Ala Ser Leu Glu Asp Leu Ile Pro Thr Val Asn Lys Leu Gln Asp
1               5                   10                  15

Val Met Tyr Asp Ser Gly Ile Asp Thr Leu Asp Leu Pro Ile Leu Ala
            20                  25                  30

Val Val Gly Ser Gln Ser Ser Gly Lys Ser Ser Ile Leu Glu Thr Leu
        35                  40                  45

Val Gly Arg Val Thr Arg Arg Pro Leu Val Leu Gln Leu Asn Asn Ile
    50                  55                  60

Ser Pro Asn Ser Pro Leu Ile Glu Glu Asp Asp Asn Ser Val Asn Pro
65                  70                  75                  80

His Asp Glu Val Thr Lys Ile Ser Gly Phe Glu Ala Gly Thr Lys Pro
                85                  90                  95

Leu Glu Tyr Arg Gly Lys Glu Arg Asn His Ala Asp Glu Trp Gly Glu
            100                 105                 110

Phe Leu His Ile Pro Gly Lys Arg Phe Tyr Glu Asn Glu Thr Ala Arg
        115                 120                 125

Ile Ala Gly Lys Asp Lys Gly Ile Ser Lys Ile Pro Ile Asn Leu Lys
    130                 135                 140

Val Phe Ser Pro His Val Leu Asn Leu Thr Leu Val Asp Leu Pro Gly
145                 150                 155                 160

Ile Thr Lys Val Pro Ile Gly Glu Gln Pro Pro Asp Ile Glu Lys Gln
                165                 170                 175

Ile Lys Asn Leu Ile Leu Asp Tyr Ile Ala Thr Pro Asn Cys Val Asp
            180                 185                 190

Leu Val Asn Ser Glu Ser Leu Lys Leu Ala Arg Glu Val Asp Pro Gln
        195                 200                 205

Gly Lys Arg Thr Ile Gly Val Ile Thr Lys Leu Asp Leu Met Asp Ser
    210                 215                 220

Gly Thr Asn Ala Leu Asp Ile Leu Ser Gly Lys Met Tyr Pro Leu Lys
225                 230                 235                 240

Leu Gly Phe Val Gly Val Val Asn Arg Ser Gln Gln Asp Ile Gln Leu
                245                 250                 255

Asn Lys Thr Val Glu Phe Arg Lys His Pro Val Tyr Arg Thr Ile Ser
            260                 265                 270

Thr Lys Cys Gly Thr Arg Tyr Leu Ala Lys Leu Leu Asn Gln Thr Leu
        275                 280                 285

Leu Ser His Ile Arg Asp Lys Leu Pro Asp Ile Lys Thr Lys Leu Asn
    290                 295                 300

Thr Leu Ile Ser Gln Thr Glu Gln Glu Leu Ala Arg Tyr Gly Gly Val
305                 310                 315                 320
```

```
Gly Ala Thr Thr Asn Glu Ser Arg Ala Ser Leu Val Asn Phe Ile Ser
                325                 330                 335

Ser Ile Asp Gly Thr Ser Ser Asp Ile Asn Thr Lys Glu Leu Cys Gly
            340                 345                 350

Gly Ala Arg Ile Tyr Tyr Ile Tyr Asn Asn Val Phe Gly Asn Ser Leu
        355                 360                 365

Lys Ser Ile Asp Pro Thr Ser Asn Leu Ser Val Leu Asp Val Arg Thr
    370                 375                 380

Ala Ile Arg Asn Ser Thr Gly Pro Arg Pro Thr Leu Phe Val Pro Glu
385                 390                 395                 400

Leu Ala Lys Leu Leu Leu Glu Pro Ser Gln Arg Cys Val Glu Leu Val
                405                 410                 415

Tyr Glu Glu Leu Met Lys Ile Cys His Lys Cys Gly Ser Ala Glu Leu
            420                 425                 430

Ala Arg Tyr Pro Lys Leu Lys Ser Met Leu Ile Glu Val Ile Ser Glu
        435                 440                 445

Leu Leu Arg Glu Arg Leu Gln Pro Thr Arg Ser Tyr Val Glu Ile Asn
    450                 455                 460

Thr Asn His Pro Asn Phe Leu Ser Ala Thr Glu Ala Met Asp Asp Ile
465                 470                 475                 480

Met Lys Thr Arg Arg Lys Arg Asn Gln Glu Leu Leu Lys Ser Lys Leu
                485                 490                 495

Ser Gln Gln Glu Asn Gly Gln Thr Asn Gly Ile Asn Gly Thr Ser Ser
            500                 505                 510

Ile Ser Ser Asn Ile Asp Gln Asp Asp Gly Ile Asp Ala Glu Ser Lys
        515                 520                 525

Gln Thr Lys Asp Lys Phe Leu Asn Tyr Phe Phe Gly Lys Asp Lys Lys
    530                 535                 540

Gly Gln Pro Val Phe Asp Ala Ser Asp Lys Lys Arg Ser Ile Ala Gly
545                 550                 555                 560

Asp Gly Asn Ile Glu Asp Phe Arg Asn Leu Gln Ile Ser Asp Phe Ser
                565                 570                 575

Leu Gly Asp Ile Asp Asp Pro Leu Thr Glu Arg Glu Glu Leu Glu Cys
            580                 585                 590

Glu Leu Ile Lys Arg Leu Ile Val Ser Tyr Phe Asp Ile Ile Arg Glu
        595                 600                 605

Met Ile Glu Asp Gln Val Pro Lys Ala Val Met Cys Leu Leu Val Asn
    610                 615                 620

Tyr Cys Lys Asp Ser Val Gln Asn Arg Leu Val Thr Lys Leu Tyr Lys
625                 630                 635                 640

Glu Thr Leu Phe Glu Glu Leu Leu Arg Glu Leu Cys Val Lys Ser Leu
                645                 650                 655

Gly Val Tyr Lys Lys Ala Ala Thr Leu Ile Ser Asn Ile Leu
            660                 665                 670


<210> SEQ ID NO 197
<211> LENGTH: 690
<212> TYPE: PRT
<213> ORGANISM: Arabidopsis thaliana

<400> SEQUENCE: 197

Met Ala Glu Val Ser Ala Lys Ser Val Thr Val Glu Glu Met Ala Glu
1               5                   10                  15

Glu Asp Asp Ala Ala Ile Glu Glu Arg Trp Ser Leu Tyr Glu Ala Tyr
            20                  25                  30
```

-continued

```
Asn Glu Leu His Ala Leu Ala Gln Glu Leu Glu Thr Pro Phe Glu Ala
        35                  40                  45

Pro Ala Val Leu Val Val Gly Gln Gln Thr Asp Gly Lys Ser Ala Leu
    50                  55                  60

Val Glu Ala Leu Met Gly Phe Lys Thr Arg Arg Pro Ile Thr Leu His
65                  70                  75                  80

Met Lys Tyr Asp Pro Gln Cys Gln Phe Pro Leu Cys His Leu Gly Ser
                85                  90                  95

Asp Asp Asp Pro Ser Val Ser Leu Pro Lys Glu Ala Glu Asn Met Arg
            100                 105                 110

Leu Glu Gln Glu Pro Cys Ser Pro Phe Ser Ala Lys Glu Ile Ile Val
        115                 120                 125

Lys Val Gln Tyr Lys Tyr Cys Pro Asn Leu Thr Ile Ile Asp Thr Pro
    130                 135                 140

Gly Leu Ile Ala Pro Ala Pro Gly Leu Lys Asn Arg Ala Leu Gln Val
145                 150                 155                 160

Gln Ala Arg Ala Val Glu Ala Leu Val Arg Ala Lys Met Gln His Lys
                165                 170                 175

Glu Ser Asp Trp Ser Ile Ala Thr Thr Arg Arg Ile Val Met Gln Val
            180                 185                 190

Asp Pro Glu Leu Ser Arg Thr Ile Val Val Ser Thr Lys Leu Asp Thr
        195                 200                 205

Lys Ile Pro Gln Phe Ser Cys Ser Ser Asp Val Glu Val Phe Leu Ser
    210                 215                 220

Pro Pro Ala Ser Ala Leu Asp Ser Ser Leu Leu Gly Asp Ser Pro Phe
225                 230                 235                 240

Phe Tyr Gly Gln Asp Ser Val Tyr Lys Ser Asn Asp Glu Phe Lys Gln
                245                 250                 255

Ala Val Ser Leu Arg Glu Met Glu Asp Ile Ala Ser Leu Glu Lys Lys
            260                 265                 270

Leu Gly Arg Leu Leu Thr Lys Gln Glu Lys Ser Arg Ile Gly Ile Ser
        275                 280                 285

Lys Leu Arg Leu Phe Leu Glu Glu Leu Leu Trp Lys Arg Tyr Lys Glu
    290                 295                 300

Ser Val Pro Leu Ile Ile Pro Leu Arg Lys Leu Asp Thr Val Ser Lys
305                 310                 315                 320

Glu Leu Ser Ser Leu Asp Glu Ala Lys Leu Lys Glu Arg Gly Arg Thr
                325                 330                 335

Phe His Asp Leu Phe Leu Thr Lys Leu Ser Leu Leu Leu Lys Gly Thr
            340                 345                 350

Val Val Ala Pro Pro Asp Lys Phe Gly Glu Thr Leu Gln Asp Glu Arg
        355                 360                 365

Thr Gln Gly Gly Ala Phe Val Gly Thr Asp Gly Leu Gln Phe Ser Arg
    370                 375                 380

Leu Tyr Gly Gly Ala Gln Tyr His Arg Ala Met Ala Glu Phe Arg Phe
385                 390                 395                 400

Leu Val Gly Ala Ile Lys Cys Pro Pro Ile Thr Arg Glu Glu Ile Val
                405                 410                 415

Asn Ala Cys Gly Val Glu Asp Ile His Asp Gly Thr Asn Tyr Ser Arg
            420                 425                 430

Thr Ala Cys Val Ile Ala Val Ala Lys Ala Arg Glu Thr Phe Glu Pro
        435                 440                 445
```

-continued

```
Phe Leu His Gln Leu Gly Leu Leu Pro Ile Ser Val Tyr Leu Leu Gln
    450                 455                 460

Lys Glu Gly Glu Tyr Leu Ser Gly His Glu Val Phe Leu Lys Arg Val
465                 470                 475                 480

Ala Ser Ala Phe Asn Ser Phe Val Glu Ser Thr Glu Lys Ser Cys Arg
                485                 490                 495

Asp Lys Cys Met Glu Asp Leu Ala Ser Thr Thr Arg Tyr Val Thr Trp
            500                 505                 510

Ser Leu His Asn Lys Asn Ser Phe Gly Gly Thr Glu His Asn Thr Thr
        515                 520                 525

Ser Gly Asn Ala Ile Gly Phe Ser Leu Pro Gln Asp Ala Leu Gly Gly
    530                 535                 540

Thr Thr Asp Thr Lys Ser Arg Ser Asp Val Lys Leu Ser His Leu Ala
545                 550                 555                 560

Ser Asn Ile Asp Ser Gly Ser Ser Ile Gln Thr Thr Glu Met Arg Leu
                565                 570                 575

Ala Asp Leu Leu Asp Ser Thr Leu Trp Asn Arg Lys Leu Ile Val Tyr
            580                 585                 590

Ala Leu Val Gln Gln Ile Phe Gln Gly Ile Arg Glu Tyr Phe Leu Ala
        595                 600                 605

Ser Ala Glu Leu Lys Phe Asn Cys Phe Leu Leu Met Pro Ile Val Asp
    610                 615                 620

Lys Leu Pro Ala Leu Leu Arg Glu Glu Leu Glu Asn Ala Phe Glu Asp
625                 630                 635                 640

Asp Leu Asp Ser Ile Phe Asp Ile Thr Asn Leu Arg Thr Glu Ile Glu
                645                 650                 655

Leu Arg Arg Val Lys Arg Ile Lys Glu Lys Phe Arg Val Met Asn Glu
            660                 665                 670

Lys Leu Asn Ser His Glu Phe Ala Gln Asn Leu Lys Ala Pro Ser Val
        675                 680                 685

Gln His
    690
```

<210> SEQ ID NO 198
<211> LENGTH: 712
<212> TYPE: DNA
<213> ORGANISM: Lactuca sativa
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t

<400> SEQUENCE: 198

```
ttgttcagct ccgccaaaag aatccaagaa ttggcgtaat ccggctcgat tcttattgtg     60

aagggaccag gtgacataac gggtggtgct tattagatct tccatgcatt tttcatggca    120

tgatctttcg gtggattcag caaagttata gaaagcagat gaaacacgtc tcaagaaaac    180

ttcatggcca cttaggaatt cgccttcttt ctgaagaaga taaacggaga tgggaagtaa    240

tctcttgaga atgtgaagaa gtcgactgcc caactgatga agaaaaggtt caaaagtatc    300

acgagctttt gcaacagcga tgacacatgc agtcctggag taatttgttc catcatgaat    360

atcttcgacc ccacatgcat tcacaatttc ttcacgtgta attgcagggc attttatccc    420

tccaacaaca aacctaaatt cagccatggc acgatgatat tgtgcacctc catatagacg    480
```

catacctgca ttaggtatta gtttgtgtgg gaactgagag ccatcaatac cgattaatgc 540
ccctccatta accctctcat cttgtagtgt ttccccaaat ttatctggag gtgcaacaac 600
tgtccctntt catagcagtg ataacttggt aaggaaaaga tcatgaaaag atctcncttt 660
ctcctttagt ttgacttcat ctaaagtgct gagttcttga tttatgtcat tt 712

<210> SEQ ID NO 199
<211> LENGTH: 666
<212> TYPE: DNA
<213> ORGANISM: Medicago truncatula
<220> FEATURE:
<221> NAME/KEY: misc_feature
<222> LOCATION: (646)..(646)
<223> OTHER INFORMATION: n is a, c, g, or t

<400> SEQUENCE: 199
atctaaagta acaaccacca caaaacacaa caatggagga agaaagagaa caccaccaac 60
tcaaagacaa agaagaaaac gagtggcgtc tctacgaagc ttacaatgaa cttcacgcgc 120
ttgctcaaga acttcacacg cctttcgacg cgccggcggt actggttgtg ggccaccaaa 180
cagacgggaa gagcgcctta gttgaggctc taatgggctt ccagttcaac cacgtcggtg 240
gtggcaccaa aacccgccgg cccattactc ttcacatgaa atatggccca cattgcgagt 300
ctccttcttg ctatcttctt tctgatgatg acccttctct ttctcaccat atgtcacttt 360
cccaaatcca gggttatatt gaagctgaga atgcgaggtt ggagcgtgac tcatgttgtc 420
aattttcagc taaggaaata atcataaaag tggaatacaa atactgtccc aatctcacca 480
taatagacac accaggatta gttgctcctg caccaggtcg taaaaatagg gcgatacagg 540
cacaggcacg agcggtagag tcactcgttc gtgcaaaaat gcagcacaag gagttcatta 600
tactctgtct tgaagattgt agtgattgga gcaatgcgac tacgangcgc gttgtaatgc 660
aaattg 666

<210> SEQ ID NO 200
<211> LENGTH: 663
<212> TYPE: DNA
<213> ORGANISM: Medicago truncatula

<400> SEQUENCE: 200
gtctttatgg gggtgcacaa tatcatcgag caatggctga atttcgtttt gtagttggag 60
gaatcaagtg ccctccaatt acccgggaag aaattgtaaa tgcttgtgga gttgaagaca 120
ttcatgatgg aacaaactac tctaggactg cttgtgtaat tgctgttgca aaggctcatg 180
atacatttga accttttctt catcagttgg ggtctagatt gttgcacata cttaagagat 240
tgctcccaat ctctttttat cttcttcaga aagattgtga gtatctaagt ggccatcagg 300
tgttcctcag gcgtgttgcc tccgccttcg acaactttgc agaatccact gaaaaatcat 360
gccgtgaaaa atgtatggag gacttggtaa gcaccacacg atatgtctca tggtctctac 420
acaataagag tcgggcagga ttacgccagt tcttagattc atttggtgga acagaacatt 480
ccaatgtttg taatgatccc actgcaactg ttctatcaca aacaaatgtg caagagaagg 540
aagacacaaa gccacaacta gaagtaaagc tcagtcacgt ggcctctgga actgatccta 600
gcacatccac ccagacagct gaaacaaagc ttgctgacct tcttgatagt acactttgga 660
atc 663

<210> SEQ ID NO 201

```
<211> LENGTH: 622
<212> TYPE: DNA
<213> ORGANISM: Prunus persica
<220> FEATURE:
<221> NAME/KEY: misc_feature
<222> LOCATION: (609)..(609)
<223> OTHER INFORMATION: n is a, c, g, or t

<400> SEQUENCE: 201

gcttatacct aacgcaggaa tgcgtttata tggtggtgca caataccacc gtgccatggc     60

tgagttccgc tttgtagttg gaggaataaa atgccctcca attacaaggg aagaaattgt    120

aaatgcatgt ggagttgaag atttacatga tggcacaaac tactcaagga cagcttgtgt    180

aatagccgtt gcaaaggccc gtgatacatt tgagcctttc cttcatcagt taggttgtag    240

actcttgcac attctaaaga gattacttcc tatatcagtc tatcttcttc agaaagatgg    300

tgagtattta agtggccatg aggtgtttct taggcgtgtt gcttctgctt tcaatgactt    360

tgcagaatct accgaaaggg catgtcgtga aaaatgcatg gaggatttag taagcaccac    420

ccgctatgtc acctggtccc ttcacaacaa gaatcgagct gggttacgtc aatttttaga    480

ctcgttcgct ggaacagaac ataacactat gggtagtaat tgcgtacctg ctggtatttc    540

ccaagattca tcctttgggt ctgttgccaa tgagaaggat actaagtcaa gggcagatgt    600

gaagctcanc catgtggcgt ct                                             622


<210> SEQ ID NO 202
<211> LENGTH: 752
<212> TYPE: DNA
<213> ORGANISM: Solanum tuberosum

<400> SEQUENCE: 202

gcgaatgtga ttcttcaaag gcaacaaagg ctgacggagg aatttgtgcc tcgtgcagat     60

ctgcttctgt ttctcatgtc tgctgatcga ccattaactg aaagtgaggt tagttttctg    120

cgttacactc agcagtggag taagaaggtc atttttgtgc tgaacaagtc tgacatatac    180

aagaataacg gcgagttgga ggaggccatt gcatttatca aagaaaatac acggaaattg    240

ctgaatacag aatccgtaac actgtatcca gtatctgcac ggctcgctct tgaatcaaag    300

ctttctactt ttgatggtgc ccttagtcaa aacaatggga gttcaaataa tgattctcac    360

tggaaaacca agagcttcta tgagcttgag aagtacttgt ctagcttttt ggattcatcc    420

acaagtactg gaattgagag aatgaagctg aagcttgaaa ctccaattgc cattgcagaa    480

caactacttt tagcttgtca aggacttgtg agacaagaat gtcagcaagc caaacaagac    540

ttgctgtttg ttgaggatct tgtcaacagc gtagaagagt gcacaaagaa gctggaagtt    600

gatagcattc tgtggaagag gcaggttcta tctctgataa actctgctca agcacgtgtt    660

gtccggcttg tagagtcaac gttacaactg tcaaatgttg atcttgtcgc tacatatgta    720

ttcagaagag aaaactctac tcaaatgcca gc                                  752


<210> SEQ ID NO 203
<211> LENGTH: 492
<212> TYPE: DNA
<213> ORGANISM: Glycine max

<400> SEQUENCE: 203

tgttgaatga agctattgaa gctatcaaga gggctgcacc tctgatggag gaggtttcac     60

ttcttaatga tgcggtttct caaattgatg agccattctt actggttata gtgggggaat    120

tcaactctgg taaatctacc gtgattaatg cgcttcttgg agaaagatat ctcaaagagg    180
```

```
gagttgttcc aacaactaat gagatcacat ttttacgata tactgactta gatattgaac    240

aacaacggtg tgaaaggcat ccagatggcc aatatatttg ctacattcct gctccaattc    300

ttaaagagat gaccattgtt gatacacctg gaactaatgt gattcttcag aggcagcagc    360

gtcttacaga ggaatttgta ccccgtgcag atttacttct ttttgtcatt tctgctgatc    420

gccctttaac tggaagtgag attgcttttc ttcgttattc tcagcagtgg aaaaagaaag    480

cggtctttgt ct                                                        492


<210> SEQ ID NO 204
<211> LENGTH: 446
<212> TYPE: DNA
<213> ORGANISM: Lycopersicon esculentum

<400> SEQUENCE: 204

gagaccatta agtacaattc tataagcagt cttttgaaaa aagatggact tcattggtga     60

atccgtctga ccaaattgag ttaggaacaa ctggtgtgct ggatagaaaa tctgaagtta    120

ccataagtgt catagaggat ttcagtgctg cagctgcttc aaaattgctt gagagagata    180

ttcgtgaagt gttcttgggt acttttggtg gtcttggagc agctggttta tcagcgtcgc    240

ttctgacatc tgttcttcaa accacattag aagacctcct tgcacttggc ctttgttctg    300

ctggcgggtt attagcggtc ttcaacttct catcccggag acagcaagtg gtagataaag    360

taaagaggac tgctgatggc ctttcacgtg aactcgaaga ggctatgcag aaggagctct    420

tggagacgac tagtaatgtg gaggac                                         446


<210> SEQ ID NO 205
<211> LENGTH: 521
<212> TYPE: DNA
<213> ORGANISM: Populus balsamifera subsp. trichocarpa

<400> SEQUENCE: 205

tggtgttgtg ctgtctgatc aagggcttcc tgcccttgtg gcaagaaata tgatgatggg     60

ttctcgaact gaatcagttg ttctaccttt ggtagccagg attgtgcaga caccatatgc    120

tgcattaaat gcgtctaatt ctgaaggtgc tgattttctt atatatgttc atggcccaga    180

ggatgatcct gatgtagaaa tgagccctgg attcgggaat gtgaagatac caatctttgt    240

cctcaatgct tcacgtgggg aggacacatt gtcggtgggg gcatcaaaat ttctgaaaac    300

cggtgctagt ggtttagttc tgtcattgga agatttgagg ttatttagcg atgatgcttt    360

gagtcagatg tttgacactc tgagtgcaac cggtaaaaac tttcaggatg accttgaaag    420

cttcagtaag ctcaaatcta tggatatgga aaatgatatt catgaaaaaa caacggtggc    480

aggctttgtt aaactggagg atagagaaaa acagctcata g                        521


<210> SEQ ID NO 206
<211> LENGTH: 324
<212> TYPE: PRT
<213> ORGANISM: Arabidopsis thaliana

<400> SEQUENCE: 206

Met Glu Ala Leu Ser His Val Gly Ile Gly Leu Ser Pro Phe Gln Leu
1               5                   10                  15

Cys Arg Leu Pro Pro Ala Thr Thr Lys Leu Arg Arg Ser His Asn Thr
            20                  25                  30

Ser Thr Thr Ile Cys Ser Ala Ser Lys Trp Ala Asp Arg Leu Leu Ser
        35                  40                  45
```

```
Asp Phe Asn Phe Thr Ser Asp Ser Ser Ser Ser Ser Phe Ala Thr Ala
    50                  55                  60

Thr Thr Thr Ala Thr Leu Val Ser Leu Pro Pro Ser Ile Asp Arg Pro
65                  70                  75                  80

Glu Arg His Val Pro Ile Pro Ile Asp Phe Tyr Gln Val Leu Gly Ala
                85                  90                  95

Gln Thr His Phe Leu Thr Asp Gly Ile Arg Arg Ala Phe Glu Ala Arg
            100                 105                 110

Val Ser Lys Pro Pro Gln Phe Gly Phe Ser Asp Asp Ala Leu Ile Ser
        115                 120                 125

Arg Arg Gln Ile Leu Gln Ala Ala Cys Glu Thr Leu Ser Asn Pro Arg
    130                 135                 140

Ser Arg Arg Glu Tyr Asn Glu Gly Leu Leu Asp Asp Glu Glu Ala Thr
145                 150                 155                 160

Val Ile Thr Asp Val Pro Trp Asp Lys Val Pro Gly Ala Leu Cys Val
                165                 170                 175

Leu Gln Glu Gly Gly Glu Thr Glu Ile Val Leu Arg Val Gly Glu Ala
            180                 185                 190

Leu Leu Lys Glu Arg Leu Pro Lys Ser Phe Lys Gln Asp Val Val Leu
        195                 200                 205

Val Met Ala Leu Ala Phe Leu Asp Val Ser Arg Asp Ala Met Ala Leu
    210                 215                 220

Asp Pro Pro Asp Phe Ile Thr Gly Tyr Glu Phe Val Glu Glu Ala Leu
225                 230                 235                 240

Lys Leu Leu Gln Glu Glu Gly Ala Ser Ser Leu Ala Pro Asp Leu Arg
                245                 250                 255

Ala Gln Ile Asp Glu Thr Leu Glu Glu Ile Thr Pro Arg Tyr Val Leu
            260                 265                 270

Glu Leu Leu Gly Leu Pro Leu Gly Asp Asp Tyr Ala Ala Lys Arg Leu
        275                 280                 285

Asn Gly Leu Ser Gly Val Arg Asn Ile Leu Trp Ser Val Gly Gly Gly
    290                 295                 300

Gly Ala Ser Ala Leu Val Gly Gly Leu Thr Arg Glu Lys Phe Met Asn
305                 310                 315                 320

Glu Ala Phe Leu


<210> SEQ ID NO 207
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 207

Cys Xaa Xaa Cys Xaa Gly Xaa Gly
1               5
```

-continued

```
<210> SEQ ID NO 208
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(21)

<400> SEQUENCE: 208

gcg ttt tta tga atg aca gct                                          21
Ala Phe Leu     Met Thr Ala
1                   5
```